(12) United States Patent
Conn et al.

(10) Patent No.: US 8,853,392 B2
(45) Date of Patent: Oct. 7, 2014

(54) BENZAMIDE MGLUR5 POSITIVE ALLOSTERIC MODULATORS AND METHODS OF MAKING AND USING SAME

(75) Inventors: P. Jeffrey Conn, Brentwood, TN (US); Craig W. Lindsley, Brentwood, TN (US); Charles David Weaver, Franklin, TN (US); Alice L. Rodriguez, Nashville, TN (US); Colleen M. Niswender, Brentwood, TN (US); Carrie K. Jones, Nashville, TN (US); Richard Williams, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 113 days.

(21) Appl. No.: 12/132,289

(22) Filed: Jun. 3, 2008

(65) Prior Publication Data
US 2009/0042855 A1    Feb. 12, 2009

Related U.S. Application Data

(60) Provisional application No. 60/941,686, filed on Jun. 3, 2007.

(51) Int. Cl.
| | |
|---|---|
| *C07D 265/30* | (2006.01) |
| *C07D 211/06* | (2006.01) |
| *C07D 207/04* | (2006.01) |
| *C07D 205/04* | (2006.01) |
| *C07C 235/70* | (2006.01) |
| *C07D 213/74* | (2006.01) |
| *C07D 211/52* | (2006.01) |
| *C07D 401/10* | (2006.01) |
| *C07D 207/09* | (2006.01) |
| *C07C 233/66* | (2006.01) |
| *C07D 409/04* | (2006.01) |
| *C07C 233/69* | (2006.01) |
| *A61K 31/4725* | (2006.01) |
| *A61K 31/472* | (2006.01) |
| *A61K 31/5377* | (2006.01) |
| *C07D 211/22* | (2006.01) |
| *C07D 211/58* | (2006.01) |
| *C07D 401/12* | (2006.01) |
| *C07D 211/46* | (2006.01) |

(Continued)

(52) U.S. Cl.
CPC ............ *C07D 211/60* (2013.01); *C07D 213/74* (2013.01); *C07D 211/52* (2013.01); *C07D 205/04* (2013.01); *C07D 401/10* (2013.01); *C07D 207/09* (2013.01); *C07C 2101/08* (2013.01); *C07C 233/66* (2013.01); *C07D 409/04* (2013.01); *C07C 233/69* (2013.01); *A61K 31/4725* (2013.01); *C07C 2101/14* (2013.01); *A61K 31/472* (2013.01); *A61K 31/5377* (2013.01); *C07C 2101/02* (2013.01); *C07D 211/22* (2013.01); *C07D 211/58* (2013.01); *C07D 401/12* (2013.01); *C07D 211/46* (2013.01); *C07C 2102/08* (2013.01); *C07D 413/12* (2013.01); *C07D 211/42* (2013.01); *C07D 211/18* (2013.01); *C07C 233/65* (2013.01); *C07D 217/06* (2013.01); *C07D 295/13* (2013.01); *C07D 295/30* (2013.01); *A61K 31/4035* (2013.01); *C07D 271/06* (2013.01); *C07D 401/04* (2013.01); *A61K 31/497* (2013.01); *C07D 295/14* (2013.01); *C07D 295/192* (2013.01)

USPC ........... 544/176; 546/248; 548/567; 548/953; 564/161

(58) Field of Classification Search
USPC ................... 544/176; 546/248; 548/567, 953; 564/161
See application file for complete search history.

(56) References Cited

U.S. PATENT DOCUMENTS

| | | | |
|---|---|---|---|
| 5,731,324 A | 3/1998 | Fisher | ............................. 514/320 |
| 6,137,002 A | 10/2000 | Fisher | ............................. 562/440 |

(Continued)

FOREIGN PATENT DOCUMENTS

| | | |
|---|---|---|
| EP | 1748048 | 1/2007 |
| JP | 43013473 | 6/1998 |

(Continued)

OTHER PUBLICATIONS

Xia, Mia. Polyethylene Glycol Supported Chloro[1,3,5]triazine: A Novel Synthetic Auxiliary for the Liquid-Phase Synthesis of Alkynyl Benzamide Derivatives. Synthetic Communications. 33(3) (2003) 403-408.*

(Continued)

*Primary Examiner* — Samantha Shterengarts
(74) *Attorney, Agent, or Firm* — Ballard Spahr LLP

(57) ABSTRACT

In one aspect, the invention relates to compounds, including phenylethynylbenzamide derivatives, cycloalkylethynylbenzamide derivatives, styrylbenzamide derivatives, 4-(3-phenyl-1,2,4-oxadiazol-5-yl)benzamide derivatives, 4-(pyridinylethynyl)benzamide derivatives, and $N^1$-phenylterephthalamide derivatives, which are useful as positive allosteric modulators of the metabotropic glutamate receptor subtype 5 (mGluR5); synthetic methods for making the compounds; pharmaceutical compositions comprising the compounds; and methods of treating neurological and psychiatric disorders associated with glutamate dysfunction using the compounds and compositions. This abstract is intended as a scanning tool for purposes of searching in the particular art and is not intended to be limiting of the present invention.

9 Claims, 17 Drawing Sheets

(51) Int. Cl.
*C07D 413/12* (2006.01)
*C07D 211/42* (2006.01)
*C07D 211/60* (2006.01)
*C07D 211/18* (2006.01)
*C07C 233/65* (2006.01)
*C07D 217/06* (2006.01)
*C07D 295/13* (2006.01)
*C07D 295/30* (2006.01)
*A61K 31/4035* (2006.01)
*C07D 271/06* (2006.01)
*C07D 401/04* (2006.01)
*A61K 31/497* (2006.01)
*C07D 295/14* (2006.01)
*C07D 295/192* (2006.01)

(56) References Cited

U.S. PATENT DOCUMENTS

| | | | |
|---|---|---|---|
| 6,656,957 B1* | 12/2003 | Allgeier et al. | 514/332 |
| 2003/0191323 A1* | 10/2003 | Ikawa et al. | 548/530 |
| 2006/0235069 A1 | 10/2006 | Duggan et al. | |

FOREIGN PATENT DOCUMENTS

| WO | WO 96/11210 | 4/1996 |
|---|---|---|
| WO | WO 98/37068 | 8/1998 |
| WO | WO-0026202 A1 | 5/2000 |
| WO | WO 00/75178 | 12/2000 |
| WO | WO 03/009807 | 2/2003 |
| WO | WO 03/059886 | 7/2003 |
| WO | WO 2004/009549 | 1/2004 |
| WO | WO-2004087048 A2 | 10/2004 |
| WO | WO 2005/040144 | 5/2005 |
| WO | WO 2005/044797 | 5/2005 |
| WO | WO 2005/046683 | 5/2005 |
| WO | WO-2005046683 A1 | 5/2005 |
| WO | WO 2005/048953 | 6/2005 |
| WO | WO-2005097773 A1 | 10/2005 |
| WO | WO 2005/108370 | 11/2005 |
| WO | WO 2006/020879 | 2/2006 |
| WO | WO 2006/089700 | 8/2006 |
| WO | WO 2006/093832 | 9/2006 |
| WO | WO 2007/093364 | 8/2007 |
| WO | WO 2008/151184 | 12/2008 |
| WO | WO 2009/047303 | 4/2009 |
| WO | WO 2009/078983 | 6/2009 |

OTHER PUBLICATIONS

Grant & Hackh's Chemical Dictionary (5th Ed. 1987) at p. 148.*
International Search Report and Written Opinion for International Application No. PCT/US2008/65647, mailed on Sep. 22, 2008.
Noeske, et al., 'Allosteric modulation of family 3 GPCRs,' QSAR & Combinatorial Science, 25(2), 134-146 (2005).
Wichmann, et al., "Functional neuroanatomy of the basal ganglia in Parkinson's disease," *Adv Neurol* 91:9-18 (2003).
Supplementary European Search Report for EP 08770045 mailed Jan. 17, 2012.
Ritzen, et al., "Discovery of a potent and brain penetrant mGluR5 positive allosteric modulator," *Bioorg. Med. Chem. Lett.*, 19 (2009) 3275-3278.
Rodriguez, et al., "Discovery of Novel Allosteric Modulators of Metabotropic Glutamate Receptor Subtype 5 Reveals Chemical and Functional Diversity and In Vivo Activity in Rat Behavioral Models of Anxiolytic and Antipsychotic Activity," *Mol Pharmacol* 78:1105-1123, 2010.
Sams, et al., "Efficacy switching SAR of mGluR5 allosteric modulators: highly potent positive and negative modulators from one chemotype," *Bioorg. Med. Chem. Lett.*, (2011).
Williams, et al., "Synthesis and SAR of centrally active mGlu5 positive allosteric modulators based on an aryl acetylenic bicyclic lactam scaffold" *Bioorg. Med. Chem. Lett.*, 21 (2011) 1350-1353.

Non-Final Office Action issued Aug. 4, 2010 for U.S. Appl. No. 12/263,224.
Response to Non-Final Office Action filed Feb. 4, 2011 for U.S. Appl. No. 12/263,224.
Kew, Pharmacology & Therapeutics, 2004, Elsevier, vol. 104, pp. 233-244.
Kato, et al., Chemical Abstract Services STN, 1990.
Gazivoda, et al., Bioorganic & Medicinal Chemistry, 2007, Elsevier, vol. 15, pp. 749-758.
International Preliminary Report on Patentability issued Dec. 7, 2009 for PCT/US2008/65647.
Alagarsamy, et al., "NMDA-Induced phosphorylation and regulation of mGluR5," Pharmacol., Biochem, Behav. (special issue devoted to metabotropic glutamate receptors) 73:299-306 (2002).
Ayala, et al., "mGluR5 positive allosteric modulators facilitate both hippocampal LTP and LTD and enhance spatial learning." Neuropsychopharmacology, 34(9):2057-71 (2009).
Chan et al., "Attenuation of ketamine-evoked behavioral responses by mGluR5 positive modulators in mice," Psychopharmacology (Berl), 198(1):141-8 (2008).
Chen, et al., "Interaction of novel positive allosteric modulators of metabotropic glutamate receptor 5 with the negative allosteric antagonist site is required for potentiation of receptor responses," Mol Pharmacol, 71(5):1389-98 (2007).
Chen, et al., "N-{4-Chloro-2-[(1,3-dioxo-1,3-dihydro-2H-isoindol-2-yl)methyl]phenyl}-2-hydroxybenzamide (CPPHA) acts through a novel site as a positive allosteric modulator of group 1 metabotropic glutamate receptors," Mol Pharmacol, 73(3):909-18 (2008).
Conn, et al., "Allosteric modulators of GPCRs: a novel approach for the treatment of CNS disorders," Nat Rev Drug Discov, 8(1):41-54 (2009).
Darrah, et al., "Interaction of N-methyl-D-aspartate and group 5 metabotropic glutamate receptors on behavioral flexibility using a novel operant set-shift paradigm," Behav Pharmacol., 19(3):225-34 (2008).
Gass JT, et al., "Positive allosteric modulation of mGluR5 receptors facilitates extinction of a cocaine contextual memory," Biol Psychiatry., 65(8):717-20 (2009).
Hodder, et al., "Identification of metabotropic glutamate receptor antagonists using an automated high-throughput screening system," Anal Biochem. 313:246-254 (2003).
Marino, et al., "Direct and indirect modulation of the N-methyl D-aspartate receptor: Potential for development of novel antipsychotic therapies," Curr Drug Targets-CNS Neurol Disord. 1: 1-16 (2002).
Marino, et al., "Glutamate receptors and Parkinson's disease: Opportunities for intervention," Drugs Aging 20:377-97 (2003).
Marino, et al., "Haloperidol-induced alteration in the physiological actions of group I mGluRs in the subthalamic nucleus and the substantia nigra pars reticulata," Neuropharmacology 43: 147-159 (2002).
Marino, et al., "Modulation of the basal ganglia by metabotropic glutamate receptors: Potential for novel therapeutics," Curr Drug Targets-CNS Neurol Disord. 1: 239-250 (2002).
Niswender, et al., "Metabotropic glutamate receptors: physiology, pharmacology, and disease," Annu Rev Pharmacol Toxicol, 50:295-322 (2010).
Niswender, et al., "A novel assay of Gi/o-linked G protein-coupled receptor coupling to potassium channels provides new insights into the pharmacology of the group III metabotropic glutamate receptors," Mol Pharmacol, 73(4):1213-24 (2008).
Okutani, et al., "Synthesis of capillarisins," Heterocycles 6:1581-9 (1977).
Poewe, et al., "Pharmacological treatment of Parkinson's disease," Movement disorders: Neurological principles and practice (Watts RL ed) pp. 201-219, McGraw-Hill, New York (1997).
Wichmann, et al., "Physiology of the basal ganglia and pathophysiology of movement desorders of basal ganglia origin" in Movement disorders: Neurological principles and practice (Watts RL ed) pp. 87-97, McGraw-Hill, New York (1997).
Wittmann, et al., "Activation of metabotropic glutamate receptor 1 inhibits glutamatergic transmission in the substantia nigra pars reticulate," Neurosci . . . 105:881-889 (2001).

(56) References Cited

OTHER PUBLICATIONS

Xia et al., Mia. Polyethylene Glycol Supported Chloro[1,3,5]triazene: A Novel Synthetic Auxiliary for the Liquid-Phase Synthesis of Alkynyl Benzamide Derivatives, Synthetic Communications, 33(3) (2003) 403-408.
Alagarsamy, et al., "Coordinate regulation of metabotropic glutamate receptors," Curr Opin Neurobiol 11:357-362 (2001).
Alagarsamy, et al., "NMDA-induced reversal of mGluR5 desensitization is mediated by activation of protein phosphatase 2B/calcineurin," J. Neurochem. (submitted) (2005).
Albin, et al., "The functional anatomy of basal ganglia disorders," Trends Neurosci 12:366-75 (1989).
Andreasen, "Scales for the Assessment of Negative Symptoms", Iowa City, Iowa (1983).
Annoura, et al., "A novel class of antagonists for metabotropic glutamate receptors, 7-(hydroxycyclopropa[b]chromen-1a-carboxylates," Bioorg. Med. Chem. Lett. 6:763-766 (1996).
Awad-Granko, et al., "Activation of groups I and III metabotropic glutamate receptors inhibits excitatory transmission in the rat subthalamic nucleus," Neuropharmacol. 41: 32-41 (2001).
Awad et al., "Activation of metabotropic glutamate receptor 5 has direct excitatory effects and potentiates NMDA receptor currents in neurons of the subthalamic nucleus," J. Neurosci. 20:7871-7879 (2000).
Berger, et al., Anil-Synthese. 20. Mitteilung . Über die Herstellung von Stilbenyl-Derivaten des 1,2,4,-Oxadiazols, Helvetica Chimica Acta, 62:1411-1428 (2004) (abstract).
Bevan, et al., "Move to the rhythm: oscillations in the subthalamic nucleus-external globus pallidus network," Trends Neurosci 25:525-31 (2002).
Boraud, et al., "From single extracellular unit recording in experimental and human Parkinsonism to the development of a functional concept of the role played by the basal ganglia in motor control," Prog Neurobiol 66:265-83 (2002).
Bradley, et al., "Immunohistochemical localization of subtype 4a metabotropic glutamate receptors in the rat and mouse basal ganglia," J Comp Neurol 407:33-46 (1999).
Braff, et al., "Sensorimotor gating and schizophrenia. Human and animal model studies," Archives of general psychiatry, 47(2):181-8 (1990).
Braff, et al., "Human studies of prepulse inhibition of startle: normal subjects, patient groups, and pharmacological studies," Psychopharmacology, 156(2-3), 234-258 (2001).
Brody, "Assessment of a prepulse inhibition deficit in a mutant mouse lacking mGlu5 receptors," Molecular Psychiatry, 9:35-41 (2004).
Chavez-Noriega et al., "Curr. Drug Targets: CNS & Neurological Disorders," 1:261-281 (2002).
Chavez-Noriega, et al., "Novel potential therapeutics for schizophrenia: focus on the modulation of metabotropic glutamate receptor function," Curr Neuropharmacol,, 3:9-34 (2005).
Chiamulera et al. Nature Neurosci. 4:873-874 (2001).
Conn, et al., "Pharmacology and functions of metabotropic glutamate receptors," Annu Rev Pharmacol Toxicol 37:205-37 (1997).
Conn, "Physiological roles and therapeutic potential of metabotropic glutamate receptors," Annals New York Acad. Sci. 1003:12-21 (2003).
Corti, et al., "Distribution and synaptic localisation of the metabotropic glutamate receptor 4 (mGluR4) in the rodent CNS," Neuroscience 110:403-20 (2002).
Daggett, et al., "Molecular and functional characterization of recombinant human metabotropic glutamate receptor subtype 5," Neuropharmacology 34:871-86 (1995).
De Blasi, et al., "Molecular determinants of metabotropic glutamate receptor signaling," Trends Pharmacol Sci. 22: 114-120 (2001).
DeLong, "Primate models of movement disorders of basal ganglia origin," Trends Neurosci 13:281-5 (1990).
Doherty, et al., "Metabotropic glutamate receptors modulate feedback inhibition in a developmentally regulated manner in rat dentate gyrus," J Physiol, 561.2:395-401 (2004).

Engers, et al., "Synthesis, SAR and Unanticipated Pharmacological Profiles of Analogues of the mGluR5 Ago-potentiator ADX-47273," ChemMedChem, 4:505-511 (2009).
Epping-Jordan et al., "In Vivo Characterization of mGluR5 Positive Allosteric Modulators as Novel Treatments for Schizophrenia and Cognitive Dysfunction," Neuropharmacology, 49:243 (2005).
Fisher et al., "Non-Peptide RGD Surrogates Which Mimic a Gly-Asp β-Turn: Potent Antagonists of Platelet Glycoprotein IIb-IIIa," J. Med. Chem., 40:2085-2101 (1997).
Gasparini et al., "2-Methyl-6-(phenylethynyl)-pyridine (MPEP), a potent, selective and systemically active mGlu5 receptor antagonist," Neuropharmacol. 38:1493-1503 (1999).
Geyer, et al., "Mouse genetic models for prepulse inhibition: an early review," Molecular Psychiatry, 7(10):1039-1053 (2002).
Geyer, M. A. 'Behavioral studies of hallucinogenic drugs in animals: implications for schizophrenia research.' Pharmacopsychiatry, 31(Suppl. 2), 73-79 (1998).
Jagadeesh, et al., "Selective C-3 monochlorination of 2-methylchromones and chromone-2-carboxaldehydes," Synthetic Comm. 28:3827-3833 (1998).
Johnson et al., "Discovery of allosteric potentiators for the metabotropic glutamate 2 receptor: synthesis and subtype selectivity of N-(4-(2-methoxyphenoxy)phenyl)-N-(2,2,2-trifluoroethylsulfonyl)pyrid-3-ylmethylamine," J. Med. Chem., 46:3189-3192 (2003).
Kay et al., Schizophrenia Bulletin 13, 261-276 (1987).
Kinney, et al., "The glycine transporter type 1 inhibitor NFPS potentiates NMDA receptor-mediated responses in vivo and produces an antipsychotic profile in rodent behavior," J. Neurosci. 23:7586-9 (2003).
Kinney, et al., "Metabotropic glutamates $_5$ (mGluR5) receptors modulate locomotor activity and sensorimotor gating in rodents," J. Pharmacol. Exp. Ther. 306:116-123 (2003).
Kinney, et al.. "A novel selective positive allosteric modulator of metabotropic glutamate receptor subtype 5 (mGluR5) has an antipsychotic profile in rat behavioral models," J. Pharmacol. Exp. Therapeut., 313(1):199-206 (2005).
Knoflach et al., "Positive allosteric modulators of metabotropic glutamate 1 receptor: characterization, mechanism of action, and binding site," Proc. Natl. Acad. Sci. USA 98:13402-13407 (2001).
Koren et al., Schizophr Bull, 32(2), 310-26 (2006).
Lavreysen, et al., "[3H]R214127: a novel high-affinity radioligand for the mGlu1 receptor reveals a common binding site shared by multiple allosteric antagonists," Mol Pharmacol 63:1082-93 (2003).
Lindenmayer et al., J Nerv Ment Dis, 182, 631-638 (1994).
Lindsley, et al., "Discovery of positive allosteric modulators for the metabotropic glutamate receptor subtype 5 from a series of N-(1,3-Diphenyl-1H-pyrazol-5-yl) benzamides that potentiate receptor function in vivo," J. Med. Chem., 47:5825-5828 (2004).
Litschig et al., "CPCCOEt, a noncompetitive metabotropic glutamate receptor 1 antagonist, inhibits receptor signaling without affecting glutamate binding," Mol. Pharmacol., 55:453-461 (1999).
Liu, et al., "ADX47273 [S-(4-Fluoro-phenyl)-{3-[3-(4-fluoro-phenyl)-[1,2,4]-oxadiazol-5-yl]-piperidin-1-yl}-methanone]: A Novel Metabotropic Glutamate Receptor 5-Selective Positive Allosteric Modulator with Preclinical Antipsychotic-Like and Procognitive Activities," J Pharmacol Exp Ther, 327:827-839, 2008.
Lloyd et al., "Design and Synthesis of 4-Substituted Benzamides as Potent, Selective, and Orally Bioavailable $I_{Ks}$ Blockers," J. Med. Chem., 44:3764-3767 (2001).
Malherbe, et al., "Mutational analysis and molecular modeling of the allosteric binding site of a novel, selective, noncompetitive antagonist of the metabotropic glutamate 1 receptor," J Biol Chem 278:8340-7 (2003).
Malherbe, et al., "Mutational analysis and molecular modeling of the binding pocket of the metabotropic glutamate 5 receptor negative modulator 2-methyl-6-(phenylethynyl)-pyridine," Mol Pharmacol 64:823-32 (2003).
Maneuf, et al., "On the role of enkephalin cotransmission in the GABAergic striatel efferents to the globus pallidus," Exp Neurol 125:65-71(1994).

(56) References Cited

OTHER PUBLICATIONS

Mannaioni et.al., "mGluR1 and mGluR5 receptors differentially regulate CA1 pyramidal cell function," *J. Neurosci.* 21:5925-5934 (2001).
Marino, et al., "Activation of group I metabotropic glutamate receptors produces a direct excitation and disinhibition of GABAergic projection neurons in the substantia nigra pars reticulata," *J. Neurosci.* 21:7001-7012 (2001).
Marino et al., "Allosteric modulation of group III metabotropic glutamate receptor 4: a potential approach to Parkinson's disease treatment," Proc. Natl. Acad. Sci. USA 100:13668-13763 (2003).
Marino, et al., "Localization and Physiological Roles of Metabotropic Glutamate Receptors in the Direct and Indirect Pathways of the Basal Ganglia," *Amino Acids.* 23:185-91 (2002).
Mathiesen, et al., "Positive allosteric modulation of the human metabotropic glutamate receptor 4 (hmGluR4) by SIB-1893 and MPEP," *Br J Pharmacol* 138:1026-30 (2003).
Mohler, et al., "A new benzodiazepine pharmacology," *J Pharmacol Exp Ther* 300:2-8 (2002).
Natesan, et al., 'Evaluation of N-Desmethylclozapine as a Potential Antipsychotic—Preclinical Studies,' *Neuropsychopharmacology*, 32(7):1540-1549 (2007).
O'Brien et al., "A family of highly selective allosteric modulators of the metabotropic glutamate receptor subtype 5," Mol. Pharmacol., 64:731-740 (2003).
O'Brien, et al., "A novel selective allosteric modulator potentiates the activity of native metabotropic glutamate receptor subtype 5 (mGluR5) in rat forebrain," *J. Pharmacol. Exp. Ther.* 309:568-577 (2004).
Ossowska et al. Neuropharmacol. 41: 413-420 (2001).
Ott, et al., "Chiral resolution, pharmacological characterization, and receptor docking of the noncompetitive mGlu1 receptor antagonist (+−)-2-hydroxyimino-1a,2-dihydro-1H-7-oxacyclopropa[b]naphthalene-7a-carboxylic acid ethyl ester," *J. Med. Chem.* 43:4428-4436 (2000).
Pagano, et al., "The non-competitive antagonists 2-methyl-6-(phenylethynyl)pyridine and 7-hydroxyiminocyclopropan[b]chromen-1a-carboxylic acid ethyl ester interact with overlapping binding pockets in the transmembrane region of group I metabotropic glutamate receptors," *J Biol Chem* 275:33750-8 R (2000).
Peavy, et al., "Differential regulation of mGluR5-mediated phosphoinositide hydrolysis and extracellular signal-regulated kinase responses by PKC in cultutred astrocytes," *J. Neurochem.* 83: 110-118 (2002).
Peavy, et al., "Metabotropic glutamate receptor 5-induced phosphorylation of extracellular signal regulated kinase in astrocytes depends on transactivation of the epidermal growth factor receptor," *J. Neurosci.* 21: 9619-9628 (2001).
Poisik, et al., "Distinct functional roles of metabotropic glutamate receptors 1 and 5 in the rat globus pallidus," *J. Neurosci.* 23:122-130 (2003).
Poisik, et al., "Metabotropic glutamate receptor 2 modulates excitatory synaptic transmission in the rat globus pallidus," *Neuropharmacol*, 49: 57-69 (2005).
Powell, et al., "Potential use of animal models to examine antipsychotic prophylaxis for schizophrenia," *Clinical Neuroscience Research*, 3(4-5):289-296 (2003).
Ritzen et al., "Discovery of a potent and brain penetrant mGluR5 positive allosteric modulator," Bioorganic & Medicinal Chemistry Letters, 19:3275-3278 (2009).
Rouse, et al., "Distribution and roles of metabotropic glutamate receptors in the basal ganglia motor circuit: implications for treatment of Parkinson's disease and related disorders," *Pharmacol Ther* 88:427-435 (2000).

Salt, et al., "Contributions of mGlu1 and mGlu5 receptors to interactions with N-methyl-D-aspartate receptor-mediated responses and nociceptive sensory responses of rat thalamic neurons," Neurosci., 100:375-380 (2001).
Schaffhauser, et al., "Pharmacological characterization and identification of amino acids involved in the positive modulation of metabotropic glutamate receptor subtype 2," *Mol Pharmacol* 64:798-810 (2003).
Schlumberger, et al., "Comparison of the mGlu5 receptor positive allosteric modulator ADX47273 and the mGlu2/3 receptor agonist LY354740 in tests for antipsychotic-like activity," Eur. J. Pharmacol., doi:10.1016/j.ejphar.2009.09.006 (2009).
Schoepp, et al., "Metabotropic glutamate receptors," *Pharmacol. Biochem. Behav.* (special issue devoted to metabotropic glutamate receptors) 74: 255-256 (2002).
Schoepp, et al., "Pharmacological agents acting at subtypes of metabotropic glutamate receptors," Neuropharmacol. 38: 1431-1476 (1999).
Sharma, et al., "Discovery of Molecular Switches That Modulate Modes of Metabotropic Glutamate Receptor Subtype 5 (mGlu5) Pharmacology in Vitro and in Vivo within a Series of Functionalized, Regioisomeric 2- and 5-(Phenylethynyl) Pyrimidines," *J. Med. Chem.*, 52:4103-4106 (2009).
Sorensen, et al., "G-protein coupled receptor kinases regulate metabotropic glutamate receptor 5 function and expression," *Neuropharmacol.* 44:699-706 (2003).
Spooren et. al. Anxiolytic-Like Effects of the Prototypical Metabotropic Glutamate Receptor 5 Antagonist 2-Methyl-6-(phenylethynyl)pyridine in Rodents, J. *Pharmacol. Exp. Therapeut.*, 295:1267-1275 (2000).
STN Database Search for Structure No. 3 (L13).
Tatarczynska et al. Br. J. Pharmacol. 132:1423-1430 (2001).
Thomsen et al., "Decreased prepulse inhibition and increased sensitivity to muscarinic, but not dopaminergic drugs in M5 muscarinic acetylcholine receptor knockout mice," Psychopharmacology, 192:97-110 (2007).
Valenti, et al., "Distinct physiological roles of the Gq coupled metabotropic glutamate receptors co-expressed in the same neuronal populations," *J. Cellular Physiol.* 191: 125-137 (2002).
Valenti, et al., "Group III metabotropic glutamate receptor-mediated modulation of the striatopallidal synapse," *J Neurosci* 23:7218-26 (2003).
Weiss, et al., "Environmental animal models for sensor motor gating deficiencies in schizophrenia: a review," *Psychopharmacology* 156(2-3):305-326 (2001).
Williams, et al., "Development of a scintillation proximity assay for analysis of $Na^+$/$Cl^-$ dependent neurotransmitter transporter activity," *Analytical Biochem.* 321:31-37 (2003).
Williams, et al., "Difference in mGluR5 interaction between positive allosteric modulators from two structural classes," *Annals New York Acad. Sci.* 1003:481-484 (2003).
Williams, et al., "Effects of typical and atypical antipsychotics on human glycine transporters," *Schizophrenia Res.* (in press) (2005).
Wittmann et al., Activation of group III mGluRs inhibits GABAergic and glutamatergic transmission in the substantia nigra pars reticulata. *J Neurophysiol* 85:1960-8 (2001).
Wittmann, et al., "Dopamine modulates the function of group II and group III metabotropic glutamate receptors in the substantia nigra pars reticulate," *J Pharmacol Exp Ther* 302:433-41 (2002).
Zheng, et al., "Allosteric interaction between the N-terminal domain and the ligand-binding domain of NR2A," *Nat Neurosci* 4: 894-901 (2001).

* cited by examiner

EC50 = 113 nM
85% Glu Max
Ki = 2.6 μM

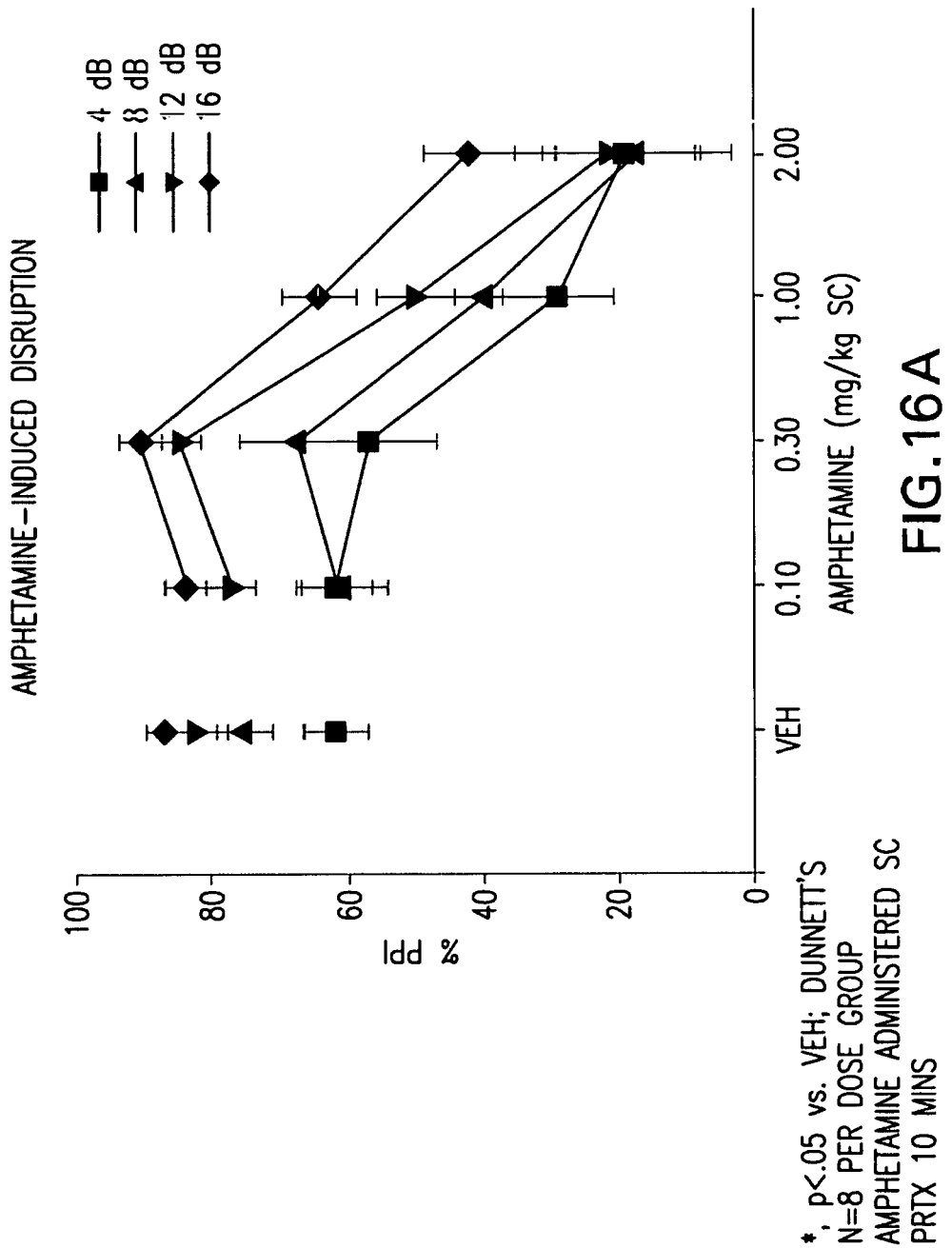

BENZAMIDE MGLUR5 POSITIVE ALLOSTERIC MODULATORS AND METHODS OF MAKING AND USING SAME

CROSS-REFERENCE TO RELATED APPLICATIONS

This application claims the benefit of U.S. Application No. 60/941,686, filed Jun. 3, 2007, which is hereby incorporated herein by reference in its entirety.

ACKNOWLEDGMENT

This invention was made with government support under Grants NIH/NIMH R01 MH062646 and F32 NS049865 awarded by the National Institutes of Health. The United States government has certain rights in the invention.

BACKGROUND

L-glutamic acid, the most commonly occurring neurotransmitter in the central nervous system, plays a role in a large number of physiological processes. The glutamate-dependent stimulus receptors are divided into two main groups. The first main group forms ligand-controlled ion channels. The second main group is metabotropic glutamate receptors (mGluRs), which belong to the family of G-protein-coupled receptors. Metabotropic glutamate receptors, including mGluR5, have been implicated in a wide range of biological functions, indicating a potential role for the mGluR5 receptor in a variety of disease processes in mammals. Ligands of metabotropic glutamate receptors can be used for the treatment or prevention of acute and/or chronic neurological and/or psychiatric disorders associated with glutamate dysfunction, such as psychosis, schizophrenia, age-related cognitive decline, and the like.

Selective positive allosteric modulators are compounds that do not directly activate receptors by themselves, but binding of these compounds increase the affinity of a glutamate-site agonist at its extracellular N-terminal binding site. Positive allosteric modulation (potentiations) is thus an attractive mechanism for enhancing appropriate physiological receptor activation.

Unfortunately, there is a scarcity of selective positive allosteric modulators for the mGluR5 receptor. Further, conventional mGluR5 receptor modulators typically lack satisfactory aqueous solubility and exhibit poor oral bioavailability. Therefore, there remains a need for methods and compositions that overcome these deficiencies and that effectively provide selective positive allosteric modulators for the mGluR5 receptor.

SUMMARY

In accordance with the purpose(s) of the invention, as embodied and broadly described herein, the invention, in one aspect, relates to compounds useful as positive allosteric modulators (i.e., potentiators) of the metabotropic glutamate receptor subtype 5 (mGluR5), methods of making same, pharmaceutical compositions comprising same, and methods of treating neurological and psychiatric disorders associated with glutamate dysfunction using same.

Disclosed are compounds having a structure represented by a formula:

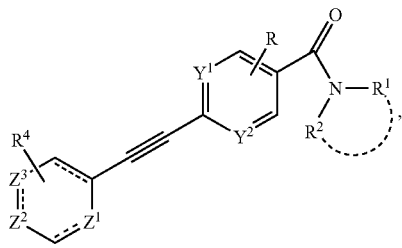

wherein $R^1$ and $R^2$ are independently optionally substituted organic radicals comprising from 1 to 12 carbon atoms; wherein each ---- is an optional covalent bond; wherein $Y^1$ and $Y^2$ are independently selected from N and C—R; wherein R comprises two to four substituents independently selected from hydrogen, halogen, hydroxyl, cyano, nitro, thiol, or an organic radical comprising 1 to 12 carbon atoms; wherein $Z^1$, $Z^2$, and $Z^3$ are independently selected from N and C—$R^4$, with the proviso that no more than two of $Z^1$, $Z^2$, and $Z^3$ are nitrogen; and wherein $R^4$ comprises up to five substituents independently selected from hydrogen, halogen, hydroxyl, cyano, nitro, thiol, optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, optionally substituted heteroaryl, optionally substituted alkoxyl, optionally substituted thioalkyl, optionally substituted alkylsulfinyl, optionally substituted alkylsulfonyl, and optionally substituted amino, thioamido, amidosulfonyl, alkoxycarbonyl, carboxamide, aminocarbonyl, and alkylamine-carbonyl; or a pharmaceutically acceptable salt or N-oxide thereof, wherein the compound exhibits potentiation of mGluR5 response to glutamate as an increase in response to non-maximal concentrations of glutamate in human embryonic kidney cells transfected with rat mGluR5 in the presence of the compound, compared to the response to glutamate in the absence of the compound.

Also disclosed are compounds having a structure represented by a formula:

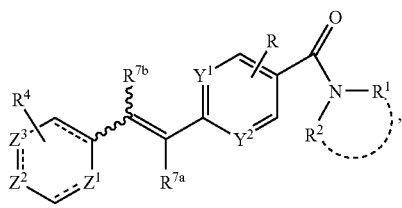

wherein $R^1$ and $R^2$ are independently hydrogen or an optionally substituted organic radical comprising from 1 to 12 carbon atoms; wherein each ---- is an optional covalent bond; wherein $Y^1$ and $Y^2$ are independently selected from N and C—R; wherein R comprises two to four substituents independently selected from hydrogen, halogen, hydroxyl, cyano, nitro, thiol, or an organic radical comprising 1 to 12 carbon atoms; wherein $Z^1$, $Z^2$, and $Z^3$ are independently selected from N and C—$R^4$, with the proviso that no more than two of $Z^1$, $Z^2$, and $Z^3$ are nitrogen; wherein $R^4$ comprises up to five substituents independently selected from hydrogen, halogen, hydroxyl, cyano, nitro, thiol, optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, optionally substituted heteroaryl, optionally substituted alkoxyl, optionally substituted thioalkyl, optionally substituted alkylsulfinyl, optionally substituted alkylsulfonyl, and optionally substituted amino, thioamido, amidosulfonyl, alkoxycarbonyl, carboxamide, amino-carbonyl, and alkylamine-carbonyl; and wherein $R^{7a}$ and $R^{7b}$ together form an optionally substituted carbocyclic or heterocyclic ring having from two to five carbons or are independently selected from hydrogen, halogen, hydroxyl, cyano, nitro, thiol, amino, and an organic radical comprising 1 to 5 carbon atoms selected from optionally substituted C1-C6 alkyl or C2-C6 alkenyl or C2-C6 alkynyl, optionally substituted C1-C6 heteroalkyl or C2-C6 heteroalkenyl or C2-C6 heteroalkynyl, optionally substituted C3-C8 cycloalkyl or C3-C8 cycloalkenyl or C6-C8 cycloalkynyl, optionally substituted C3-C8 heterocycloalkyl or C3-C8 heterocycloalkenyl or C6-C8 heterocycloalkynyl, optionally substituted aryl, optionally substituted heteroaryl, optionally substituted alkoxyl, optionally substituted thioalkyl, optionally substituted alkylsulfinyl, optionally substituted alkylsulfonyl, and optionally substituted amino, thioamido, amidosulfonyl, alkoxycarbonyl, carboxamide, amino-carbonyl, and alkylamine-carbonyl; or a pharmaceutically acceptable salt or N-oxide thereof, wherein the compound exhibits potentiation of mGluR5 response to glutamate as an increase in response to non-maximal concentrations of glutamate in human embryonic kidney cells transfected with rat mGluR5 in the presence of the compound, compared to the response to glutamate in the absence of the compound.

Also disclosed are compounds having a structure represented by a formula:

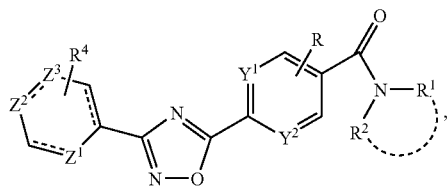

wherein $R^1$ and $R^2$ are independently optionally substituted organic radicals comprising from 1 to 12 carbon atoms; wherein each ----- is an optional covalent bond; wherein $Y^1$ and $Y^2$ are independently selected from N and C—R; wherein R comprises two to four substituents independently selected from hydrogen, halogen, hydroxyl, cyano, nitro, thiol, or an organic radical comprising 1 to 12 carbon atoms; wherein $Z^1$, $Z^2$, and $Z^3$ are independently selected from N and C—$R^4$, with the proviso that no more than two of $Z^1$, $Z^2$, and $Z^3$ are nitrogen; and wherein $R^4$ comprises up to five substituents independently selected from hydrogen, halogen, hydroxyl, cyano, nitro, thiol, optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, optionally substituted heteroaryl, optionally substituted alkoxyl, optionally substituted thioalkyl, optionally substituted alkylsulfinyl, optionally substituted alkylsulfonyl, and optionally substituted amino, thioamido, amidosulfonyl, alkoxycarbonyl, carboxamide, aminocarbonyl, and alkylamine-carbonyl; or a pharmaceutically acceptable salt or N-oxide thereof, wherein the compound exhibits potentiation of mGluR5 response to glutamate as an increase in response to non-maximal concentrations of glutamate in human embryonic kidney cells transfected with rat mGluR5 in the presence of the compound, compared to the response to glutamate in the absence of the compound.

Also disclosed are compounds having a structure represented by a formula:

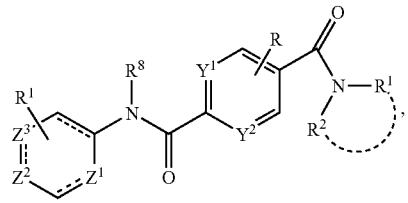

wherein $R^1$ and $R^2$ are independently hydrogen or an optionally substituted organic radical comprising from 1 to 12 carbon atoms; wherein each ----- is an optional covalent bond; wherein $Y^1$ and $Y^2$ are independently selected from N and C—R; wherein R comprises two to four substituents independently selected from hydrogen, halogen, hydroxyl, cyano, nitro, thiol, or an organic radical comprising 1 to 12 carbon atoms; wherein $Z^1$, $Z^2$, and $Z^3$ are independently selected from N and C—$R^4$, with the proviso that no more than two of $Z^1$, $Z^2$, and $Z^3$ are nitrogen; wherein $R^4$ comprises up to five substituents independently selected from hydrogen, halogen, hydroxyl, cyano, nitro, thiol, optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, optionally substituted heteroaryl, optionally substituted alkoxyl, optionally substituted thioalkyl, optionally substituted alkylsulfinyl, optionally substituted alkylsulfonyl, and optionally substituted amino, thioamido, amidosulfonyl, alkoxycarbonyl, carboxamide, amino-carbonyl, and alkylamine-carbonyl; and wherein $R^8$ is selected from hydrogen and lower alkyl; or a pharmaceutically acceptable salt or N-oxide thereof, wherein the compound exhibits potentiation of mGluR5 response to glutamate as an increase in response to non-maximal concentrations of glutamate in human embryonic kidney cells transfected with rat mGluR5 in the presence of the compound, compared to the response to glutamate in the absence of the compound.

Also disclosed are methods for the treatment of a neurological and/or psychiatric disorder associated with glutamate dysfunction in a mammal comprising the step of administering to the mammal at least one compound having a structure represented by a formula:

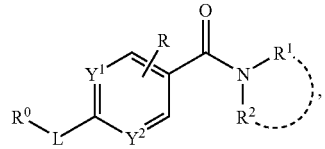

wherein ----- is an optional covalent bond; wherein $Y^1$ and $Y^2$ are independently selected from N and C—R; wherein R comprises two to four substituents independently selected from hydrogen, halogen, hydroxyl, cyano, nitro, thiol, or an organic radical comprising 1 to 12 carbon atoms; wherein $R^1$ and $R^2$ are independently hydrogen or an optionally substituted organic radical comprising from 1 to 12 carbon atoms; wherein $R^0$ is an optionally substituted organic radical comprising 4 to 14 carbon atoms, wherein L is an organic divalent radical comprising 1 to 7 carbon atoms and is selected from:

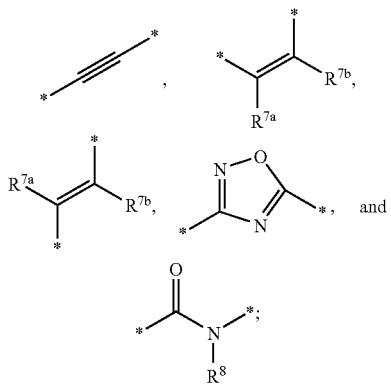

wherein $R^{7a}$ and $R^{7b}$ together form an optionally substituted carbocyclic or heterocyclic ring having from two to five carbons or are independently selected from hydrogen, halogen, hydroxyl, cyano, nitro, thiol, amino, and an organic radical comprising 1 to 5 carbon atoms selected from optionally substituted C1-C5 alkyl or C2-C5 alkenyl or C2-C5 alkynyl, optionally substituted C1-C5 heteroalkyl or C2-C5 heteroalkenyl or C2-C5 heteroalkynyl, optionally substituted C3-C5 cycloalkyl or C3-C5 cycloalkenyl, optionally substituted C3-C5 heterocycloalkyl or C3-C5 heterocycloalkenyl, optionally substituted aryl, optionally substituted heteroaryl, optionally substituted alkoxyl, optionally substituted thioalkyl, optionally substituted alkylsulfinyl, optionally substituted alkylsulfonyl, and optionally substituted amino, thioamido, amidosulfonyl, alkoxycarbonyl, carboxamide, aminocarbonyl, and alkylamine-carbonyl; and wherein $R^8$ is selected from hydrogen, and an organic radical comprising 1 to 6 carbon atoms selected from optionally substituted C1-C6 alkyl or C2-C6 alkenyl or C2-C6 alkynyl, optionally substituted C1-C6 heteroalkyl or C2-C6 heteroalkenyl or C2-C6 heteroalkynyl, optionally substituted C3-C6 cycloalkyl or C3-C6 cycloalkenyl or C6 cycloalkynyl, optionally substituted C3-C6 heterocycloalkyl or C3-C6 heterocycloalkenyl or C6 heterocycloalkynyl, optionally substituted aryl, and optionally substituted heteroaryl; or a pharmaceutically acceptable salt or N-oxide thereof, in a dosage and amount effective to treat the neurological and/or psychiatric disorder associated with glutamate dysfunction in the mammal.

Also disclosed are methods for potentiation of metabotropic glutamate receptor activity in a mammal comprising the step of administering to the mammal at least one compound having a structure represented by a formula:

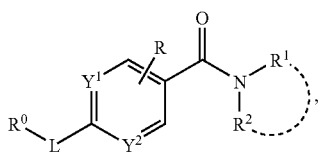

wherein ---- is an optional covalent bond; wherein $Y^1$ and $Y^2$ are independently selected from N and C—R; wherein R comprises two to four substituents independently selected from hydrogen, halogen, hydroxyl, cyano, nitro, thiol, or an organic radical comprising 1 to 12 carbon atoms; wherein $R^1$ and $R^2$ are independently hydrogen or an optionally substituted organic radical comprising from 1 to 12 carbon atoms; wherein $R^0$ is an optionally substituted organic radical comprising 4 to 14 carbon atoms; and wherein L is an organic divalent radical comprising 1 to 7 carbon atoms and is selected from:

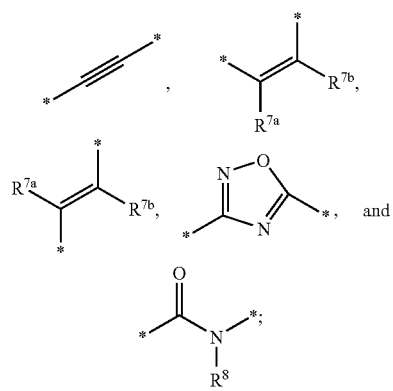

wherein $R^{7a}$ and $R^{7b}$ together form an optionally substituted carbocyclic or heterocyclic ring having from two to five carbons or are independently selected from hydrogen, halogen, hydroxyl, cyano, nitro, thiol, amino, and an organic radical comprising 1 to 5 carbon atoms selected from optionally substituted C1-C5 alkyl or C2-C5 alkenyl or C2-C5 alkynyl, optionally substituted C1-C5 heteroalkyl or C2-C5 heteroalkenyl or C2-C5 heteroalkynyl, optionally substituted C3-C5 cycloalkyl or C3-C5 cycloalkenyl, optionally substituted C3-C5 heterocycloalkyl or C3-C5 heterocycloalkenyl, optionally substituted aryl, optionally substituted heteroaryl, optionally substituted alkoxyl, optionally substituted thioalkyl, optionally substituted alkylsulfinyl, optionally substituted alkylsulfonyl, and optionally substituted amino, thioamido, amidosulfonyl, alkoxycarbonyl, carboxamide, aminocarbonyl, and alkylamine-carbonyl; or a pharmaceutically acceptable salt or N-oxide thereof, in a dosage and amount effective to potentiate metabotropic glutamate receptor activity in the mammal.

Also disclosed are methods for partial agonism of metabotropic glutamate receptor activity in a mammal comprising the step of administering to the mammal at least one compound having a structure represented by a formula:

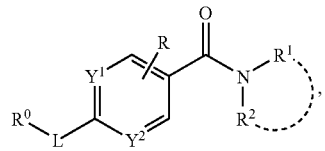

wherein each ---- is an optional covalent bond; wherein $Y^1$ and $Y^2$ are independently selected from N and C—R; wherein R comprises two to four substituents independently selected from hydrogen, halogen, hydroxyl, cyano, nitro, thiol, or an organic radical comprising 1 to 12 carbon atoms; wherein $R^1$ and $R^2$ are independently hydrogen or an optionally substituted organic radical comprising 1 to 12 carbon atoms; wherein $R^0$ is an optionally substituted organic radical comprising 4 to 14 carbon atoms, wherein L is an organic divalent radical comprising 1 to 7 carbon atoms and is selected from:

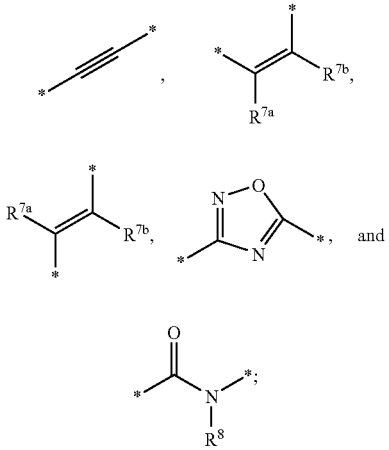

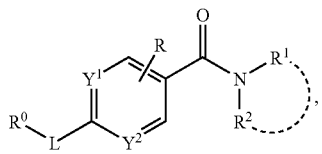

wherein $R^{7a}$ and $R^{7b}$ together form an optionally substituted carbocyclic or heterocyclic ring having from two to five carbons or are independently selected from hydrogen, halogen, hydroxyl, cyano, nitro, thiol, amino, and an organic radical comprising 1 to 5 carbon atoms selected from optionally substituted C1-C5 alkyl or C2-C5 alkenyl or C2-C5 alkynyl, optionally substituted C1-C5 heteroalkyl or C2-C5 heteroalkenyl or C2-C5 heteroalkynyl, optionally substituted C3-C5 cycloalkyl or C3-C5 cycloalkenyl, optionally substituted C3-C5 heterocycloalkyl or C3-C5 heterocycloalkenyl, optionally substituted aryl, optionally substituted heteroaryl, optionally substituted alkoxyl, optionally substituted thioalkyl, optionally substituted alkylsulfinyl, optionally substituted alkylsulfonyl, and optionally substituted amino, thioamido, amidosulfonyl, alkoxycarbonyl, carboxamide, aminocarbonyl, and alkylamine-carbonyl; and or a pharmaceutically acceptable salt or N-oxide thereof, in a dosage and amount effective to exhibit partial agonism of metabotropic glutamate receptor activity in the mammal.

Also disclosed are methods for enhancing cognition in a mammal comprising the step of administering to the mammal at least one compound having a structure represented by a formula:

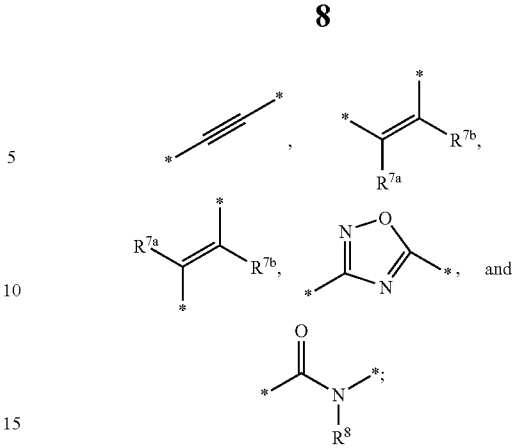

wherein each ----- is an optional covalent bond; wherein $Y^1$ and $Y^2$ are independently selected from N and C—R; wherein R comprises two to four substituents independently selected from hydrogen, halogen, hydroxyl, cyano, nitro, thiol, or an organic radical comprising 1 to 12 carbon atoms; wherein $R^1$ and $R^2$ are independently hydrogen or an optionally substituted organic radical comprising from 1 to 12 carbon atoms; wherein $R^0$ is an optionally substituted organic radical comprising 4 to 14 carbon atoms, wherein L is an organic divalent radical comprising 1 to 7 carbon atoms and is selected from:

wherein $R^{7a}$ and $R^{7b}$ together form an optionally substituted carbocyclic or heterocyclic ring having from two to five carbons or are independently selected from hydrogen, halogen, hydroxyl, cyano, nitro, thiol, amino, and an organic radical comprising 1 to 5 carbon atoms selected from optionally substituted C1-C5 alkyl or C2-C5 alkenyl or C2-C5 alkynyl, optionally substituted C1-C5 heteroalkyl or C2-C5 heteroalkenyl or C2-C5 heteroalkynyl, optionally substituted C3-C5 cycloalkyl or C3-C5 cycloalkenyl, optionally substituted C3-C5 heterocycloalkyl or C3-C5 heterocycloalkenyl, optionally substituted aryl, optionally substituted heteroaryl, optionally substituted alkoxyl, optionally substituted thioalkyl, optionally substituted alkylsulfinyl, optionally substituted alkylsulfonyl, and optionally substituted amino, thioamido, amidosulfonyl, alkoxycarbonyl, carboxamide, aminocarbonyl, and alkylamine-carbonyl; and or a pharmaceutically acceptable salt or N-oxide thereof, in a dosage and amount effective to enhance cognition in the mammal.

Also disclosed are methods for preparing a phenylethynylbenzamide derivative comprising the steps of coupling an arylacetylene with an aryl halide, wherein one of the arylacetylene or the aryl halide bears a carboxyl functionality; and forming an amide derivative of the carboxyl functionality by reaction with an amine.

Also disclosed are methods for preparing a phenylethynylbenzamide derivative comprising the steps of coupling an arylacetylene with an aryl halide, wherein one of the arylacetylene or the aryl halide bears a carboxyl functionality; and forming an amide derivative of the carboxyl functionality by reaction with an amine.

Also disclosed are methods for preparing a styrylbenzamide derivative comprising the steps of coupling a styryl bornonic acid or a styryl boronic ester with an aryl halide, wherein one of the styryl bornonic acid or styryl boronic ester or the aryl halide bears a carboxyl functionality; and forming an amide derivative of the carboxyl functionality by reaction with an amine.

Also disclosed are methods for preparing a 4-(3-phenyl-1, 2,4-oxadiazol-5-yl)benzamide derivative comprising the steps of condensing an N'-hydroxybenzimidamide with an aryl carboxylic acid, wherein one of the N'-hydroxybenzimidamide or the aryl carboxylic acid bears an ester functionality; and forming an amide derivative of the ester functionality by reaction with an amine.

Also disclosed are methods for preparing a 4-(pyridinylethynyl)benzamide derivative comprising the steps of coupling an arylacetylene with an aryl halide, wherein one of the arylacetylene or the aryl halide bears a carboxyl functionality; and forming an amide derivative of the carboxyl functionality by reaction with an amine.

Also disclosed are methods for preparing a N'-phenyl-terephthalamide derivative comprising the steps of reacting an aniline compound with a benzoic acid compound, wherein the benzoic acid compound bears a carboxyl functionality; and forming an amide derivative of the carboxyl functionality by reaction with an amine.

Also disclosed are the products of the disclosed methods.

Also disclosed are pharmaceutical compositions comprising the disclosed compounds. For example, the compositions can comprise a therapeutically effective amount of one or more phenylethynylbenzamide derivatives, cycloalkylethynylbenzamide derivatives, styrylbenzamide derivatives, 4-(3-phenyl-1,2,4-oxadiazol-5-yl)benzamide derivatives, 4-(pyridinylethynyl)benzamide derivatives, and/or $N^1$-phenylterephthalamide derivatives at least one phenylethynylbenzamide derivative and a pharmaceutically acceptable carrier.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

Figure 1:
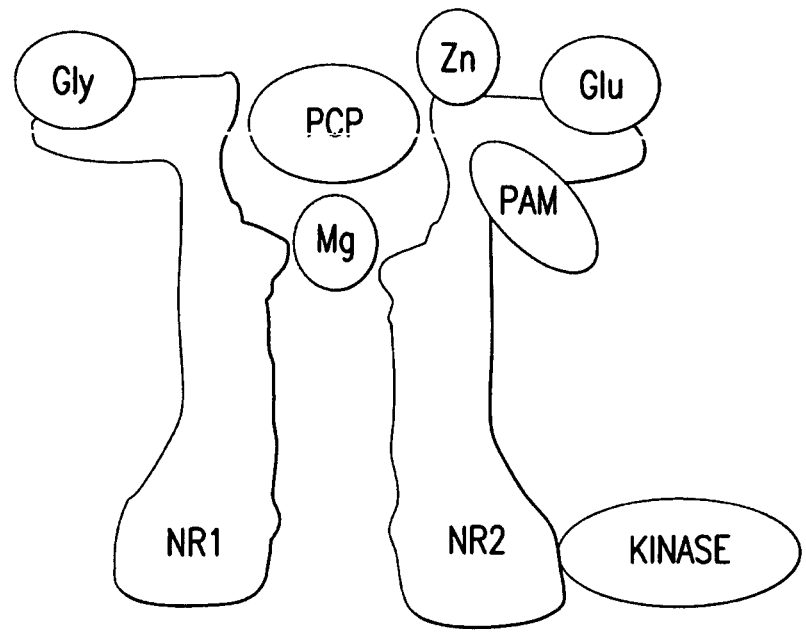
FIG. 1 shows a schematic of the NMDA receptor.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can need to be independently confirmed.

A. DEFINITIONS

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —$OCH_2CH_2O$— units in the polyester, regardless of whether ethylene glycol was used to prepare the polyester. Similarly, a sebacic acid residue in a polyester refers to one or more —$CO(CH_2)_8CO$— moieties in the polyester, regardless of whether the residue is obtained by reacting sebacic acid or an ester thereof to obtain the polyester.

As used herein, the terms "optional" or "optionally" means that the subsequently described event or circumstance can or can not occur, and that the description includes instances where said event or circumstance occurs and instances where it does not.

As used herein, the term "mGluR5 receptor positive allosteric modulator" refers to any exogenously administered compound or agent that directly or indirectly augments the activity of the mGluR5 receptor in the presence or in the absence of the endogenous ligand (such as glutamate) in an animal, in particular a mammal, for example a human. The term "mGluR5 receptor positive allosteric modulator" includes a compound that is an "mGluR5 receptor allosteric potentiator" or an "mGluR5 receptor allosteric agonist," as well as a compound that has mixed activity as both an "mGluR5 receptor allosteric potentiator" and an "mGluR5 receptor allosteric agonist."

As used herein, the term "mGluR5 receptor allosteric potentiator" refers to any exogenously administered compound or agent that directly or indirectly augments the response produced by the endogenous ligand (such as glutamate) when it binds to the orthosteric site of the mGluR5 receptor in an animal, in particular a mammal, for example a human. The mGluR5 receptor allosteric potentiator binds to a site other than the orthosteric site (an allosteric site) and positively augments the response of the receptor to an agonist. Because it does not induce desensitization of the receptor, activity of a compound as an mGluR5 receptor allosteric potentiator provides advantages over the use of a pure mGluR5 receptor allosteric agonist. Such advantages can include, for example, increased safety margin, higher tolerability, diminished potential for abuse, and reduced toxicity.

As used herein, the term "mGluR5 receptor allosteric agonist" refers to any exogenously administered compound or agent that directly augments the activity of the mGluR5 receptor in the absence of the endogenous ligand (such as glutamate) in an animal, in particular a mammal, for example a human. The mGluR5 receptor allosteric agonist binds to the orthosteric glutamate site of the mGluR5 receptor and directly influences the orthosteric site of the mGluR5 receptor. Because it does not require the presence of the endogenous ligand, activity of a compound as an mGluR5 receptor allosteric agonist provides advantages over the use of a pure mGluR5 receptor allosteric potentiator, such as more rapid onset of action.

By "treatment" is meant the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

By "prevent" or "preventing" is meant to preclude, avert, obviate, forestall, stop, or hinder something from happening, especially by advance action. It is understood that where reduce, inhibit or prevent are used herein, unless specifically indicated otherwise, the use of the other two words is also expressly disclosed.

As used herein, "diagnosed with a need for potentiation of metabotropic glutamate receptor activity" means having been subjected to a physical examination by a person of skill, for example, a physician, and found to have a condition that can be diagnosed or treated by potentiation of metabotropic glutamate receptor activity. As used herein, "diagnosed with a need for partial agonism of metabotropic glutamate receptor activity" means having been subjected to a physical examination by a person of skill, for example, a physician, and found to have a condition that can be diagnosed or treated by partial agonism of metabotropic glutamate receptor activity. As used herein, "diagnosed with a need for treatment of one or more neurological and/or psychiatric disorder associated with glutamate dysfunction" means having been subjected to a physical examination by a person of skill, for example, a physician, and found to have one or more neurological and/or psychiatric disorder associated with glutamate dysfunction.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, a "therapeutically effective amount" refers to an amount that is sufficient to achieve the desired therapeutic result or to have an effect on undesired symptoms, but is generally insufficient to cause adverse side affects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, a "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity may be maintained, for example, by the use of coating materials such as lecithin, by the maintenance of the required particle size in the case of dispersions and by the use of surfactants. These compositions may also contain adjuvants such as preservatives, wetting agents, emulsifying agents and dispersing agents. Prevention of the action of microorganisms may be ensured by the inclusion of various antibacterial and antifungal agents such as paraben, chlorobutanol, phenol, sorbic acid and the like. It may also be desirable to include isotonic agents such as sugars, sodium chloride and the like. Prolonged absorption of the injectable pharmaceutical form may be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations may be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, optionally substituted alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula —$(CH_2)_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$-$(OA^2)_a$-$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula $NA^1A^2A^3$, where $A^1$, $A^2$, and $A^3$ can be, independently, hydrogen or optionally substituted alkyl, cycloalkyl, alkenyl, cycloalkenyl, alkynyl, cycloalkynyl, aryl, or heteroaryl group as described herein.

The term "carboxylic acid" as used herein is represented by the formula —C(O)OH.

The term "ester" as used herein is represented by the formula —$OC(O)A^1$ or —$C(O)OA^1$, where $A^1$ can be an optionally substituted alkyl, cycloalkyl, alkenyl, cycloalkenyl, alkynyl, cycloalkynyl, aryl, or heteroaryl group as described herein. The term "polyester" as used herein is represented by the formula -$(A^1O(O)C-A^2-C(O)O)_a$— or -$(A^1O(O)C-A^2-OC(O))_a$—, where $A^1$ and $A^2$ can be, independently, an optionally substituted alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an optionally substituted alkyl, cycloalkyl, alkenyl, cycloalkenyl, alkynyl, cycloalkynyl, aryl, or heteroaryl group described herein. The term "polyether" as used herein is represented by the formula -$(A^1O-A^2O)_a$—, where $A^1$ and $A^2$ can be, independently, an optionally substituted alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "hydroxyl" as used herein is represented by the formula —OH.

The term "ketone" as used herein is represented by the formula $A^1C(O)A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The term "nitrile" as used herein is represented by the formula —CN.

The term "silyl" as used herein is represented by the formula —$SiA^1A^2A^3$, where $A^1$, $A^2$, and $A^3$ can be, independently, hydrogen or an optionally substituted alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, —$S(O)_2A^1$, —$OS(O)_2A^1$, or —$OS(O)_2OA^1$, where $A^1$ can be hydrogen or an optionally substituted alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2A^1$, where $A^1$ can be hydrogen or an optionally substituted alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein.

The term "thiol" as used herein is represented by the formula —SH.

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure

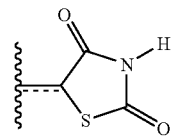

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5,6,7,8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

The following abbreviations are used herein. DMF: dimethyl formamide. EtOAc: ethyl acetate. THF: tetrahydrofuran. DIPEA or DIEA: diisopropylethylamine. HOBt: 1-hydroxybenzotriazole. EDC: 1-ethyl-3-[3-dimethylaminopropyl]carbodiimide hydrochloride. DMSO: dimethylsulfoxide. DMAP: 4-Dimethylaminopyridine. RT: Room temperature. H: Hours. Min: Minutes. DCM: Dichloromethane. MeCN: Acetonitrile. MeOH: methanol. iPrOH: 2-Propanol. n-BuOH: 1-Butanol.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. DEVELOPMENT OF NOVEL ALLOSTERIC POTENTIATORS OF mGluR5

Figure 2:
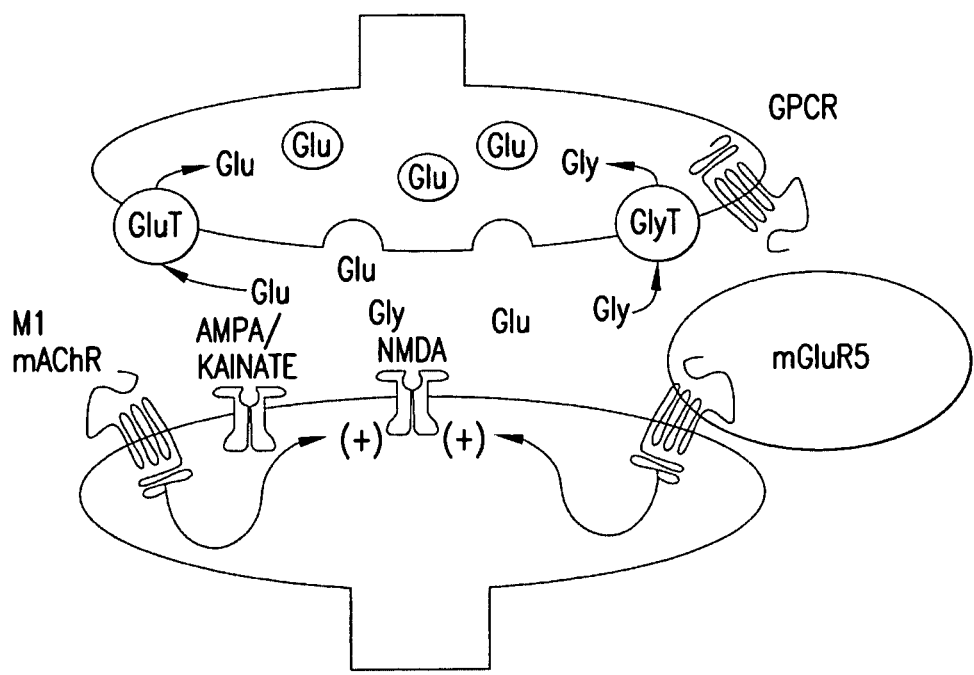
FIG. 2 shows a schematic illustrating that activation of mGluR5 potentiates NMDA receptor function.
Figure 3:
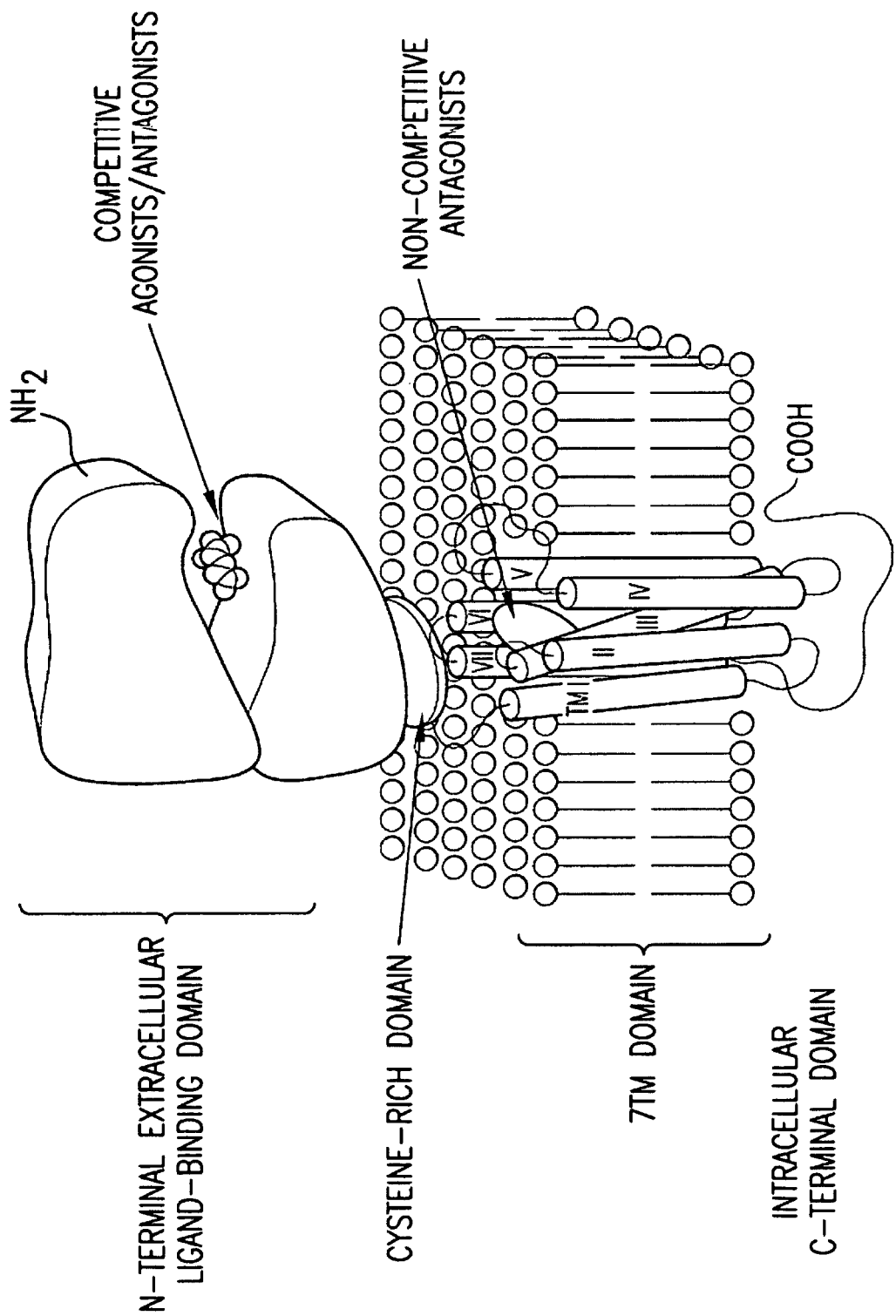
FIG. 3 illustrates allosteric modulation of mGluR5.

Phencyclidine (PCP) and other NMDA receptor antagonists induce a psychotic state in humans similar to schizophrenia. In schizophrenia patients, PCP and ketamine exacerbate/precipitate preexisting positive and negative symptoms in stable patients. Treatment with NMDA receptor co-agonists can improve positive and negative symptoms. A schematic of the NMDA receptor is shown in FIG. 1. Activation of mGluR5 potentiates NMDA receptor function. See FIG. 2. Orthosteric ligands lack subtype selectivity and may cause unwanted side effects. Allosteric modulators (see FIG. 3) targeting transmembrane domain offer alternative: TMD is significantly less conserved.

Figure 4:
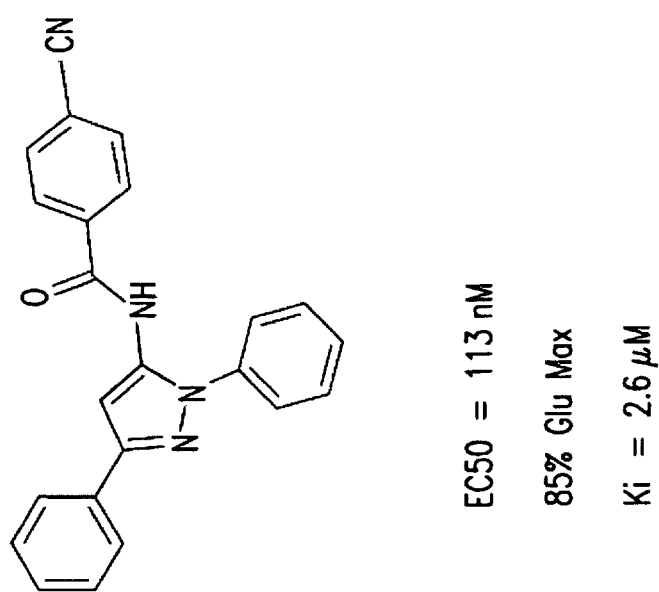
FIG. 4 shows CDPPB as a potent and selective mGluR5 potentiator having modest efficacy in rodent behavioral models for antipsychoticic activity.
Figure 4:
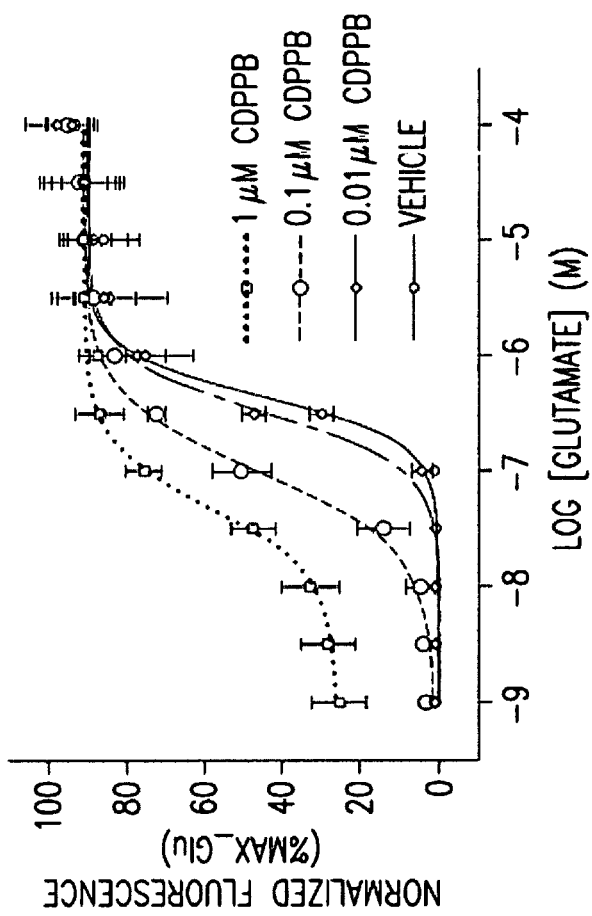
Figure 5:
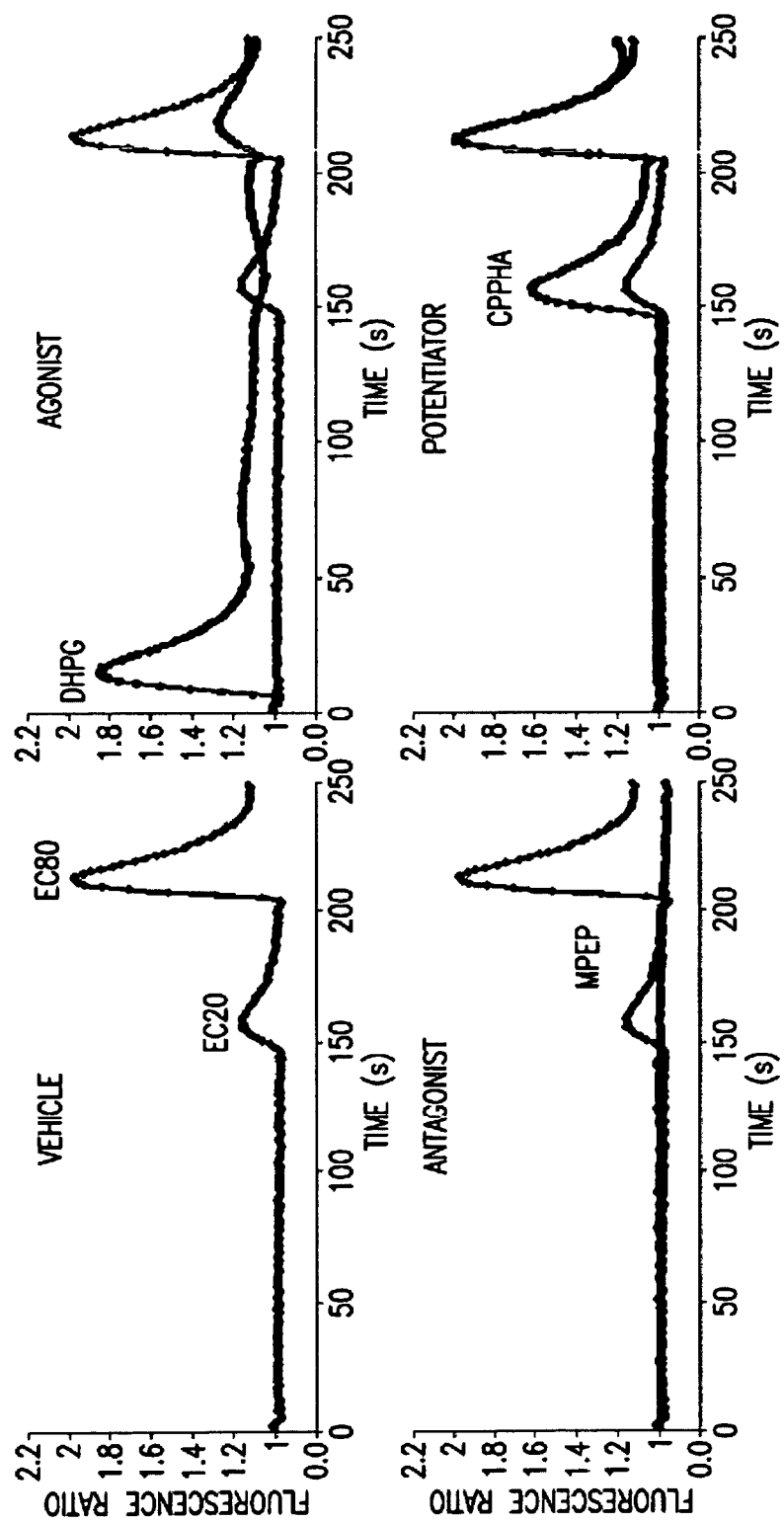
FIG. 5 shows classification of compounds as agonists, potentiators, and antagonists.
Figure 6:
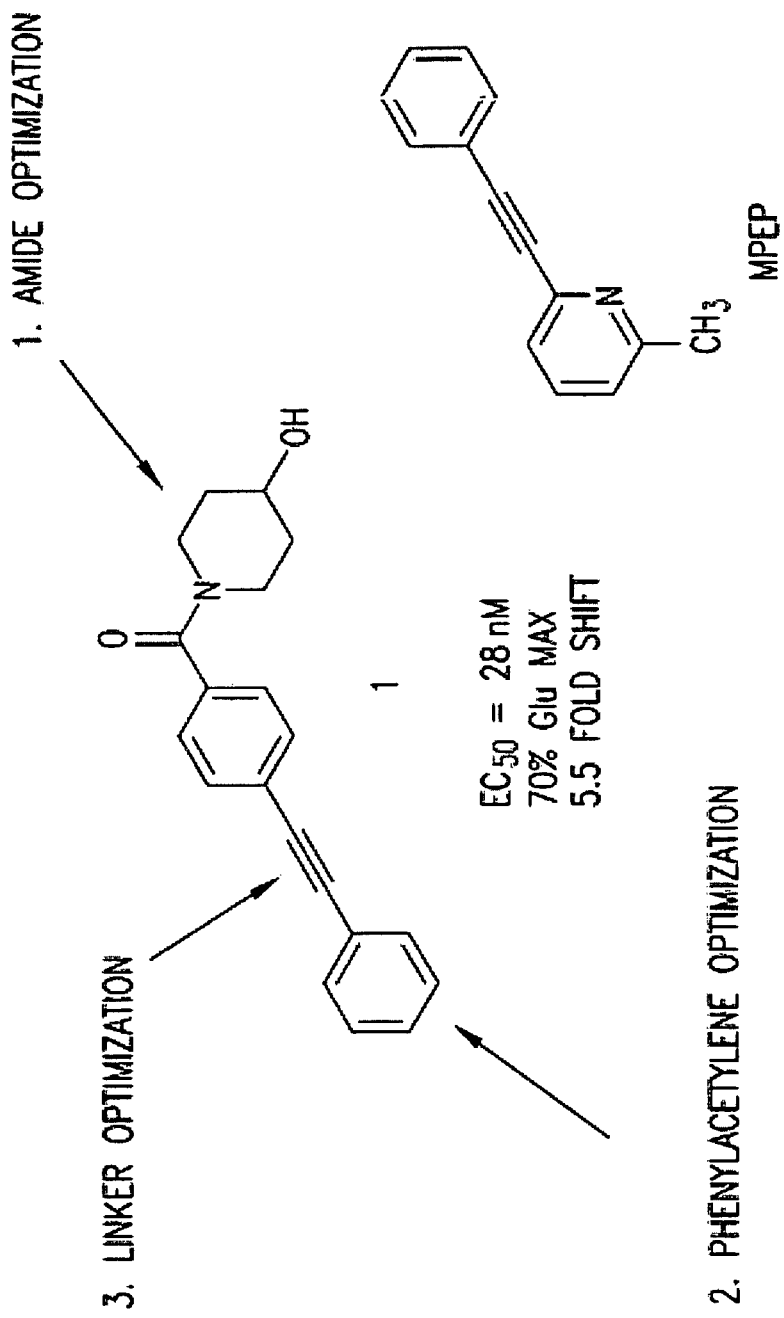
FIG. 6 shows a schematic illustrating optimization of candidates.

4-Cyano-N-(1,3-diphenyl-1H-pyrazol-5-yl)benzamide (CDPPB) is a potent and selective mGluR5 potentiator having modest efficacy in rodent behavioral models for antipsychoticic activity. See FIG. 4. However, this compound lacks satisfactory aqueous solubility and exhibits poor oral bioavailability. Approximately 160,000 compounds were screened as potential mGluR5 modulators. After verification, compounds were classified as agonists, potentiators, and antagonists. See FIG. 5.

As shown below, based upon identified structures, an amide library could be prepared.

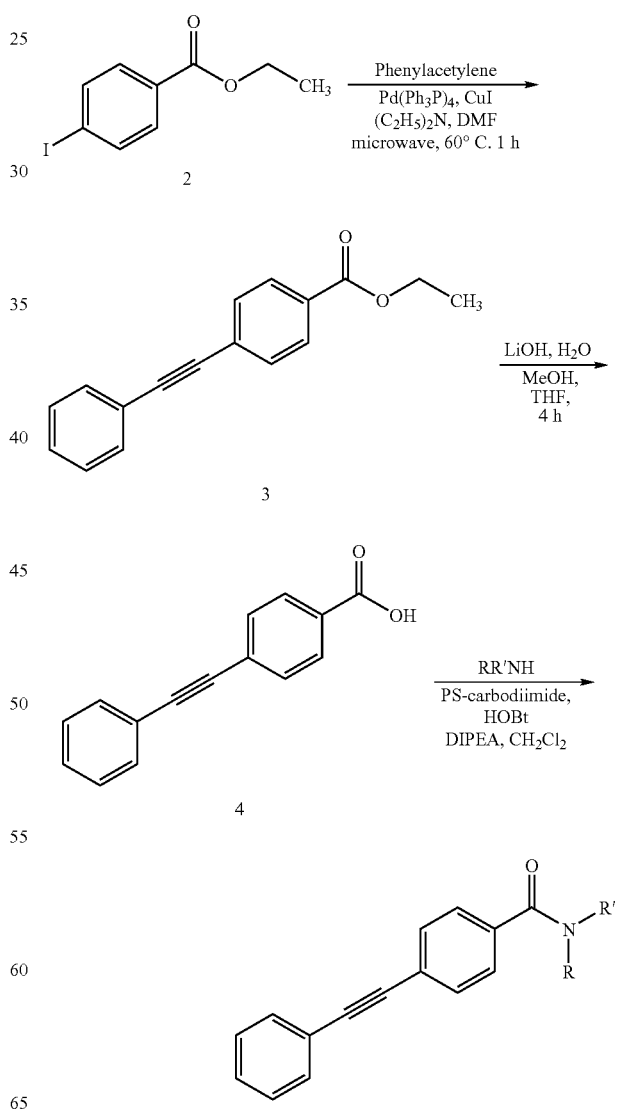

Typically, small, non-polar, and morpholino side chains gave highest potency. Also, typically, increasing ring size and steric bulk decreased activity. Polar side chains were tolerated but typically decreased activity. Additionally, the side chains could be further modified, as shown below.

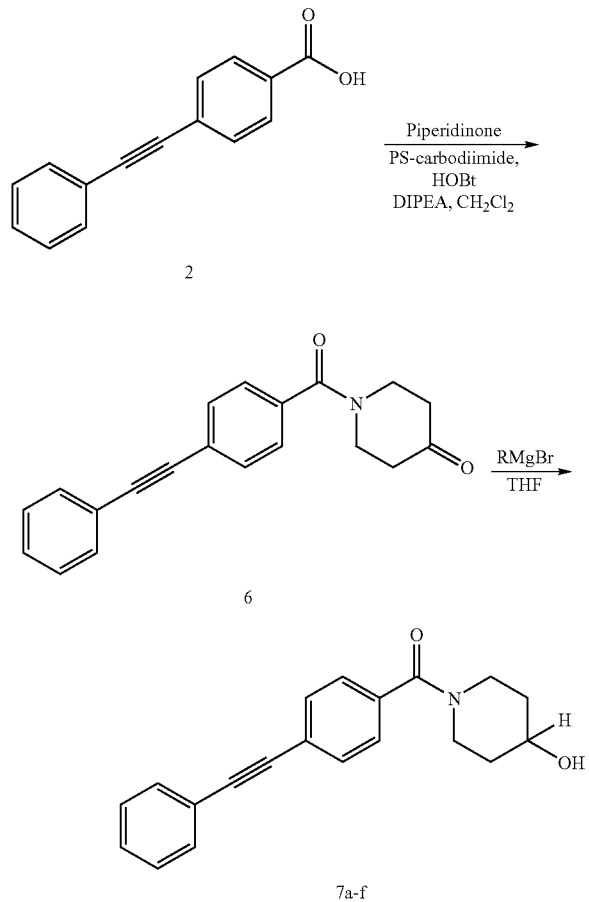

Relevant data are tabulated below. In general, methyl substitution provided superior results.

| Compound | R | EC$_{50}$ (nM) | % Glu Max |
|---|---|---|---|
| 7a | CH$_3$ | 3.5 | 82.5 |
| 7b | CH$_2$CH$_2$CH$_3$ | 1250 | 90.1 |
| 7c | CH(CH$_3$)$_2$ | 1770 | 89.1 |
| 7d | thiophene | 1000 | 95 |
| 7e | 4-F-phenyl | 1190 | 87 |
| 7f | 3-F-phenyl | 1600 | 92 |
| 7g | 4-methoxy-phenyl | 2450 | 91 |

| Compound | R | EC$_{50}$ (nM) | % Glu Max |
|---|---|---|---|
| 9a | H | 212 | 67.3 |
| 9b | Me | 89 | 82 |
| 9c | n-propyl | 423 | 59.8 |
| 9d | thiophene | 1470 | 43.7 |

Replacement of hydroxypiperidine with azitidine was tolerated, with small R-groups typically preferred.

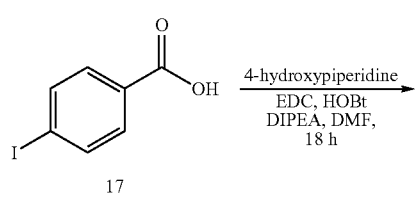

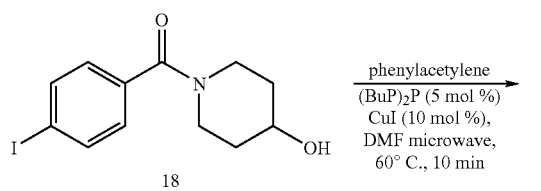

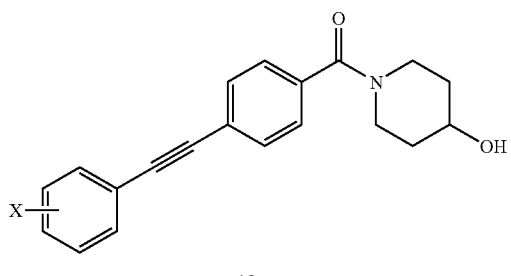

| Compound | X | EC$_{50}$ (nM) | % Glu Max |
|---|---|---|---|
| 19a | 2-fluoro | 27.3 | 80 |
| 19b | 3-fluoro | 3.25 | 77 |
| 19c | 4-fluoro | 14.7 | 63 |
| 19d | 3,4-difluoro | 68.7 | 52 |
| 19e | 3,5-difluoro | 593 | 67 |
| 19f | 4-fluoro-3-methyl | 500 | 76 |
| 19g | 2,4-difluoro | 1970 | 58 |
| 19h | 4-methyl | inactive | — |
| 19i | 3-trifluoromethyl | 2060 | 68 |
| 19j | 4-pyridinyl | 7880 | 24 |
| 19k | 2-pyridinyl | 2210 | 49 |
| 19l | imidazole | inactive | — |
| 19m | cyclohexyl | 1790 | 77 |

Typically, incorporation of mono-fluoro substituents increased potency and efficacy.

Lead compounds were then identified; all identified compounds provided near maximal response, with 3-fluoro substitution and morpholino amide providing satisfactory results.

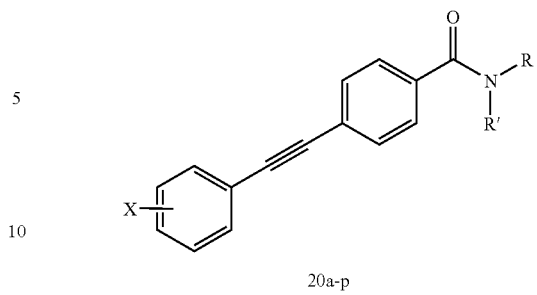

| Compound | X | NRR' | EC$_{50}$ (nM) | % Glu Max |
|---|---|---|---|---|
| 20a | 2-fluoro | | 34.9 | 86 |
| 20b | 3-fluoro | | 19.4 | 92 |
| 20c | 4-fluoro | | 39.4 | 91 |
| 20d | 3,4-difluoro | | 137 | 91 |
| 20e | 2-fluoro | | 20.6 | 88 |
| 20f | 3-fluoro | | 11.9 | 86 |
| 20g | 4-fluoro | | 24.7 | 95 |
| 20h | 3,4-difluoro | | 76.3 | 104 |
| 20i | 2-fluoro | | 12.0 | 105 |
| 20j | 3-fluoro | | 5.3 | 112 |
| 20k | 4-fluoro | | 23.6 | 107 |
| 20l | 3,4-difluoro | | 33.5 | 114 |
| 20m | 2-fluoro | | 166.2 | 98 |
| 20n | 3-fluoro | | 59.5 | 104 |
| 20o | 4-fluoro | | 155.5 | 103 |
| 20p | 3,4-difluoro | | 314.0 | 88 |

Linkers were investigated as shown in the following schematic:

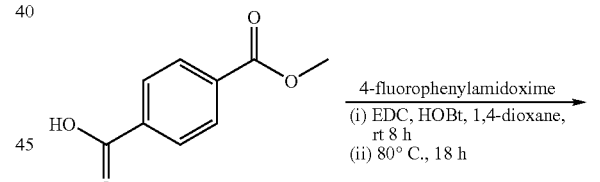

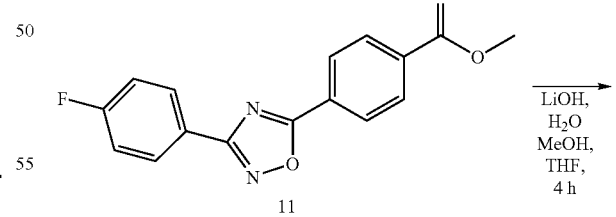

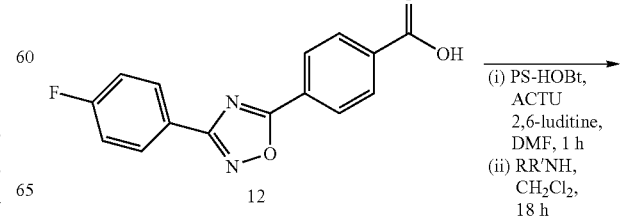

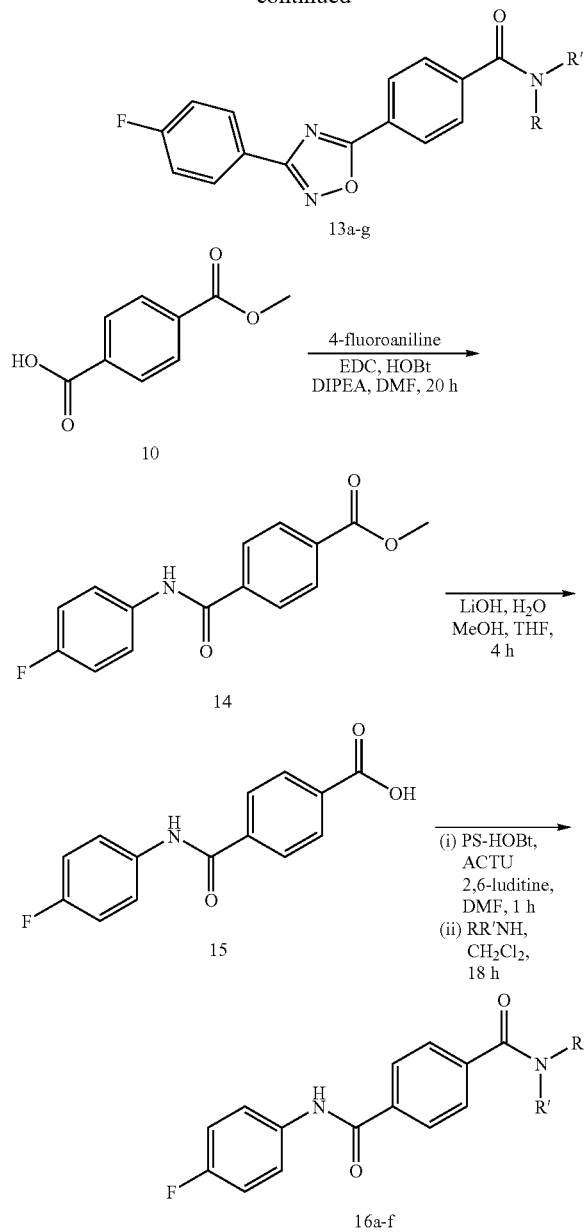

Figure 7:
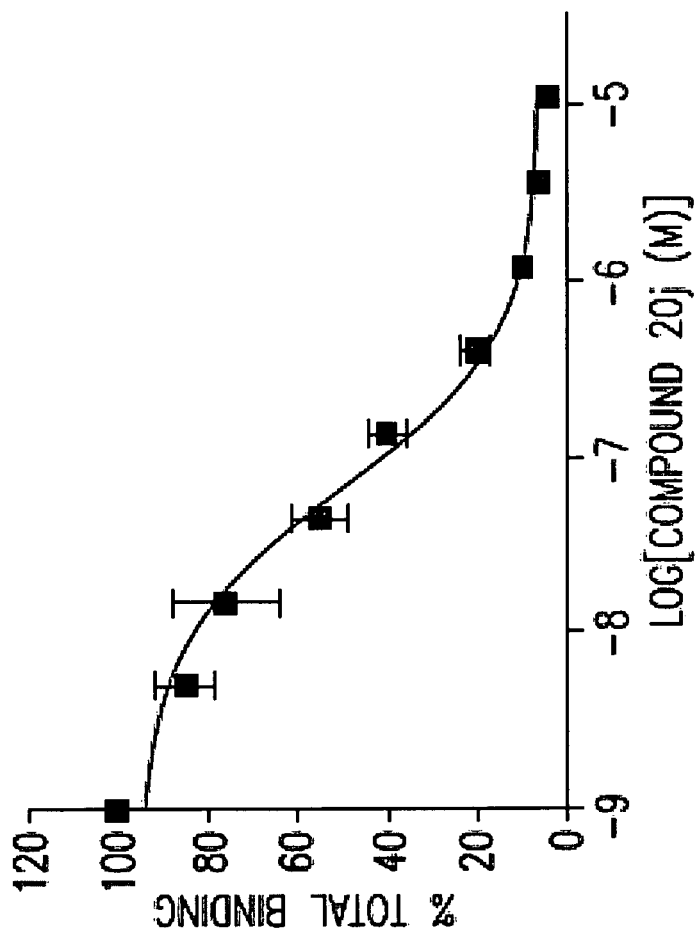
FIG. 7 tabulates displacement of [3H]methoxyPEPy and shows binding to the MPEP site with varying affinities.

The displacement of [3H]methoxyPEPy was then investigated. The compounds were found to bind to MPEP site with varying affinities. See FIG. 7. The compounds were also tested for activity on other receptors (e.g., mGluR1, mGluR4, mGluR7, M3). Initial testing demonstrates selectivity for mGluR5. The compounds were also tested for stability in rat liver microsomes. Typically, the compounds retain 90% of parent over time course of 45 min Compounds were then evaluated for activity on amphetamine-induced hyperlocomotion. See FIG. 8, FIG. 9, and FIG. 10.

C. COMPOUNDS

In one aspect, the invention relates to compounds useful as positive allosteric modulators (potentiators) of the metabotropic glutamate receptor subtype 5 (mGluR5). More specifically, the present invention relates to compounds that allosterically modulate mGluR5 receptor activity, affecting the sensitivity of mGluR5 receptors to agonists without acting as orthosteric agonists themselves. The compounds of the invention are useful in the treatment neurological and psychiatric disorders associated with glutamate dysfunction and other diseases in which metabotropic glutamate receptors are involved, as further described herein.

In a further aspect, the invention relates to a compound or pharmaceutically acceptable salt thereof selected from N-cyclopentyl-4-(phenylethynyl)benzamide; (4-((3-fluorophenyl)ethynyl)phenyl)(4-hydroxypiperidin-1-yl)methanone; morpholino(4-(phenylethynyl)phenyl)methanone; (4-((3-fluorophenyl)ethynyl)phenyl)(morpholino)methanone; N-cyclohexyl-4-(phenylethynyl)benzamide; (4-((3-fluorophenyl)ethynyl)phenyl)(4-(hydroxymethyl)piperidin-1-yl)methanone; (4-((2-fluorophenyl)ethynyl)phenyl)(morpholino)methanone; (4-hydroxypiperidin-1-yl)(4-(phenylethynyl)phenyl)methanone; 4-(phenylethynyl)-N-propylbenzamide; (4-((4-fluorophenyl)ethynyl)phenyl)(4-hydroxypiperidin-1-yl)methanone; N-(3,3-dimethylbutyl)-4-(phenylethynyl)benzamide; (4-((3-fluorophenyl)ethynyl)phenyl)(4-hydroxy-4-methylpiperidin-1-yl)methanone; (4-((2-fluorophenyl)ethynyl)phenyl)(4-(hydroxymethyl)piperidin-1-yl)methanone; (4-((4-fluorophenyl)ethynyl)phenyl)(morpholino)methanone; (4-((4-fluorophenyl)ethynyl)phenyl)(4-(hydroxymethyl)piperidin-1-yl)methanone; N-isopentyl-4-(phenylethynyl)benzamide; (4-((2-fluorophenyl)ethynyl)phenyl)(4-hydroxypiperidin-1-yl)methanone; (4-hydroxypiperidin-1-yl)(4-(phenylethynyl)phenyl)methanone; N-(3-methoxypropyl)-4-(phenylethynyl)benzamide; (4-(hydroxymethyl)piperidin-1-yl)(4-(phenylethynyl)phenyl)methanone; N-butyl-4-(phenylethynyl)benzamide; (R)-4-(phenylethynyl)-N-(2-phenylpropyl)benzamide; (4-((3,4-difluorophenyl)ethynyl)phenyl)(morpholino)methanone; (4-((2-fluorophenyl)ethynyl)phenyl)(4-hydroxy-4-methylpiperidin-1-yl)methanone; (4-hydroxy-4-methylpiperidin-1-yl)(4-(phenylethynyl)phenyl)methanone; (4-(hydroxymethyl)piperidin-1-yl)(4-(phenylethynyl)phenyl)methanone; (4-((4-fluorophenyl)ethynyl)phenyl)(4-hydroxy-4-methylpiperidin-1-yl)methanone; (4-(pentan-2-ylamino)piperidin-1-yl)(4-(phenylethynyl)phenyl)methanone; N-(cyclohexylmethyl)-4-(phenylethynyl)benzamide; (4-((3-fluorophenyl)ethynyl)phenyl)(3-hydroxyazetidin-1-yl) methanone; (4-((3,4-difluorophenyl)ethynyl)phenyl)(4-hydroxypiperidin-1-yl)methanone; N-(2-cyclohexenylethyl)-4-(phenylethynyl)benzamide; N-(4-methylcyclohexyl)-4-(phenylethynyl)benzamide; (4-(cyclohexylamino)piperidin-1-yl)(4-(phenylethynyl)phenyl)methanone; (4-((3,4-difluorophenyl)ethynyl)phenyl)(4-(hydroxymethyl)piperidin-1-yl)methanone; N-(3-hydroxypropyl)-4-(phenylethynyl)benzamide; (2,6-dimethylmorpholino)(4-(phenylethynyl)phenyl)methanone; (4-(phenylethynyl)phenyl)(4-(4-(pyridin-4-yl)piperazin-1-yl)piperidin-1-yl) methanone; (3-hydroxy-3-methylazetidin-1-yl)(4-(phenylethynyl)phenyl)methanone; (S)-(4-(1-cyclohexylethylamino)piperidin-1-yl)(4-(phenylethynyl) phenyl)methanone; (4-(4-methylpiperazin-1-yl)piperidin-1-yl)(4-(phenylethynyl)phenyl)methanone; (3-hydroxypiperidin-1-yl)(4-(phenylethynyl)phenyl)methanone; N-(2-chlorophenethyl)-4-(phenylethynyl)benzamide; N-(2-morpholinoethyl)-4-(phenylethynyl)benzamide; N-(2,3-dihydro-1H-inden-1-yl)-4-(phenylethynyl)benzamide; (4-((3,4-difluorophenyl)ethynyl)phenyl)(4-hydroxy-4-methylpiperidin-1-yl)methanone; N-(2,3-dihydro-1H-inden-2-yl)-4-(phenylethynyl)benzamide; (4-((4-fluorophenyl)ethynyl)phenyl)(3-hydroxyazetidin-1-yl)methanone;

(4-methylpiperazin-1-yl)(4-(phenylethynyl)phenyl)methanone; N-(4-chlorophenethyl)-4-(phenylethynyl)benzamide; (4-((2-fluorophenyl)ethynyl)phenyl)(3-hydroxyazetidin-1-yl)methanone; N-(3-chlorophenethyl)-4-(phenylethynyl)benzamide; (4-(cyclobutylamino)piperidin-1-yl)(4-(phenylethynyl)phenyl)methanone; N-(4-bromophenethyl)-4-(phenylethynyl)benzamide; (3-hydroxyazetidin-1-yl)(4-(phenylethynyl)phenyl)methanone; (4-(2-morpholinoethylamino)piperidin-1-yl)(4-(phenylethynyl)phenyl)methanone; (4-((3,4-difluorophenyl)ethynyl)phenyl)(3-hydroxyazetidin-1-yl)methanone; N-(3,3-dimethylbutyl)-4-(3-(4-fluorophenyl)-1,2,4-oxadiazol-5-yl)benzamide; (4-(4-chloro-2-(trifluoromethyl)phenyl)-4-hydroxypiperidin-1-yl)(4-(phenylethynyl)phenyl)methanone; (3-hydroxy-3-propylazetidin-1-yl)(4-(phenylethynyl)phenyl)methanone; (octahydroisoquinolin-2(1H)-yl)(4-(phenylethynyl)phenyl)methanone; (4-((4-fluoro-3-methylphenyl)ethynyl)phenyl)(4-hydroxypiperidin-1-yl)methanone; (4-((3,5-difluorophenyl)ethynyl)phenyl)(4-hydroxypiperidin-1-yl)methanone; (S)—N-((1-ethylpyrrolidin-2-yl)methyl)-4-(phenylethynyl)benzamide; (4-hydroxy-4-(thiophen-2-yl)piperidin-1-yl)(4-(phenylethynyl)phenyl)methanone; (4-(azetidin-1-yl)piperidin-1-yl)(4-(phenylethynyl)phenyl)methanone; 4-(3-(4-fluorophenyl)-1,2,4-oxadiazol-5-yl)-N-(3-methoxypropyl)benzamide; 4-phenyl-1-(4-(phenylethynyl)benzoyl)piperidine-4-carbonitrile; N-(3,3-dimethylbutyl)-4-(3-phenyl-1,2,4-oxadiazol-5-yl)benzamide; (4-isopropylpiperazin-1-yl)(4-(phenylethynyl)phenyl)methanone; (4-(2-methoxyethylamino)piperidin-1-yl)(4-(phenylethynyl)phenyl)methanone; N-(3-morpholinopropyl)-4-(phenylethynyl)benzamide; (4-(4-fluorophenyl)-4-hydroxypiperidin-1-yl)(4-(phenylethynyl)phenyl)methanone; 1-(4-phenyl-1-(4-(phenylethynyl)benzoyl)piperidin-4-yl)ethanone; 1-(1-(4-(phenylethynyl)benzoyl)piperidin-4-yl)-1H-benzo[d]imidazol-2(3H)-one; (4-hydroxy-4-propylpiperidin-1-yl)(4-(phenylethynyl)phenyl)methanone; (3-hydroxy-3-(thiophen-2-yl)azetidin-1-yl)(4-(phenylethynyl)phenyl)methanone; (4-(3-fluorophenyl)-4-hydroxypiperidin-1-yl)(4-(phenylethynyl)phenyl)methanone; 4-(phenylethynyl)-N-(2-(piperidin-1-yl)ethyl)benzamide; (4-hydroxy-4-isopropylpiperidin-1-yl)(4-(phenylethynyl)phenyl)methanone; (4-(cyclohexylethynyl)phenyl)(4-hydroxypiperidin-1-yl)methanone; (E)-(4-hydroxypiperidin-1-yl)(4-styrylphenyl)methanone; 4-(3-(4-fluorophenyl)-1,2,4-oxadiazol-5-yl)-N-propylbenzamide; (4-((2,4-difluorophenyl)ethynyl)phenyl)(4-hydroxypiperidin-1-yl)methanone; (4-(phenylethynyl)phenyl)(4-phenylpiperazin-1-yl)methanone; (4-(2-methoxyphenyl)piperazin-1-yl)(4-(phenylethynyl)phenyl)methanone; (4-hydroxypiperidin-1-yl)(4-((3-(trifluoromethyl)phenyl)ethynyl)phenyl)methanone; 4-3-phenyl-1,2,4-oxadiazol-5-yl)-N-propylbenzamide; (4-hydroxypiperidin-1-yl)(4-(pyridin-2-ylethynyl)phenyl)methanone; (4-(4-bromophenyl)-4-hydroxypiperidin-1-yl)(4-(phenylethynyl)phenyl)methanone; (4-hydroxy-4-(4-methoxyphenyl)piperidin-1-yl)(4-(phenylethynyl)phenyl)methanone; (4-(cyclopropylmethylamino)piperidin-1-yl)(4-(phenylethyny)phenyl)methanone; (4-(phenylethynyl)phenyl)(4-(pyridin-2-yl)piperazin-1-yl)methanone; N-(2-(dimethylamino)ethyl)-4-(phenylethynyl)benzamide; N-(4-fluorophenyl)-4-(2-methylpiperidine-1-carbonyl)benzamide; N-(2-(1-methylpyrrolidin-2-yl)ethyl)-4-(phenylethynyl)benzamide; (4-hydroxy-4-phenylpiperidin-1-yl)(4-(phenylethynyl)phenyl)methanone; (4-(phenylethynyl)phenyl)(4-(pyridin-4-yl)piperazin-1-yl)methanone; 5-chloro-1-(4-(phenylethynyl)benzoyl)-3-(piperidin-4-yl)-1H-benzo[d]imidazol-2(3H)-one; (4-(phenylethynyl)phenyl)(4-(pyrrolidin-1-yl)piperidin-1-yl)methanone; 2-(4-(4-(phenylethynyl)benzoyl)piperazin-1-yl)benzonitrile; (4-(3-(4-fluorophenyl)-1,2,4-oxadiazol-5-yl)phenyl)(4-(pyridin-4-yl)piperazin-1-yl)methanone; (4-(phenylethynyl)phenyl)(piperazin-1-yl)methanone; (4-(2-fluorophenyl)piperazin-1-yl)(4-(phenylethynyl)phenyl)methanone; and (4-(4-chlorophenyl)-4-hydroxypiperidin-1-yl)(4-(phenylethynyl)phenyl)methanone.

In a further aspect, the compound is selected from (2,6-dimethylmorpholino)(4-(phenylethynyl)phenyl)methanone; (3-hydroxy-3-(thiophen-2-yl)azetidin-1-yl)(4-(phenylethynyl)phenyl)methanone; (3-hydroxy-3-methylazetidin-1-yl)(4-(phenylethynyl)phenyl)methanone; (3-hydroxy-3-propylazetidin-1-yl)(4-(phenylethynyl)phenyl)methanone; (3-hydroxyazetidin-1-yl)(4-(phenylethynyl)phenyl)methanone; (3-hydroxypiperidin-1-yl)(4-(phenylethynyl)phenyl)methanone; (4-((2,4-difluorophenyl)ethynyl)phenyl)(4-hydroxypiperidin-1-yl)methanone; (4-((2-fluorophenyl)ethynyl)phenyl)(3-hydroxyazetidin-1-yl)methanone; (4-((2-fluorophenyl)ethynyl)phenyl)(4-(hydroxymethyl)piperidin-1-yl)methanone; (4-((2-fluorophenyl)ethynyl)phenyl)(4-hydroxy-4-methylpiperidin-1-yl)methanone; (4-((2-fluorophenyl)ethynyl)phenyl)(4-hydroxypiperidin-1-yl)methanone; (4-((2-fluorophenyl)ethynyl)phenyl)(morpholino)methanone; (4-((3,4-difluorophenyl)ethynyl)phenyl)(3-hydroxyazetidin-1-yl)methanone; (4-((3,4-difluorophenyl)ethynyl)phenyl)(4-(hydroxymethyl)piperidin-1-yl)methanone; (4-((3,4-difluorophenyl)ethynyl)phenyl)(4-hydroxy-4-methylpiperidin-1-yl)methanone; (4-((3,4-difluorophenyl)ethynyl)phenyl)(4-hydroxypiperidin-1-yl)methanone; (4-((3,4-difluorophenyl)ethynyl)phenyl)(morpholino)methanone; (4-((3,5-difluorophenyl)ethynyl)phenyl)(4-hydroxypiperidin-1-yl)methanone; (4-((3-fluorophenyl)ethynyl)phenyl)(3-hydroxyazetidin-1-yl)methanone; (4-((3-fluorophenyl)ethynyl)phenyl)(4-(hydroxymethyl)piperidin-1-yl)methanone; (4-((3-fluorophenyl)ethynyl)phenyl)(4-hydroxy-4-methylpiperidin-1-yl)methanone; (4-((3-fluorophenyl)ethynyl)phenyl)(4-hydroxypiperidin-1-yl)methanone; (4-((3-fluorophenyl)ethynyl)phenyl)(morpholino)methanone; (4-((4-fluoro-3-methylphenyl)ethynyl)phenyl)(4-hydroxypiperidin-1-yl)methanone; (4-((4-fluorophenyl)ethynyl)phenyl)(3-hydroxyazetidin-1-yl)methanone; (4-((4-fluorophenyl)ethynyl)phenyl)(4-(hydroxymethyl)piperidin-1-yl)methanone; (4-((4-fluorophenyl)ethynyl)phenyl)(4-hydroxy-4-methylpiperidin-1-yl)methanone; (4-((4-fluorophenyl)ethynyl)phenyl)(4-hydroxypiperidin-1-yl)methanone; (4-((4-fluorophenyl)ethynyl)phenyl)(morpholino)methanone; (4-(2-fluorophenyl)piperazin-1-yl)(4-(phenylethynyl)phenyl)methanone; (4-(2-methoxyethylamino)piperidin-1-yl)(4-(phenylethynyl)phenyl)methanone; (4-(2-methoxyphenyl)piperazin-1-yl)(4-(phenylethynyl)phenyl)methanone; (4-(2-morpholinoethylamino)piperidin-1-yl)(4-(phenylethynyl)phenyl)methanone; (4-(3-fluorophenyl)-4-hydroxypiperidin-1-yl)(4-(phenylethynyl)phenyl)methanone; (4-(4-bromophenyl)-4-hydroxypiperidin-1-yl)(4-(phenylethynyl)phenyl)methanone; (4-(4-chloro-2-(trifluoromethyl)phenyl)-4-hydroxypiperidin-1-yl)(4-(phenylethynyl)phenyl)methanone; (4-(4-chlorophenyl)-4-hydroxypiperidin-1-yl)(4-(phenylethynyl)phenyl)methanone; (4-(4-fluorophenyl)-4-hydroxypiperidin-1-yl)(4-(phenylethynyl)phenyl)methanone; (4-(4-methylpiperazin-1-yl)piperidin-1-yl)(4-(phenylethynyl)phenyl)methanone; (4-(azetidin-1-yl)piperidin-1-yl)(4-(phenylethynyl)phenyl)methanone; (4-(cyclobutylamino)piperidin-1-yl)(4-(phenylethynyl)phenyl)methanone; (4-

(cyclohexylamino)piperidin-1-yl)(4-(phenylethynyl)phenyl)methanone; (4-(cyclopropylmethylamino)piperidin-1-yl)(4-(phenylethynyl)phenyl)methanone; (4-(hydroxymethyl)piperidin-1-yl)(4-(phenylethynyl)phenyl)methanone; (4-(hydroxymethyl)piperidin-1-yl)(4-(phenylethynyl)phenyl)methanone; (4-(pentan-2-ylamino)piperidin-1-yl)(4-(phenylethynyl)phenyl)methanone; (4-(phenylethynyl)phenyl)(4-(4-(pyridin-4-yl)piperazin-1-yl)piperidin-1-yl)methanone; (4-(phenylethynyl)phenyl)(4-(pyridin-2-yl)piperazin-1-yl)methanone; (4-(phenylethynyl)phenyl)(4-(pyridin-4-yl)piperazin-1-yl)methanone; (4-(phenylethynyl)phenyl)(4-(pyrrolidin-1-yl)piperidin-1-yl)methanone; (4-(phenylethynyl)phenyl)(4-phenylpiperazin-1-yl)methanone; (4-(phenylethynyl)phenyl)(piperazin-1-yl)methanone; (4-hydroxy-4-(4-methoxyphenyl)piperidin-1-yl)(4-(phenylethynyl)phenyl)methanone; (4-hydroxy-4-(thiophen-2-yl)piperidin-1-yl)(4-(phenylethynyl)phenyl)methanone; (4-hydroxy-4-isopropylpiperidin-1-yl)(4-(phenylethynyl)phenyl)methanone; (4-hydroxy-4-methylpiperidin-1-yl)(4-(phenylethynyl)phenyl)methanone; (4-hydroxy-4-phenylpiperidin-1-yl)(4-(phenylethynyl)phenyl)methanone; (4-hydroxy-4-propylpiperidin-1-yl)(4-(phenylethynyl)phenyl)methanone; (4-hydroxypiperidin-1-yl)(4-((3-(trifluoromethyl)phenyl)ethynyl)phenyl)methanone; (4-hydroxypiperidin-1-yl)(4-(phenylethynyl)phenyl)methanone; (4-hydroxypiperidin-1-yl)(4-(phenylethynyl)phenyl)methanone; (4-isopropylpiperazin-1-yl)(4-(phenylethynyl)phenyl)methanone; (4-methylpiperazin-1-yl)(4-(phenylethynyl)phenyl)methanone; (octahydroisoquinolin-2(1H)-yl)(4-(phenylethynyl)phenyl)methanone; (R)-4-(phenylethynyl)-N-(2-phenylpropyl)benzamide; (S)-(4-(1-cyclohexylethylamino)piperidin-1-yl)(4-(phenylethynyl)phenyl)methanone; (S)—N-((1-ethylpyrrolidin-2-yl)methyl)-4-(phenylethynyl)benzamide; 1-(1-(4-(phenylethynyl)benzoyl)piperidin-4-yl)-1H-benzo[d]imidazol-2(3H)-one; 1-(4-phenyl-1-(4-(phenylethynyl)benzoyl)piperidin-4-yl)ethanone; 2-(4-(4-(phenylethynyl)benzoyl)piperazin-1-yl)benzonitrile; 4-(phenylethynyl)-N-(2-(piperidin-1-yl)ethyl)benzamide; 4-(phenylethynyl)-N-propylbenzamide; 4-phenyl-1-(4-(phenylethynyl)benzoyl)piperidine-4-carbonitrile; 5-chloro-1-(4-(phenylethynyl)benzoyl)-3-(piperidin-4-yl)-1H-benzo[d]imidazol-2(3H)-one; morpholino(4-(phenylethynyl)phenyl)methanone; N-(2-(1-methylpyrrolidin-2-yl)ethyl)-4-(phenylethynyl)benzamide; N-(2-(dimethylamino)ethyl)-4-(phenylethynyl)benzamide; N-(2,3-dihydro-1H-inden-1-yl)-4-(phenylethynyl)benzamide; N-(2,3-dihydro-1H-inden-2-yl)-4-(phenylethynyl)benzamide; N-(2-chlorophenethyl)-4-(phenylethynyl)benzamide; N-(2-cyclohexenylethyl)-4-(phenylethynyl)benzamide; N-(2-morpholinoethyl)-4-(phenylethynyl)benzamide; N-(3,3-dimethylbutyl)-4-(phenylethynyl)benzamide; N-(3-chlorophenethyl)-4-(phenylethynyl)benzamide; N-(3-hydroxypropyl)-4-(phenylethynyl)benzamide; N-(3-methoxypropyl)-4-(phenylethynyl)benzamide; N-(3-morpholinopropyl)-4-(phenylethynyl)benzamide; N-(4-bromophenethyl)-4-(phenylethynyl)benzamide; N-(4-chlorophenethyl)-4-(phenylethynyl)benzamide; N-(4-methylcyclohexyl)-4-(phenylethynyl)benzamide; N-(cyclohexylmethyl)-4-(phenylethynyl)benzamide; N-butyl-4-(phenylethynyl)benzamide; N-cyclohexyl-4-(phenylethynyl)benzamide; N-cyclopentyl-4-(phenylethynyl)benzamide; and N-isopentyl-4-(phenylethynyl)benzamide.

In a further aspect, the compound is selected from N-cyclopentyl-4-(phenylethynyl)benzamide; N-cyclohexyl-4-(phenylethynyl)benzamide; 4-(phenylethynyl)-N-propylbenzamide; N-(3,3-dimethylbutyl)-4-(phenylethynyl)benzamide; N-isopentyl-4-(phenylethynyl)benzamide; N-(3-methoxypropyl)-4-(phenylethynyl)benzamide; N-butyl-4-(phenylethynyl)benzamide; (R)-4-(phenylethynyl)-N-(2-phenylpropyl)benzamide; N-(cyclohexylmethyl)-4-(phenylethynyl)benzamide; N-(2-cyclohexenylethyl)-4-(phenylethynyl)benzamide; N-(4-methylcyclohexyl)-4-(phenylethynyl)benzamide; N-(3-hydroxypropyl)-4-(phenylethynyl)benzamide; N-(2-chlorophenethyl)-4-(phenylethynyl)benzamide; N-(2-morpholinoethyl)-4-(phenylethynyl)benzamide; N-(2,3-dihydro-1H-inden-1-yl)-4-(phenylethynyl)benzamide; N-(2,3-dihydro-1H-inden-2-yl)-4-(phenylethynyl)benzamide; N-(4-chlorophenethyl)-4-(phenylethynyl)benzamide; N-(3-chlorophenethyl)-4-(phenylethynyl)benzamide; N-(4-bromophenethyl)-4-(phenylethynyl)benzamide; (S)—N-((1-ethylpyrrolidin-2-yl)methyl)-4-(phenylethynyl)benzamide; N-(3-morpholinopropyl)-4-(phenylethynyl)benzamide; 4-(phenylethynyl)-N-(2-(piperidin-1-yl)ethyl)benzamide; N-(2-(dimethylamino)ethyl)-4-(phenylethynyl)benzamide; and N-(2-(1-methylpyrrolidin-2-yl)ethyl)-4-(phenylethynyl)benzamide.

In a further aspect, the compound is selected from (4-((3-fluorophenyl)ethynyl)phenyl)(4-hydroxypiperidin-1-yl)methanone; morpholino(4-(phenylethynyl)phenyl)methanone; (4-((3-fluorophenyl)ethynyl)phenyl)(morpholino)methanone; (4-((3-fluorophenyl)ethynyl)phenyl)(4-(hydroxymethyl)piperidin-1-yl)methanone; (4-((2-fluorophenyl)ethynyl)phenyl)(morpholino)methanone; (4-hydroxypiperidin-1-yl)(4-(phenylethynyl)phenyl)methanone; (4-((4-fluorophenyl)ethynyl)phenyl)(4-hydroxypiperidin-1-yl)methanone; (4-((3-fluorophenyl)ethynyl)phenyl)(4-hydroxy-4-methylpiperidin-1-yl)methanone; (4-((2-fluorophenyl)ethynyl)phenyl)(4-(hydroxymethyl)piperidin-1-yl)methanone; (4-((4-fluorophenyl)ethynyl)phenyl)(morpholino)methanone; (4-((4-fluorophenyl)ethynyl)phenyl)(4-(hydroxymethyl)piperidin-1-yl)methanone; (4-((2-fluorophenyl)ethynyl)phenyl)(4-hydroxypiperidin-1-yl)methanone; (4-hydroxypiperidin-1-yl)(4-(phenylethynyl)phenyl)methanone; (4-(hydroxymethyl)piperidin-1-yl)(4-(phenylethynyl)phenyl)methanone; (4-((3,4-difluorophenyl)ethynyl)phenyl)(morpholino)methanone; (4-((2-fluorophenyl)ethynyl)phenyl)(4-hydroxy-4-methylpiperidin-1-yl)methanone; (4-hydroxy-4-methylpiperidin-1-yl)(4-(phenylethynyl)phenyl)methanone; (4-(hydroxymethyl)piperidin-1-yl)(4-(phenylethynyl)phenyl)methanone; (4-((4-fluorophenyl)ethynyl)phenyl)(4-hydroxy-4-methylpiperidin-1-yl)methanone; (4-(pentan-2-ylamino)piperidin-1-yl)(4-(phenylethynyl)phenyl)methanone; (4-((3-fluorophenyl)ethynyl)phenyl)(3-hydroxyazetidin-1-yl)methanone; (4-((3,4-difluorophenyl)ethynyl)phenyl)(4-hydroxypiperidin-1-yl)methanone; (4-(cyclohexylamino)piperidin-1-yl)(4-(phenylethynyl)phenyl)methanone; (4-((3,4-difluorophenyl)ethynyl)phenyl)(4-(hydroxymethyl)piperidin-1-yl)methanone; (2,6-dimethylmorpholino)(4-(phenylethynyl)phenyl)methanone; (4-(phenylethynyl)phenyl)(4-(4-(pyridin-4-yl)piperazin-1-yl)piperidin-1-yl)methanone; (3-hydroxy-3-methylazetidin-1-yl)(4-(phenylethynyl)phenyl)methanone; (S)-(4-(1-cyclohexylethylamino)piperidin-1-yl)(4-(phenylethynyl)phenyl)methanone; (4-(4-methylpiperazin-1-yl)piperidin-1-yl)(4-(phenylethynyl)phenyl)methanone; (3-hydroxypiperidin-1-yl)(4-(phenylethynyl)phenyl)methanone; (4-((3,4-difluorophenyl)ethynyl)phenyl)(4-hydroxy-4-methylpiperidin-1-yl)methanone; (4-((4-fluorophenyl)ethynyl)phenyl)(3-hydroxyazetidin-1-yl)methanone; (4-methylpiperazin-1-yl)(4-(phenylethynyl)phenyl)methanone; (4-((2-fluorophenyl)ethynyl)phenyl)(3-hydroxyazetidin-1-yl)methanone; (4-(cyclobutylamino)piperidin-1-yl)(4-(phenylethynyl)phenyl)methanone; (3-hydroxyazetidin-1-yl)(4-(phenylethynyl)phenyl)methanone; (4-(2-morpholinoethylamino)piperidin-1-yl)(4-(phenylethynyl)phenyl)methanone; (4-((3,4-difluorophenyl)ethynyl)phenyl)(3-hydroxyazetidin-1-yl)methanone; (4-(4-chloro-2-(trifluoromethyl)phenyl)-4-hydroxypiperidin-1-yl)(4-(phenylethynyl)phenyl)methanone; (3-hydroxy-3-propylazetidin-1-yl)(4-(phenylethynyl)phenyl)methanone; (octahydroisoquinolin-2(1H)-yl)(4-(phenylethynyl)phenyl)methanone; (4-((4-fluoro-3-methylphenyl)ethynyl)phenyl)(4-hydroxypiperidin-1-yl)methanone; (4-((3,5-difluorophenyl)ethynyl)phenyl)(4-hydroxypiperidin-1-yl)methanone; (4-hydroxy-4-(thiophen-2-yl)piperidin-1-yl)(4-(phenylethynyl)phenyl)methanone; (4-(azetidin-1-yl)piperidin-1-yl)(4-(phenylethynyl)phenyl)methanone; 4-phenyl-1-(4-(phenylethynyl)benzoyl)piperidine-4-carbonitrile; (4-isopropylpiperazin-1-yl)(4-(phenylethynyl)phenyl)methanone; (4-(2-methoxyethylamino)piperidin-1-yl)(4-(phenylethynyl)phenyl)methanone; (4-(4-fluorophenyl)-4-hydroxypiperidin-1-yl)(4-(phenylethynyl)phenyl)methanone; 1-(4-phenyl-1-(4-(phenylethynyl)benzoyl)piperidin-4-yl)ethanone; 1-(1-(4-(phenylethynyl)benzoyl)piperidin-4-yl)-1H-benzo[d]imidazol-2(3H)-one; (4-hydroxy-4-propylpiperidin-1-yl)(4-(phenylethynyl)phenyl)methanone; (3-hydroxy-3-(thiophen-2-yl)azetidin-1-yl)(4-(phenylethynyl)phenyl)methanone; (4-(3-fluorophenyl)-4-hydroxypiperidin-1-yl)(4-(phenylethynyl)phenyl)methanone; (4-hydroxy-4-isopropylpiperidin-1-yl)(4-(phenylethynyl)phenyl)methanone; (4-((2,4-difluorophenyl)ethynyl)phenyl)(4-hydroxypiperidin-1-yl)methanone; (4-(phenylethynyl)phenyl)(4-phenylpiperazin-1-yl)methanone; (4-(2-methoxyphenyl)piperazin-1-yl)(4-(phenylethynyl)phenyl)methanone; (4-hydroxypiperidin-1-yl)(4-((3-(trifluoromethyl)phenyl)ethynyl)phenyl)methanone; (4-(4-bromophenyl)-4-hydroxypiperidin-1-yl)(4-(phenylethynyl)phenyl)methanone; (4-hydroxy-4-(4-methoxyphenyl)piperidin-1-yl)(4-(phenylethynyl)phenyl)methanone; (4-(cyclopropylmethylamino)piperidin-1-yl)(4-(phenylethynyl)phenyl)methanone; (4-(phenylethynyl)phenyl)(4-(pyridin-2-yl)piperazin-1-yl)methanone; (4-hydroxy-4-phenylpiperidin-1-yl)(4-(phenylethynyl)phenyl)methanone; (4-(phenylethynyl)phenyl)(4-(pyridin-4-yl)piperazin-1-yl)methanone; 5-chloro-1-(4-(phenylethynyl)benzoyl)-3-(piperidin-4-yl)-1H-benzo[d]imidazol-2(3H)-one; (4-(phenylethynyl)phenyl)(4-(pyrrolidin-1-yl)piperidin-1-yl)methanone; 2-(4-(4-(phenylethynyl)benzoyl)piperazin-1-yl)benzonitrile; (4-(phenylethynyl)phenyl)(piperazin-1-yl)methanone; (4-(2-fluorophenyl)piperazin-1-yl)(4-(phenylethynyl)phenyl)methanone; and (4-(4-chlorophenyl)-4-hydroxypiperidin-1-yl)(4-(phenylethynyl)phenyl)methanone.

In a further aspect, the compound is selected from 4-(3-(4-fluorophenyl)-1,2,4-oxadiazol-5-yl)-N-(3-methoxypropyl)benzamide; N-(3,3-dimethylbutyl)-4-(3-phenyl-1,2,4-oxadiazol-5-yl)benzamide; 4-(3-(4-fluorophenyl)-1,2,4-oxadiazol-5-yl)-N-propylbenzamide; 4-(3-phenyl-1,2,4-oxadiazol-5-yl)-N-propylbenzamide; (4-(3-(4-fluorophenyl)-1,2,4-oxadiazol-5-yl)phenyl)(4-(pyridin-4-yl)piperazin-1-yl)methanone; N-(3,3-dimethylbutyl)-4-(3-(4-fluorophenyl)-1,2,4-oxadiazol-5-yl)benzamide; (E)-(4-hydroxypiperidin-1-yl)(4-styrylphenyl)methanone; (4-hydroxypiperidin-1-yl)(4-(pyridin-2-ylethynyl)phenyl)methanone; (4-(cyclohexylethynyl)phenyl)(4-hydroxypiperidin-1-yl)methanone; and N-(4-fluorophenyl)-4-(2-methylpiperidine-1-carbonyl)benzamide.

In a further aspect, the compound is selected from 4-(3-(4-fluorophenyl)-1,2,4-oxadiazol-5-yl)-N-(3-methoxypropyl)benzamide; N-(3,3-dimethylbutyl)-4-(3-phenyl-1,2,4-oxadiazol-5-yl)benzamide; 4-(3-(4-fluorophenyl)-1,2,4-oxadiazol-5-yl)-N-propylbenzamide; 4-(3-phenyl-1,2,4-oxadiazol-5-yl)-N-propylbenzamide; (4-(3-(4-fluorophenyl)-1,2,4-oxadiazol-5-yl)phenyl)(4-(pyridin-4-yl)piperazin-1-yl)methanone; and N-(3,3-dimethylbutyl)-4-(3-(4-fluorophenyl)-1,2,4-oxadiazol-5-yl)benzamide.

In a yet further aspect, the compound is (E)-(4-hydroxypiperidin-1-yl)(4-styrylphenyl)methanone. In a yet further aspect, the compound is (4-hydroxypiperidin-1-yl)(4-(pyridin-2-ylethynyl)phenyl)methanone. In a yet further aspect, the compound is (4-(cyclohexylethynyl)phenyl)(4-hydroxypiperidin-1-yl)methanone. In a yet further aspect, the compound is N-(4-fluorophenyl)-4-(2-methylpiperidine-1-carbonyl)benzamide.

In a further aspect, the compound is selected from N-cyclopentyl-4-(phenylethynyl)benzamide; (4-((3-fluorophenyl)ethynyl)phenyl)(4-hydroxypiperidin-1-yl)methanone; morpholino(4-(phenylethynyl)phenyl)methanone; (4-((3-fluorophenyl)ethynyl)phenyl)(morpholino)methanone; N-cyclohexyl-4-(phenylethynyl)benzamide; (4-((3-fluorophenyl)ethynyl)phenyl)(4-(hydroxymethyl)piperidin-1-yl)methanone; (4-((2-fluorophenyl)ethynyl)phenyl)(morpholino)methanone; (4-hydroxypiperidin-1-yl)(4-(phenylethynyl)phenyl)methanone; 4-(phenylethynyl)-N-propylbenzamide; (4-((4-fluorophenyl)ethynyl)phenyl)(4-hydroxypiperidin-1-yl)methanone; N-(3,3-dimethylbutyl)-4-(phenylethynyl)benzamide; (4-((3-fluorophenyl)ethynyl)phenyl)(4-hydroxy-4-methylpiperidin-1-yl)methanone; (4-((2-fluorophenyl)ethynyl)phenyl)(4-(hydroxymethyl)piperidin-1-yl)methanone; (4-((4-fluorophenyl)ethynyl)phenyl)(morpholino)methanone; (4-((4-fluorophenyl)ethynyl)phenyl)(4-(hydroxymethyl)piperidin-1-yl)methanone; N-isopentyl-4-(phenylethynyl)benzamide; (4-((2-fluorophenyl)ethynyl)phenyl)(4-hydroxypiperidin-1-yl)methanone; (4-hydroxypiperidin-1-yl)(4-(phenylethynyl)phenyl)methanone; N-(3-methoxypropyl)-4-(phenylethynyl)benzamide; (4-(hydroxymethyl)piperidin-1-yl)(4-(phenylethynyl)phenyl)methanone; N-butyl-4-(phenylethynyl)benzamide; (R)-4-(phenylethynyl)-N-(2-phenylpropyl)benzamide; (4-((3,4-difluorophenyl)ethynyl)phenyl)(morpholino)methanone; (4-((2-fluorophenyl)ethynyl)phenyl)(4-hydroxy-4-methylpiperidin-1-yl)methanone; (4-hydroxy-4-methylpiperidin-1-yl)(4-(phenylethynyl)phenyl)methanone; (4-(hydroxymethyl)piperidin-1-yl)(4-(phenylethynyl)phenyl)methanone; (4-((4-fluorophenyl)ethynyl)phenyl)(4-hydroxy-4-methylpiperidin-1-yl)methanone; (4-(pentan-2-ylamino)piperidin-1-yl)(4-(phenylethynyl)phenyl)methanone; N-(cyclohexylmethyl)-4-(phenylethynyl)benzamide; (4-((3-fluorophenyl)ethynyl)phenyl)(3-hydroxyazetidin-1-yl)methanone; (4-((3,4-difluorophenyl)ethynyl)phenyl)(4-hydroxypiperidin-1-yl)methanone; N-(2-cyclohexenylethyl)-4-(phenylethynyl)benzamide; N-(4-methylcyclohexyl)-4-(phenylethynyl)benzamide; (4-(cyclohexylamino)piperidin-1-yl)(4-(phenylethynyl)phenyl)methanone; (4-((3,4-difluorophenyl)ethynyl)phenyl)(4-(hydroxymethyl)piperidin-1-yl)methanone; N-(3-hydroxypropyl)-4-(phenylethynyl)benzamide; (2,6-dimethylmorpholino)(4-(phenylethynyl)phenyl)methanone; (4-(phenylethynyl)phenyl)(4-(4-(pyridin-4-yl)piperazin-1-yl)piperidin-1-yl)methanone; (3-hydroxy-3-methylazetidin-1-yl)(4-(phenylethynyl)phenyl)methanone; (S)-(4-(1-cyclohexylethylamino)piperidin-1-yl)(4-(phenylethynyl)phenyl)methanone; (4-(4-methylpiperazin-1-yl)piperidin-1- yl)(4-(phenylethynyl)phenyl)methanone; (3-hydroxypiperidin-1-yl)(4-(phenylethynyl)phenyl)methanone; N-(2-chlorophenethyl)-4-(phenylethynyl)benzamide; N-(2-morpholinoethyl)-4-(phenylethynyl)benzamide; N-(2,3-dihydro-1H-inden-1-yl)-4-(phenylethynyl)benzamide; (4-((3,4-difluorophenyl)ethynyl)phenyl)(4-hydroxy-4-methylpiperidin-1-yl)methanone; N-(2,3-dihydro-1H-inden-2-yl)-4-(phenylethynyl)benzamide; (4-((4-fluorophenyl)ethynyl)phenyl)(3-hydroxyazetidin-1-yl)methanone; (4-methylpiperazin-1-yl)(4-(phenylethynyl)phenyl)methanone; N-(4-chlorophenethyl)-4-(phenylethynyl)benzamide; (4-((2-fluorophenyl)ethynyl)phenyl)(3-hydroxyazetidin-1-yl)methanone; N-(3-chlorophenethyl)-4-(phenylethynyl)benzamide; (4-(cyclobutylamino)piperidin-1-yl)(4-(phenylethynyl)phenyl)methanone; N-(4-bromophenethyl)-4-(phenylethynyl)benzamide; (3-hydroxyazetidin-1-yl)(4-(phenylethynyl)phenyl)methanone; (4-(2-morpholinoethylamino)piperidin-1-yl)(4-(phenylethynyl)phenyl)methanone; (4-((3,4-difluorophenyl)ethynyl)phenyl)(3-hydroxyazetidin-1-yl)methanone; N-(3,3-dimethylbutyl)-4-(3-(4-fluorophenyl)-1,2,4-oxadiazol-5-yl)benzamide; (4-(4-chloro-2-(trifluoromethyl)phenyl)-4-hydroxypiperidin-1-yl)(4-(phenylethynyl)phenyl)methanone; (3-hydroxy-3-propylazetidin-1-yl)(4-(phenylethynyl)phenyl)methanone; (octahydroisoquinolin-2(1H)-yl)(4-(phenylethynyl)phenyl)methanone; and (4-((4-fluoro-3-methylphenyl)ethynyl)phenyl)(4-hydroxypiperidin-1-yl)methanone.

In a further aspect, the compound is selected from N-cyclopentyl-4-(phenylethynyl)benzamide; (4-((3-fluorophenyl)ethynyl)phenyl)(4-hydroxypiperidin-1-yl)methanone; morpholino(4-(phenylethynyl)phenyl)methanone; (4-((3-fluorophenyl)ethynyl)phenyl)(morpholino)methanone; N-cyclohexyl-4-(phenylethynyl)benzamide; (4-((3-fluorophenyl)ethynyl)phenyl)(4-(hydroxymethyl)piperidin-1-yl)methanone; (4-((2-fluorophenyl)ethynyl)phenyl)(morpholino)methanone; (4-hydroxypiperidin-1-yl)(4-(phenylethynyl)phenyl)methanone; 4-(phenylethynyl)-N-propylbenzamide; (4-((4-fluorophenyl)ethynyl)phenyl)(4-hydroxypiperidin-1-yl)methanone; N-(3,3-dimethylbutyl)-4-(phenylethynyl)benzamide; (4-((3-fluorophenyl)ethynyl)phenyl)(4-hydroxy-4-methylpiperidin-1-yl)methanone; (4-((2-fluorophenyl)ethynyl)phenyl)(4-(hydroxymethyl)piperidin-1-yl)methanone; (4-((4-fluorophenyl)ethynyl)phenyl)(morpholino)methanone; (4-((4-fluorophenyl)ethynyl)phenyl)(4-(hydroxymethyl)piperidin-1-yl)methanone; N-isopentyl-4-(phenylethynyl)benzamide; (4-((2-fluorophenyl)ethynyl)phenyl)(4-hydroxypiperidin-1-yl)methanone; (4-hydroxypiperidin-1-yl)(4-(phenylethynyl)phenyl)methanone; N-(3-methoxypropyl)-4-(phenylethynyl)benzamide; (4-(hydroxymethyl)piperidin-1-yl)(4-(phenylethynyl)phenyl)methanone; N-butyl-4-(phenylethynyl)benzamide; (R)-4-(phenylethynyl)-N-(2-phenylpropyl)benzamide; (4-((3,4-difluorophenyl)ethynyl)phenyl)(morpholino)methanone; (4-((2-fluorophenyl)ethynyl)phenyl)(4-hydroxy-4-methylpiperidin-1-yl)methanone; (4-hydroxy-4-methylpiperidin-1-yl)(4-(phenylethynyl)phenyl)methanone; (4-(hydroxymethyl)piperidin-1-yl)(4-(phenylethynyl)phenyl)methanone; (4-((4-fluorophenyl)ethynyl)phenyl)(4-hydroxy-4-methylpiperidin-1-yl)methanone; (4-(pentan-2-ylamino)piperidin-1-yl)(4-(phenylethynyl)phenyl)methanone; N-(cyclohexylmethyl)-4-(phenylethynyl)benzamide; (4-((3-fluorophenyl)ethynyl)phenyl)(3-hydroxyazetidin-1-yl)methanone; (4-((3,4-difluorophenyl)ethynyl)phenyl)(4-hydroxypiperidin-1-yl)methanone; N-(2-cyclohexenylethyl)-4-(phenylethynyl)benzamide; N-(4-methylcyclohexyl)-4-(phenylethynyl)benzamide; (4-(cyclohexylamino)piperidin-1-yl)(4-(phenylethynyl)phenyl)methanone; (4-((3,4-difluorophenyl)ethynyl)phenyl)(4-(hydroxymethyl)piperidin-1-yl)methanone; N-(3-hydroxypropyl)-4-(phenylethynyl)benzamide; and (2,6-dimethylmorpholino)(4-(phenylethynyl)phenyl)methanone.

In a further aspect, the compound is selected from N-cyclopentyl-4-(phenylethynyl)benzamide; (4-((3-fluorophenyl)ethynyl)phenyl)(4-hydroxypiperidin-1-yl)methanone; morpholino(4-(phenylethynyl)phenyl)methanone; and (4-((3-fluorophenyl)ethynyl)phenyl)(morpholino)methanone.

In a still further aspect, the compound can be a phenylethynylbenzamide derivative, a cycloalkylethynylbenzamide derivative, a styrylbenzamide derivative, a 4-(3-phenyl-1,2,4-oxadiazol-5-yl)benzamide derivative, a 4-(pyridinylethynyl)benzamide derivative, or a $N^1$-phenylterephthalamide derivative.

1. Phenylethynylbenzamide Derivatives

In a further aspect, the invention relates to compounds having a structure represented by a formula:

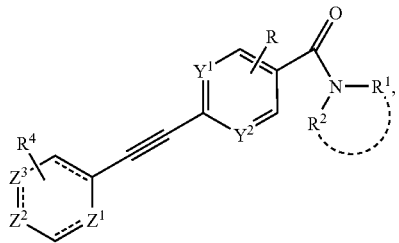

wherein $R^1$ and $R^2$ are independently optionally substituted organic radicals comprising from 1 to 12 carbon atoms; wherein each ----- is an optional covalent bond; wherein $Y^1$ and $Y^2$ are independently selected from N and C—R; wherein R comprises two to four substituents independently selected from hydrogen, halogen, hydroxyl, cyano, nitro, thiol, or an organic radical comprising 1 to 12 carbon atoms; wherein $Z^1$, $Z^2$, and $Z^3$ are independently selected from N and C—$R^4$, with the proviso that no more than two of $Z^1$, $Z^2$, and $Z^3$ are nitrogen; and wherein $R^4$ comprises up to five substituents independently selected from hydrogen, halogen, hydroxyl, cyano, nitro, thiol, optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, optionally substituted heteroaryl, optionally substituted alkoxyl, optionally substituted thioalkyl, optionally substituted alkylsulfinyl, optionally substituted alkylsulfonyl, and optionally substituted amino, thioamido, amidosulfonyl, alkoxycarbonyl, carboxamide, aminocarbonyl, and alkylamine-carbonyl; or a pharmaceutically acceptable salt or N-oxide thereof, wherein the compound exhibits potentiation of mGluR5 response to glutamate as an increase in response to non-maximal concentrations of glutamate in human embryonic kidney cells transfected with rat mGluR5 in the presence of the compound, compared to the response to glutamate in the absence of the compound.

In a further aspect, $R^1$ and $R^2$ are independently alkyl having from 1 to 6 carbons. In a further aspect, N, $R^1$, and $R^2$ together comprise an optionally substituted heterocyclic ring having from two to seven carbons. In a further aspect, all of $Z^1$, $Z^2$, and $Z^3$ are carbon. In a further aspect, $R^4$ comprises up to five substituents independently selected from hydrogen, halogen, and lower alkyl. In a further aspect, both of $Y^1$ and $Y^2$ are carbon.

In a yet further aspect, the compound has a structure represented by a formula:

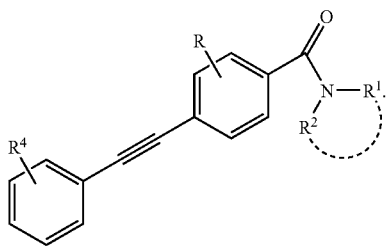

In a further aspect, $R^1$ and $R^2$ are independently alkyl having from 1 to 6 carbons or N, $R^1$, and $R^2$ together comprise an optionally substituted heterocyclic ring having from two to seven carbons; R comprises four substituents independently selected from hydrogen, halogen, and lower alkyl; and $R^4$ comprises five substituents independently selected from hydrogen, halogen, and lower alkyl.

In a further aspect, the invention relates to phenylethynylbenzamide derivatives. In one aspect, the compound is a compound or pharmaceutically acceptable salt thereof comprising the structure:

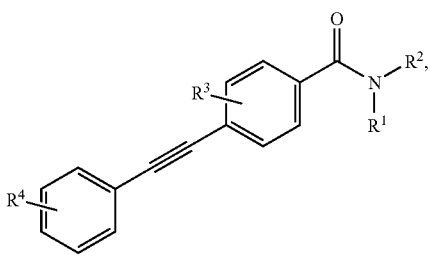

wherein $R^1$ and $R^2$ are independently selected from optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, and optionally substituted heteroaryl, or wherein N, $R^1$, and $R^2$ together comprise an optionally substituted hetrocyclic ring having from two to seven carbons; wherein $R^3$ comprises four substituents independently selected from hydrogen, halogen, hydroxyl, cyano, nitro, thiol, optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, optionally substituted heteroaryl, optionally substituted alkoxyl, optionally substituted thioalkyl, optionally substituted alkylsulfinyl, optionally substituted alkylsulfonyl, and optionally substituted amino, thioamido, amidosulfonyl, alkoxycarbonyl, carboxamide, amino-carbonyl, and alkylamine-carbonyl; wherein $R^4$ comprises five substituents independently selected from hydrogen, halogen, hydroxyl, cyano, nitro, thiol, optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, optionally substituted heteroaryl, optionally substituted alkoxyl, optionally substituted thioalkyl, optionally substituted alkylsulfinyl, optionally substituted alkylsulfonyl, and optionally substituted amino, thioamido, amidosulfonyl, alkoxycarbonyl, carboxamide, amino-carbonyl, and alkylamine-carbonyl; and wherein the compound exhibits potentiation of glutamate as an increase in response to non-maximal concentrations of glutamate in human embryonic kidney cells transfected with rat mGluR5 in the presence of the compound, compared to the response to glutamate in the absence of the compound.

In one aspect, the compound exhibits potentiation with an $EC_{50}$ of less than about $10 \times 10^{-6}$. For example, the compound can exhibit potentiation with an $EC_{50}$ of less than about $10 \times 10^{-7}$. As a further example, the compound can exhibit potentiation with an $EC_{50}$ of less than about $1.0 \times 10^8$.

In a further aspect, $R^1$ is selected from optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, and optionally substituted heteroaryl and has from two to seven carbons.

In a further aspect, $R^2$ is selected from optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, and optionally substituted heteroaryl and has from two to seven carbons.

In a further aspect, one or more substitutents of $R^3$ are selected from optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, and optionally substituted heteroaryl and have from two to seven carbons.

In a further aspect, one or more substitutents of $R_4$ are selected from optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, and optionally substituted heteroaryl and have from two to seven carbons.

In one aspect, each of $R^1$, $R^2$, $R^3$, and/or $R_4$ comprises an optionally substituted alkyl or an optionally substituted cycloalkyl. In one aspect, the optionally substituted alkyl of $R^1$, $R^2$, $R^3$, and/or $R_4$ comprises a C1 to C6 substituent; that is, a substituent having from one to six carbons. For example, in one aspect, the optionally substituted alkyl can be methyl, ethyl, propyl, isopropyl, butyl, isobutyl, sec-butyl, pentyl, or hexyl. In a further aspect, all of $R^3$ are hydrogen.

In a further aspect, at least one of $R^4$ is halogen selected from F and Cl. In a further aspect, $R^4$ comprises four hydrogens and one or two substituents selected from hydrogen, F, and Cl.

In one aspect, the compound can have a structure represented by a formula:

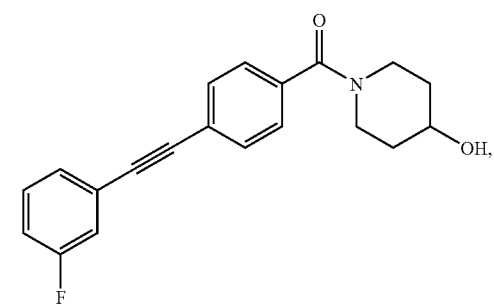
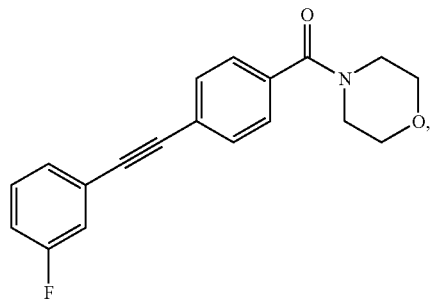
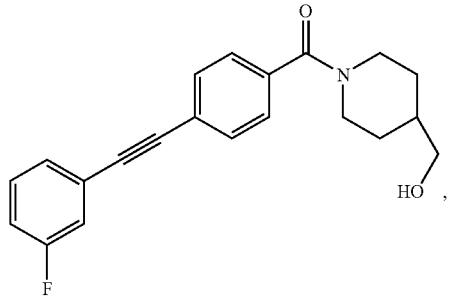
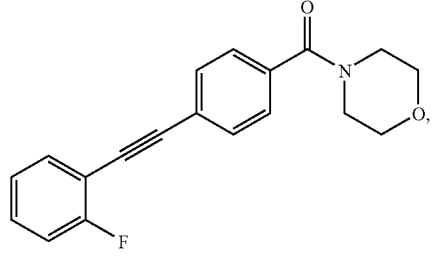
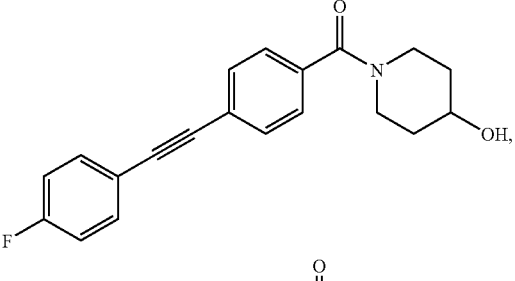
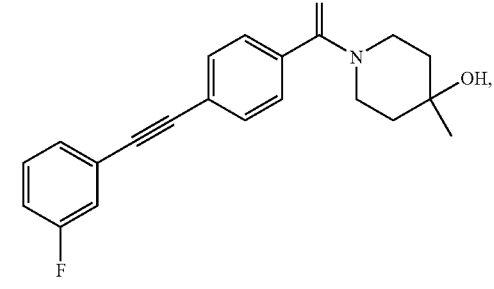
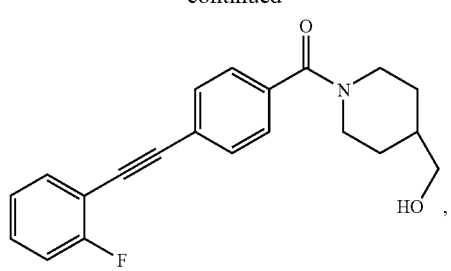
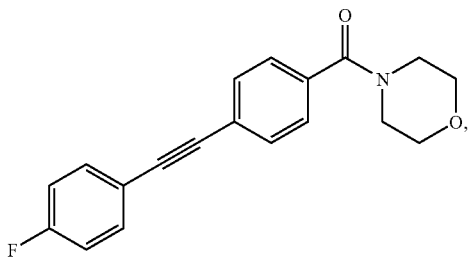
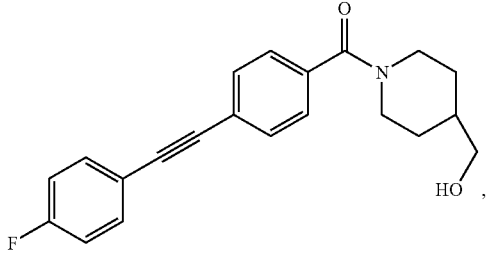
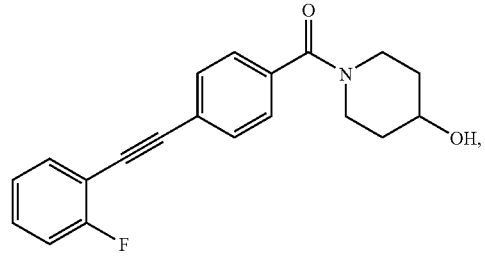
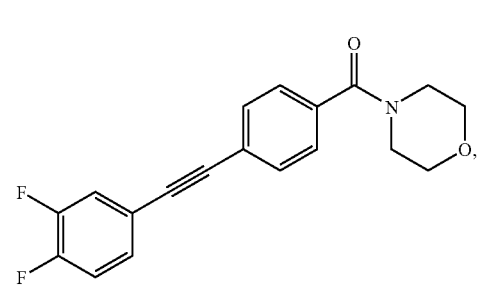
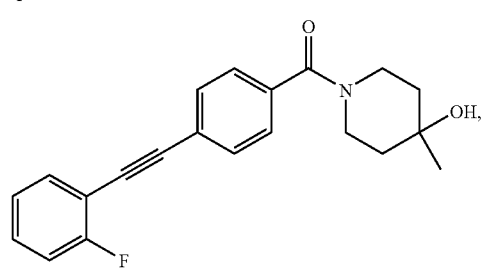

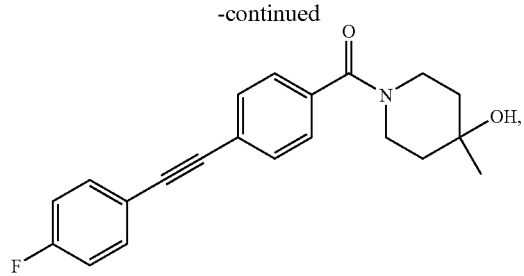
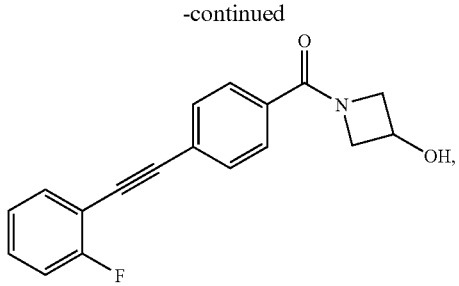
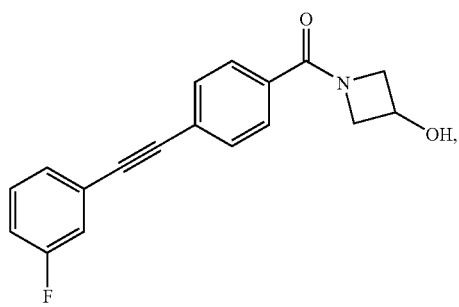
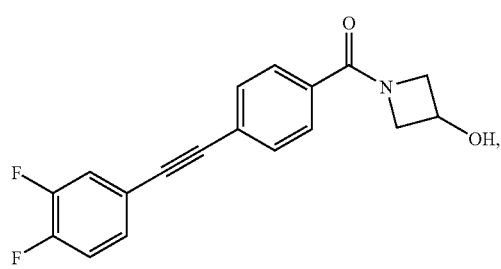
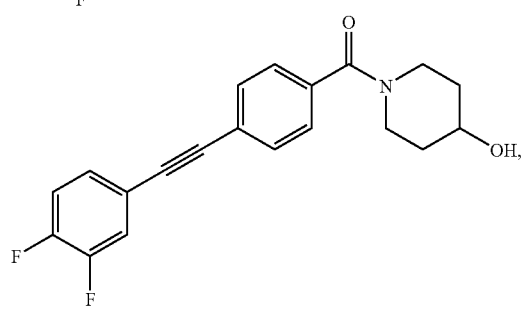
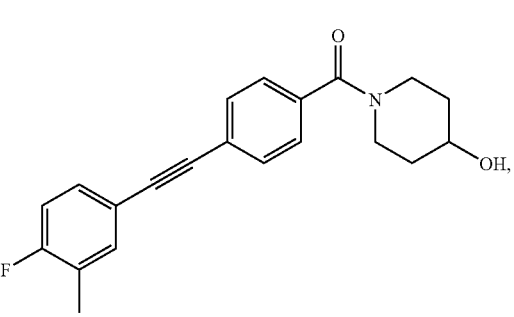
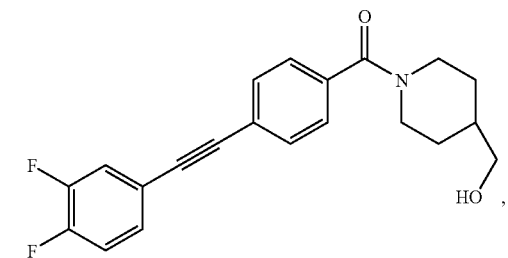
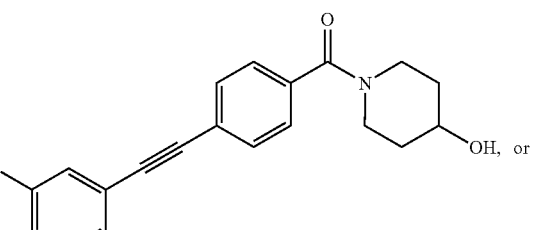
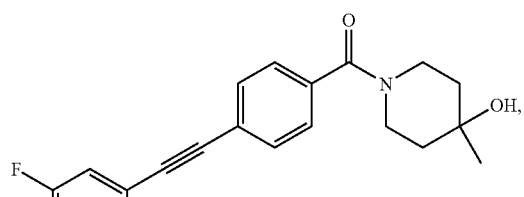
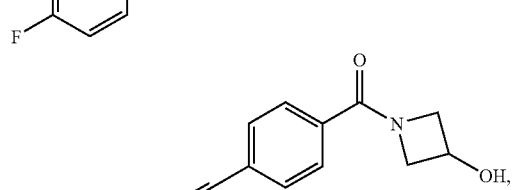
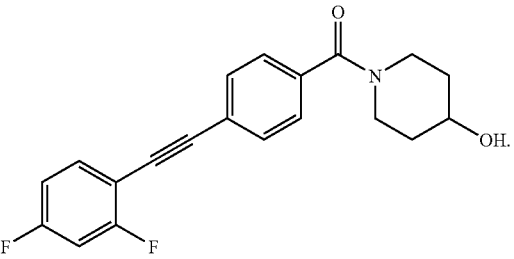
In one aspect, at least one of $R^4$ is optionally substituted alkyl selected from methyl and trifluoromethyl. In a further aspect, the compound can have a structure represented by a formula:

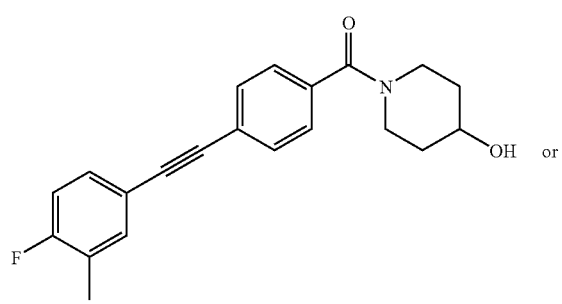
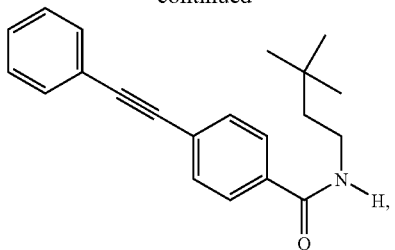
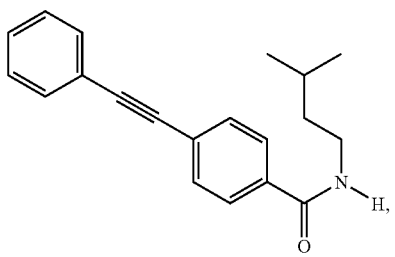
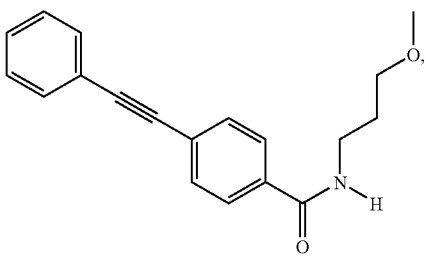
In a further aspect, $R^4$ comprises five hydrogens and one optionally substituted alkyl. In a further aspect, all of $R^4$ are hydrogen.
In a further aspect, the compound has a structure represented by a formula:
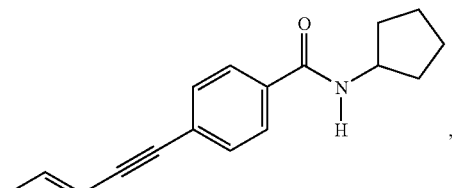
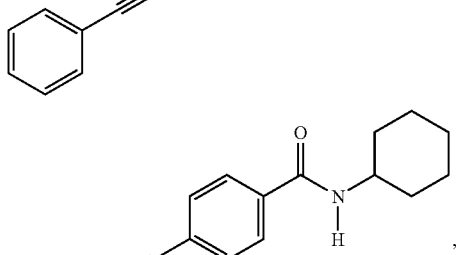
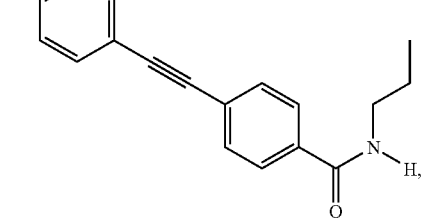

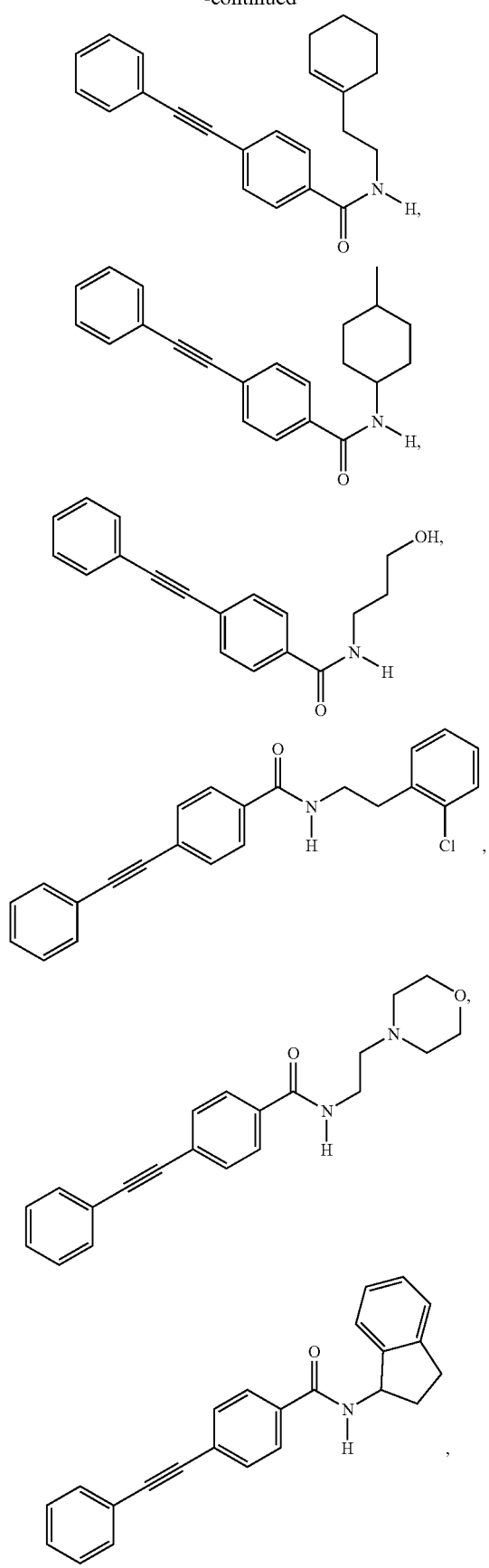
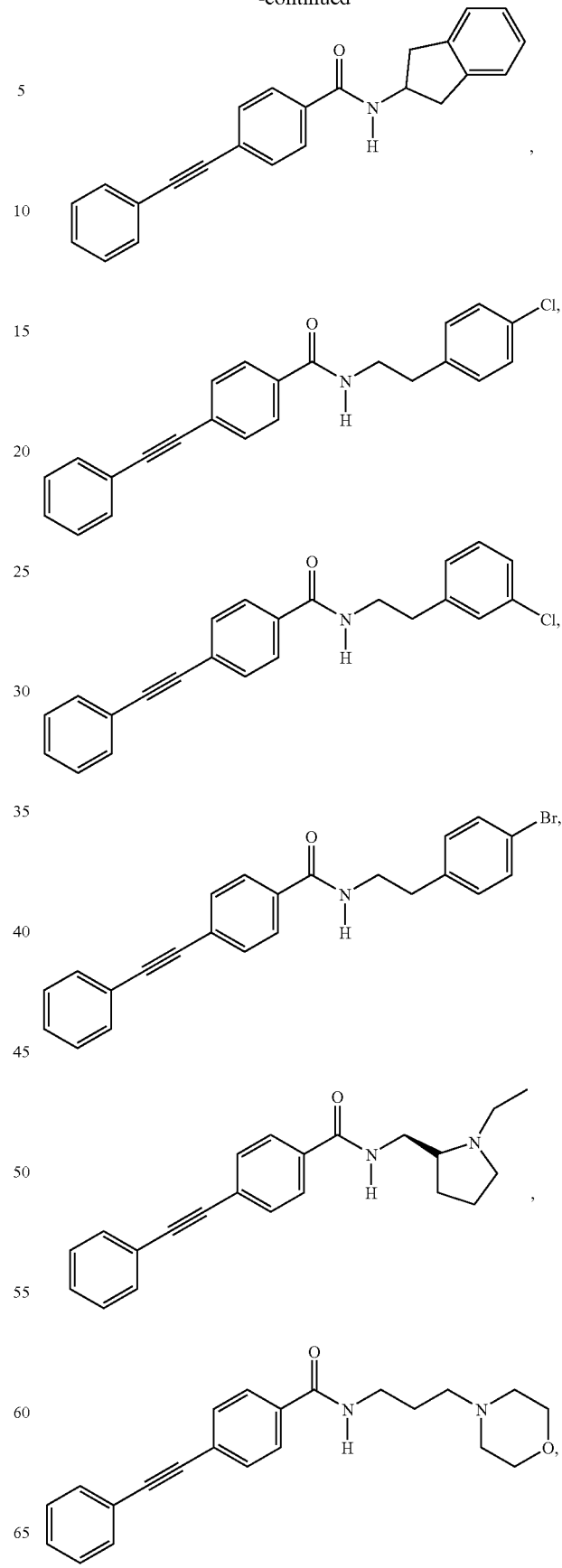

45
-continued
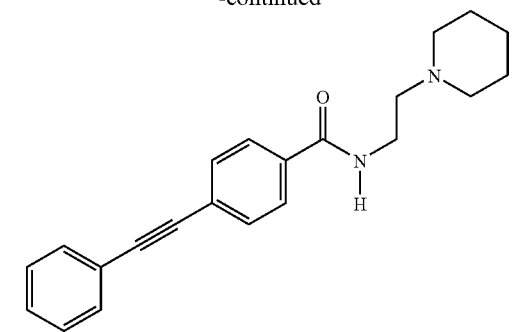
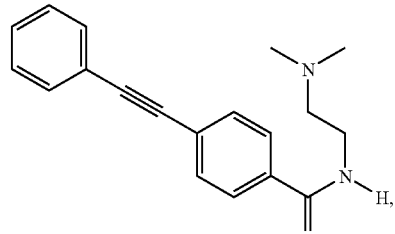
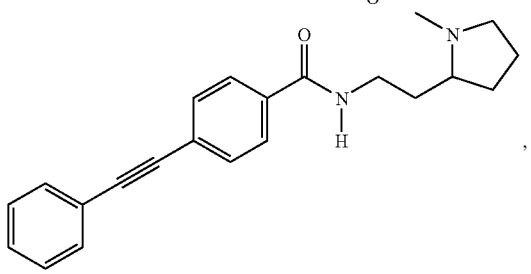
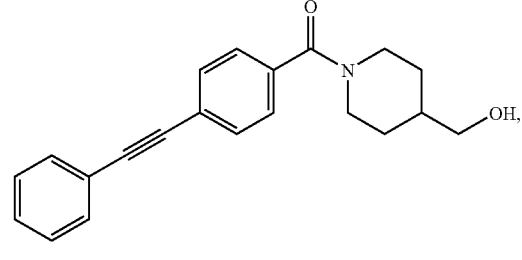
46
-continued
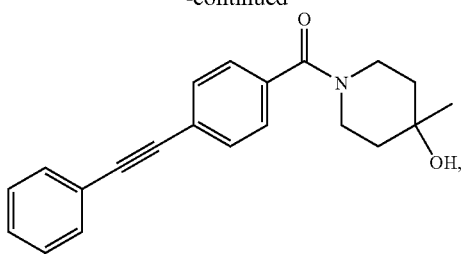
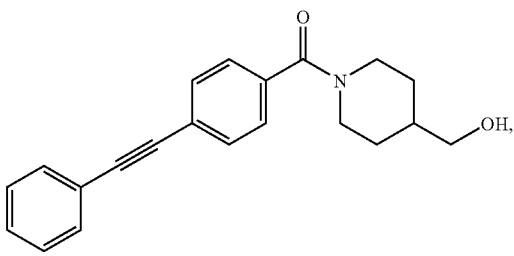
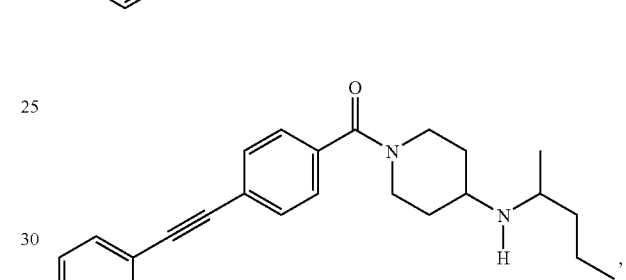
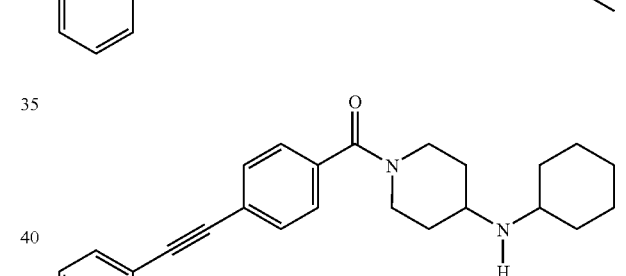
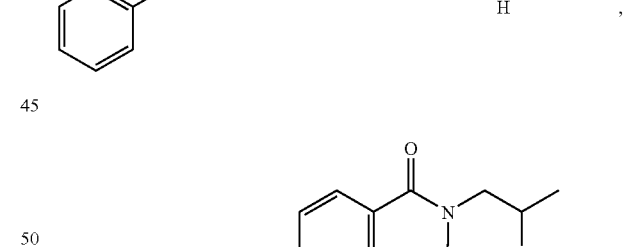
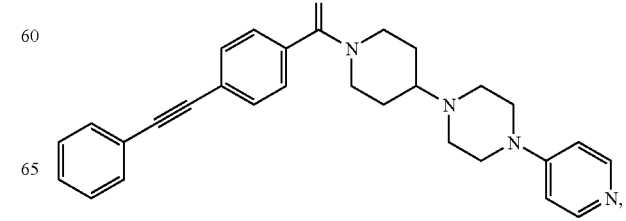

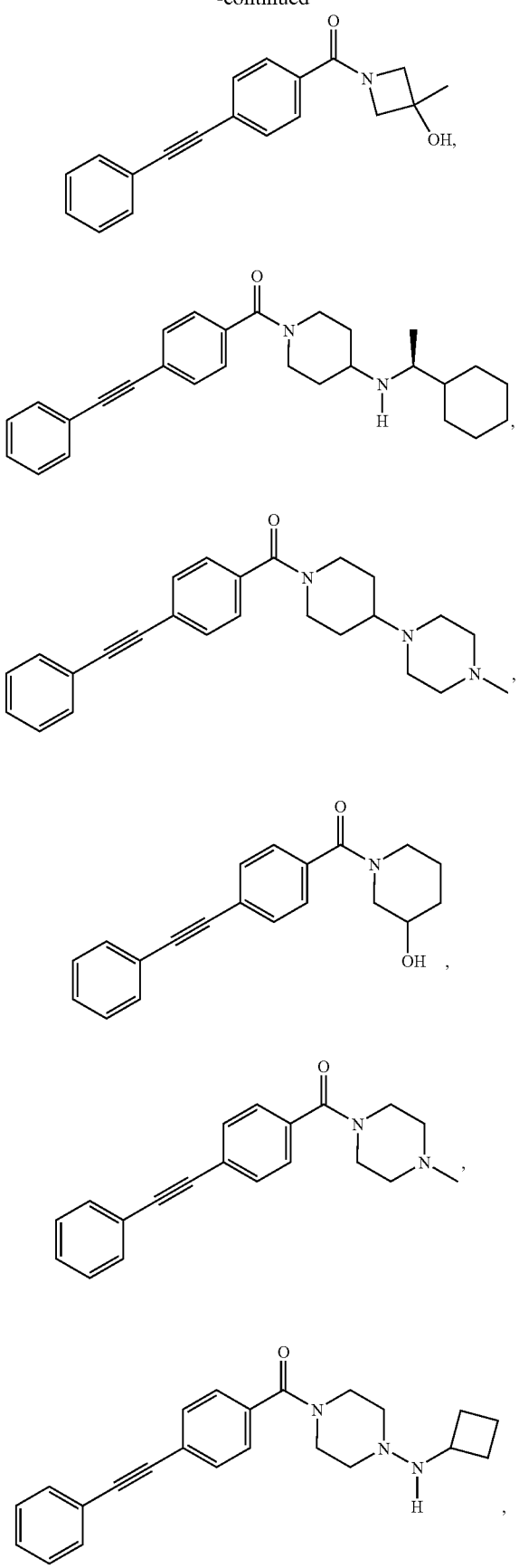
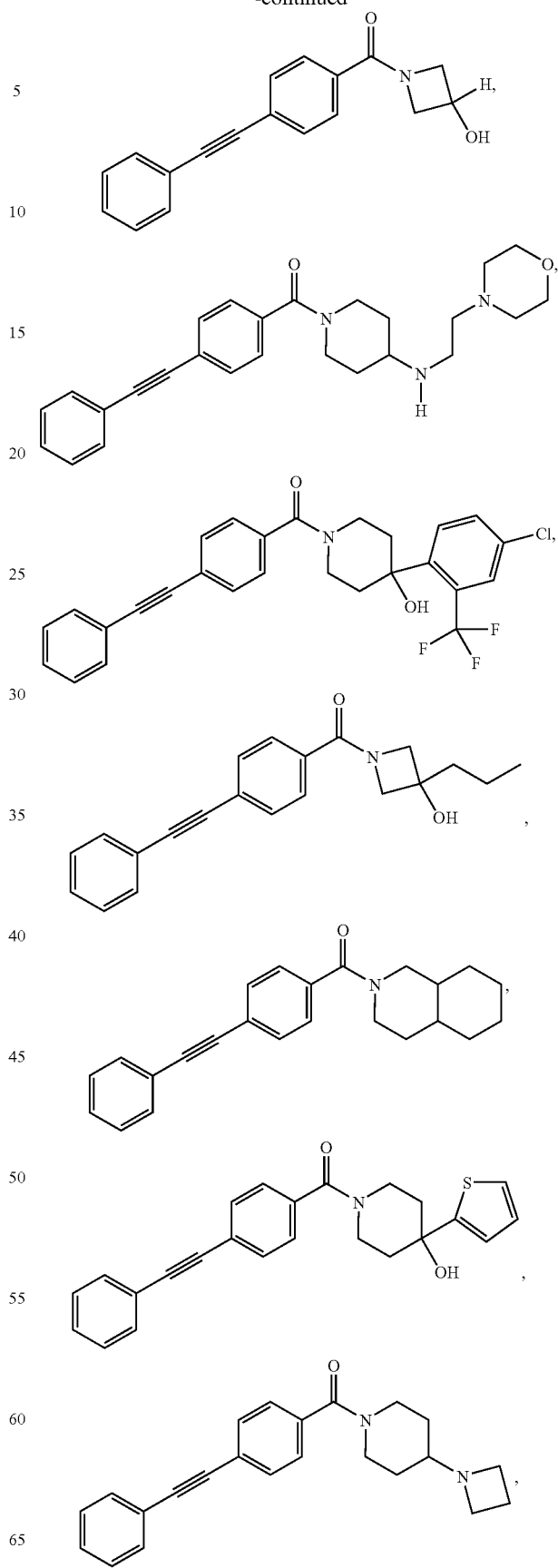

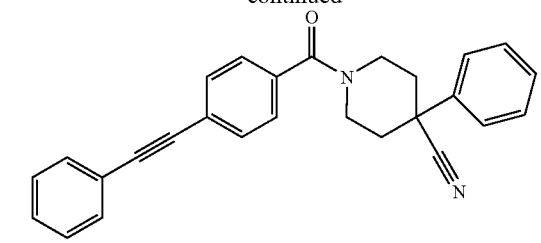,
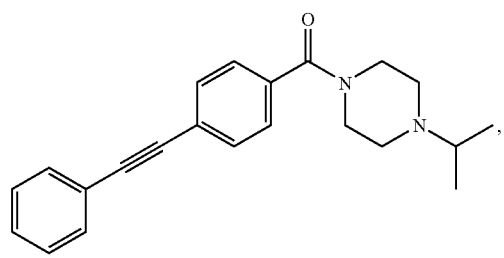,
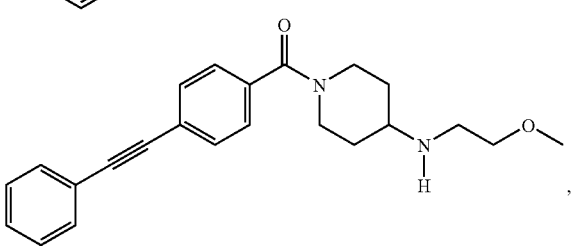,
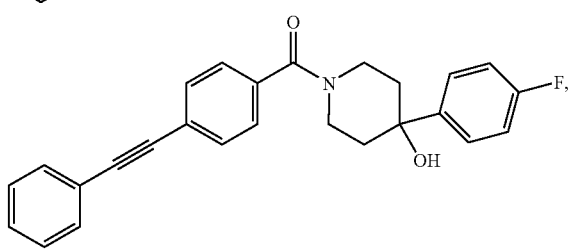,
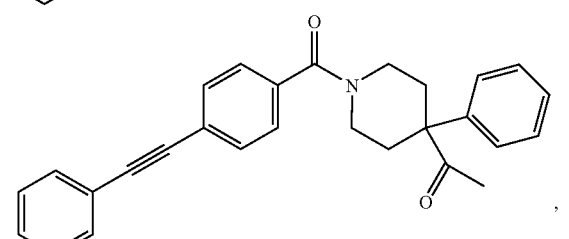,
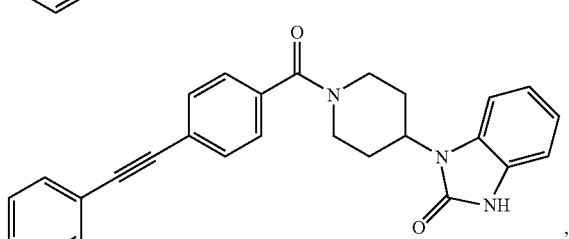,
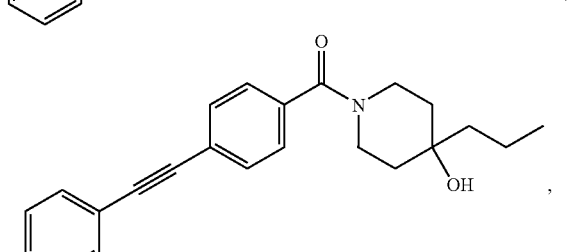,
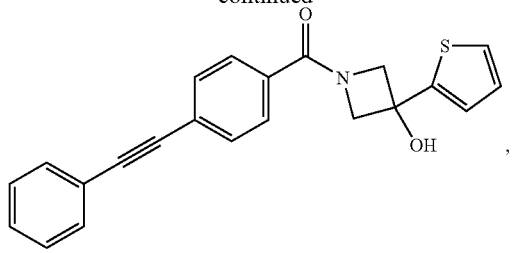,
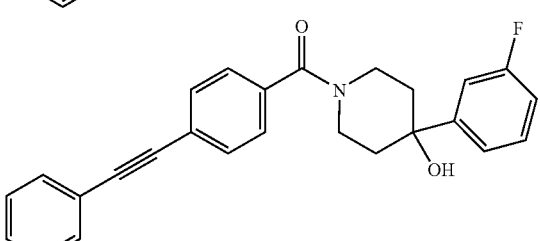,
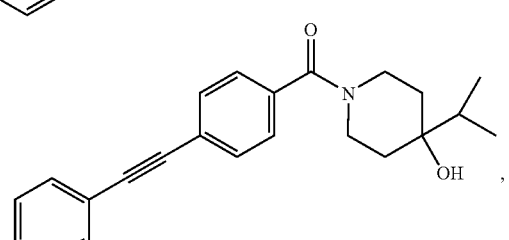,
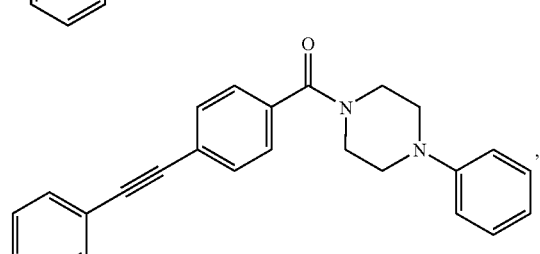,
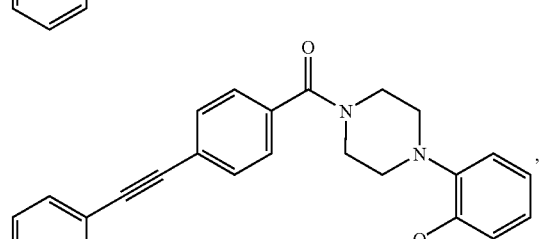,
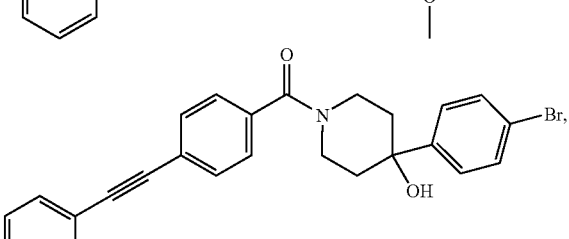,
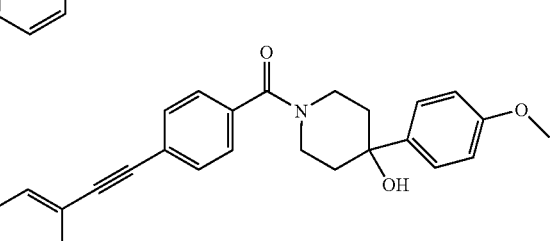,

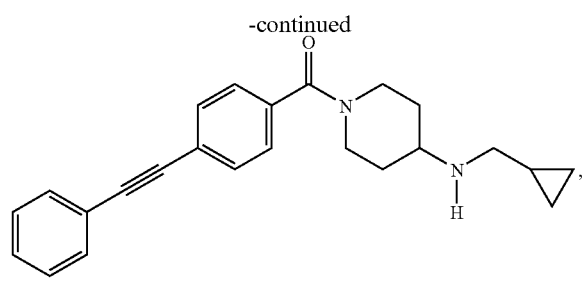

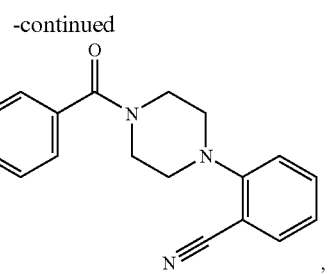

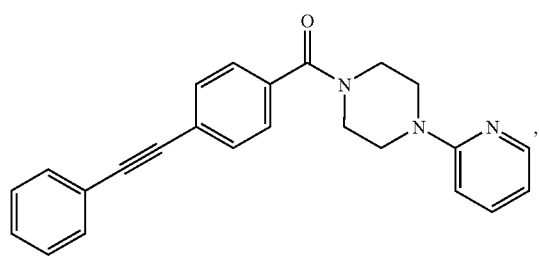

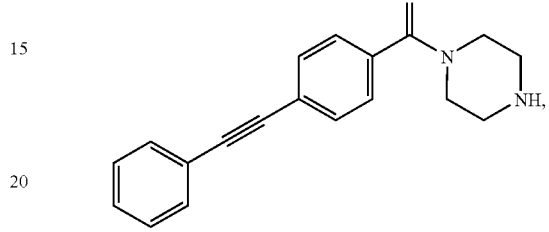

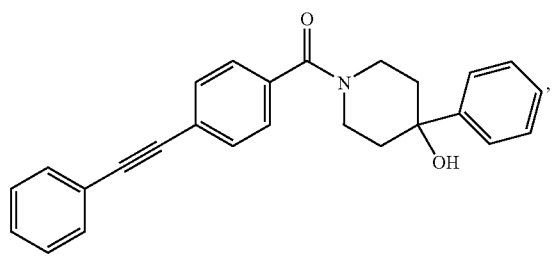

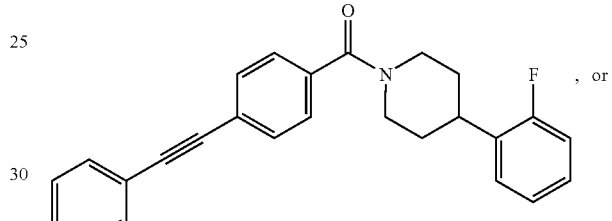, or

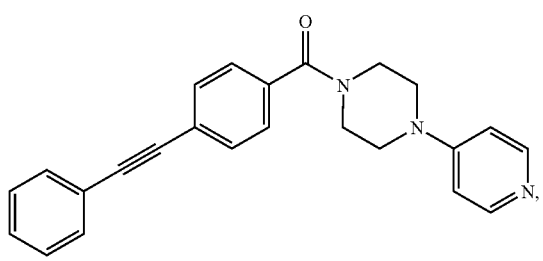

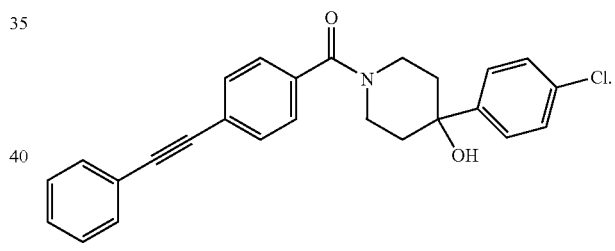

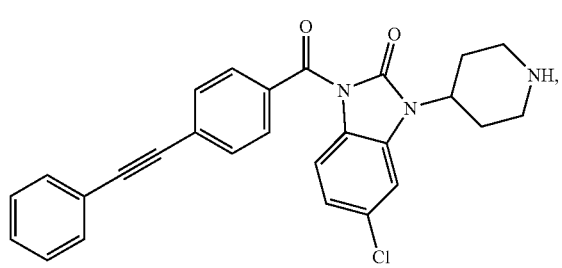

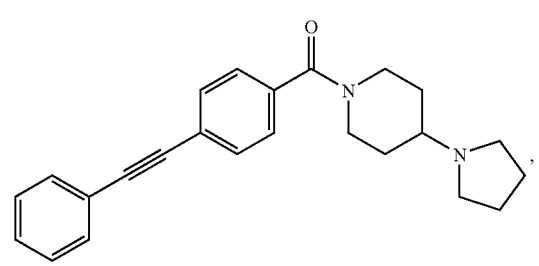

In a further aspect, $R^1$ and $R^2$ are independently selected from hydrogen, (1-ethylpyrrolidin-2-yl)methyl; 2-(1-methylpyrrolidin-2-yl)ethyl; 2-(dimethylamino)ethyl; 2-(piperidin-1-yl)ethyl; 2,3-dihydro-1H-inden-1-yl; 2-chlorophenethyl; 2-morpholinoethyl; 2-phenylpropyl; 3,3-dimethylbutyl; 3-chlorophenethyl; 3-hydroxypropyl; 3-methoxypropyl; 3-morpholinopropyl; 4-bromophenethyl; 4-chlorophenethyl; butyl; cyclohexenylethyl; cyclohexylcyclohexylmethylcyclopentyl; isopentyl; methylcyclohexyl; and propyl. In a yet further aspect, $R^1$ and $R^2$ are independently selected from (1-ethylpyrrolidin-2-yl)methyl; 2-(1-methylpyrrolidin-2-yl)ethyl; 2-(dimethylamino)ethyl; 2-(piperidin-1-yl)ethyl; 2,3-dihydro-1H-inden-1-yl; 2-chlorophenethyl; 2-morpholinoethyl; 2-phenylpropyl; 3,3-dimethylbutyl; 3-chlorophenethyl; 3-hydroxypropyl; 3-methoxypropyl; 3-morpholinopropyl; 4-bromophenethyl; 4-chlorophenethyl; butyl; cyclohexenylethyl; cyclohexylcyclohexylmethylcyclopentyl; isopentyl; methylcyclohexyl; and propyl.

In a still further aspect, the compound has a structure represented by a formula:

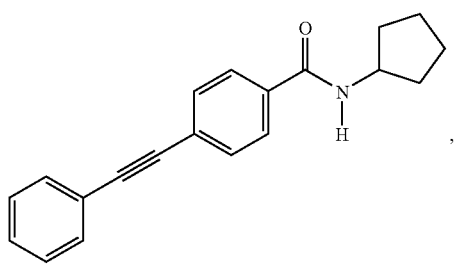
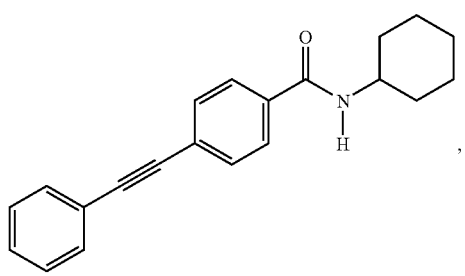
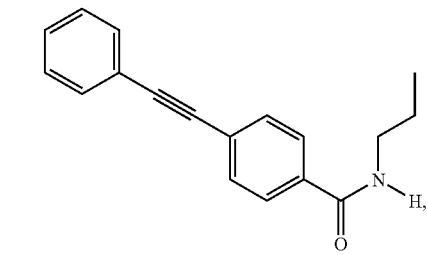
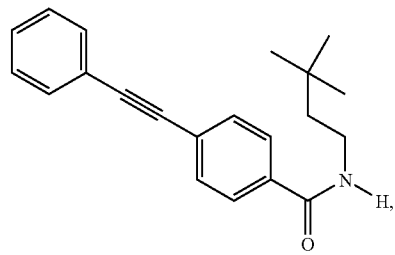
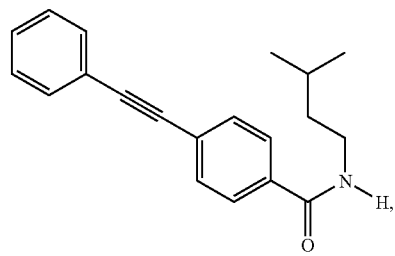
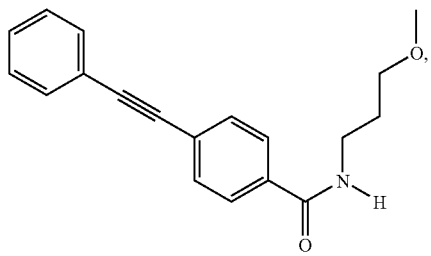
-continued
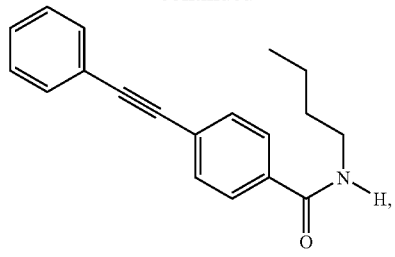
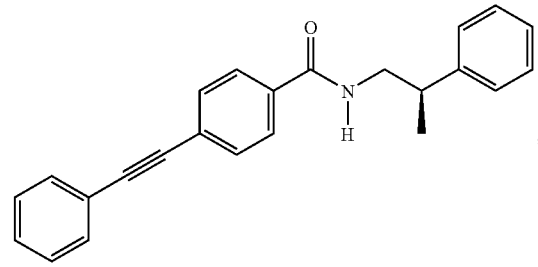
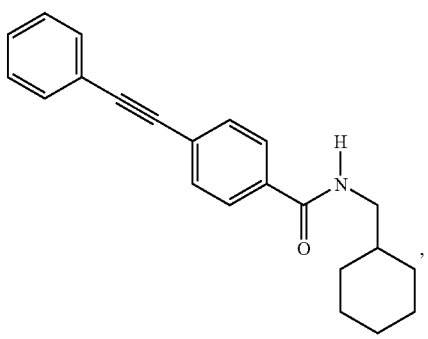
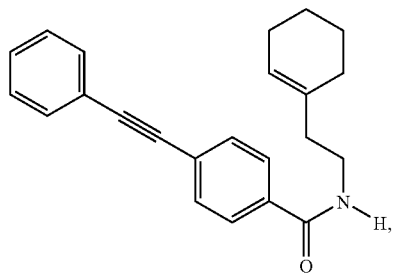
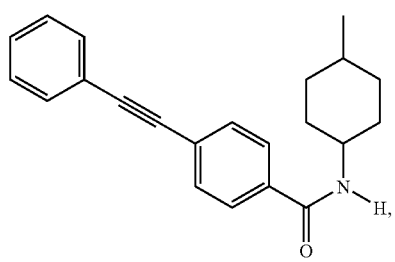
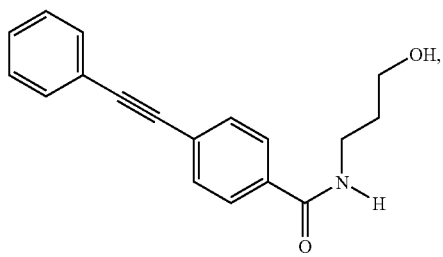

55
-continued
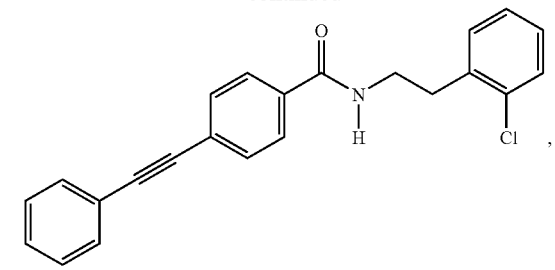
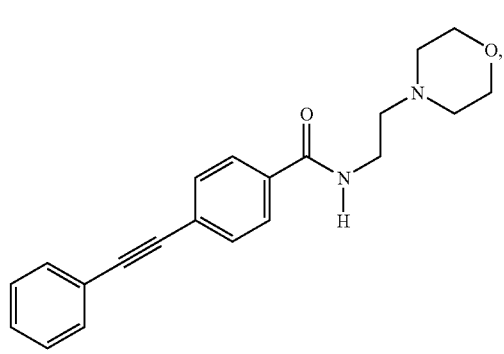
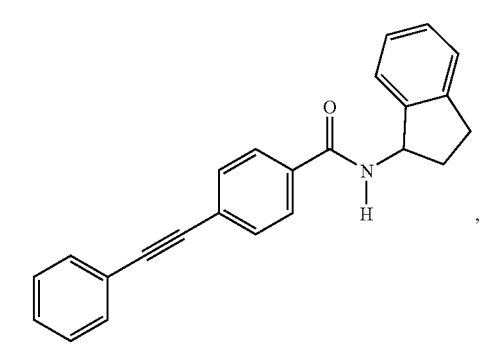
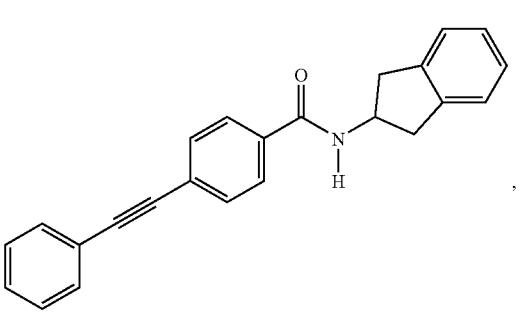
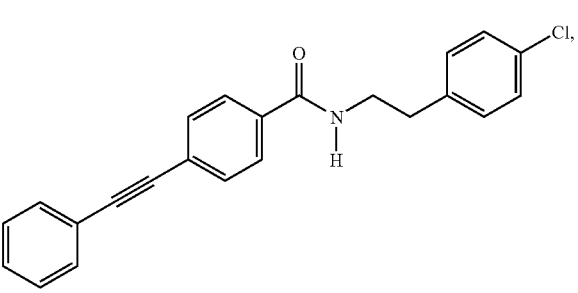
56
-continued
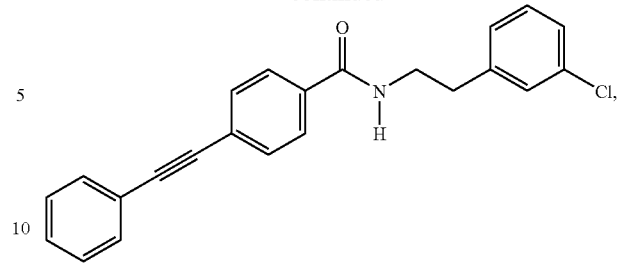
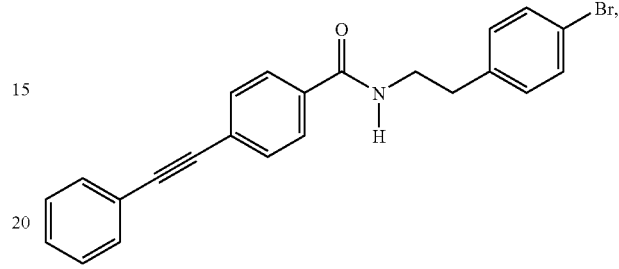
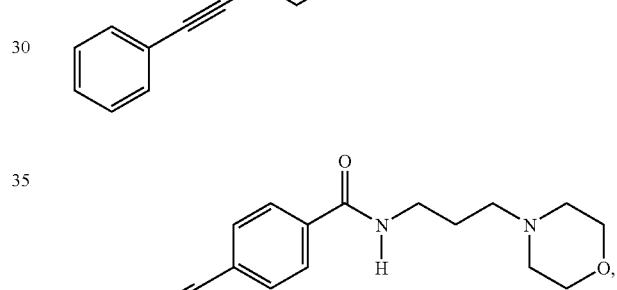
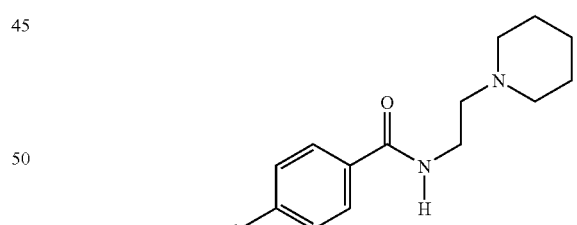
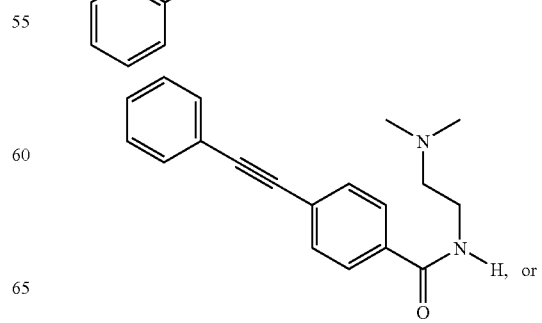

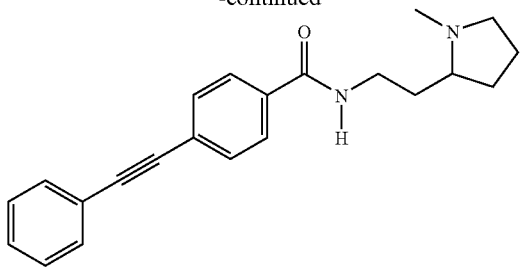

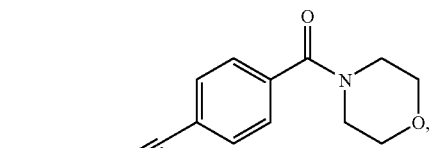

In a still further aspect, N, R[1], and R[2] together comprise a cyclic optionally substituted alkyl residue. In a further aspect, the cyclic optionally substituted alkyl residue is selected from (E)-4-hydroxypiperidin-1-yl; (S)-(4-(1-cyclohexylethylamino)piperidin-1-yl; 1-(piperidin-4-yl)-1H-benzo[d]imidazol-2(3H)-one; 1-(piperidin-4-yl)ethanone; 2-(piperazin-1-yl)benzonitrile; 2,6-dimethylmorpholino; 2-morpholinoethyl; 3-hydroxy-3-(thiophen-2-yl)azetidin-1-yl; 3-hydroxy-3-methylazetidin-1-yl; 3-hydroxy-3-propylazetidin-1-yl; 3-hydroxyazetidin-1-yl; 3-hydroxypiperidin-1-yl; 4-(2-fluorophenyl)piperazin-1-yl; 4-(2-methoxyethylamino)piperidin-1-yl; 4-(2-methoxyphenyl)piperazin-1-yl; 4-(2-morpholinoethylamino)piperidin-1-yl; 4-(3-fluorophenyl)-4-hydroxypiperidin-1-yl; 4-(4-(pyridin-4-yl)piperazin-1-yl)piperidin-1-yl; 4-(4-bromophenyl)-4-hydroxypiperidin-1-yl; 4-(4-chloro-2-(trifluoromethyl)phenyl)-4-hydroxypiperidin-1-yl; 4-(4-chlorophenyl)-4-hydroxypiperidin-1-yl; 4-(4-fluorophenyl)-4-hydroxypiperidin-1-yl; 4-(4-methylpiperazin-1-yl)piperidin-1-yl; 4-(azetidin-1-yl)piperidin-1-yl; 4-(cyclobutylamino)piperidin-1-yl; 4-(cyclopropylmethylamino)piperidin-1-yl; 4-(hydroxymethyl)piperidin-1-yl; 4-(pyridin-2-yl)piperazin-1-yl; 4-(pyrrolidin-1-yl)piperidin-1-yl; 4-hydroxy-4-(4-methoxyphenyl)piperidin-1-yl; 4-hydroxy-4-(thiophen-2-yl)piperidin-1-yl; 4-hydroxy-4-isopropylpiperidin-1-yl; 4-hydroxy-4-methylpiperidin-1-yl; 4-hydroxypiperidin-1-yl; 4-isopropylpiperazin-1-yl; 4-methylpiperazin-1-yl; 4-phenyl-1-piperidine-4-carbonitrile; 6-chloro-1-(piperidin-4-yl)-1H-benzo[d]imidazol-2(3H)-one; morpholino; octahydroisoquinolin-2(1H)-yl; and piperazin-1-yl.

In a further aspect, the compound has a structure represented by a formula:

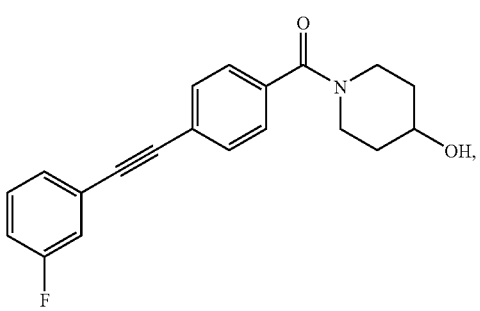

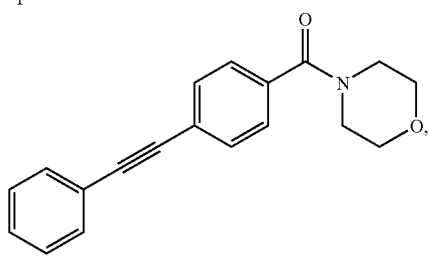

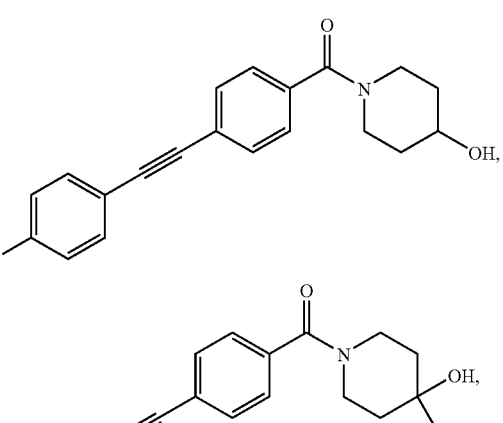

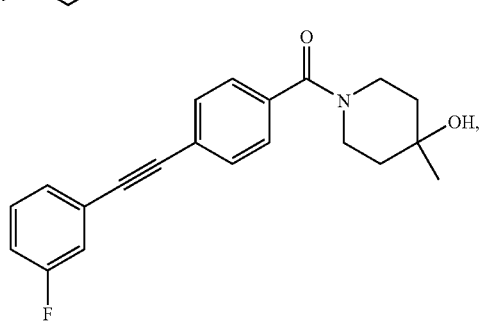

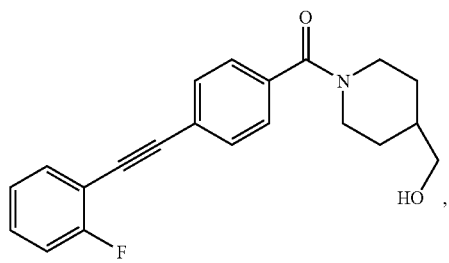
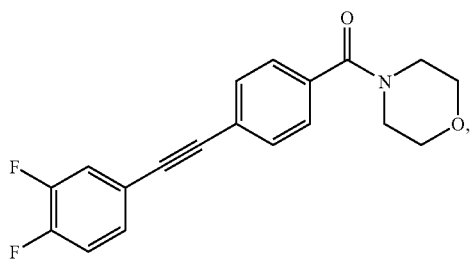

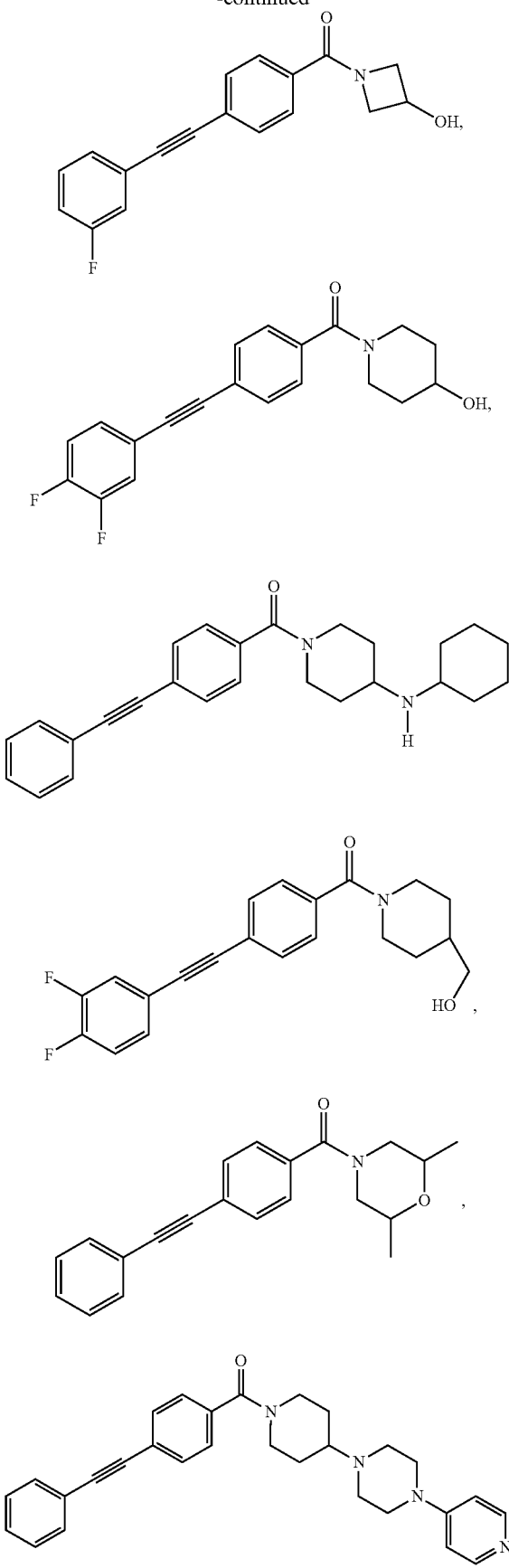
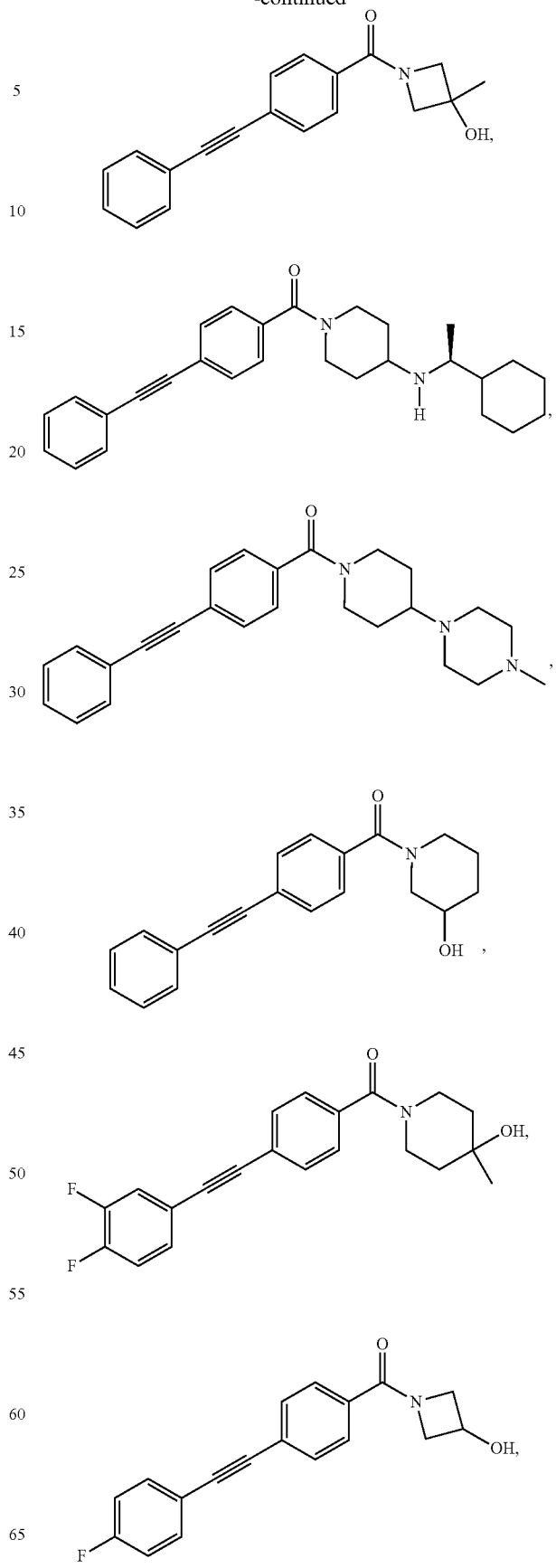

63
-continued
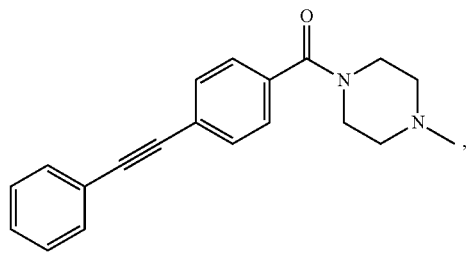
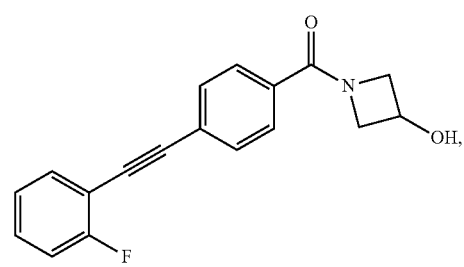
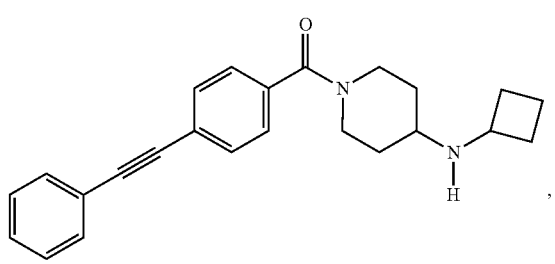
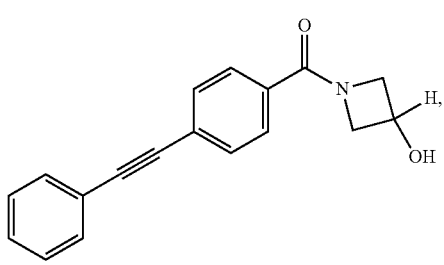
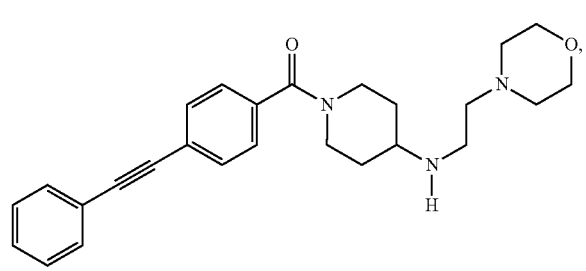
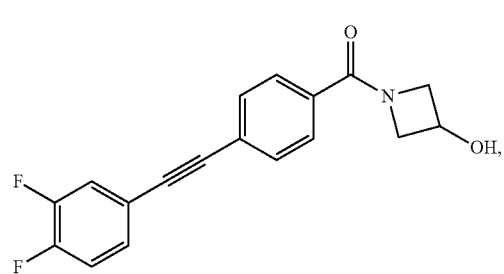
64
-continued
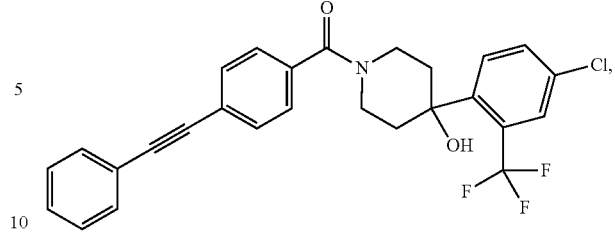
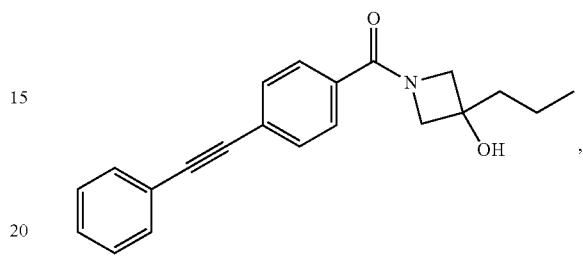
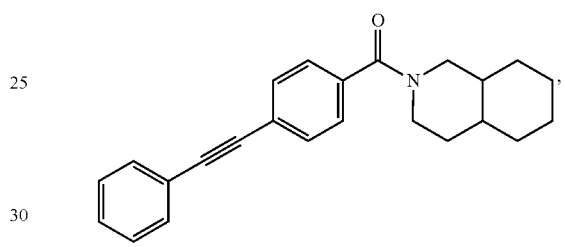
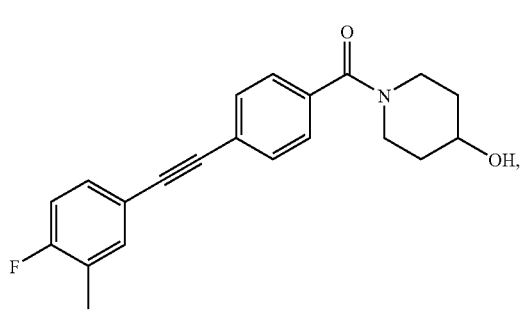
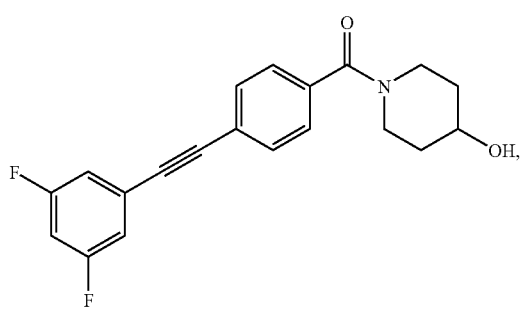
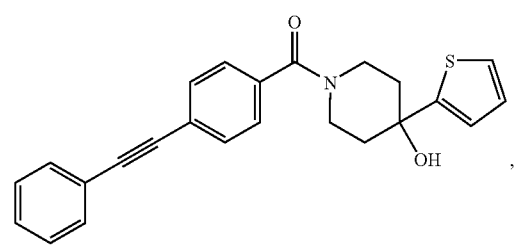

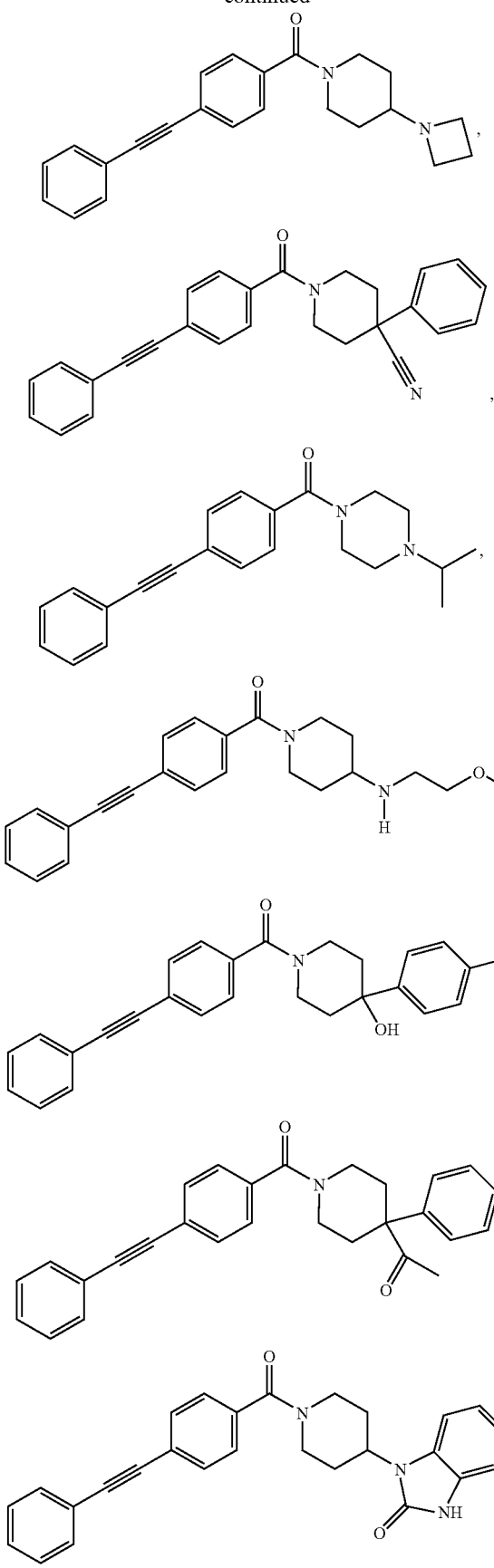
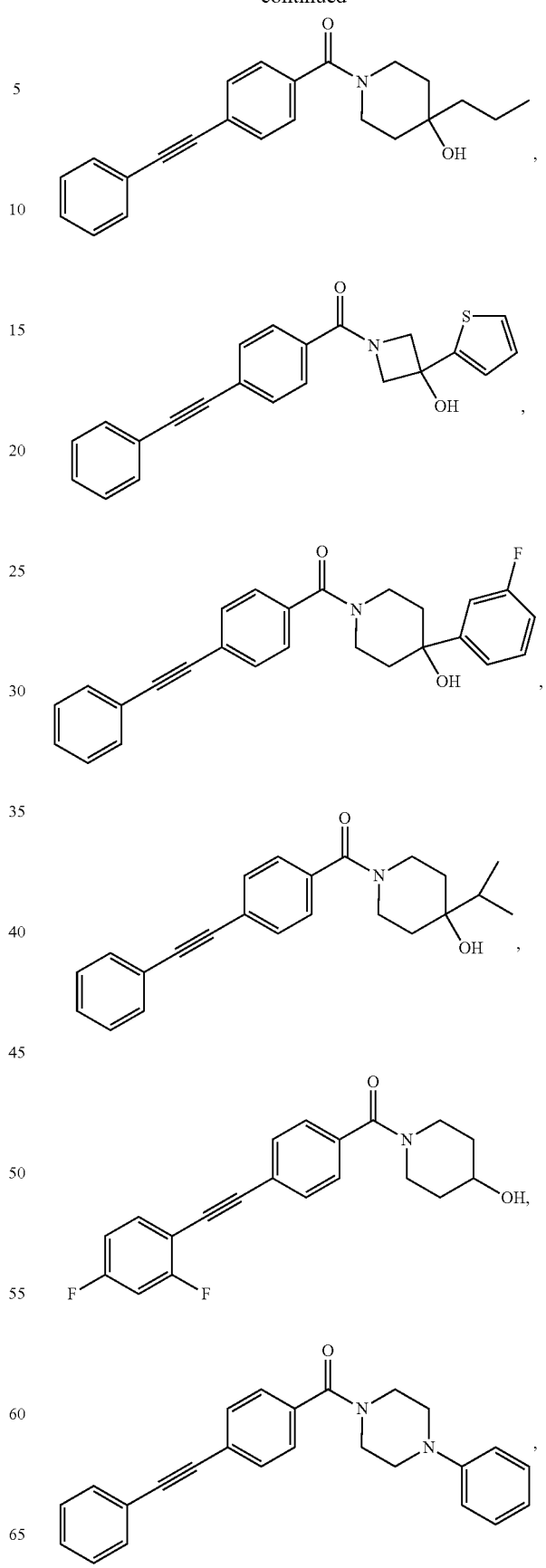

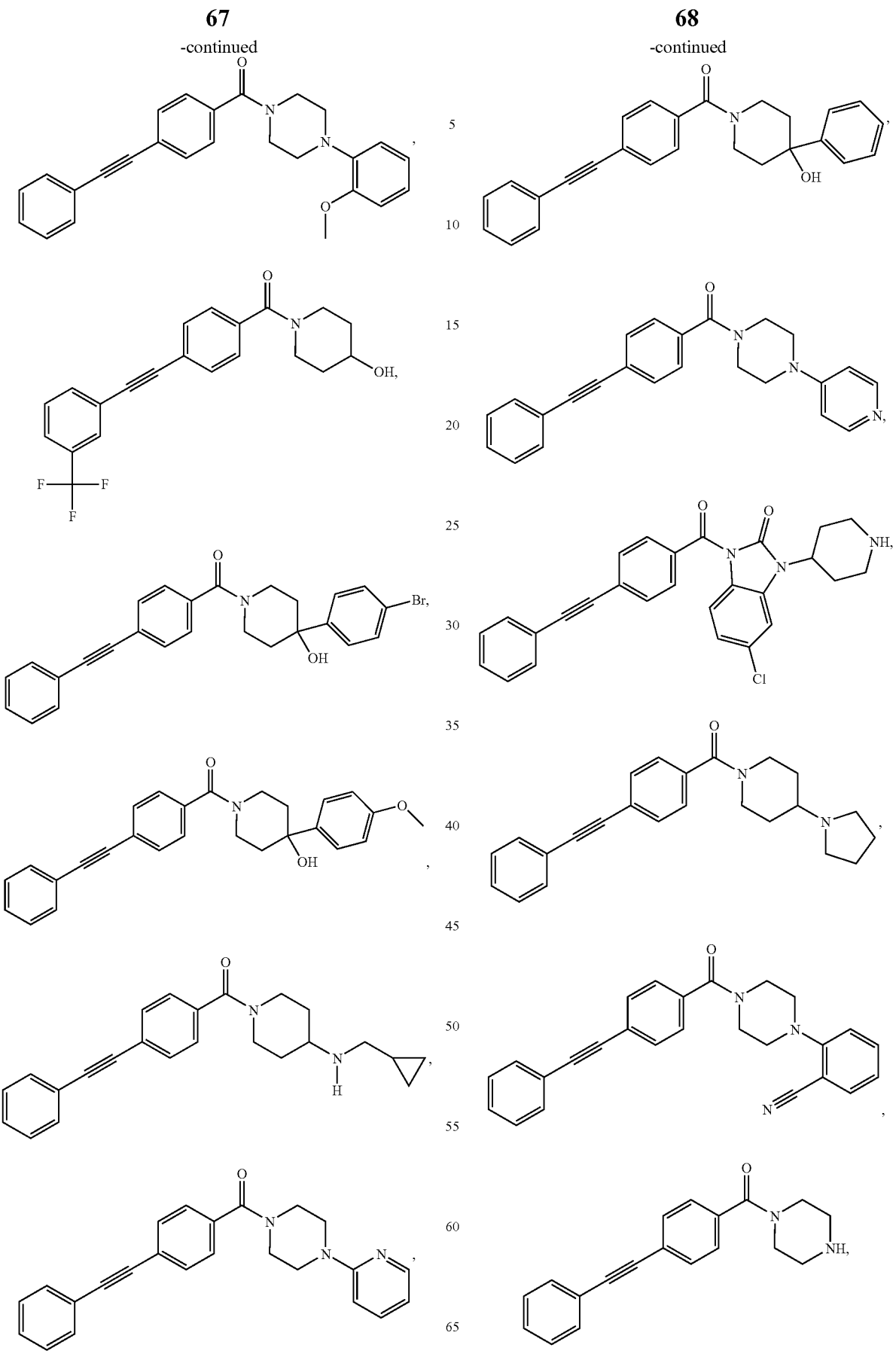

-continued

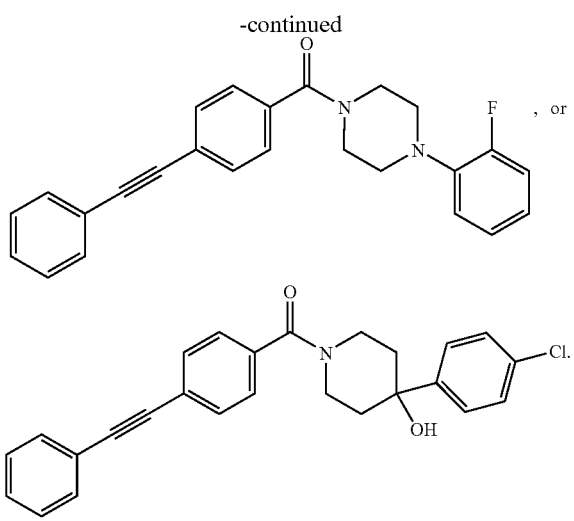

It is understood that the compound can be provided by the disclosed methods of making, can be employed in the disclosed compositions, and can be used in the disclosed methods of using.

2. Cycloalkylethynylbenzamide Derivatives

In one aspect, the invention relates to cycloalkylethynylbenzamide derivatives. In one aspect, the compound is a compound or pharmaceutically acceptable salt thereof comprising the structure:

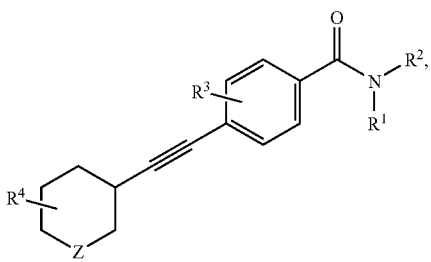

wherein $R^1$ and $R^2$ are independently selected from hydrogen, optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, and optionally substituted heteroaryl, or wherein N, $R^1$, and $R^2$ together comprise an optionally substituted hetrocyclic ring having from two to seven carbons;

wherein $R^3$ comprises four substituents independently selected from hydrogen, halogen, hydroxyl, cyano, nitro, thiol, optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, optionally substituted heteroaryl, optionally substituted alkoxyl, optionally substituted thioalkyl, optionally substituted alkylsulfinyl, optionally substituted alkylsulfonyl, and optionally substituted amino, thioamido, amidosulfonyl, alkoxycarbonyl, carboxamide, amino-carbonyl, and alkylamine-carbonyl;

wherein Z comprises from zero to two carbons;

wherein $R^4$ comprises nine to thirteen substituents independently selected from hydrogen, halogen, hydroxyl, cyano, nitro, thiol, optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, optionally substituted heteroaryl, optionally substituted alkoxyl, optionally substituted thioalkyl, optionally substituted alkylsulfinyl, optionally substituted alkylsulfonyl, and optionally substituted amino, thioamido, amidosulfonyl, alkoxycarbonyl, carboxamide, amino-carbonyl, and alkylamine-carbonyl; and wherein the compound exhibits potentiation of glutamate as an increase in response to non-maximal concentrations of glutamate in human embryonic kidney cells transfected with rat mGluR5 in the presence of the compound, compared to the response to glutamate in the absence of the compound.

In one aspect, the compound exhibits potentiation with an $EC_{50}$ of less than about $1.0 \times 10^{-6}$. For example, the compound can exhibit potentiation with an $EC_{50}$ of less than about $10 \times 10^{-7}$. As a further example, the compound can exhibit potentiation with an $EC_{50}$ of less than about $1.0 \times 10^8$.

In a further aspect, $R^1$ is selected from optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, and optionally substituted heteroaryl and has from two to seven carbons.

In a further aspect, $R^2$ is selected from optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, and optionally substituted heteroaryl and has from two to seven carbons.

In a further aspect, one or more substitutents of $R^3$ are selected from optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, and optionally substituted heteroaryl and have from two to seven carbons.

In a further aspect, one or more substitutents of $R^4$ are selected from optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, and optionally substituted heteroaryl and have from two to seven carbons.

In one aspect, the optionally substituted alkyl of $R^1$, $R^2$, $R^3$, and/or $R_4$ comprises an optionally substituted alkyl or an optionally substituted cycloalkyl. In a further aspect, all of $R^3$ are hydrogen. In a further aspect, N, $R^1$, and $R^2$ together comprise an optionally substituted hetrocyclic ring having from two to seven carbons. In a further aspect, N, $R^1$, and $R^2$ together comprise 4-hydroxypiperidin-1-yl. In a further aspect, Z is one and $R^4$ comprises eleven substituents. In a further aspect, at least one of $R^4$ is halogen selected from F and Cl. In a further aspect, all of $R^4$ are hydrogen.

In one aspect, the compound has a structure represented by a formula:

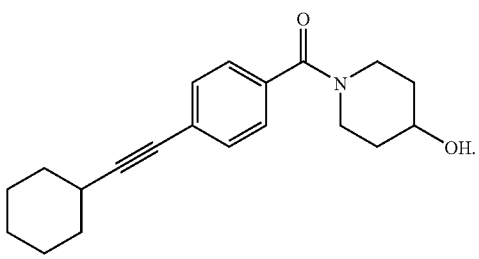 [SMILES: O=C(c1ccc(C#CC2CCCCC2)cc1)N1CCC(O)CC1]

It is understood that the compound can be provided by the disclosed methods of making, can be employed in the disclosed compositions, and can be used in the disclosed methods of using.

3. Styrylbenzamide Derivatives

In one aspect, the invention relates to a compound having a structure represented by a formula:

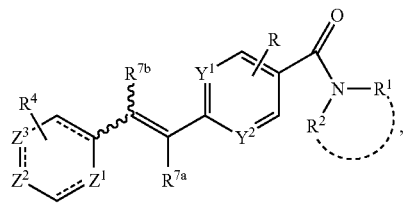

wherein $R^1$ and $R^2$ are independently hydrogen or an optionally substituted organic radical comprising from 1 to 12 carbon atoms; wherein each ----- is an optional covalent bond; wherein $Y^1$ and $Y^2$ are independently selected from N and C—R; wherein R comprises two to four substituents independently selected from hydrogen, halogen, hydroxyl, cyano, nitro, thiol, or an organic radical comprising 1 to 12 carbon atoms; wherein $Z^1$, $Z^2$, and $Z^3$ are independently selected from N and C—$R^4$, with the proviso that no more than two of $Z^1$, $Z^2$, and $Z^3$ are nitrogen; wherein $R^4$ comprises up to five substituents independently selected from hydrogen, halogen, hydroxyl, cyano, nitro, thiol, optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, optionally substituted heteroaryl, optionally substituted alkoxyl, optionally substituted thioalkyl, optionally substituted alkylsulfinyl, optionally substituted alkylsulfonyl, and optionally substituted amino, thioamido, amidosulfonyl, alkoxycarbonyl, carboxamide, amino-carbonyl, and alkylamine-carbonyl; and wherein $R^{7a}$ and $R^{7b}$ together form an optionally substituted carbocyclic or heterocyclic ring having from two to five carbons or are independently selected from hydrogen, halogen, hydroxyl, cyano, nitro, thiol, amino, and an organic radical comprising 1 to 5 carbon atoms selected from optionally substituted C1-C6 alkyl or C2-C6 alkenyl or C2-C6 alkynyl, optionally substituted C1-C6 heteroalkyl or C2-C6 heteroalkenyl or C2-C6 heteroalkynyl, optionally substituted C3-C8 cycloalkyl or C3-C8 cycloalkenyl or C6-C8 cycloalkynyl, optionally substituted C3-C8 heterocycloalkyl or C3-C8 heterocycloalkenyl or C6-C8 heterocycloalkynyl, optionally substituted aryl, optionally substituted heteroaryl, optionally substituted alkoxyl, optionally substituted thioalkyl, optionally substituted alkylsulfinyl, optionally substituted alkylsulfonyl, and optionally substituted amino, thioamido, amidosulfonyl, alkoxycarbonyl, carboxamide, amino-carbonyl, and alkylamine-carbonyl; or a pharmaceutically acceptable salt or N-oxide thereof, wherein the compound exhibits potentiation of mGluR5 response to glutamate as an increase in response to non-maximal concentrations of glutamate in human embryonic kidney cells transfected with rat mGluR5 in the presence of the compound, compared to the response to glutamate in the absence of the compound.

In a further aspect, $R^1$ and $R^2$ are independently hydrogen or alkyl having from 1 to 6 carbons. In a further aspect, N, $R^1$, and $R^2$ together comprise an optionally substituted heterocyclic ring having from two to seven carbons. In a further aspect, all of $Z^1$, $Z^2$, and $Z^3$ are carbon. In a further aspect, $R^4$ comprises up to five substituents independently selected from hydrogen, halogen, and lower alkyl. In a further aspect, both of $Y^1$ and $Y^2$ are carbon. In a further aspect, both of $R^{7a}$ and $R^{7b}$ are hydrogen.

In a further aspect, the compound has a structure represented by a formula:

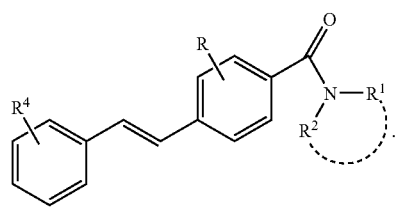

In a further aspect, $R^1$ and $R^2$ are independently hydrogen or alkyl having from 1 to 6 carbons or N, $R^1$, and $R^2$ together comprise an optionally substituted heterocyclic ring having from two to seven carbons; R comprises four substituents independently selected from hydrogen, halogen, and lower alkyl; and $R^4$ comprises five substituents independently selected from hydrogen, halogen, and lower alkyl.

In one aspect, the invention relates to styrylbenzamide derivatives. In one aspect, the compound is a compound or pharmaceutically acceptable salt thereof comprising the structure:

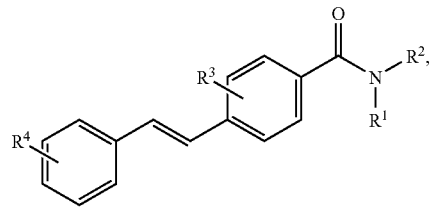

wherein $R^1$ and $R^2$ are independently selected from hydrogen, optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, and optionally substituted heteroaryl, or wherein N, $R^1$, and $R^2$ together comprise an optionally substituted hetrocyclic ring having from two to seven carbons; wherein $R^3$ comprises four substituents independently selected from hydrogen, halogen, hydroxyl, cyano, nitro, thiol, optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, optionally substituted heteroaryl, optionally substituted alkoxyl, optionally substituted thioalkyl, optionally substituted alkylsulfinyl, optionally substituted alkylsulfonyl, and optionally substituted amino, thioamido, amidosulfonyl, alkoxycarbonyl, carboxamide, amino-carbonyl, and alkylamine-carbonyl; wherein $R^4$ comprises five substituents independently selected from hydrogen, halogen, hydroxyl, cyano, nitro, thiol, optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, optionally substituted heteroaryl, optionally substituted alkoxyl, optionally substituted thioalkyl, optionally substituted alkylsulfinyl, optionally substituted alkylsulfonyl, and optionally substituted amino, thioamido, amidosulfonyl, alkoxycarbonyl, carboxamide, amino-carbonyl, and alkylamine-carbonyl; and wherein the compound exhibits potentiation of glutamate as an increase in response to non-maximal concentrations of glutamate in human embryonic kidney cells transfected with rat mGluR5 in the presence of the compound, compared to the response to glutamate in the absence of the compound.

In one aspect, the compound exhibits potentiation with an $EC_{50}$ of less than about $1.0 \times 10^{-6}$. For example, the compound can exhibit potentiation with an $EC_{50}$ of less than about $1.0 \times 10^{-7}$. As a further example, the compound can exhibit potentiation with an $EC_{50}$ of less than about $1.0 \times 10^8$.

In a further aspect, $R^1$ is selected from optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, and optionally substituted heteroaryl and has from two to seven carbons.

In a further aspect, $R^2$ is selected from optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, and optionally substituted heteroaryl and has from two to seven carbons.

In a further aspect, one or more substitutents of $R^3$ are selected from optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, and optionally substituted heteroaryl and have from two to seven carbons.

In a further aspect, one or more substitutents of $R^4$ are selected from optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, and optionally substituted heteroaryl and have from two to seven carbons.

In a further aspect, N, $R^1$, and $R^2$ together comprise an optionally substituted hetrocyclic ring having from two to seven carbons. In a further aspect, N, $R^1$, and $R^2$ together comprise 4-hydroxypiperidin-1-yl.

In a further aspect, the optionally substituted alkyl of $R^1$, $R^2$, $R^3$, and/or $R_4$ comprises an optionally substituted alkyl or an optionally substituted cycloalkyl. n a further aspect, all of $R^3$ are hydrogen.

In a further aspect, at least one of $R^4$ is halogen selected from F and Cl. In a further aspect, all of $R^4$ are hydrogen. In a further aspect, the compound has a structure represented by a formula:

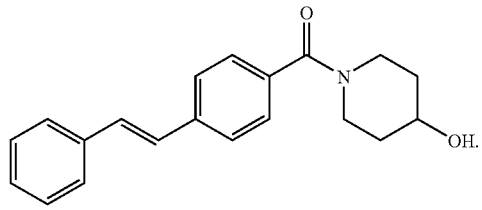 [SMILES: O=C(c1ccc(/C=C/c2ccccc2)cc1)N1CCC(O)CC1]

It is understood that the compound can be provided by the disclosed methods of making, can be employed in the disclosed compositions, and can be used in the disclosed methods of using.

4. 4-(3-Phenyl-1,2,4-oxadiazol-5-yl)benzamide derivatives

In one aspect, the invention relates to a compound having a structure represented by a formula:

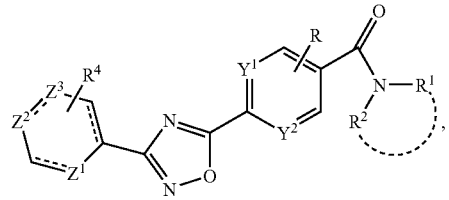

wherein $R^1$ and $R^2$ are independently optionally substituted organic radicals comprising from 1 to 12 carbon atoms; wherein each ----- is an optional covalent bond; wherein $Y^1$ and $Y^2$ are independently selected from N and C—R; wherein R comprises two to four substituents independently selected from hydrogen, halogen, hydroxyl, cyano, nitro, thiol, or an organic radical comprising 1 to 12 carbon atoms; wherein $Z^1$, $Z^2$, and $Z^3$ are independently selected from N and C—$R^4$, with the proviso that no more than two of $Z^1$, $Z^2$, and $Z^3$ are nitrogen; and wherein $R^4$ comprises up to five substituents independently selected from hydrogen, halogen, hydroxyl, cyano, nitro, thiol, optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, optionally substituted heteroaryl, optionally substituted alkoxyl, optionally substituted thioalkyl, optionally substituted alkylsulfinyl, optionally substituted alkylsulfonyl, and optionally substituted amino, thioamido, amidosulfonyl, alkoxycarbonyl, carboxamide, amino-carbonyl, and alkylamine-carbonyl; or a pharmaceutically acceptable salt or N-oxide thereof, wherein the compound exhibits potentiation of mGluR5 response to glutamate as an increase in response to non-maximal concentrations of glutamate in human embryonic kidney cells transfected with rat mGluR5 in the presence of the compound, compared to the response to glutamate in the absence of the compound.

In a further aspect, $R^1$ and $R^2$ are independently hydrogen or alkyl having from 1 to 6 carbons. In a further aspect, N, $R^1$, and $R^2$ together comprise an optionally substituted heterocyclic ring having from two to seven carbons. In a further aspect, all of $Z^1$, $Z^2$, and $Z^3$ are carbon. In a further aspect, $R^4$ comprises up to five substituents independently selected from hydrogen, halogen, and lower alkyl. In a further aspect, both of $Y^1$ and $Y^2$ are carbon.

In a further aspect, the compound has a structure represented by a formula:

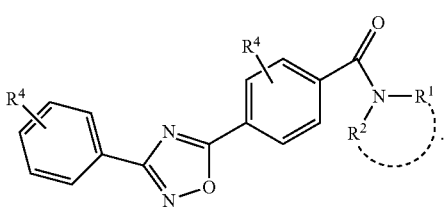

In a further aspect, $R^1$ and $R^2$ are independently alkyl having from 1 to 6 carbons or N, $R^1$, and $R^2$ together comprise an optionally substituted heterocyclic ring having from two to seven carbons; R comprises four substituents independently selected from hydrogen, halogen, and lower alkyl; and $R^4$ comprises five substituents independently selected from hydrogen, halogen, and lower alkyl.

In one aspect, the invention relates to 4-(3-phenyl-1,2,4-oxadiazol-5-yl)benzamide derivatives. In one aspect, the compound is a compound or pharmaceutically acceptable salt thereof comprising the structure:

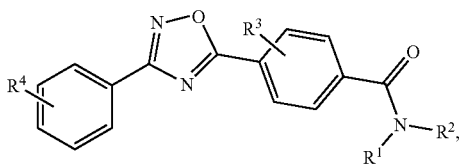

wherein $R^1$ and $R^2$ are independently selected from optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, and optionally substituted heteroaryl, or wherein N, $R^1$, and $R^2$ together comprise an optionally substituted hetrocyclic ring having from two to seven carbons; wherein $R^3$ comprises four substituents independently selected from hydrogen, halogen, hydroxyl, cyano, nitro, thiol, optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, optionally substituted heteroaryl, optionally substituted alkoxyl, optionally substituted thioalkyl, optionally substituted alkylsulfinyl, optionally substituted alkylsulfonyl, and optionally substituted amino, thioamido, amidosulfonyl, alkoxycarbonyl, carboxamide, amino-carbonyl, and alkylamine-carbonyl; wherein $R^4$ comprises five substituents independently selected from hydrogen, halogen, hydroxyl, cyano, nitro, thiol, optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, optionally substituted heteroaryl, optionally substituted alkoxyl, optionally substituted thioalkyl, optionally substituted alkylsulfinyl, optionally substituted alkylsulfonyl, and optionally substituted amino, thioamido, amidosulfonyl, alkoxycarbonyl, carboxamide, amino-carbonyl, and alkylamine-carbonyl; and wherein the compound exhibits potentiation of glutamate as an increase in response to non-maximal concentrations of glutamate in human embryonic kidney cells transfected with rat mGluR5 in the presence of the compound, compared to the response to glutamate in the absence of the compound.

In one aspect, the compound exhibits potentiation with an $EC_{50}$ of less than about $1.0 \times 10^{-6}$. For example, the compound can exhibit potentiation with an $EC_{50}$ of less than about $1.0 \times 10^{-7}$. As a further example, the compound can exhibit potentiation with an $EC_{50}$ of less than about $1.0 \times 10^{-8}$.

In a further aspect, $R^1$ is selected from optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, and optionally substituted heteroaryl and has from two to seven carbons.

In a further aspect, $R^2$ is selected from optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, and optionally substituted heteroaryl and has from two to seven carbons.

In a further aspect, one or more substitutents of $R^3$ are selected from optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, and optionally substituted heteroaryl and have from two to seven carbons.

In a further aspect, one or more substitutents of $R^4$ are selected from optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, and optionally substituted heteroaryl and have from two to seven carbons.

In a further aspect, N, $R^1$, and $R^2$ together comprise an optionally substituted hetrocyclic ring having from two to seven carbons. In a further aspect, N, $R^1$, and $R^2$ together comprise 4-(pyridin-4-yl)piperazin-1-yl.

In a further aspect, the optionally substituted alkyl of $R^1$, $R^2$, $R^3$, and/or $R_4$ comprises an optionally substituted alkyl or an optionally substituted cycloalkyl. In a further aspect, $R^1$ and $R^2$ are independently selected from H; 3-methoxypropyl; 3,3-dimethylbutyl; and N-propyl.

In a further aspect, the compound has a structure represented by a formula:

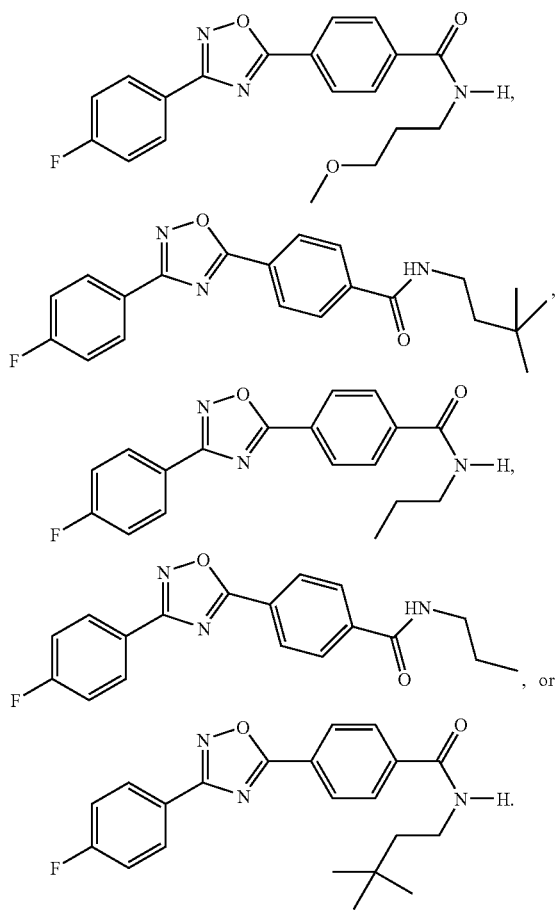

In a further aspect, the compound has a structure represented by a formula:

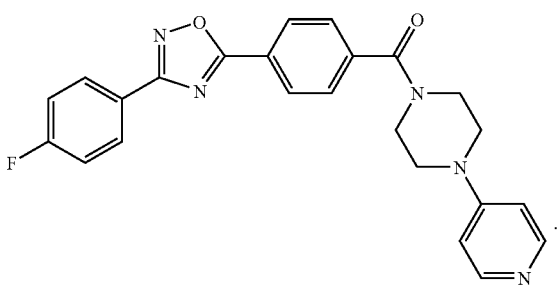 [SMILES: O=C(c1ccc(-c2nc(-c3ccc(F)cc3)no2)cc1)N1CCN(c2ccncc2)CC1]

In a further aspect, all of $R^3$ are hydrogen. In a further aspect, at least one of $R^4$ is halogen selected from F and Cl. In a further aspect, four of $R^4$ are hydrogen and one of $R^4$ is F.

It is understood that the compound can be provided by the disclosed methods of making, can be employed in the disclosed compositions, and can be used in the disclosed methods of using.

5. 4-(Pyridinylethynyl)benzamide derivatives

In a further aspect, the invention relates to compounds having a structure represented by a formula:

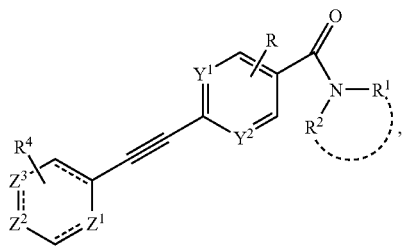

wherein $R^1$ and $R^2$ are independently hydrogen or optionally substituted organic radicals comprising from 1 to 12 carbon atoms; wherein each ---- is an optional covalent bond; wherein $Y^1$ and $Y^2$ are independently selected from N and C—R; wherein R comprises two to four substituents independently selected from hydrogen, halogen, hydroxyl, cyano, nitro, thiol, or an organic radical comprising 1 to 12 carbon atoms; wherein $Z^1$, $Z^2$, and $Z^3$ are independently selected from N and C—$R^4$, with the proviso that only of $Z^1$, $Z^2$, and $Z^3$ are nitrogen; and wherein $R^4$ comprises up to five substituents independently selected from hydrogen, halogen, hydroxyl, cyano, nitro, thiol, optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, optionally substituted heteroaryl, optionally substituted alkoxyl, optionally substituted thioalkyl, optionally substituted alkylsulfinyl, optionally substituted alkylsulfonyl, and optionally substituted amino, thioamido, amidosulfonyl, alkoxycarbonyl, carboxamide, amino-carbonyl, and alkylamine-carbonyl; or a pharmaceutically acceptable salt or N-oxide thereof, wherein the compound exhibits potentiation of mGluR5 response to glutamate as an increase in response to non-maximal concentrations of glutamate in human embryonic kidney cells transfected with rat mGluR5 in the presence of the compound, compared to the response to glutamate in the absence of the compound.

In a further aspect, $R^1$ and $R^2$ are independently hydrogen or alkyl having from 1 to 6 carbons. In a further aspect, N, $R^1$, and $R^2$ together comprise an optionally substituted heterocyclic ring having from two to seven carbons. In a further aspect, $R^4$ comprises four substituents independently selected from hydrogen, halogen, and lower alkyl. In a further aspect, both of $Y^1$ and $Y^2$ are carbon.

In a yet further aspect, the compound has a structure represented by a formula:

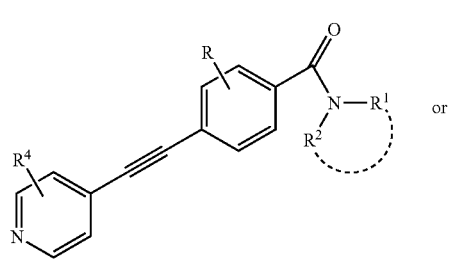

-continued

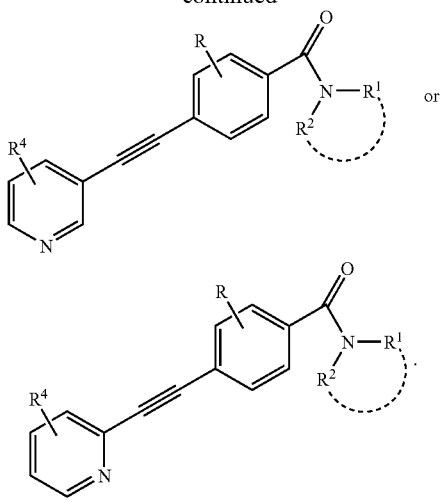

In a further aspect, $R^1$ and $R^2$ are independently alkyl having from 1 to 6 carbons or N, $R^1$, and $R^2$ together comprise an optionally substituted heterocyclic ring having from two to seven carbons; R comprises four substituents independently selected from hydrogen, halogen, and lower alkyl; and $R^4$ comprises five substituents independently selected from hydrogen, halogen, and lower alkyl.

In a yet further aspect, the invention relates to 4-(pyridinylethynyl)benzamide derivatives. In one aspect, the compound is a compound or pharmaceutically acceptable salt thereof comprising a structure selected from:

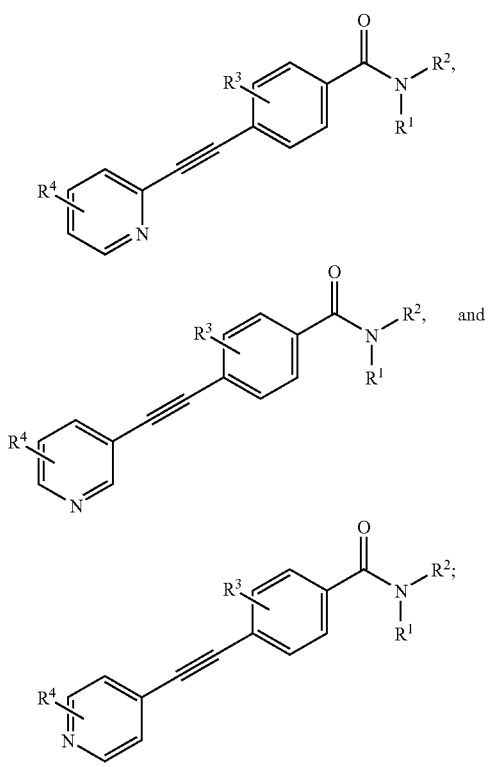

wherein $R^1$ and $R^2$ are independently selected from hydrogen, optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted heteroaryl, or wherein N, $R^1$, and $R^2$ together comprise an optionally substituted hetrocyclic ring having from two to seven carbons; wherein $R^3$ comprises four substituents independently selected from hydrogen, halogen, hydroxyl, cyano, nitro, thiol, optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, optionally substituted heteroaryl, optionally substituted alkoxyl, optionally substituted thioalkyl, optionally substituted alkylsulfinyl, optionally substituted alkylsulfonyl, and optionally substituted amino, thioamido, amidosulfonyl, alkoxycarbonyl, carboxamide, amino-carbonyl, and alkylamine-carbonyl; wherein $R^4$ comprises four substituents independently selected from hydrogen, halogen, hydroxyl, cyano, nitro, thiol, optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, optionally substituted heteroaryl, optionally substituted alkoxyl, optionally substituted thioalkyl, optionally substituted alkylsulfinyl, optionally substituted alkylsulfonyl, and optionally substituted amino, thioamido, amidosulfonyl, alkoxycarbonyl, carboxamide, amino-carbonyl, and alkylamine-carbonyl; and wherein the compound exhibits potentiation of glutamate as an increase in response to non-maximal concentrations of glutamate in human embryonic kidney cells transfected with rat mGluR5 in the presence of the compound, compared to the response to glutamate in the absence of the compound.

In one aspect, the compound exhibits potentiation with an $EC_{50}$ of less than about $1.0 \times 10^{-6}$. For example, the compound can exhibit potentiation with an $EC_{50}$ of less than about $1.0 \times 10^{-7}$. As a further example, the compound can exhibit potentiation with an $EC_{50}$ of less than about $1.0 \times 10^{8}$.

In a further aspect, $R^1$ is selected from hydrogen, optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, and optionally substituted heteroaryl and has from two to seven carbons.

In a further aspect, $R^2$ is selected from hydrogen, optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, and optionally substituted heteroaryl and has from two to seven carbons.

In a further aspect, one or more substitutents of $R^3$ are selected from optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, and optionally substituted heteroaryl and have from two to seven carbons.

In a further aspect, one or more substitutents of $R_4$ are selected from optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, and optionally substituted heteroaryl and have from two to seven carbons.

In a further aspect, the optionally substituted alkyl of $R^1$, $R^2$, $R^3$, and/or $R_4$ comprises an optionally substituted alkyl or an optionally substituted cycloalkyl.

In a further aspect, N, $R^1$, and $R^2$ together comprise an optionally substituted hetrocyclic ring having from two to seven carbons. In a further aspect, N, $R^1$, and $R^2$ together comprise 2-methylpiperidinyl.

In a further aspect, the compound has a structure represented by a formula:

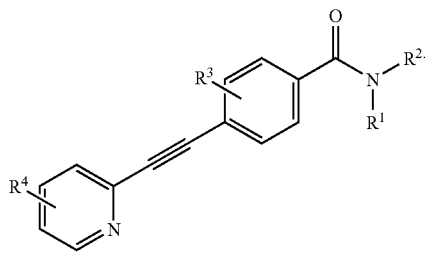

In a further aspect, N, $R^1$, and $R^2$ together comprise a cyclic optionally substituted alkyl residue. In a further aspect, the cyclic optionally substituted alkyl residue is 2-methylpiperidinyl. In a further aspect, all of $R^3$ are hydrogen. In a further aspect, at least one of $R^4$ is halogen selected from F and Cl. In a further aspect, all of $R^4$ are hydrogen. In a further aspect, the compound has a structure represented by a formula:

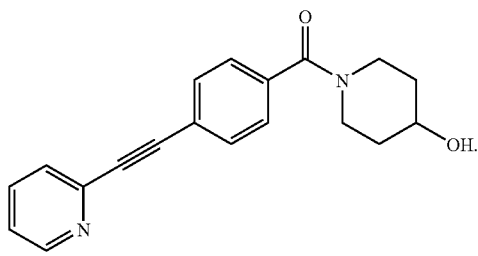 [SMILES: O=C(c1ccc(C#Cc2ccccn2)cc1)N1CCC(O)CC1]

It is understood that the compound can be provided by the disclosed methods of making, can be employed in the disclosed compositions, and can be used in the disclosed methods of using.

6. $N^1$-Phenylterephthalamide Derivatives

In one aspect, the invention relates to a compound having a structure represented by a formula:

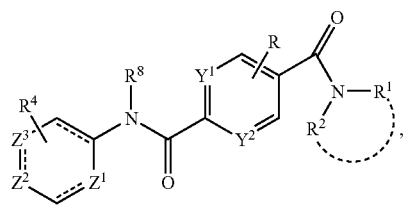

wherein $R^1$ and $R^2$ are independently hydrogen or an optionally substituted organic radical comprising from 1 to 12 carbon atoms; wherein each ----- is an optional covalent bond;

wherein $Y^1$ and $Y^2$ are independently selected from N and C—R; wherein R comprises two to four substituents independently selected from hydrogen, halogen, hydroxyl, cyano, nitro, thiol, or an organic radical comprising 1 to 12 carbon atoms; wherein $Z^1$, $Z^2$, and $Z^3$ are independently selected from N and C—$R^4$, with the proviso that no more than two of $Z^1$, $Z^2$, and $Z^3$ are nitrogen; wherein $R^4$ comprises up to five substituents independently selected from hydrogen, halogen, hydroxyl, cyano, nitro, thiol, optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, optionally substituted heteroaryl, optionally substituted alkoxyl, optionally substituted thioalkyl, optionally substituted alkylsulfinyl, optionally substituted alkylsulfonyl, and optionally substituted amino, thioamido, amidosulfonyl, alkoxycarbonyl, carboxamide, amino-carbonyl, and alkylamine-carbonyl; and wherein $R^8$ is selected from hydrogen and lower alkyl; or a pharmaceutically acceptable salt or N-oxide thereof, wherein the compound exhibits potentiation of mGluR5 response to glutamate as an increase in response to non-maximal concentrations of glutamate in human embryonic kidney cells transfected with rat mGluR5 in the presence of the compound, compared to the response to glutamate in the absence of the compound.

In a further aspect, $R^1$ and $R^2$ are independently hydrogen or alkyl having from 1 to 6 carbons. In a further aspect, N, $R^1$, and $R^2$ together comprise an optionally substituted heterocyclic ring having from two to seven carbons. In a further aspect, all of $Z^1$, $Z^2$, and $Z^3$ are carbon. In a further aspect, $R^4$ comprises up to five substituents independently selected from hydrogen, halogen, and lower alkyl. In a further aspect, both of $Y^1$ and $Y^2$ are carbon. In a further aspect, $R^8$ is hydrogen.

In a yet further aspect, the compound has a structure represented by a formula:

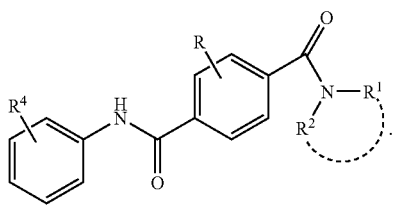

In a further aspect, $R^1$ and $R^2$ are independently hydrogen or alkyl having from 1 to 6 carbons or N, $R^1$, and $R^2$ together comprise an optionally substituted heterocyclic ring having from two to seven carbons; R comprises four substituents independently selected from hydrogen, halogen, and lower alkyl; and $R^4$ comprises five substituents independently selected from hydrogen, halogen, and lower alkyl.

In one aspect, the invention relates to $N^1$-phenylterephthalamide derivatives. In one aspect, the compound is a compound or pharmaceutically acceptable salt thereof comprising the structure:

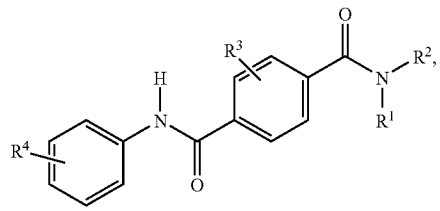

wherein $R^1$ and $R^2$ are independently selected from hydrogen, optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, and optionally substituted heteroaryl, or wherein N, $R^1$, and $R^2$ together comprise an optionally substituted hetrocyclic ring having from two to seven carbons; wherein $R^3$ comprises four substituents independently selected from hydrogen, halogen, hydroxyl, cyano, nitro, thiol, optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, optionally substituted heteroaryl, optionally substituted alkoxyl, optionally substituted thioalkyl, optionally substituted alkylsulfinyl, optionally substituted alkylsulfonyl, and optionally substituted amino, thioamido, amidosulfonyl, alkoxycarbonyl, carboxamide, amino-carbonyl, and alkylamine-carbonyl; wherein $R^4$ comprises five substituents independently selected from hydrogen, halogen, hydroxyl, cyano, nitro, thiol, optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, optionally substituted heteroaryl, optionally substituted alkoxyl, optionally substituted thioalkyl, optionally substituted alkylsulfinyl, optionally substituted alkylsulfonyl, and optionally substituted amino, thioamido, amidosulfonyl, alkoxycarbonyl, carboxamide, amino-carbonyl, and alkylamine-carbonyl; and wherein the compound exhibits potentiation of glutamate as an increase in response to non-maximal concentrations of glutamate in human embryonic kidney cells transfected with rat mGluR5 in the presence of the compound, compared to the response to glutamate in the absence of the compound.

In one aspect, the compound exhibits potentiation with an $EC_{50}$ of less than about $1.0 \times 10^{-6}$. For example, the compound can exhibit potentiation with an $EC_{50}$ of less than about $1.0 \times 10^{-7}$. As a further example, the compound can exhibit potentiation with an $EC_{50}$ of less than about $1.0 \times 10^8$.

In a further aspect, $R^1$ is selected from optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, and optionally substituted heteroaryl and has from two to seven carbons.

In a further aspect, $R^2$ is selected from optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, and optionally substituted heteroaryl and has from two to seven carbons.

In a further aspect, one or more substitutents of $R^3$ are selected from optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, and optionally substituted heteroaryl and have from two to seven carbons.

In a further aspect, one or more substitutents of $R^4$ are selected from optionally substituted alkyl or alkenyl or alkynyl, optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, and optionally substituted heteroaryl and have from two to seven carbons.

In a further aspect, N, $R^1$, and $R^2$ together comprise an optionally substituted hetrocyclic ring having from two to seven carbons. In a further aspect, N, $R^1$, and $R^2$ together comprise 2-methylpiperidinyl.

In a further aspect, the optionally substituted alkyl of $R^1$, $R^2$, $R^3$, and/or $R_4$ comprises an optionally substituted alkyl or an optionally substituted cycloalkyl. In a further aspect, all of $R^3$ are hydrogen.

In a further aspect, at least one of $R^4$ is halogen selected from F and Cl. In a further aspect, four of $R^4$ are hydrogen and one of $R^4$ is F. In a further aspect, the compound has a structure represented by a formula:

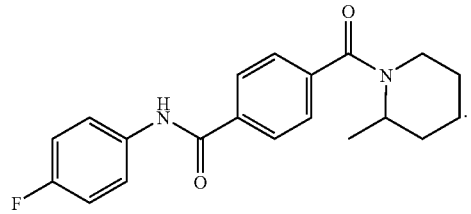 [SMILES: CC1CCCCN1C(=O)c1ccc(C(=O)Nc2ccc(F)cc2)cc1]

It is understood that the compound can be provided by the disclosed methods of making, can be employed in the disclosed compositions, and can be used in the disclosed methods of using.

D. METABOTROPIC GLUTAMATE RECEPTOR ACTIVITY

The utility of the compounds in accordance with the present invention as potentiators of metabotropic glutamate receptor activity, in particular mGluR5 activity, can be demonstrated by methodology known in the art. Human embryonic kidney (HEK) cells transfected with rat mGluR5 were plated in clear bottom assay plates for assay in a Functional Drug Screening System (FDSS). The cells were loaded with a $Ca^{2+}$-sensitive fluorescent dye (e.g., Fluo-4), and the plates were washed and placed in the FDSS instrument. After establishment of a fluorescence baseline for twelve seconds, the compounds of the present invention were added to the cells, and the response in cells was measured. Five minutes later, an mGluR5 agonist (e.g., glutamate, 3,5-dihydroxyphenylglycine, or quisqualate) was added to the cells, and the response of the cells was measured. Potentiation of the agonist response of mGluR5 by the compounds in the present invention was observed as an increase in response to non-maximal concentrations of agonist (here, glutamate) in the presence of compound compared to the response to agonist in the absence of compound.

The above described assay operated in two modes. In the first mode, a range of concentrations of the present compounds were added to cells, followed by a single fixed concentration of agonist. If a compound acted as a potentiator, an $EC_{50}$ value for potentiation and a maximum extent of potentiation by the compound at this concentration of agonist was determined by non-linear curve fitting. In the second mode, several fixed concentrations of the present compounds were added to various wells on a plate, followed by a range of concentrations of agonist for each concentration of present compound; the $EC_{50}$ values for the agonist at each concentration of compound were determined by non-linear curve fitting. A decrease in the $EC_{50}$ value of the agonist with increasing concentrations of the present compounds (a leftward shift of the agonist concentration-response curve) is an indication of the degree of mGluR5 potentiation at a given concentration of the present compound. An increase in the $EC_{50}$ value of the agonist with increasing concentrations of the present compounds (a rightward shift of the agonist concentration-response curve) is an indication of the degree of mGluR5 antagonism at a given concentration of the present compound. The second mode also indicates whether the present compounds also affect the maximum response to mGluR5 to agonists.

In particular, the disclosed compounds had activity in potentiating the mGluR5 receptor in the aforementioned assays, generally with an $EC_{50}$ for potentiation of less than about 10 µM. Preferred compounds within the present invention had activity in potentiating the mGluR5 receptor with an $EC_{50}$ for potentiation of less than about 500 nM. Preferred compounds further caused a leftward shift of the agonist $EC_{50}$ by greater than 3-fold. These compounds did not cause mGluR5 to respond in the absence of agonist, and they did not elicit a significant increase in the maximal response of mGluR5 to agonists. These compounds are positive allosteric modulators (potentiators) of human and rat mGluR5 and were selective for mGluR5 compared to the other seven subtypes of metabotropic glutamate receptors.

With respect to the disclosed compounds, $EC_{50}$ for potentiating the mGluR5 receptor are listed in Table 1 below:

TABLE 1

| mGluR5 Potentiator | $EC_{50}$ | Nomenclature |
| --- | --- | --- |
|  | 2.78E-09 | N-cyclopentyl-4-(phenylethynyl)benzamide |
|  | 3.25E-09 | (4-((3-fluorophenyl)ethynyl)phenyl)(4-hydroxypiperidin-1-yl)methanone |
|  | 5.28E-09 | morpholino(4-(phenylethynyl)phenyl)methanone |
|  | 5.32E-09 | (4-((3-fluorophenyl)ethynyl)phenyl)(morpholino)methanone |

TABLE 1-continued

| mGluR5 Potentiator | EC$_{50}$ | Nomenclature |
|---|---|---|
| | 6.22E-09 | N-cyclohexyl-4-(phenylethyl)benzamide |
| | 1.19E-08 | (4-((3-fluorophenyl)ethynyl)phenyl)(4-(hydroxymethyl)piperidin-1-yl)methanone |
| | 1.20E-08 | (4-((2-fluorophenyl)ethynyl)phenyl)(morpholino)methanone |
| | 1.43E-08 | (4-hydroxypiperidin-1-yl)(4-(phenylethynyl)phenyl)methanone |
| | 1.47E-08 | 4-(phenylethynyl)-N-propylbenzamide |

TABLE 1-continued

| mGluR5 Potentiator | EC$_{50}$ | Nomenclature |
|---|---|---|
| | 1.52E-08 | (4-((4-fluorophenyl)ethynyl)phenyl)(4-hydroxypiperidin-1-yl)methanone |
| | 1.94E-08 | N-(3,3-dimethylbutyl)-4-(phenylethynyl)benzamide |
| | 2.06E-08 | (4-((3-fluorophenyl)ethynyl)phenyl)(4-hydroxy-4-methylpiperidin-1-yl)methanone |
| | 2.36E-08 | (4-((2-fluorophenyl)ethynyl)phenyl)(4-(hydroxymethyl)piperidin-1-yl)methanone |
| | 2.47E-08 | (4-((4-fluorophenyl)ethynyl)phenyl)(morpholino)methanone |

TABLE 1-continued

| mGluR5 Potentiator | EC$_{50}$ | Nomenclature |
|---|---|---|
| | 2.61E-08 | (4-((4-fluorophenyl)ethynyl)phenyl)(4-(hydroxymethyl)piperidin-1-yl)methanone |
| | 2.73E-08 | N-isopentyl-4-(phenylethynyl)benzamide |
| | 2.81E-08 | (4-((2-fluorophenyl)ethynyl)phenyl)(4-hydroxypiperidin-1-yl)methanone |
| | 2.83E-08 | (4-hydroxypiperidin-1-yl)(4-(phenylethynyl)phenyl)methanone |
| | 3.22E-08 | N-(3-methoxypropyl)-4-(phenylethynyl)benzamide |
| | 3.27E-08 | (4-(hydroxymethyl)piperidin-1-yl)(4-(phenylethynyl)phenyl)methanone |

TABLE 1-continued

| mGluR5 Potentiator | EC$_{50}$ | Nomenclature |
|---|---|---|
| | 3.35E-08 | N-butyl-4-(phenylethynyl)benzamide |
| | 3.49E-08 | (R)-4-(phenylethynyl)-N-(2-phenylpropyl)benzamide |
| | 3.51E-08 | (4-((3,4-difluoro-phenyl)ethynyl)phenyl)(morpholino)methanone |
| | 3.79E-08 | (4-((2-fluorophenyl)ethynyl)phenyl)(4-hydroxy-4-methylpiperidin-1-yl)methanone |
| | 3.94E-08 | (4-hydroxy-4-methylpiperidin-1-yl)(4-(phenylethynyl)phenyl)methanone |
| | 4.34E-08 | (4-(hydroxymethyl)piperidin-1-yl)(4-(phenylethynyl)phenyl)methanone |

TABLE 1-continued

| mGluR5 Potentiator | EC$_{50}$ | Nomenclature |
|---|---|---|
| | 5.42E-08 | (4-((4-fluorophenyl)ethynyl)phenyl)(4-hydroxy-4-methylpiperidin-1-yl)methanone |
| | 5.95E-08 | (4-(pentan-2-ylamino)piperidin-1-yl)(4-(phenylethynyl)phenyl)methanone |
| | 6.87E-08 | N-(cyclohexylmethyl)-4-(phenylethynyl)benzamide |
| | 7.30E-08 | (4-((3-fluorophenyl)ethynyl)phenyl)(3-hydroxyazetidin-1-yl)methanone |
| | 7.39E-08 | (4-((3,4-difluorophenyl)ethynyl)phenyl)(4-hydroxypiperidin-1-yl)methanone |

TABLE 1-continued

| mGluR5 Potentiator | EC$_{50}$ | Nomenclature |
|---|---|---|
| | 7.53E-08 | N-(2-cyclohexenylethyl)-4-(phenylethynyl)benzamide |
| | 7.63E-08 | N-(4-methylcyclohexyl)-4-(phenylethynyl)benzamide |
| | 7.80E-08 | (4-(cyclohexylamino)piperidin-1-yl)(4-(phenylethynyl)phenyl)methanone |
| | 8.17E-08 | (4-((3,4-difluorophenyl)ethynyl)phenyl)(4-(hydroxymethyl)piperidin-1-yl)methanone |
| | 8.62E-08 | N-(3-hydroxypropyl)-4-(phenylethynyl)benzamide |
| | 8.89E-08 | (2,6-dimethylmorpholino)(4-(phenylethynyl)phenyl)methanone |

TABLE 1-continued

| mGluR5 Potentiator | EC$_{50}$ | Nomenclature |
|---|---|---|
| 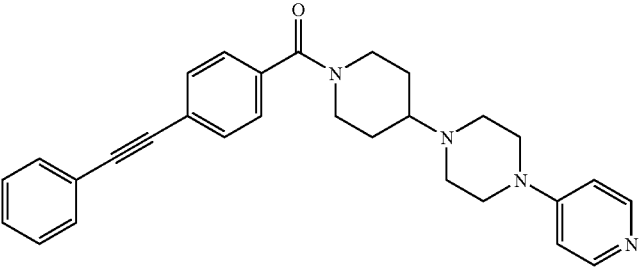 [SMILES: O=C(c1ccc(C#Cc2ccccc2)cc1)N1CCC(N2CCN(c3ccncc3)CC2)CC1] | 1.13E-07 | (4-(phenylethynyl)phenyl)(4-(4-(pyridin-4-yl)piperazin-1-yl)piperidin-1-yl)methanone |
| 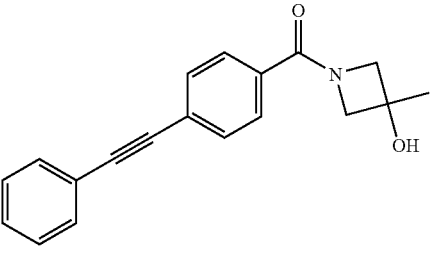 [SMILES: CC1(O)CN(C(=O)c2ccc(C#Cc3ccccc3)cc2)C1] | 1.19E-07 | (3-hydroxy-3-methylazetidin-1-yl)(4-(phenylethynyl)phenyl)methanone |
| 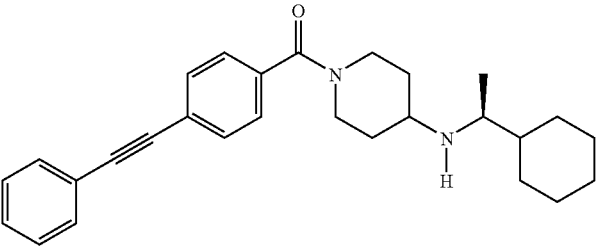 [SMILES: C[C@H](NC1CCN(C(=O)c2ccc(C#Cc3ccccc3)cc2)CC1)C1CCCCC1] | 1.29E-07 | (S)-(4-(1-cyclohexylethylamino)piperidin-1-yl)(4-(phenylethynyl)phenyl)methanone |
| 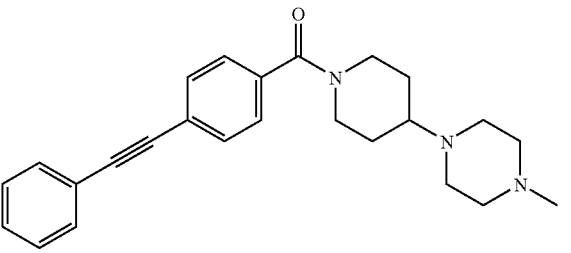 [SMILES: CN1CCN(C2CCN(C(=O)c3ccc(C#Cc4ccccc4)cc3)CC2)CC1] | 1.32E-07 | (4-(4-methylpiperazin-1-yl)piperidin-1-yl)(4-(phenylethynyl)phenyl)methanone |
| 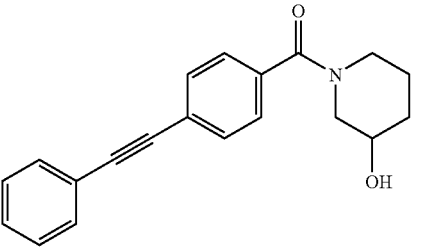 [SMILES: O=C(c1ccc(C#Cc2ccccc2)cc1)N1CCCC(O)C1] | 1.34E-07 | (3-hydroxypiperidin-1-yl)(4-(phenylethynyl)phenyl)methanone |

TABLE 1-continued
| mGluR5 Potentiator | EC$_{50}$ | Nomenclature |
|---|---|---|
| 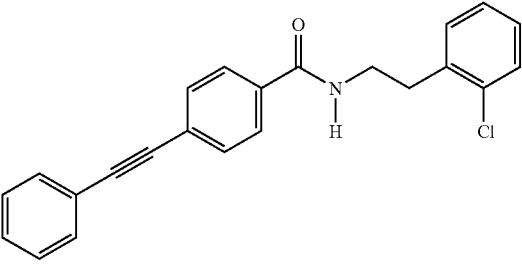 [SMILES: O=C(NCCc1ccccc1Cl)c1ccc(C#Cc2ccccc2)cc1] | 1.35E-07 | N-(2-chlorophenethyl)-4-(phenylethynyl)benzamide |
| 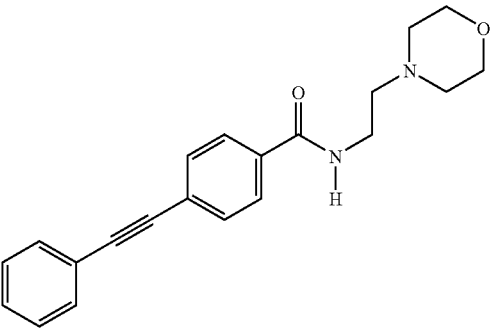 [SMILES: O=C(NCCN1CCOCC1)c1ccc(C#Cc2ccccc2)cc1] | 1.37E-07 | N-(2-morpholinoethyl)-4-(phenylethynyl)benzamide |
| 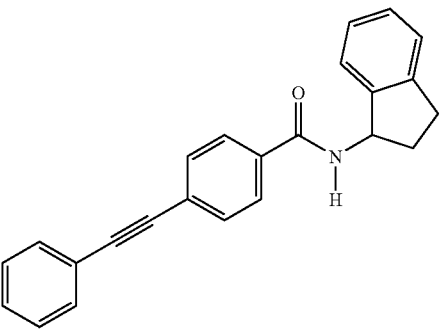 [SMILES: O=C(NC1CCc2ccccc21)c1ccc(C#Cc2ccccc2)cc1] | 1.46E-07 | N-(2,3-dihydro-1H-inden-1-yl)-4-(phenylethynyl)benzamide |
| 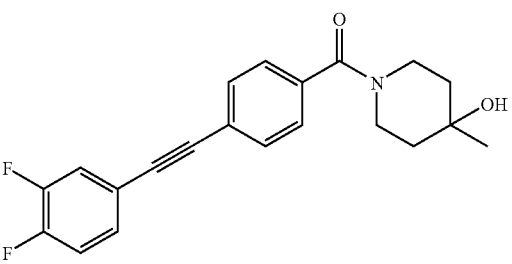 [SMILES: CC1(O)CCN(C(=O)c2ccc(C#Cc3ccc(F)c(F)c3)cc2)CC1] | 1.56E-07 | (4-((3,4-difluorophenyl)ethynyl)phenyl)(4-hydroxy-4-methylpiperidin-1-yl)methanone |
| 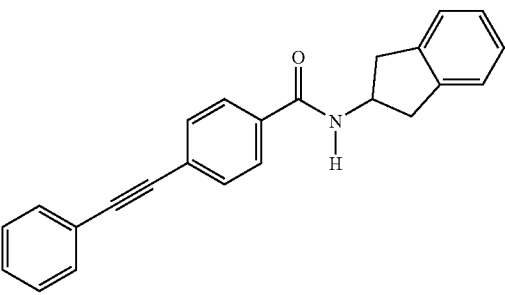 [SMILES: O=C(NC1Cc2ccccc2C1)c1ccc(C#Cc2ccccc2)cc1] | 1.59E-07 | N-(2,3-dihydro-1H-inden-2-yl)-4-(phenylethynyl)benzamide |

TABLE 1-continued

| mGluR5 Potentiator | EC$_{50}$ | Nomenclature |
|---|---|---|
| | 1.62E-07 | (4-((4-fluorophenyl)ethynyl)phenyl)(3-hydroxyazetidin-1-yl)methanone |
| | 1.66E-07 | (4-methylpiperazin-1-yl)(4-(phenylethynyl)phenyl)methanone |
| | 1.77E-07 | N-(4-chlorophenethyl)-4-(phenylethynyl)benzamide |
| | 1.87E-07 | (4-((2-fluorophenyl)ethynyl)phenyl)(3-hydroxyazetidin-1-yl)methanone |
| | 2.06E-07 | N-(3-chlorophenethyl)-4-(phenylethynyl)benzamide |

TABLE 1-continued

| mGluR5 Potentiator | EC$_{50}$ | Nomenclature |
|---|---|---|
| | 2.12E-07 | (4-(cyclobutylamino)piperidin-1-yl)(4-(phenylethynyl)phenyl)methanone |
| | 2.37E-07 | N-(4-bromophenethyl)-4-(phenylethynyl)benzamide |
| | 3.14E-07 | (3-hydroxyazetidin-1-yl)(4-(phenylethynyl)phenyl)methanone |
| | 3.83E-07 | (4-(2-morpholinoethylamino)piperidin-1-yl)(4-(phenylethynyl)phenyl)methanone |
| | 3.87E-07 | (4-((3,4-difluorophenyl)ethynyl)phenyl)(3-hydroxyazetidin-1-yl)methanone |
| | 4.23E-07 | N-(3,3-dimethylbutyl)-4-(3-(4-fluorophenyl)-1,2,4-oxadiazol-5-yl)benzamide |

TABLE 1-continued

| mGluR5 Potentiator | EC$_{50}$ | Nomenclature |
|---|---|---|
| | 4.77E-07 | (4-(4-chloro-2-(trifluoromethyl)phenyl)-4-hydroxypiperidin-1-yl)(4-(phenylethynyl)phenyl)methanone |
| | 5.00E-07 | (3-hydroxy-3-propylazetidin-1-yl)(4-(phenylethynyl)phenyl)methanone |
| | 5.93E-07 | (octahydroisoquinolin-2(1H)-yl)(4-(phenylethynyl)phenyl)methanone |
| | 8.32E-07 | (4-((4-fluoro-3-methylphenyl)ethynyl)phenyl)(4-hydroxypiperidin-1-yl)methanone |
| | 1.00E-06 | (4-((3,5-difluorophenyl)ethynyl)phenyl)(4-hydroxypiperidin-1-yl)methanone |

TABLE 1-continued

| mGluR5 Potentiator | EC₅₀ | Nomenclature |
|---|---|---|
| 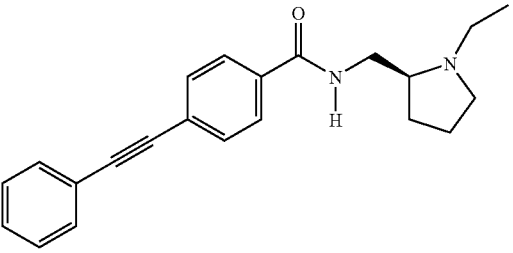 [SMILES: CCN1CCC[C@H]1CNC(=O)c1ccc(C#Cc2ccccc2)cc1] | 1.03E-06 | (S)-N-((1-ethylpyrrolidin-2-yl)methyl)-4-(phenylethynyl)benzamide |
| 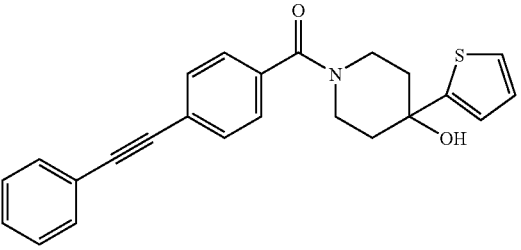 [SMILES: O=C(c1ccc(C#Cc2ccccc2)cc1)N1CCC(O)(c2cccs2)CC1] | 1.07E-06 | (4-hydroxy-4-(thiophen-2-yl)piperidin-1-yl)(4-(phenylethynyl)phenyl)methanone |
| 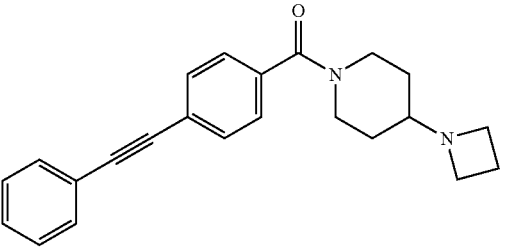 [SMILES: O=C(c1ccc(C#Cc2ccccc2)cc1)N1CCC(N2CCC2)CC1] | 1.11E-06 | (4-(azetidin-1-yl)piperidin-1-yl)(4-(phenylethynyl)phenyl)methanone |
| 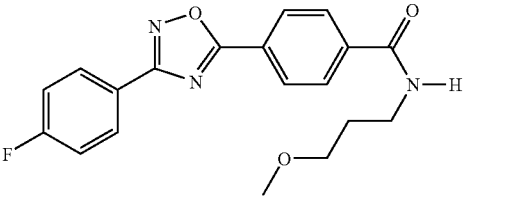 [SMILES: COCCCNC(=O)c1ccc(-c2nc(-c3ccc(F)cc3)no2)cc1] | 1.12E-06 | 4-(3-(4-fluorophenyl)-1,2,4-oxadiazol-5-yl)-N-(3-methoxypropyl)benzamide |
| 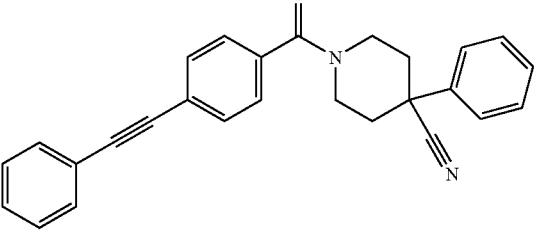 | 1.14E-06 | 4-phenyl-1-(4-(phenylethynyl)benzoyl)piperidine-4-carbonitrile |
| 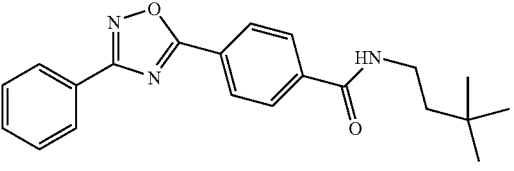 [SMILES: CC(C)(C)CCNC(=O)c1ccc(-c2nc(-c3ccccc3)no2)cc1] | 1.16E-06 | N-(3,3-dimethylbutyl)-4-(3-phenyl-1,2,4-oxadiazol-5-yl)benzamide |

TABLE 1-continued

| mGluR5 Potentiator | EC$_{50}$ | Nomenclature |
|---|---|---|
| 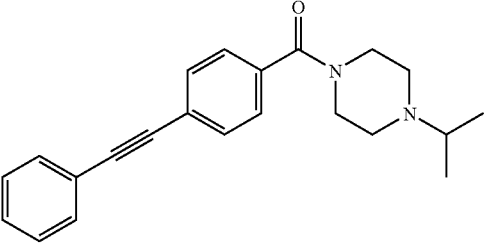 [SMILES: CC(C)N1CCN(C(=O)c2ccc(C#Cc3ccccc3)cc2)CC1] | 1.19E-06 | (4-isopropylpiperazin-1-yl)(4-(phenylethynyl)phenyl)methanone |
| 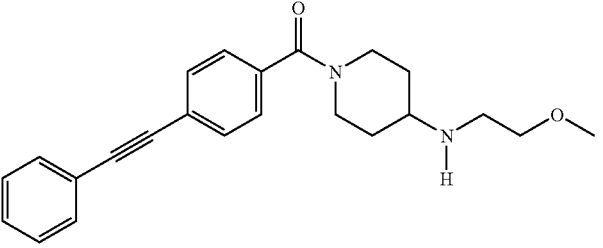 [SMILES: COCCNC1CCN(C(=O)c2ccc(C#Cc3ccccc3)cc2)CC1] | 1.19E-06 | (4-(2-methoxyethylamino)piperidin-1-yl)(4-(phenylethynyl)phenyl)methanone |
| 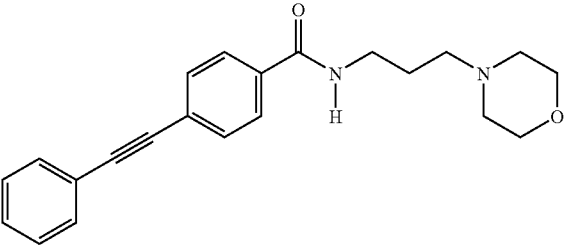 [SMILES: O=C(NCCCN1CCOCC1)c1ccc(C#Cc2ccccc2)cc1] | 1.23E-06 | N-(3-morpholinopropyl)-4-(phenylethynyl)benzamide |
| 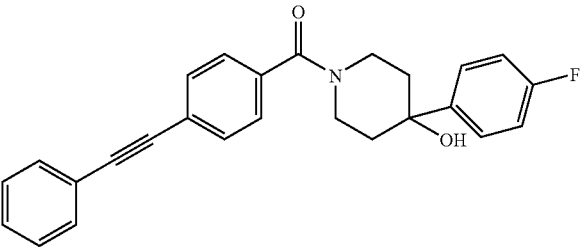 [SMILES: O=C(c1ccc(C#Cc2ccccc2)cc1)N1CCC(O)(c2ccc(F)cc2)CC1] | 1.25E-06 | (4-(4-fluorophenyl)-4-hydroxypiperidin-1-yl)(4-(phenylethynyl)phenyl)methanone |
| 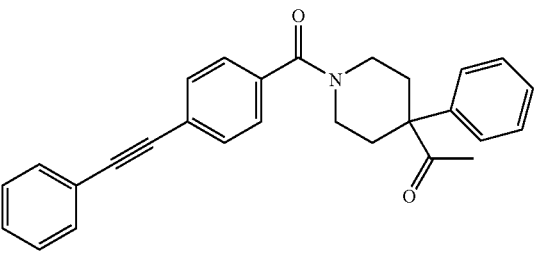 [SMILES: CC(=O)C1(c2ccccc2)CCN(C(=O)c2ccc(C#Cc3ccccc3)cc2)CC1] | 1.25E-06 | 1-(4-phenyl-1-(4-(phenylethynyl)benzoyl)piperidin-4-yl)ethanone |
| 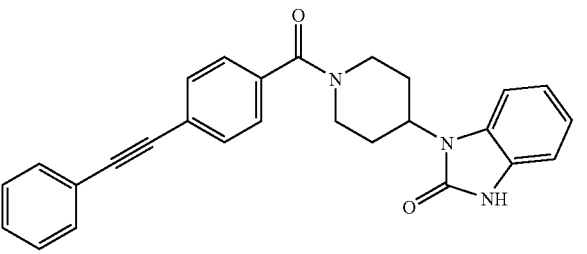 [SMILES: O=C(c1ccc(C#Cc2ccccc2)cc1)N1CCC(n2c(=O)[nH]c3ccccc32)CC1] | 1.47E-06 | 1-(1-(4-(phenylethynyl)benzoyl)piperidin-4-yl)-1H-benzo[d]imidazol-2(3H)-one |

TABLE 1-continued

| mGluR5 Potentiator | EC$_{50}$ | Nomenclature |
|---|---|---|
| | 1.61E-06 | (4-hydroxy-4-propylpiperidn-1-yl)(4-(phenylethynyl)phenyl)methanone |
| | 1.71E-06 | (3-hydroxy-3-(thiophen-2-yl)azetidin-1-yl)(4-(phenylethynyl)phenyl)methanone |
| | 1.77E-06 | (4-(3-fluorophenyl)-4-hydroxypiperidin-1-yl)(4-(phenylethynyl)phenyl)methanone |
| | 1.79E-06 | 4-(phenylethynyl)-N-(2-(piperidin-1-yl)ethyl)benzamide |
| | 1.80E-06 | (4-hydroxy-4-isopropylpiperidin-1-yl)(4-(phenylethynyl)phenyl)methanone |

TABLE 1-continued

| mGluR5 Potentiator | EC$_{50}$ | Nomenclature |
|---|---|---|
| (structure) | 1.87E-06 | (4-(cyclohexylethynyl)phenyl)(4-hydroxypiperidin-1-yl)methanone |
| (structure) | 1.97E-06 | (E)-(4-hydroxypiperidin-1-yl)(4-styrylphenyl)methanone |
| (structure) | 2.03E-06 | 4-(3-(4-fluorophenyl)-1,2,4-oxadiazol-5-yl)-N-propylbenzamide |
| (structure) | 2.03E-06 | (4-((2,4-difluorophenyl)ethynyl)phenyl)(4-hydroxypiperidin-1-yl)methanone |
| (structure) | 2.06E-06 | (4-(phenylethynyl)phenyl)(4-phenylpiperazin-1-yl)methanone |
| (structure) | 2.10E-06 | (4-(2-methoxyphenyl)piperazin-1-yl)(4-(phenylethynyl)phenyl)methanone |

TABLE 1-continued

| mGluR5 Potentiator | EC₅₀ | Nomenclature |
|---|---|---|
| | 2.21E-06 | (4-hydroxypiperidin-1-yl)(4-((3-(trifluoromethyl)phenyl)ethynyl)phenyl)methanone |
| | 2.27E-06 | 4-(3-phenyl-1,2,4-oxadiazol-5-yl)-N-propylbenzamide |
| | 2.45E-06 | (4-hydroxypiperidin-1-yl)(4-pyridin-2-ylethynyl)phenyl)methanone |
| | 2.46E-06 | (4-(4-bromophenyl)-4-hydroxypiperidin-1-yl)(4-(phenylethynyl)phenyl)methanone |
| | 2.63E-06 | (4-hydroxy-4-(4-methoxyphenyl)piperidin-1-yl)(4-(phenylethynyl)phenyl)methanone |

TABLE 1-continued

| mGluR5 Potentiator | EC$_{50}$ | Nomenclature |
|---|---|---|
| | 2.79E-06 | (4-(cyclopropylmethylamino)piperidin-1-yl)(4-(phenylethynyl)phenyl)methanone |
| | 2.92E-06 | (4-(phenylethynyl)phenyl)(4-(pyridin-2-yl)piperazin-1-yl)methanone |
| | 2.99E-06 | N-(2-(dimethylamino)ethyl)-4-(phenylethynyl)benzamide |
| | 3.33E-06 | N-(4-fluorophenyl)-4-(2-methylpiperidine-1-carbonyl)benzamide |
| | 3.53E-06 | N-(2-(1-methylpyrrolidin-2-yl)ethyl)-4-(phenylethynyl)benzamide |
| | 3.66E-06 | (4-hydroxy-4-phenylpiperidin-1-yl)(4-(phenylethynyl)phenyl)methanone |

TABLE 1-continued

| mGluR5 Potentiator | EC$_{50}$ | Nomenclature |
|---|---|---|
| | 3.68E-06 | (4-(phenylethynyl)phenyl)(4-(pyridin-4-yl)piperazin-1-yl)methanone |
| | 3.72E-06 | 5-chloro-1-(4-(phenylethynyl)benzoyl)-3-(piperidin-4-yl)-1H-benzo[d]imidazol-2(3H)-one |
| | 3.73E-06 | (4-(phenylethynyl)phenyl)(4-(pyrrolidin-1-yl)piperidin-1-yl)methanone |
| | 4.20E-06 | 2-(4-(4-phenylethynyl)benzoyl)piperazin-1-yl)benzonitrile |
| | 4.21E-06 | (4-(3-(4-fluorophenyl)-1,2,4-oxadiazol-5-yl)phenyl)(4-(pyridin-4-yl)piperazin-1-yl)methanone |
| | 4.79E-06 | (4-(phenylethynyl)phenyl)(piperazin-1-yl)methanone |

TABLE 1-continued

| mGluR5 Potentiator | EC$_{50}$ | Nomenclature |
|---|---|---|
| (structure) | 5.14E-06 | (4-(2-fluorophenyl)piperazin-1-yl)(4-(phenylethynyl)phenyl)methanone |
| (structure) | 6.46E-06 | (4-(4-chlorophenyl)-4-hydroxypiperidin-1-yl)(4-(phenylethynyl)phenyl)methanone |

Preferred compounds of the present invention also showed in vivo efficacy in a number of preclinical rat behavioral model where known, clinically useful antipsychotics display similar positive responses. For example, compounds of the present invention reverse amphetamine-induced hyperlocomotion in male Sprague-Dawley rats at doses ranging from 1 to 100 mg/kg i.p. Data for three example compounds follow:

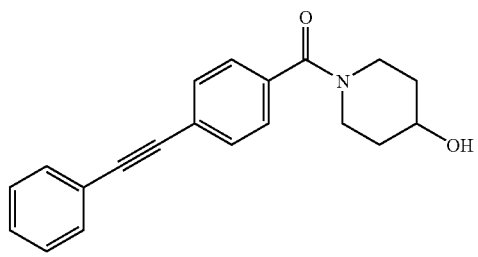 [SMILES: O=C(c1ccc(C#Cc2ccccc2)cc1)N1CCC(O)CC1]

Figure 8:
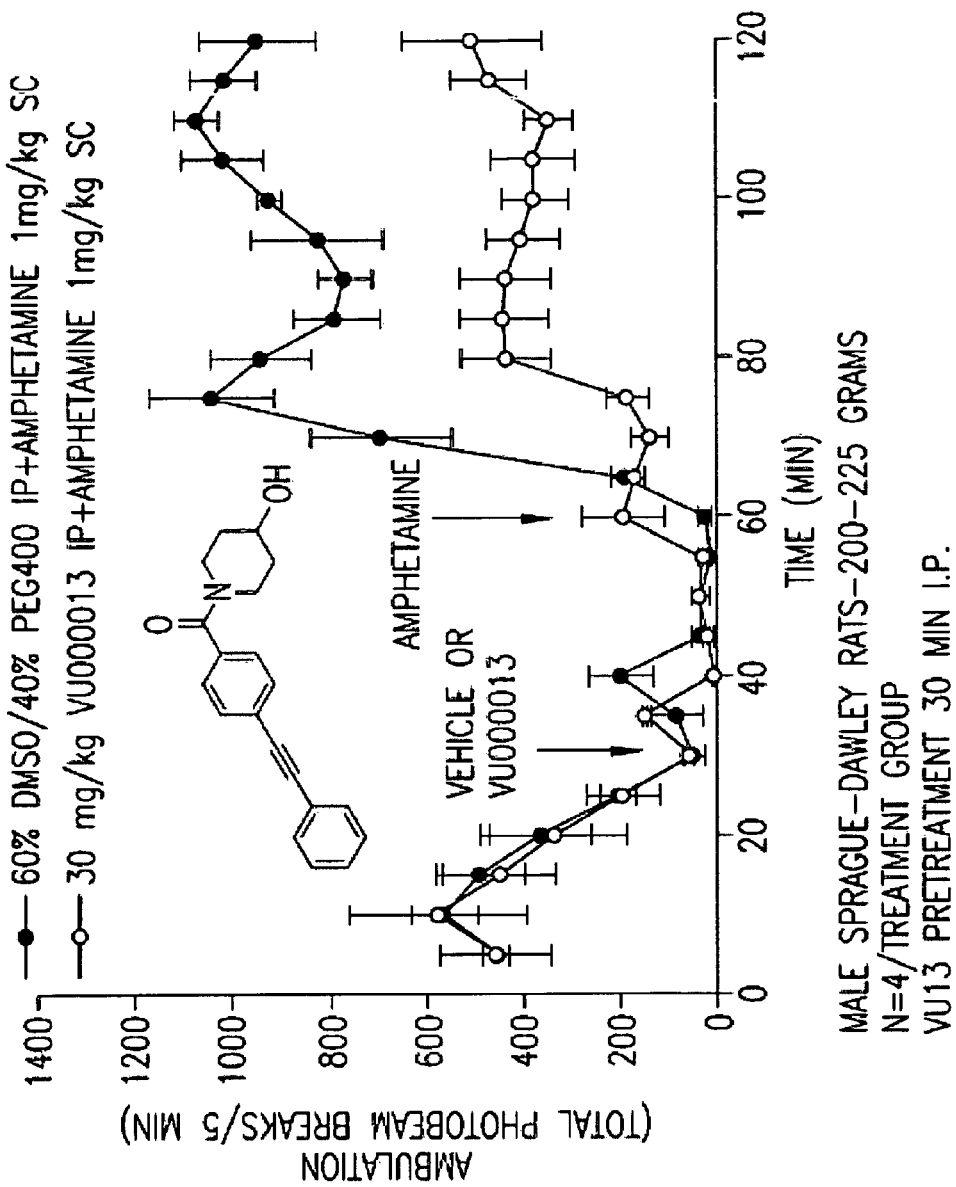
FIG. 8 shows in vivo efficacy for (4-hydroxypiperidin-1-yl)(4-(phenylethynyl)phenyl)methanone (Compound VU13).

FIG. 8 shows efficacy in reversing amphetamine-induced hyperlocomotion for (4-hydroxypiperidin-1-yl)(4-(phenylethynyl)phenyl)methanone (Compound VU13; In vitro: 13.6 nm; 50% Glu Max).

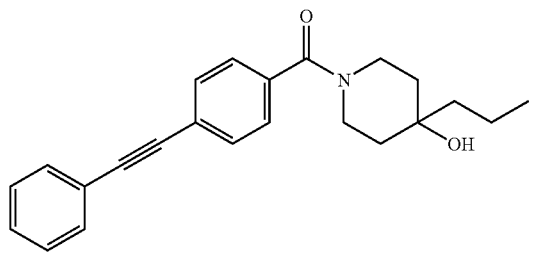 [SMILES: CCCC1(O)CCN(C(=O)c2ccc(C#Cc3ccccc3)cc2)CC1]

Figure 9:
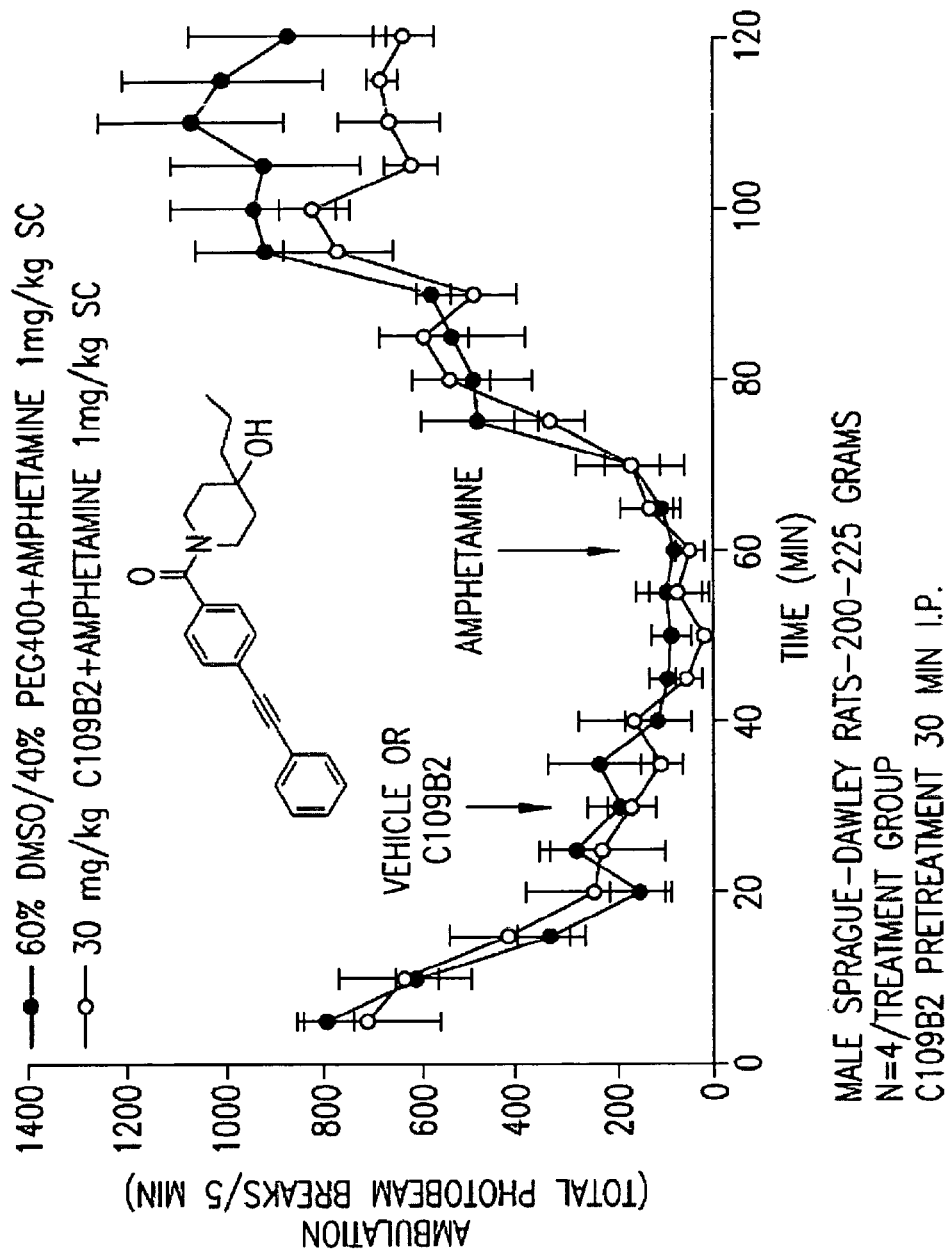
FIG. 9 shows in vivo efficacy for (4-hydroxy-4-propylpiperidin-1-yl)(4-(phenylethynyl)phenyl)methanone (Compound VU60).

FIG. 9 shows efficacy in reversing amphetamine-induced hyperlocomotion for (4-hydroxy-4-propylpiperidin-1-yl)(4-(phenylethynyl)phenyl)methanone (Compound VU60/C109B2; In vitro: 1250 nm; 90% Glu Max).

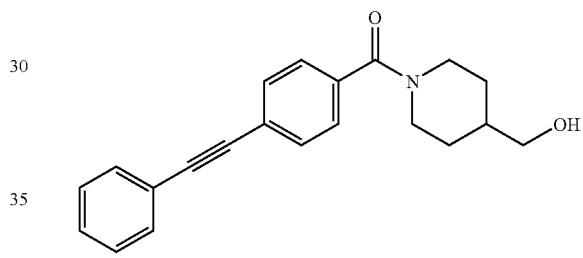

Figure 10:
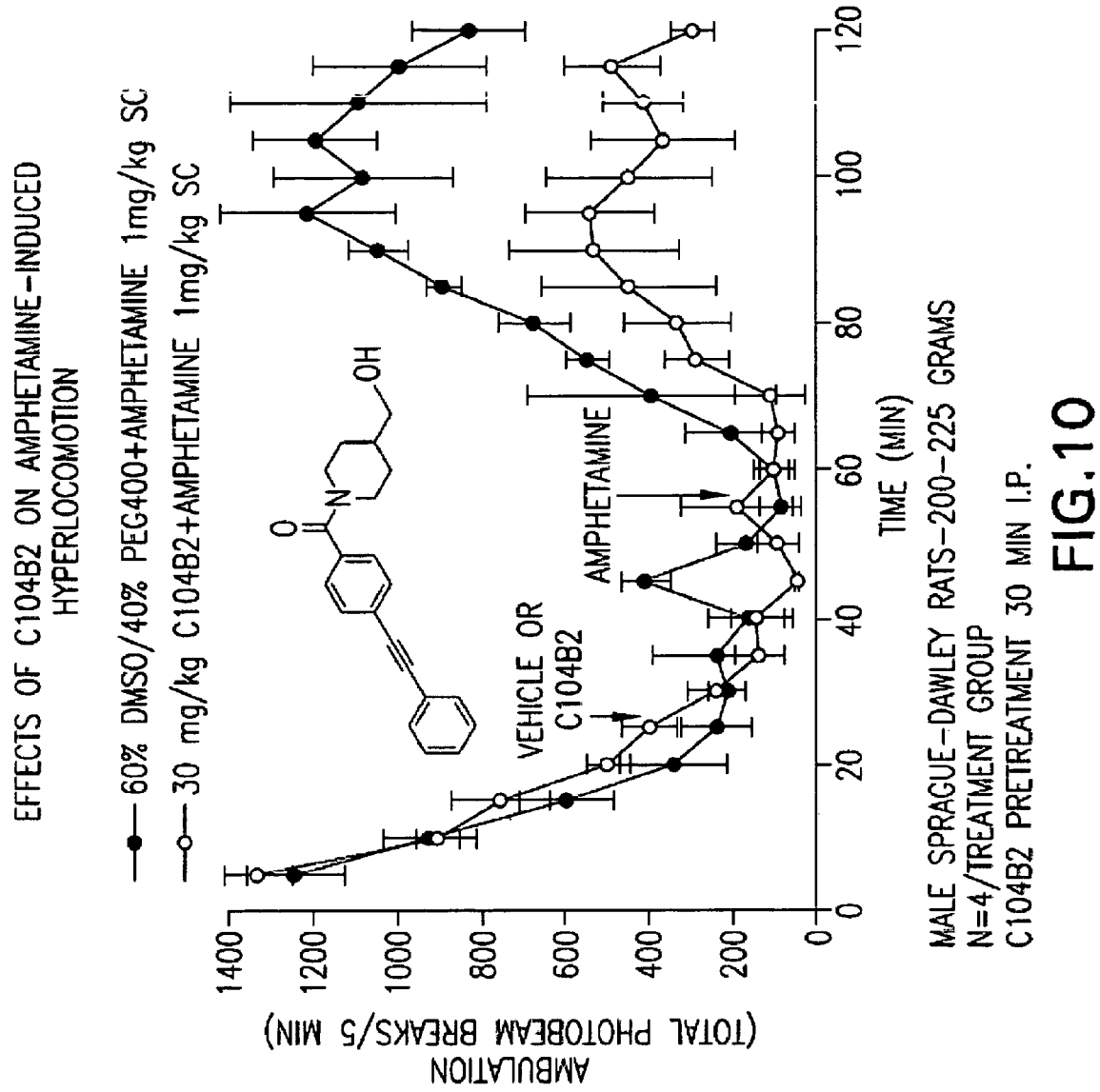
FIG. 10 shows in vivo efficacy for (4-(hydroxymethyl)piperidin-1-yl)(4-(phenylethynyl)phenyl)methanone (Compound VU14/C104B2).

FIG. 10 shows efficacy in reversing amphetamine-induced hyperlocomotion for (4-(hydroxymethyl)piperidin-1-yl)(4-(phenylethynyl)phenyl)methanone (Compound VU14/C104B2; In vitro: 29.6 nm; 41% Glu Max).

Schizophrenic patients show decreased measures of sensorimotor gating, such as prepulse inhibition (PPI) of startle, and preclinical models of PPI in rats are routinely used to predict antipsychotic efficacy. In fact, PPI can be measured in humans and rats employing identical stimulus parameters yielding similar responses (Braff, D. L.; Geyer, M. A.; Swerdlow, N. R. 'Human studies of prepulse inhibition of startle: normal subjects, patient groups, and pharmacological studies.' Psychopharmacology 2001, 156(2-3), 234-258; Braff, D. L.; Geyer, M. A. 'Sensorimotor gating and schizophrenia. Human and animal model studies.' Archives of general psychiatry 1990, 47(2), 181-8; Braff, D. L.; Geyer, M. A.; Swerdlow, N. R. 'Human studies of prepulse inhibition of startle: normal subjects, patient groups, and pharmacological studies.' Psychopharmacology 2001, 156(2-3), 234-258; Weiss, I. C.; Feldon, J. 'Environmental animal models for sensor motor gating deficiencies in schizophrenia: a review.' Psychopharmacology 2001, 156(2-3), 305-326; Thomsen, M.; Woertwein, G.; Fink-Jensen, A.; Woldbye, D. P. D.; Wess, J.; Caine, S. B. 'Decreased prepulse inhibition and increased sensitivity to muscarinic, but not dopaminergic drugs in M5 muscarinic acetylcholine receptor knockout mice.' Psychopharmacology 2007, 192(1), 97-110.). In addition, all clinically relevant antipsychotic agents (both typical and atypical)

display efficacy in preclinical models of PPI and amphetamine-induced hyperlocomotion, and these preclinical models are employed to guide the development of novel antipsychotic agents (Geyer, M. A. 'Behavioral studies of hallucinogenic drugs in animals: implications for schizophrenia research.' *Pharmacopsychiatry* 1998, 31(Suppl. 2), 73-79; Geyer, M. A.; McIlwain, K. L.; Paylor, R. 'Mouse genetic models for prepulse inhibition: an early review.' *Molecular Psychiatry* 2002, 7(10), 1039-1053; Powell, S. B.; Risbrough, V. B.; Geyer, M. A. 'Potential use of animal models to examine antipsychotic prophylaxis for schizophrenia.' *Clinical Neuroscience Research* 2003, 3(4-5), 289-296.).

Figure 12:
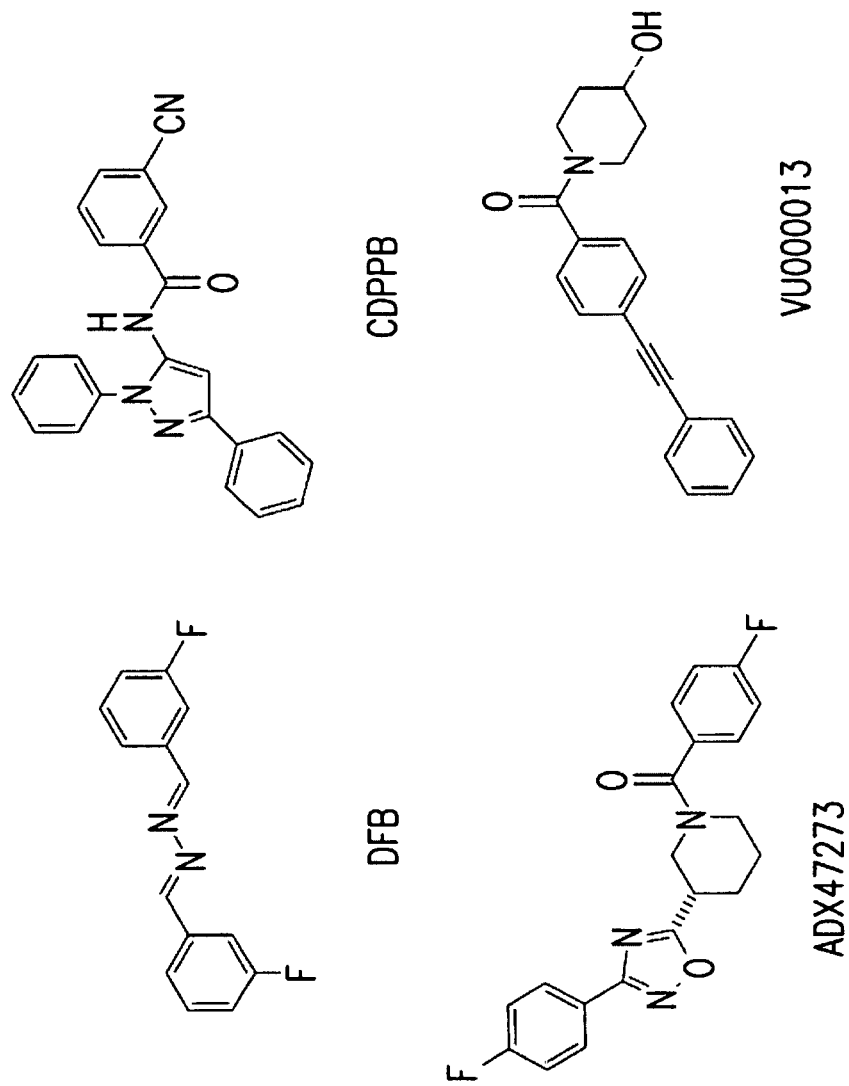
FIG. 12 shows the chemical structures of mGluR5 PAMs with in vivo activity in preclinical antipsychotic models.

Positive allosteric modulators (PAMs) of mGluR5 from distinct structural series (FIG. 12) have displayed antipsychotic-like effects in rat behavioral models predictive of antipsychotic efficacy in humans (Lindsley, C. W.; Wisnoski, D. D.; Leister, W. H.; O'Brien, J. A.; Lemiare, W.; Williams, Jr., D. L.; Burno, M.; Sur, C.; Kinney, G. G.; Pettibone, D. J.; Miller, P. R.; Smith, S.; Duggan, M. E.; Hartman, G. D.; Conn, P. J.; Huff, J. R. 'Discovery of positive allosteric modulators for the metabotropic glutamate receptor subtype 5 from a series of N-(1,3-Diphenyl-1H-pyrazol-5-yl)benzamides that potentiate receptor function in vivo' *J. Med. Chem.* 2004, 47, 5825; Kinney, G. G.; O'Brien, Lemaire, W.; Burno, M.' Bickel, D. J.; Clements, M. K.; Wisnoski, D. D.; Lindsley, C. W.; Tiller, P. R.; Smith, S.; Jacobson, M. A.; Sur, C.; Duggan, M. E.; Pettibone, D. J.; Williams, Jr., D. W. 'A novel selective allosteric modulator of metabotropic glutamate receptor subtype 5 (mGluR5) has an antipsychotic profile in rat behavioral models' *J. Pharmacol. Exp. Therapeut.* 2005, 313(1), 199; Epping-Jordan M. P., Nayak, S., Derouet, F., Dominguez, H., Bessis A. S., Le Poul E., Ludwig B. L. Mutel V., Poli S. M. and Rocher J. P. In Vivo Characterization of mGluR5 Positive Allosteric Modulators as Novel Treatments for Schizophrenia and Cognitive Dysfunction *Neuropharmacology* 2005, 49, 243).

Figure 13A:
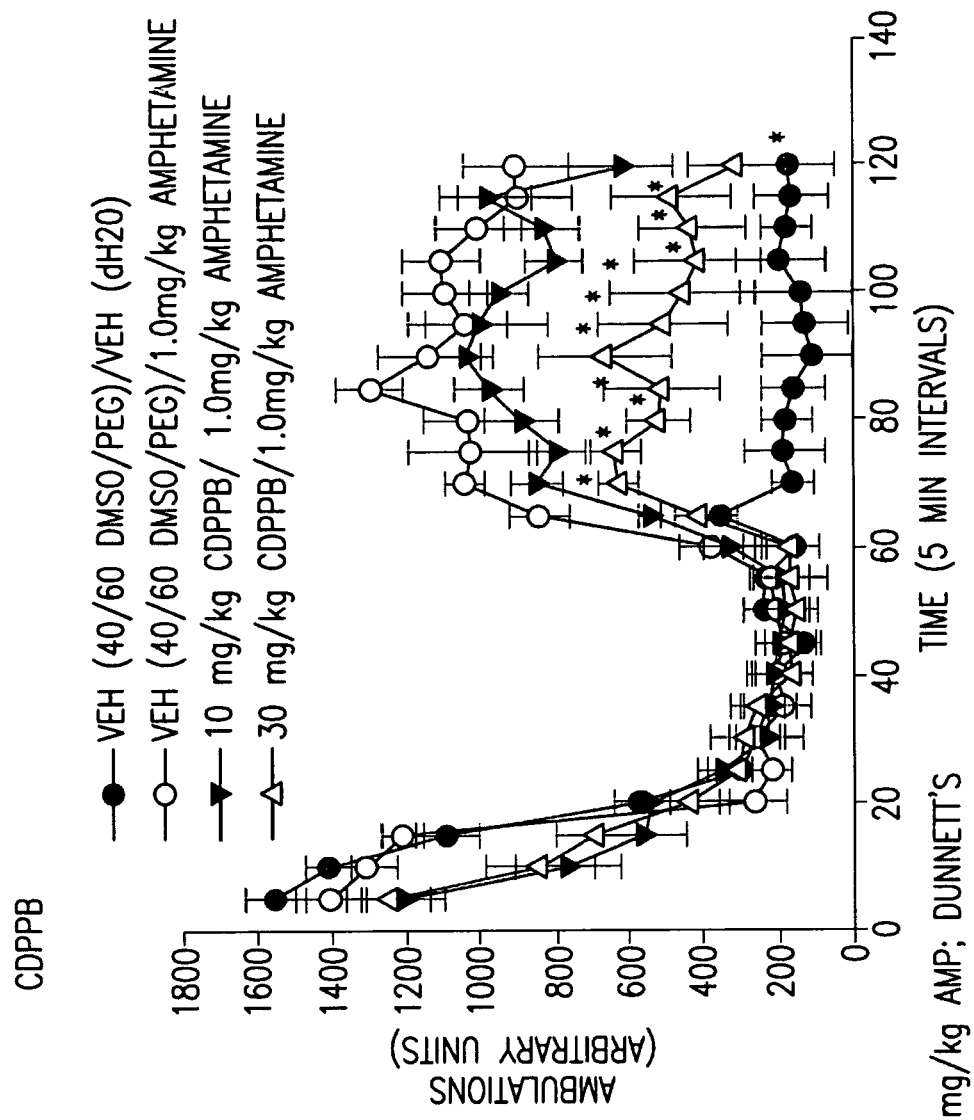
FIG. 13 shows reversal of amphetamine-induced hyperlocomotion by CDPPB and ADX47273.
Figure 13B:
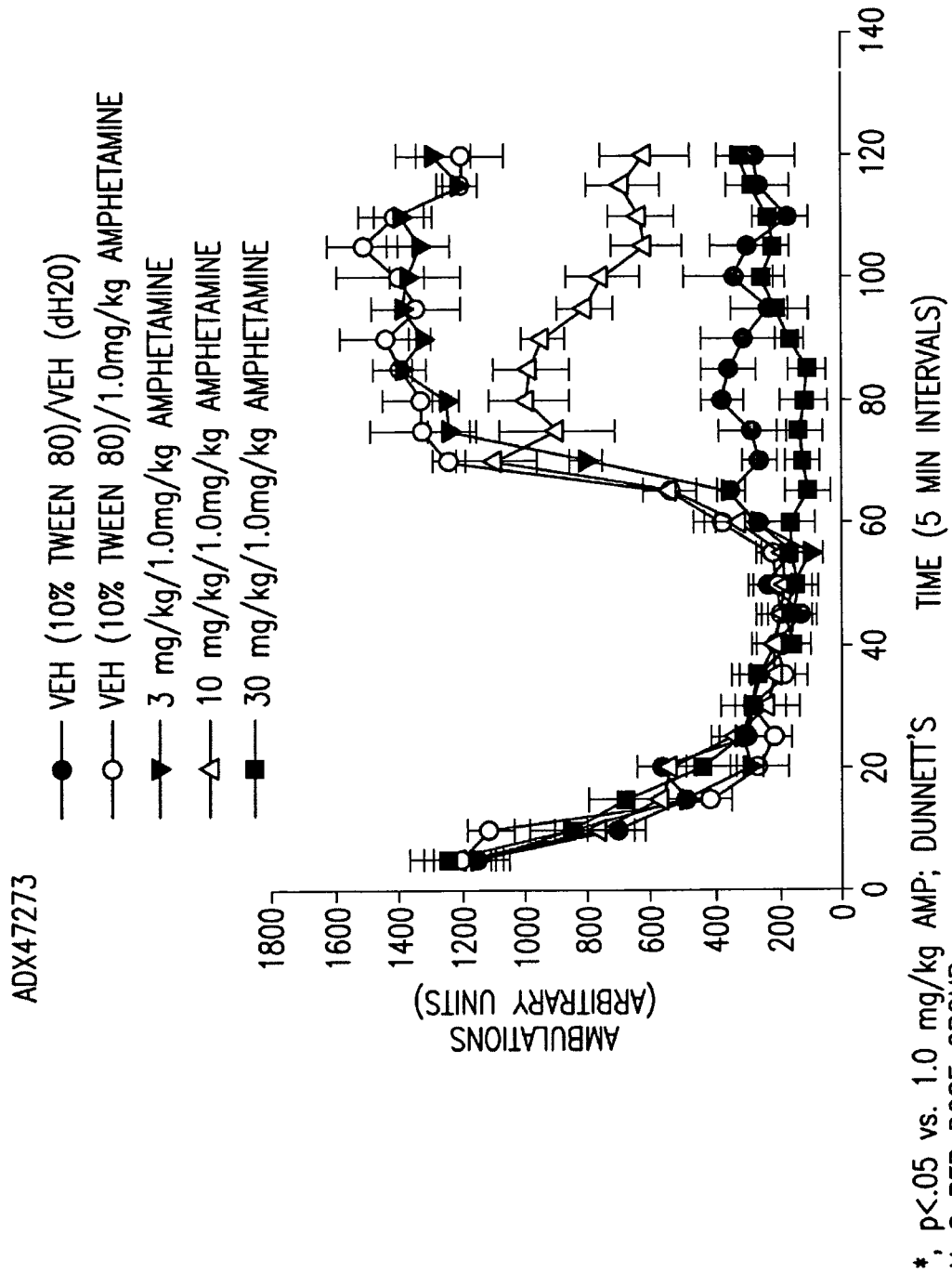
Figure 14:
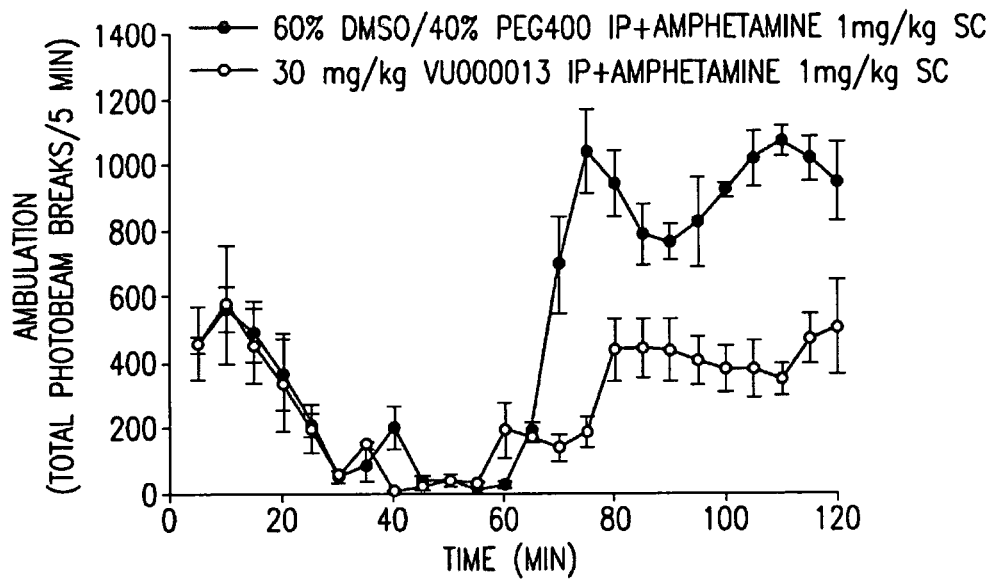
FIG. 14 shows reversal of amphetamine-induced hyperlocomotion by VU00013.

CDPPB (Lindsley, C. W.; Wisnoski, D. D.; Leister, W. H.; O'Brien, J. A.; Lemiare, W.; Williams, Jr., D. L.; Burno, M.; Sur, C.; Kinney, G. G.; Pettibone, D. J.; iller, P. R.; Smith, S.; Duggan, M. E.; Hartman, G. D.; Conn, P. J.; Huff, J. R. 'Discovery of positive allosteric modulators for the metabotropic glutamate receptor subtype 5 from a series of N-(1,3-Diphenyl-1H-pyrazol-5-yl)benzamides that potentiate receptor function in vivo' *J. Med. Chem.* 2004, 47, 5825; Kinney, G. G.; O'Brien, Lemaire, W.; Burno, M.' Bickel, D. J.; Clements, M. K.; Wisnoski, D. D.; Lindsley, C. W.; Tiller, P. R.; Smith, S.; Jacobson, M. A.; Sur, C.; Duggan, M. E.; Pettibone, D. J.; Williams, Jr., D. W. 'A novel selective allosteric modulator of metabotropic glutamate receptor subtype 5 (mGluR5) has an antipsychotic profile in rat behavioral models' *J. Pharmacol. Exp. Therapeut.* 2005, 313(1), 199) was the first centrally active mGlur5 PAM which reversed amphetamine-induced hyperlomotion in rats, and recent data with the structurally distinct ADX47273 afforded similar results (FIG. 13). Recently, similar data has been reported with DFB. A new mGluR5 PAM (FIG. 14; VU000013) affords similar results as well, suggesting positive allosteric modulation of mGluR5 provides antipsychotic-like efficacy in this preclinical model.

Figure 15:
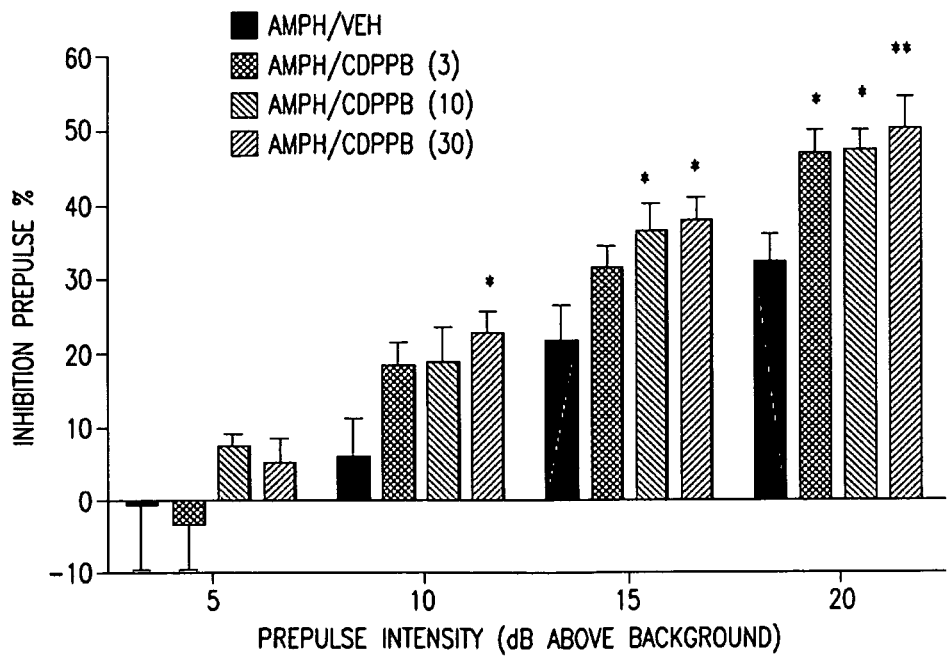
FIG. 15 shows reversal of amphetamine-induced prepulse inhibition (PPI) by CDPPB.
Figure 16B:
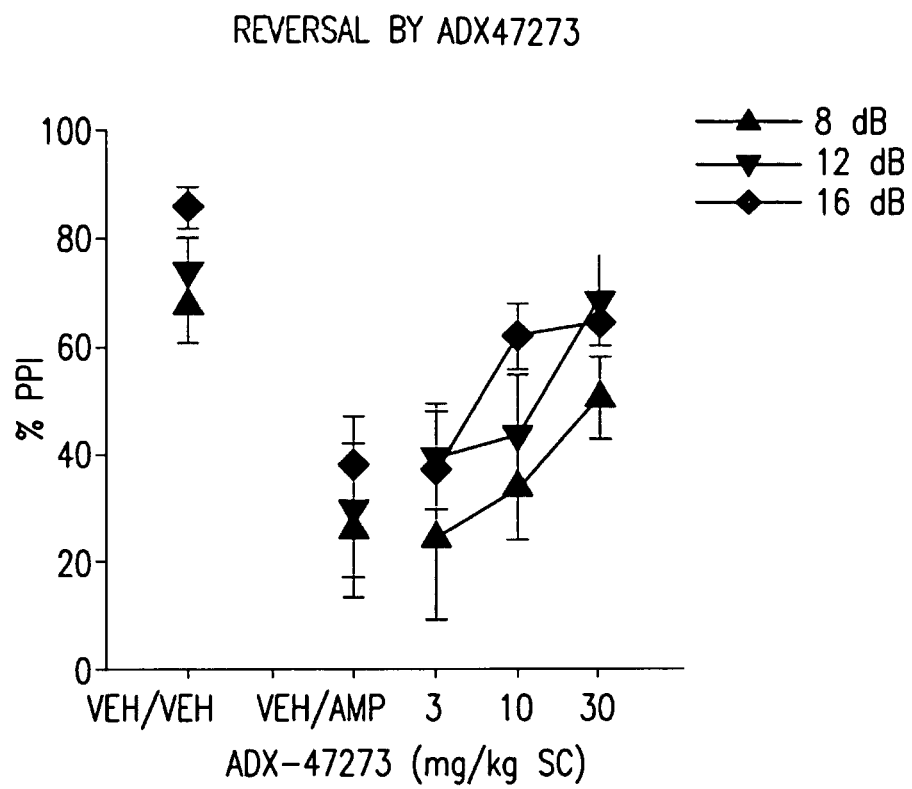
FIG. 16 shows reversal of amphetamine-induced prepulse inhibition (PPI) by ADX47273.

Both CDPPB and ADX47273 also demonstrated efficacy in PPI, a preclinical model with direct relevance to clinical efficacy, and a behavior identical in schizophrenic patients. As shown in FIG. 15, CDPPB reverses PPI in a dose-dependent manner at four different prepulse intensities above background. ADX47273 affords similar results (FIG. 16).

E. METHODS OF MAKING THE COMPOUNDS

In one aspect, the invention relates to methods of making compounds useful as positive allosteric modulators (potentiators) of the metabotropic glutamate receptor subtype 5 (mGluR5), which can be useful in the treatment neurological and psychiatric disorders associated with glutamate dysfunction and other diseases in which metabotropic glutamate receptors are involved. In a further aspect, the invention relates to methods of making phenylethynylbenzamide derivatives, cycloalkylethynylbenzamide derivatives, styrylbenzamide derivatives, 4-(3-phenyl-1,2,4-oxadiazol-5-yl) benzamide derivatives, 4-(pyridinylethynyl)benzamide derivatives, and $N^1$-phenylterephthalamide derivatives.

1. Phenylethynylbenzamide Derivatives

In one aspect, the invention relates to a method for preparing a phenylethynylbenzamide derivative comprising the steps of coupling an arylacetylene with an aryl halide, wherein one of the arylacetylene or the aryl halide bears a carboxyl functionality; and forming an amide derivative of the carboxyl functionality by reaction with an amine. Typically, a method involves a coupling reaction (e.g., transition metal catalyzed cross coupling reaction) and a reaction forming an amide moiety. Such a method can be represented in the following schematic:

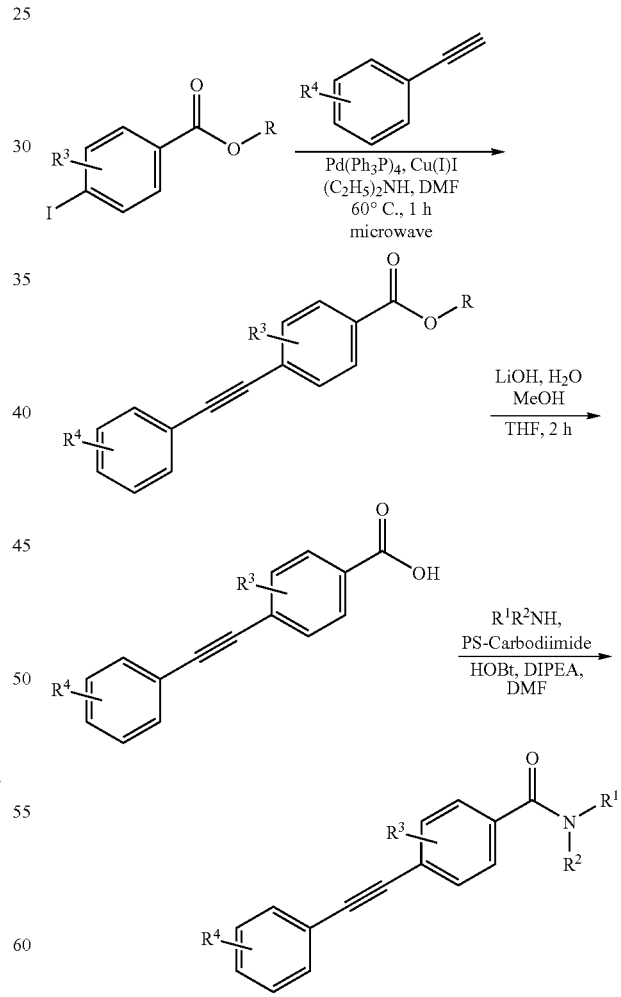

In a further aspect, the method can be represented in the following schematic, which illustrates a synthetic method useful for preparation of larger amounts of the disclosed compounds:

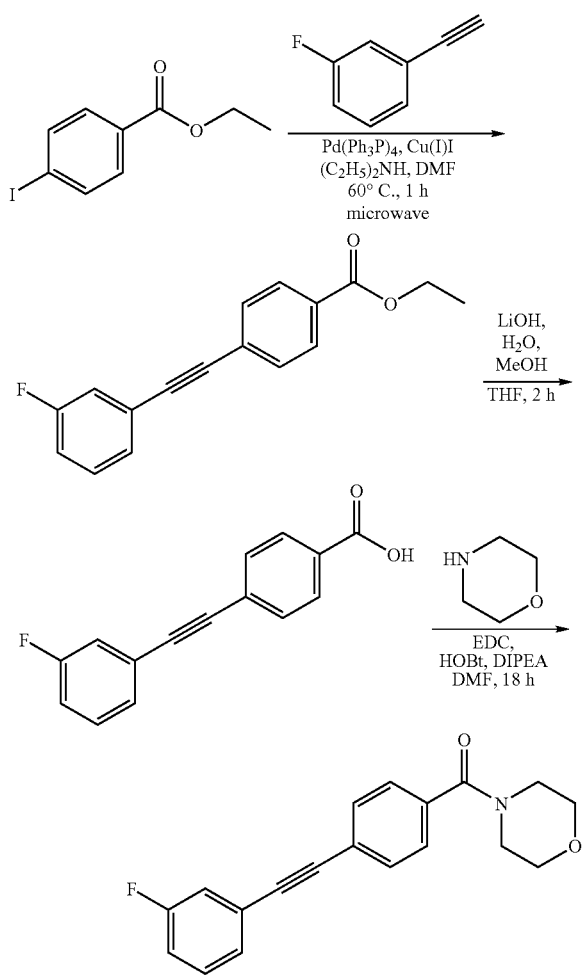

In one aspect, the coupling step is performed prior to the forming step. In a further aspect, the method further comprises the step of converting the carboxyl functionality to a carboxylic acid. In one aspect, the carboxyl functionality is an ester moiety. In one aspect, the aryl halide bears the carboxyl functionality. The halide can be Br or I. It is understood that a pseudohalide can be substituted for a halide.

In one aspect, the amine is an optionally substituted primary amine or an optionally substituted secondary amine. In a further aspect, the amine is an optionally substituted cyclic amine.

In one aspect, the coupling step is palladium-catalyzed cross-coupling.

In one aspect, the forming step is performed with PS-carbodiimide and 1-hydroxybenzotriazole.

In one aspect, the aryl halide has a structure represented by a formula:

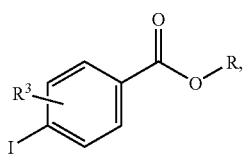

wherein R is optionally substituted alkyl; and wherein $R^3$ comprises four substituents independently selected from hydrogen, halogen, and optionally substituted alkyl.

In a further aspect, the arylacetylene has a structure represented by a formula:

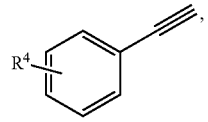

wherein $R^4$ comprises five substituents independently selected from hydrogen, halogen, and optionally substituted alkyl.

It is understood that the method can be used to provide the disclosed compounds.

2. Cycloalkylethynylbenzamide Derivatives

In one aspect, the invention relates to a method for preparing a cycloalkylethynylbenzamide derivative comprising the steps of coupling an cycloalkylacetylene with an aryl halide, wherein the aryl halide bears a carboxyl functionality; and forming an amide derivative of the carboxyl functionality by reaction with an amine. Typically, a method involves a coupling reaction (e.g., transition metal catalyzed cross coupling reaction) and a reaction forming an amide moiety. Such a method can be represented in the following schematic:

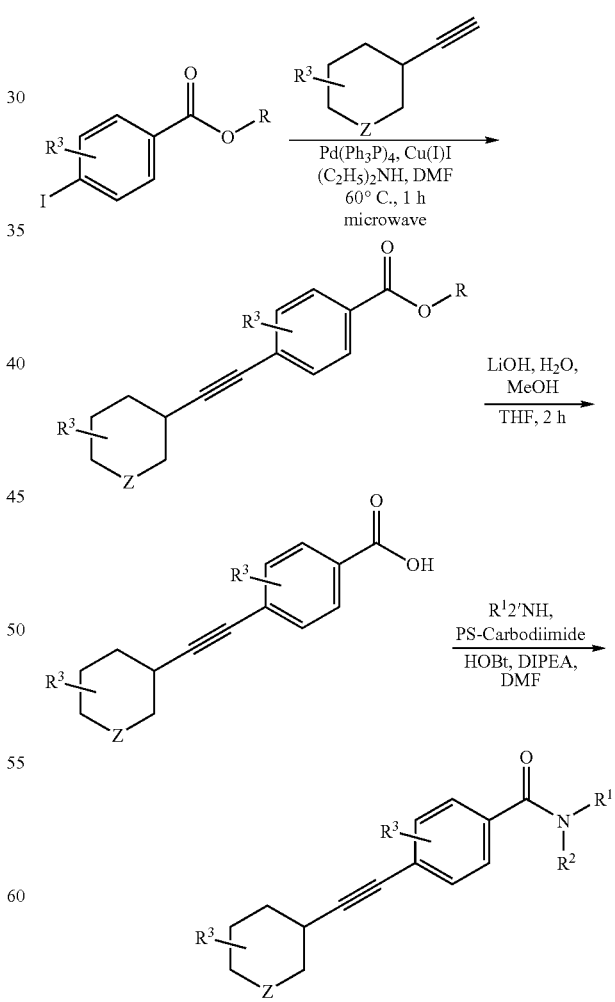

In one aspect, the coupling step is performed prior to the forming step.

In one aspect, the method further comprises the step of converting the carboxyl functionality to a carboxylic acid. In a further aspect, the carboxyl functionality is an ester moiety.

In one aspect, the halide is Br, I, or pseudohalide.

In one aspect, the amine is an optionally substituted primary amine or an optionally substituted secondary amine. In a further aspect, the amine is an optionally substituted cyclic amine.

In one aspect, the coupling step is palladium-catalyzed cross-coupling.

In one aspect, the forming step is performed with PS-carbodiimide and 1-hydroxybenzotriazole.

In one aspect, the aryl halide has a structure represented by a formula:

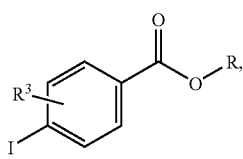

wherein R is optionally substituted alkyl; and wherein $R^3$ comprises four substituents independently selected from hydrogen, halogen, and optionally substituted alkyl.

In one aspect, the cycloalkylacetylene has a structure represented by a formula:

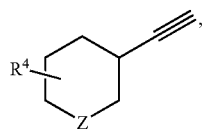

wherein Z comprises from zero to two carbons; and wherein $R^4$ comprises nine to thirteen substituents independently selected from hydrogen, halogen, and optionally substituted alkyl.

It is understood that the method can be used to provide the disclosed compounds.

3. Styrylbenzamide Derivatives

In one aspect, the invention relates to a method for preparing a styrylbenzamide derivative comprising the steps of coupling a styryl bornonic acid or a styryl boronic ester with an aryl halide, wherein one of the styryl bornonic acid or styryl boronic ester or the aryl halide bears a carboxyl functionality; and forming an amide derivative of the carboxyl functionality by reaction with an amine. Typically, a method involves a coupling reaction (e.g., transition metal catalyzed cross coupling reaction) and a reaction forming an amide moiety. Such a method can be represented in the following schematic:

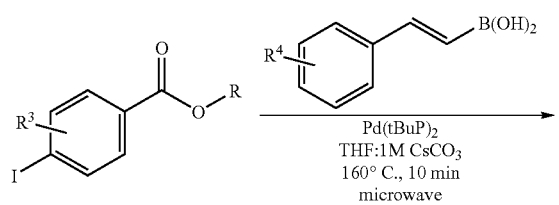

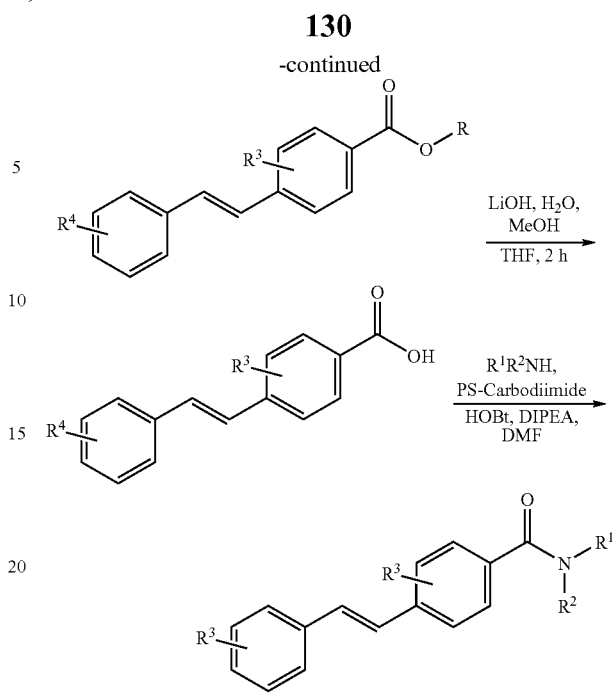

In a further aspect, the method can be represented in the following schematic, which illustrates a synthetic method useful for preparation of larger amounts of the disclosed compounds:

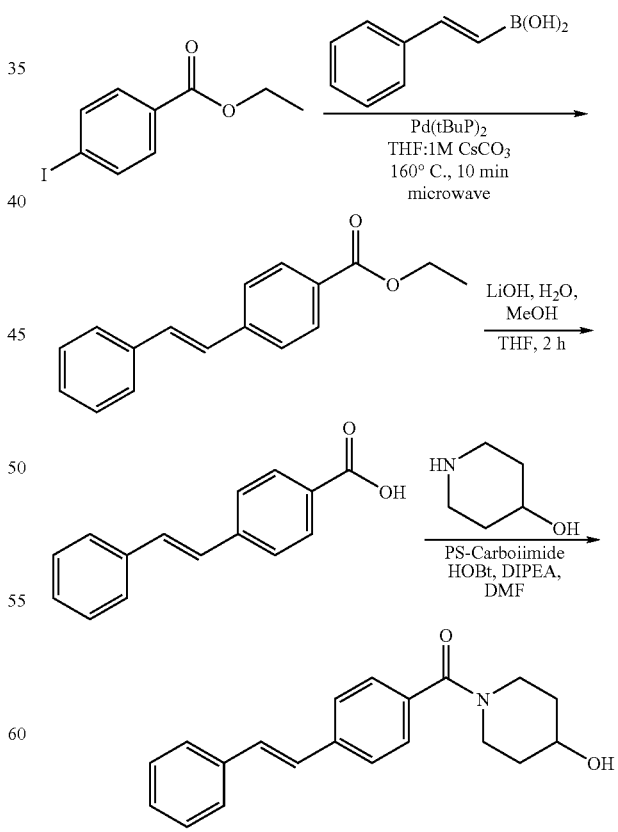

In one aspect, the coupling step is performed prior to the forming step.

In one aspect, the method further comprises the step of converting the carboxyl functionality to a carboxylic acid. In one aspect, the carboxyl functionality is an ester moiety.

In a further aspect, the aryl halide bears the carboxyl functionality.

In one aspect, the halide is Br, I, or pseudohalide.

In one aspect, the amine is an optionally substituted primary amine or an optionally substituted secondary amine. In a further aspect, the amine is an optionally substituted cyclic amine.

In one aspect, the coupling step is palladium-catalyzed cross-coupling.

In one aspect, the forming step is performed with PS-carbodiimide and 1-hydroxybenzotriazole.

In one aspect, the aryl halide has a structure represented by a formula:

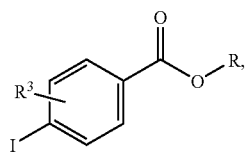

wherein R is optionally substituted alkyl; and wherein $R^3$ comprises four substituents independently selected from hydrogen, halogen, and optionally substituted alkyl.

In one aspect, the styryl bornonic acid or styryl boronic ester has a structure represented by a formula:

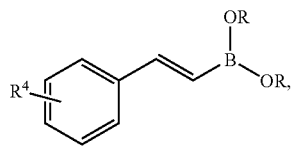

wherein R is H or optionally substituted alkyl; and wherein $R^4$ comprises five substituents independently selected from hydrogen, halogen, and optionally substituted alkyl.

It is understood that the method can be used to provide the disclosed compounds.

4. 4-(3-Phenyl-1,2,4-oxadiazol-5-yl)benzamide derivatives

In one aspect, the invention relates to a method for preparing a 4-(3-phenyl-1,2,4-oxadiazol-5-yl)benzamide derivative comprising the steps of condensing an N'-hydroxybenzimidamide with an aryl carboxylic acid, wherein one of the N'-hydroxybenzimidamide or the aryl carboxylic acid bears an ester functionality; and forming an amide derivative of the ester functionality by reaction with an amine. Typically, a method involves a condensing reaction (e.g., formation of an oxadiazol) and a reaction forming an amide moiety. Such a method can be represented in the following schematic:

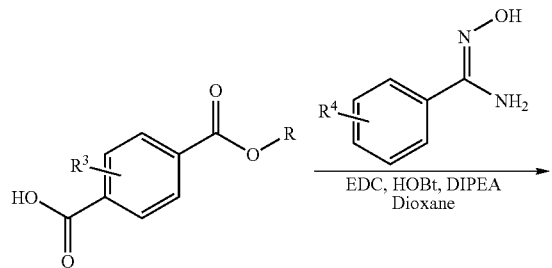

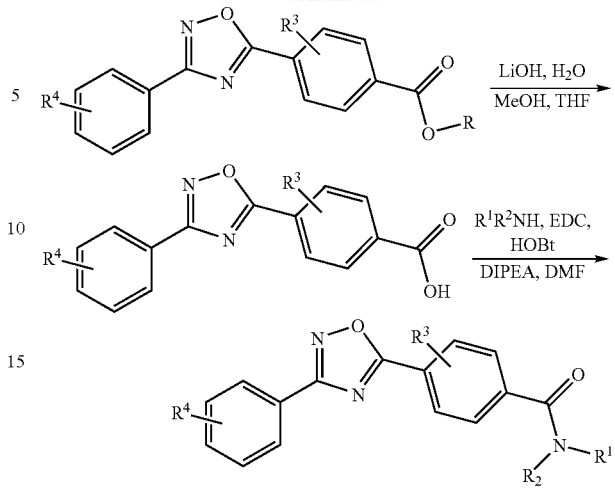

In one aspect, the condensing step is performed prior to the forming step.

In one aspect, the method further comprises the step of converting the ester functionality to a carboxylic acid. In a further aspect, the aryl carboxylic acid bears the ester functionality.

In one aspect, the amine is an optionally substituted primary amine or an optionally substituted secondary amine. In a further aspect, the amine is an optionally substituted cyclic amine.

In one aspect, one or both of the condensing step and the forming step is performed with 1-ethyl-3-[3-dimethylaminopropyl]carbodiimide hydrochloride and 1-hydroxybenzotriazole.

In one aspect, the aryl carboxylic acid has a structure represented by a formula:

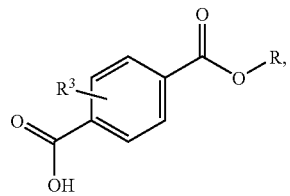

wherein R is optionally substituted alkyl; and wherein $R^3$ comprises four substituents independently selected from hydrogen, halogen, and optionally substituted alkyl.

In one aspect, the N'-hydroxybenzimidamide has a structure represented by a formula:

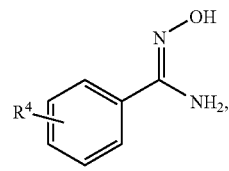

wherein $R^4$ comprises five substituents independently selected from hydrogen, halogen, and optionally substituted alkyl.

It is understood that the method can be used to provide the disclosed compounds.

5. 4-(Pyridinylethynyl)benzamide derivatives

In one aspect, the invention relates to a method for preparing a 4-(pyridinylethynyl)benzamide derivative comprising the steps of coupling an arylacetylene with an aryl halide, wherein one of the arylacetylene or the aryl halide bears a carboxyl functionality; and forming an amide derivative of the carboxyl functionality by reaction with an amine. Typically, a method involves a coupling reaction (e.g., transition metal catalyzed cross coupling reaction) and a reaction forming an amide moiety. Such a method can be represented in the following schematic:

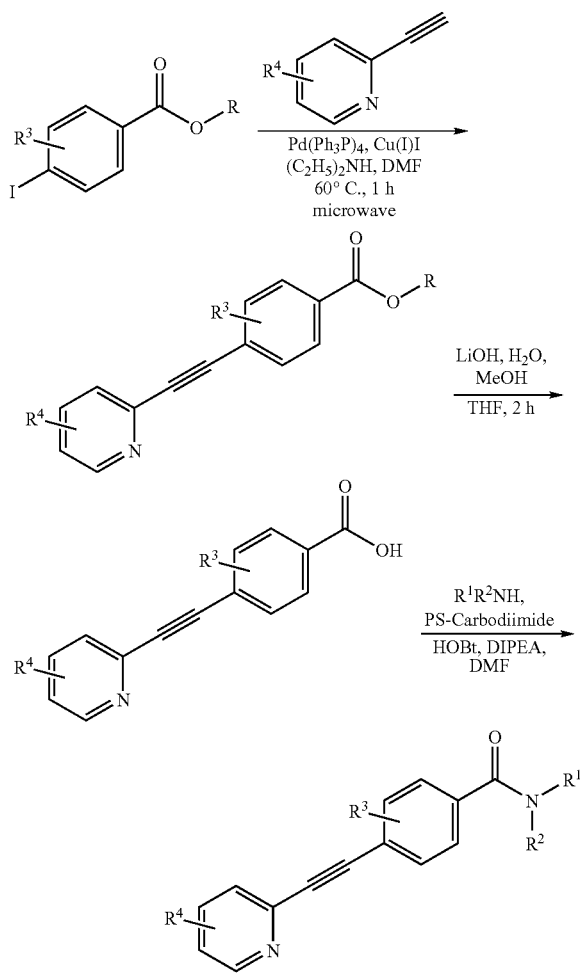

In one aspect, the coupling step is performed prior to the forming step.

In one aspect, the method further comprises the step of converting the carboxyl functionality to a carboxylic acid. In one aspect, the carboxyl functionality is an ester moiety.

In a further aspect, the aryl halide bears the carboxyl functionality.

In one aspect, the halide is Br, I, or pseudohalide.

In one aspect, the amine is an optionally substituted primary amine or an optionally substituted secondary amine. In a further aspect, the amine is an optionally substituted cyclic amine.

In one aspect, the coupling step is palladium-catalyzed cross-coupling.

In one aspect, the forming step is performed with PS-carbodiimide and 1-hydroxybenzotriazole.

In one aspect, the aryl halide has a structure represented by a formula:

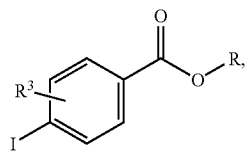

wherein R is optionally substituted alkyl; and wherein $R^3$ comprises four substituents independently selected from hydrogen, halogen, and optionally substituted alkyl.

In one aspect, the arylacetylene has a structure represented by a formula:

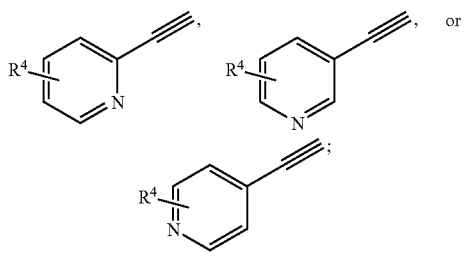

wherein $R^4$ comprises four substituents independently selected from hydrogen, halogen, and optionally substituted alkyl.

It is understood that the method can be used to provide the disclosed compounds.

6. $N^1$-Phenylterephthalamide derivatives

In one aspect, in the invention relates to a method for preparing a $N^1$-phenylterephthalamide derivative comprising the steps of reacting an aniline compound with a benzoic acid compound, wherein the benzoic acid compound bears a carboxyl functionality; and forming an amide derivative of the carboxyl functionality by reaction with an amine. Typically, a method involves two separate reactions forming amide moieties. Such a method can be represented in the following schematic:

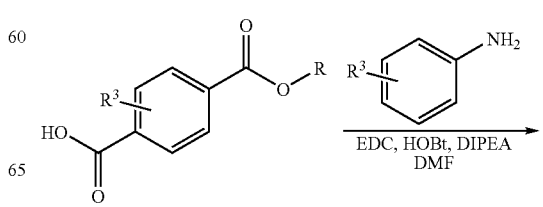

-continued

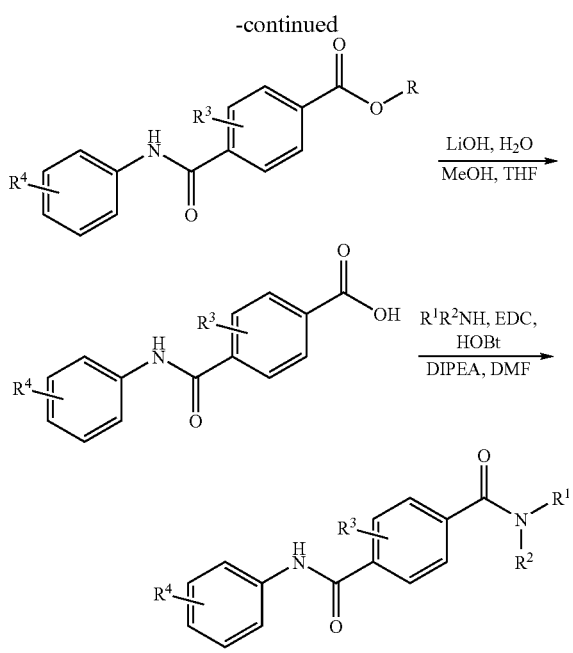

In one aspect, the reacting step is performed prior to the forming step.

In one aspect, the method further comprises the step of converting the carboxyl functionality to a carboxylic acid. In a further aspect, the carboxyl functionality is an ester moiety.

In one aspect, the amine is an optionally substituted primary amine or an optionally substituted secondary amine. In a further aspect, the amine is an optionally substituted cyclic amine.

In one aspect, the reacting step is performed with 1-ethyl-3-[3-dimethylaminopropyl]carbodiimide hydrochloride and 1-hydroxybenzotriazole.

In one aspect, the forming step is performed with 1-ethyl-3-[3-dimethylaminopropyl]carbodiimide hydrochloride and 1-hydroxybenzotriazole.

In one aspect, the benzoic acid compound has a structure represented by a formula:

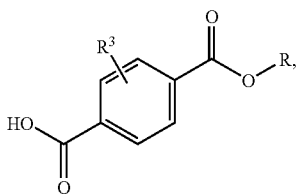

wherein R is optionally substituted alkyl; and wherein $R^3$ comprises four substituents independently selected from hydrogen, halogen, and optionally substituted alkyl.

In one aspect, the aniline compound has a structure represented by a formula:

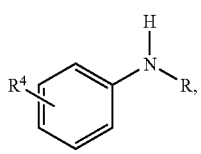

wherein R is H or optionally substituted alkyl; and wherein $R^4$ comprises five substituents independently selected from hydrogen, halogen, and optionally substituted alkyl.

It is understood that the method can be used to provide the disclosed compounds.

F. PHARMACEUTICAL COMPOSITIONS

In one aspect, the invention relates to pharmaceutical compositions comprising the disclosed compounds. For example, the compositions can comprise one or more phenylethynylbenzamide derivatives, cycloalkylethynylbenzamide derivatives, styrylbenzamide derivatives, 4-(3-phenyl-1,2,4-oxadiazol-5-yl)benzamide derivatives, 4-(pyridinylethynyl)benzamide derivatives, and/or $N^1$-phenylterephthalamide derivatives.

In a further aspect, a pharmaceutical composition comprises a therapeutically effective amount of at least one disclosed compound and a pharmaceutically acceptable carrier. In a further aspect, a pharmaceutical composition comprises a therapeutically effective amount of at least one product of a disclosed method and a pharmaceutically acceptable carrier. In a further aspect, a pharmaceutical composition comprising a therapeutically effective amount of at least one phenylethynylbenzamide derivative and a pharmaceutically acceptable carrier. In a further aspect, a pharmaceutical composition comprises a therapeutically effective amount of at least one cycloalkylethynylbenzamide derivative and a pharmaceutically acceptable carrier. In a further aspect, a pharmaceutical composition comprises a therapeutically effective amount of at least one styrylbenzamide derivative and a pharmaceutically acceptable carrier. In a further aspect, a pharmaceutical composition comprises a therapeutically effective amount of at least one 4-(3-phenyl-1,2,4-oxadiazol-5-yl)benzamide derivative and a pharmaceutically acceptable carrier. In a further aspect, a pharmaceutical composition comprises a therapeutically effective amount of at least one 4-(pyridinylethynyl)benzamide derivative and a pharmaceutically acceptable carrier. In a further aspect, a pharmaceutical composition comprises a therapeutically effective amount of at least one $N^1$-phenylterephthalamide derivative and a pharmaceutically acceptable carrier.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in moulds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including antioxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

A potentiated amount of an mGluR agonist to be administered in combination with an effective amount of a compound of formula I is expected to vary from about 0.1 milligram per kilogram of body weight per day (mg/kg/day) to about 100 mg/kg/day and is expected to be less than the amount that is required to provide the same effect when administered without an effective amount of a disclosed compound. Preferred amounts of a co-administered mGluR agonist are able to be determined by one skilled in the art.

The present invention is further directed to a method for the manufacture of a medicament for potenating glutamate receptor activity (e.g., treatment of one or more neurological and/or psychiatric disorder associated with glutamate dysfunction) in mammals (e.g., humans) comprising combining a compound of the present invention with a pharmaceutically acceptable carrier or diluent.

Thus, in one aspect, the invention relates to pharmaceutical compositions comprising the disclosed compounds. That is, a pharmaceutical composition can be provided comprising a therapeutically effective amount of at least one disclosed compound or at least one product of a disclosed method and a pharmaceutically acceptable carrier.

The disclosed pharmaceutical compositions can further comprise other therapeutically active compounds, which are usually applied in the treatment of the above mentioned pathological conditions. For example, the disclosed compounds and compositions can be coadministered with one or more antipsychotic agents. In one aspect, an antipsychotic agent can be any compound that has been shown to be useful or is believed to be useful in treating at least a positive symptom of schizophrenia.

Antipsychotic agents useful in treating at least a positive symptom of schizophrenia include typical antipsychotic agents, atypical antipsychotic agents, and other antipsychotic agents that may or may not be classified as typical or atypical antipsychotic agents. In certain embodiments, an antipsychotic agent is a typical antipsychotic agent. In certain embodiments, an antipsychotic agent is a dopamine D2 receptor antagonist, which may be a selective dopamine D2 receptor antagonist or a partial dopamine D2 receptor antagonist. Typical antipsychotic agents are generally recognized as selective dopamine D2 receptor antagonists.

Antipsychotic agents useful in treating positive symptoms of schizophrenia include, but are not limited to, acetophenazine, alseroxylon, amitriptyline, aripiprazole, astemizole, benzquinamide, carphenazine, chlormezanone, chlorpromazine, chlorprothixene, clozapine, desipramine, droperidol, aloperidol, fluphenazine, flupenthixol, glycine, oxapine, mesoridazine, molindone, olanzapine, ondansetron, perphenazine, pimozide, prochlorperazine, procyclidine, promazine, propiomazine, quetiapine, remoxipride, reserpine, risperidone, sertindole, sulpiride, terfenadine, thiethylperzaine, thioridazine, thiothixene, trifluoperazine, triflupromazine, trimeprazine, and ziprasidone. Examples of typical antipsychotic agents useful for treating positive symptoms of schizophrenia include acetophenazine, chlorpromazine, chlorprothixene, droperidol, fluphenazine, haloperidol, loxapine, mesoridazine, methotrimeprazine, molindone, perphenazine, pimozide, raclopride, remoxipride, thioridazine, thiothixene, and trifluoperazine. Examples of atypical antipsychotic agents useful for treating positive symptoms of schizophrenia include aripiprazole, clozapine, olanzapine, quetiapine, risperidone, sertindole, and ziprasidone.

Other antipsychotic agents useful for treating positive symptoms of schizophrenia include amisulpride, balaperidone, blonanserin, butaperazine, carphenazine, eplavanserin, iloperidone, lamictal, onsanetant, paliperidone, perospirone, piperacetazine, raclopride, remoxipride, sarizotan, sonepiprazole, sulpiride, ziprasidone, and zotepine; serotonin and dopamine (5HT/D2) agonists such as asenapine and bifeprunox; neurokinin 3 antagonists such as talnetant and osanetant; AMPAkines such as CX-516, galantamine, memantine, modafinil, ocaperidone, and tolcapone; and .alpha.-amino acids such as D-serine, D-alanine, D-cycloserine, and N-methylglycine. Thus, antipsychotic agents include typical antipsychotic agents, atypical antipsychotic agents, and other compounds useful for treating schizophrenia in a patient, and particularly useful for treating the positive symptoms of schizophrenia.

Thus, in one aspect, the invention also relates to methods of coadminstering to a mammal at least one disclosed compound and one or more other therapeutically active compounds, which are usually applied in the treatment of the above mentioned pathological conditions. For example, the disclosed methods can relate to coadministration of therapeutically effective amounts of one or more disclosed compound with one or more antipsychotic agents.

In a further aspect, the invention also relates to kits comprising at least one disclosed compound and one or more other therapeutically active compounds, which are usually applied in the treatment of the above mentioned pathological conditions. For example, the disclosed kits can comprise therapeutically effective amounts of one or more disclosed compound and one or more antipsychotic agents. The kits can be co-packaged, co-formulated, and/or co-delivered with the antipsychotic agents. For example, a drug manufacturer, a drug reseller, a physician, or a pharmacist can provide a disclosed kit for delivery to a patient.

In the treatment conditions which require potentiation of metabotropic glutamate receptor activity an appropriate dosage level will generally be about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the from of tablets containing 1.0 to 1000 miligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

It is understood that the disclosed compositions can be employed in the disclosed methods of using.

G. METHODS OF USING THE COMPOUNDS AND COMPOSITIONS

The amino acid L-glutamate (referred to herein simply as glutamate) is the principal excitatory neurotransmitter in the mammalian central nervous system (CNS). Within the CNS, glutamate plays a key role in synaptic plasticity (e.g., long term potentiation (the basis of learning and memory)), motor control and sensory perception. It is now well understood that a variety of neurological and psychiatric disorders, including, but not limited to, schizophrenia general psychosis and cognitive deficits, are associated with dysfunctions in the glutamatergic system. Thus, modulation of the glutamatergic system is an important therapeutic goal. Glutamate acts through two distinct receptors: ionotropic and metabotropic glutamate receptors. The first class, the ionotropic glutamate receptors, are multi-subunit ligand-gated ion channels that mediate excitatory post-synaptic currents. Three subtypes of ionotropic glutamate receptors have been identified, and despite glutamate serving as agonist for all three receptor subtypes, selective ligands have been discovered that activate each subtype. The ionotropic glutamate receptors are named after their respective selective ligands: kainite receptors, AMPA receptors and NMDA receptors.

The second class of glutamate receptor, termed metabotropic glutamate receptors, (mGluRs), are G-protein coupled receptors (GPCRs) that modulate neurotransmitter release or the strength of synaptic transmission, based on their location (pre- or post-synaptic). The mGluRs are family C GPCR, characterized by a large (~560 amino acid) "venus fly trap" agonist binding domain in the amino-terminal domain of the receptor. This unique agonist binding domain distinguishes family C GPCRs from family A and B GPCRs wherein the agonist binding domains are located within the 7-strand transmembrane spanning (7TM) region or within the extracellular loops that connect the strands to this region. To date, eight distinct mGluRs have been identified, cloned and sequenced. Based on structural similarity, primary coupling to intracellular signaling pathways and pharmacology, the mGluRs have been assigned to three groups: Group I (mGluR1 and mGluR5), Group II (mGluR2 and mGluR3) and Group III (mGluR4, mGluR6, mGluR7 and mGluR8). Group I mGluRs are coupled through Gαq/11 to increase inositol phosphate and metabolism and resultant increases in intracellular calcium. Group I mGluRs are primarily located post-synaptically and have a modulatory effect on ion channel activity and neuronal excitability. Group II (mGluR2 and mGluR3) and Group III (mGluR4, mGluR6, mGluR7 and mGluR8) mGluRs are primarily located pre-synaptically where they regulate the release of neurotransmitters, such as glutamate. Group II and Group III mGluRs are coupled to G☐i and its associated effectors such as adenylate cyclase.

Post-synaptic mGluRs are known to functionally interact with post-synaptic ionotropic glutamate receptors, such as the NMDA receptor. For example, activation of mGluR5 by a selective agonist has been shown to increase post-synaptic NMDA currents (Mannaioni et. al. J. Neurosci. 21:5925-5934 (2001)). Therefore, modulation of mGluRs is an approach to modulating glutamatergic transmission. Numerous reports indicate that mGluR5 plays a role in a number of disease states including anxiety (Spooren et. al. J. Pharmacol. Exp. Therapeut. 295:1267-1275 (2000), Tatarczynska et al. Br. J. Pharmacol. 132:1423-1430 (2001)), schizophrenia (reviewed in Chavez-Noriega et al. Curr. Drug Targets: CNS & Neurological Disorders 1:261-281 (2002), Kinney, G. G. et al. J. Pharmacol. Exp. Therapeut. 313:199-206 (2005), addiction to cocaine (Chiamulera et al. Nature Neurosci. 4:873-874 (2001), Parkinson's disease (Awad et al. J. Neurosci. 20:7871-7879 (2000), Ossowska et al. Neuropharmacol. 41:413-420 (2001) and pain (Salt and Binns Neurosci. 100:375-380 (2001).

In some aspects, the mGluR of the disclosed methods is a type I mGluR. In some aspects, the mGluR of the disclosed methods is mGluR5.

1. Treatment Methods

The compounds disclosed herein are useful for treating, preventing, ameliorating, controlling or reducing the risk of a variety of neurological and psychiatric disorders associated with glutamate dysfunction. Thus, provided is a method of treating or preventing a disorder in a subject comprising the step of administering to the subject at least one disclosed compound; at least one disclosed pharmaceutical composition; and/or at least one disclosed product in a dosage and amount effective to treat the disorder in the subject.

Also provided is a method for the treatment of one or more neurological and/or psychiatric disorders associated with glutamate dysfunction in a subject comprising the step of administering to the subject at least one disclosed compound; at least one disclosed pharmaceutical composition; and/or at least one disclosed product in a dosage and amount effective to treat the disorder in the subject.

Examples of disorders associated with glutamate dysfunction include: acute and chronic neurological and psychiatric disorders such as cerebral deficits subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, ocular damage, retinopathy, cognitive disorders, idiopathic and drug-induced Parkinson's disease, muscular spasms and disorders associated with muscular spasticity including tremors, epilepsy, convulsions, migraine (including migraine headache), urinary incontinence, substance tolerance, addictive behavior, including addiction to substances (including opiates, nicotine, tobacco products, alcohol, benzodiazepines, cocaine, sedatives, hypnotics, etc.), withdrawal from such addictive substances (including substances such as opiates, nicotine, tobacco products, alcohol, benzodiazepines, cocaine, sedatives, hypnotics, etc.), obesity, psychosis, schizophrenia, anxiety (including generalized anxiety disorder, panic disorder, and obsessive compulsive disorder), mood disorders (including depression, mania, bipolar disorders), trigeminal neuralgia, hearing loss, tinnitus, macular degeneration of the eye, emesis, brain edema, pain (including acute and chronic pain states, severe pain, intractable pain, neuropathic pain, and post-traumatic pain), tardive dyskinesia, sleep disorders (including narcolepsy), attention deficit/hyperactivity disorder, and conduct disorder.

Anxiety disorders that can be treated or prevented by the compositions disclosed herein include generalized anxiety disorder, panic disorder, and obsessive compulsive disorder. Addictive behaviors include addiction to substances (including opiates, nicotine, tobacco products, alcohol, benzodiazepines, cocaine, sedatives, hypnotics, etc.), withdrawal from such addictive substances (including substances such as opiates, nicotine, tobacco products, alcohol, benzodiazepines, cocaine, sedatives, hypnotics, etc.) and substance tolerance.

Thus, in some aspects of the disclosed method, the disorder is dementia, delirium, amnestic disorders, age-related cognitive decline, schizophrenia, psychosis including schizophrenia, schizophreniform disorder, schizoaffective disorder, delusional disorder, brief psychotic disorder, substance-related disorder, movement disorders, epilepsy, chorea, pain, migraine, diabetes, dystonia, obesity, eating disorders, brain edema, sleep disorder, narcolepsy, anxiety, affective disorder, panic attacks, unipolar depression, bipolar disorder, psychotic depression.

Thus, provided is a method for treating or prevention schizophrenia, comprising: administering to a subject at least one disclosed compound; at least one disclosed pharmaceutical composition; and/or at least one disclosed product in a dosage and amount effective to treat the disorder in the subject. At present, the fourth edition of the Diagnostic and Statistical Manual of Mental Disorders (DSM-IV) (1994, American Psychiatric Association, Washington, D.C.), provides a diagnostic tool including schizophrenia and related disorders.

Also provided is a method for treating or prevention anxiety, comprising: administering to a subject at least one disclosed compound; at least one disclosed pharmaceutical composition; and/or at least one disclosed product in a dosage and amount effective to treat the disorder in the subject. At present, the fourth edition of the Diagnostic and Statistical Manual of Mental Disorders (DSM-IV) (1994, American Psychiatric Association, Washington, D.C.), provides a diagnostic tool including anxiety and related disorders. These include: panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder and anxiety disorder not otherwise specified.

a. Potentiation of Metabotropic Glutamate Receptor Activity

In one aspect, the invention relates to a method for potentiation of metabotropic glutamate receptor activity in a mammal comprising the step of administering to the mammal at least one compound having a structure represented by a formula:

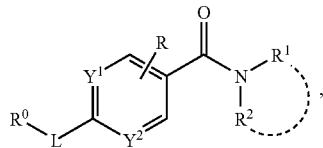

wherein ----- is an optional covalent bond; wherein $Y^1$ and $Y^2$ are independently selected from N and C—R; wherein R comprises two to four substituents independently selected from hydrogen, halogen, hydroxyl, cyano, nitro, thiol, or an organic radical comprising 1 to 12 carbon atoms; wherein $R^1$ and $R^2$ are independently hydrogen or an optionally substituted organic radical comprising from 1 to 12 carbon atoms; wherein $R^0$ is an optionally substituted organic radical comprising 4 to 14 carbon atoms; and wherein L is an organic divalent radical comprising 1 to 7 carbon atoms and is selected from:

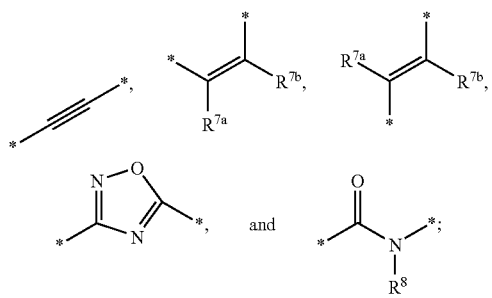

wherein $R^{7a}$ and $R^{7b}$ together form an optionally substituted carbocyclic or heterocyclic ring having from two to five carbons or are independently selected from hydrogen, halogen, hydroxyl, cyano, nitro, thiol, amino, and an organic radical comprising 1 to 5 carbon atoms selected from optionally substituted C1-C5 alkyl or C2-C5 alkenyl or C2-C5 alkynyl, optionally substituted C1-C5 heteroalkyl or C2-C5 heteroalkenyl or C2-C5 heteroalkynyl, optionally substituted C3-C5 cycloalkyl or C3-C5 cycloalkenyl, optionally substituted C3-C5 heterocycloalkyl or C3-C5 heterocycloalkenyl, optionally substituted aryl, optionally substituted heteroaryl, optionally substituted alkoxyl, optionally substituted thioalkyl, optionally substituted alkylsulfinyl, optionally substituted alkylsulfonyl, and optionally substituted amino, thioamido, amidosulfonyl, alkoxycarbonyl, carboxamide, aminocarbonyl, and alkylamine-carbonyl; or a pharmaceutically acceptable salt or N-oxide thereof, in a dosage and amount effective to potentiate metabotropic glutamate receptor activity in the mammal.

In one aspect, the mammal is a human. In a further aspect, the method further comprises identifying a mammal with a need for potentiation of metabotropic glutamate receptor activity. In a further aspect, the mammal has a need for potentiation of metabotropic glutamate receptor activity prior to administration. In a further aspect, the mammal has been diagnosed with a need for potentiation of metabotropic glutamate receptor activity prior to administration.

b. Partial Agonism of Metabotropic Glutamate Receptor Activity

In one aspect, the invention relates to a method for partial agonism of metabotropic glutamate receptor activity in a mammal comprising the step of administering to the mammal at least one compound having a structure represented by a formula:

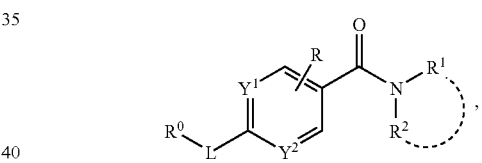

wherein each ----- is an optional covalent bond; wherein $Y^1$ and $Y^2$ are independently selected from N and C—R; wherein R comprises two to four substituents independently selected from hydrogen, halogen, hydroxyl, cyano, nitro, thiol, or an organic radical comprising 1 to 12 carbon atoms; wherein $R^1$ and $R^2$ are independently hydrogen or an optionally substituted organic radical comprising from 1 to 12 carbon atoms; wherein $R^0$ is an optionally substituted organic radical comprising 4 to 14 carbon atoms, wherein L is an organic divalent radical comprising 1 to 7 carbon atoms and is selected from:

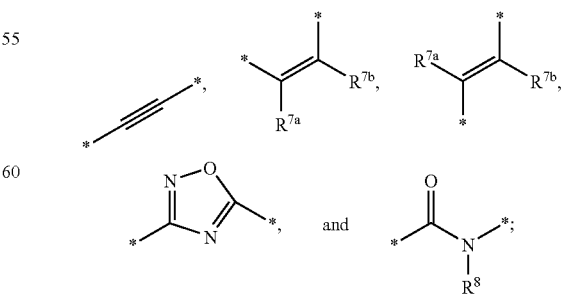

wherein $R^{7a}$ and $R^{7b}$ together form an optionally substituted carbocyclic or heterocyclic ring having from two to five carbons or are independently selected from hydrogen, halogen, hydroxyl, cyano, nitro, thiol, amino, and an organic radical comprising 1 to 5 carbon atoms selected from optionally substituted C1-C5 alkyl or C2-C5 alkenyl or C2-C5 alkynyl, optionally substituted C1-C5 heteroalkyl or C2-C5 heteroalkenyl or C2-C5 heteroalkynyl, optionally substituted C3-C5 cycloalkyl or C3-C5 cycloalkenyl, optionally substituted C3-C5 heterocycloalkyl or C3-C5 heterocycloalkenyl, optionally substituted aryl, optionally substituted heteroaryl, optionally substituted alkoxyl, optionally substituted thioalkyl, optionally substituted alkylsulfinyl, optionally substituted alkylsulfonyl, and optionally substituted amino, thioamido, amidosulfonyl, alkoxycarbonyl, carboxamide, aminocarbonyl, and alkylamine-carbonyl; or a pharmaceutically acceptable salt or N-oxide thereof, in a dosage and amount effective to exhibit partial agonism of metabotropic glutamate receptor activity in the mammal.

In one aspect, $Y^1$ is selected from N and C—$R^4$. In a further aspect, $Y^2$ is selected from N and C—H. In a further aspect, each $R^{3a}$ and $R^{3b}$ is independently hydrogen, halogen, hydroxyl, cyano, nitro, thiol, amino, or an organic radical comprising 1 to 6 carbon atoms. In a further aspect, $R^4$ is hydrogen, halogen, hydroxyl, cyano, nitro, thiol, or an organic radical comprising 1 to 12 carbon atoms.

In a further aspect, L is an organic divalent radical comprising 1 to 7 carbon atoms and is selected from:

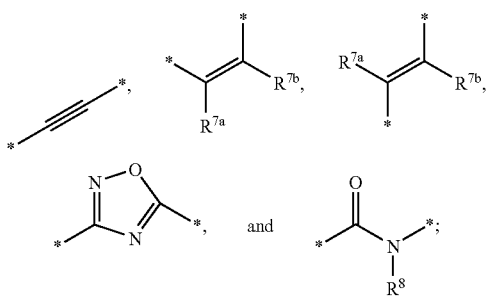

wherein $R^{7a}$ and $R^{7b}$ together form an optionally substituted carbocyclic or heterocyclic ring having from two to five carbons or are independently selected from hydrogen, halogen, hydroxyl, cyano, nitro, thiol, amino, and an organic radical comprising 1 to 5 carbon atoms selected from optionally substituted C1-C5 alkyl or C2-C5 alkenyl or C2-C5 alkynyl, optionally substituted C1-C5 heteroalkyl or C2-C5 heteroalkenyl or C2-C5 heteroalkynyl, optionally substituted C3-C5 cycloalkyl or C3-C5 cycloalkenyl, optionally substituted C3-C5 heterocycloalkyl or C3-C5 heterocycloalkenyl, optionally substituted aryl, optionally substituted heteroaryl, optionally substituted alkoxyl, optionally substituted thioalkyl, optionally substituted alkylsulfinyl, optionally substituted alkylsulfonyl, and optionally substituted amino, thioamido, amidosulfonyl, alkoxycarbonyl, carboxamide, aminocarbonyl, and alkylamine-carbonyl; and wherein $R^8$ is selected from hydrogen, and an organic radical comprising 1 to 6 carbon atoms selected from optionally substituted C1-C6 alkyl or C2-C6 alkenyl or C2-C6 alkynyl, optionally substituted C1-C6 heteroalkyl or C2-C6 heteroalkenyl or C2-C6 heteroalkynyl, optionally substituted C3-C6 cycloalkyl or C3-C6 cycloalkenyl or C6 cycloalkynyl, optionally substituted C3-C6 heterocycloalkyl or C3-C6 heterocycloalkenyl or C6 heterocycloalkynyl, optionally substituted aryl, and optionally substituted heteroaryl.

In one aspect, the mammal is a human. In a further aspect, the method further comprises identifying a mammal with a need for partial agonism of metabotropic glutamate receptor activity. In a further aspect, the mammal has a need for partial agonism of metabotropic glutamate receptor activity prior to administration. In a further aspect, the mammal has been diagnosed with a need for partial agonism of metabotropic glutamate receptor activity prior to administration.

c. Treatment of a Disorder in a Mammal

In one aspect, the invention relates to a method for the treatment of a neurological and/or psychiatric disorder associated with glutamate dysfunction in a mammal comprising the step of administering to the mammal at least one compound having a structure represented by a formula:

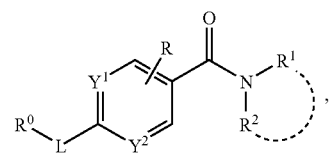

wherein ----- is an optional covalent bond; wherein $Y^1$ and $Y^2$ are independently selected from N and C—R; wherein R comprises two to four substituents independently selected from hydrogen, halogen, hydroxyl, cyano, nitro, thiol, or an organic radical comprising 1 to 12 carbon atoms; wherein $R^1$ and $R^2$ are independently hydrogen or an optionally substituted organic radical comprising from 1 to 12 carbon atoms; wherein $R^0$ is an optionally substituted organic radical comprising 4 to 14 carbon atoms, wherein L is an organic divalent radical comprising 1 to 7 carbon atoms and is selected from:

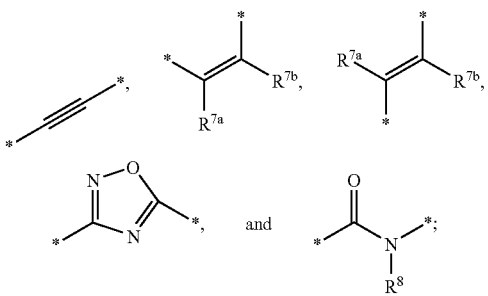

wherein $R^{7a}$ and $R^{7b}$ together form an optionally substituted carbocyclic or heterocyclic ring having from two to five carbons or are independently selected from hydrogen, halogen, hydroxyl, cyano, nitro, thiol, amino, and an organic radical comprising 1 to 5 carbon atoms selected from optionally substituted C1-C5 alkyl or C2-C5 alkenyl or C2-C5 alkynyl, optionally substituted C1-C5 heteroalkyl or C2-C5 heteroalkenyl or C2-C5 heteroalkynyl, optionally substituted C3-C5 cycloalkyl or C3-C5 cycloalkenyl, optionally substituted C3-C5 heterocycloalkyl or C3-C5 heterocycloalkenyl, optionally substituted aryl, optionally substituted heteroaryl, optionally substituted alkoxyl, optionally substituted thioalkyl, optionally substituted alkylsulfinyl, optionally substituted alkylsulfonyl, and optionally substituted amino, thioamido, amidosulfonyl, alkoxycarbonyl, carboxamide, aminocarbonyl, and alkylamine-carbonyl; and wherein $R^8$ is selected from hydrogen, and an organic radical comprising 1 to 6 carbon atoms selected from optionally substituted C1-C6 alkyl or C2-C6 alkenyl or C2-C6 alkynyl, optionally substituted C1-C6 heteroalkyl or C2-C6 heteroalkenyl or C2-C6 heteroalkynyl, optionally substituted C3-C6 cycloalkyl or C3-C6 cycloalkenyl or C6 cycloalkynyl, optionally substituted C3-C6 heterocycloalkyl or C3-C6 heterocycloalkenyl or C6 heterocycloalkynyl, optionally substituted aryl, and optionally substituted heteroaryl; or a pharmaceutically acceptable salt or N-oxide thereof, in a dosage and amount effective to treat the neurological and/or psychiatric disorder associated with glutamate dysfunction in the mammal.

In one aspect, the mammal is a human. In a further aspect, the method further comprises identifying a mammal with a need for treatment of the disorder. In a further aspect, the mammal has a need for treatment of the disorder prior to administration. In a further aspect, the mammal has been diagnosed with a need for treatment of the disorder prior to administration.

In one aspect, the disorder is one or more neurological and/or psychiatric disorder associated with glutamate dysfunction in the mammal. For example, the disorder can be one or more of dementia, delirium, amnestic disorders, age-related cognitive decline, schizophrenia, psychosis including schizophrenia, schizophreniform disorder, schizoaffective disorder, delusional disorder, brief psychotic disorder, substance-related disorder, movement disorders, epilepsy, chorea, pain, migraine, diabetes, dystonia, obesity, eating disorders, brain edema, sleep disorder, narcolepsy, anxiety, affective disorder, panic attacks, unipolar depression, bipolar disorder, and psychotic depression.

In a further aspect, $Y^1$ is selected from N and C—$R^4$. In a further aspect, $Y^2$ is selected from N and C—H. In a further aspect, each $R^{3a}$ and $R^{3b}$ is independently hydrogen, halogen, hydroxyl, cyano, nitro, thiol, amino, or an organic radical comprising 1 to 6 carbon atoms. In a further aspect, $R^4$ is hydrogen, halogen, hydroxyl, cyano, nitro, thiol, or an organic radical comprising 1 to 12 carbon atoms.

In a further aspect, L is an organic divalent radical comprising 1 to 7 carbon atoms and is selected from:

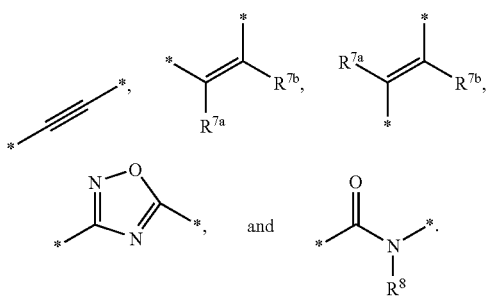

In a further aspect, $R^{7a}$ and $R^{7b}$ together form an optionally substituted carbocyclic or heterocyclic ring having from two to five carbons or are independently selected from hydrogen, halogen, hydroxyl, cyano, nitro, thiol, amino, and an organic radical comprising 1 to 5 carbon atoms selected from optionally substituted C1-C5 alkyl or C2-C5 alkenyl or C2-C5 alkynyl, optionally substituted C1-C5 heteroalkyl or C2-C5 heteroalkenyl or C2-C5 heteroalkynyl, optionally substituted C3-C5 cycloalkyl or C3-C5 cycloalkenyl, optionally substituted C3-C5 heterocycloalkyl or C3-C5 heterocycloalkenyl, optionally substituted aryl, optionally substituted heteroaryl, optionally substituted alkoxyl, optionally substituted thioalkyl, optionally substituted alkylsulfinyl, optionally substituted alkylsulfonyl, and optionally substituted amino, thioamido, amidosulfonyl, alkoxycarbonyl, carboxamide, aminocarbonyl, and alkylamine-carbonyl.

In a further aspect, $R^8$ is selected from hydrogen, and an organic radical comprising 1 to 6 carbon atoms selected from optionally substituted C1-C6 alkyl or C2-C6 alkenyl or C2-C6 alkynyl, optionally substituted C1-C6 heteroalkyl or C2-C6 heteroalkenyl or C2-C6 heteroalkynyl, optionally substituted C3-C6 cycloalkyl or C3-C6 cycloalkenyl or C6 cycloalkynyl, optionally substituted C3-C6 heterocycloalkyl or C3-C6 heterocycloalkenyl or C6 heterocycloalkynyl, optionally substituted aryl, and optionally substituted heteroaryl.

In a further aspect, the disorder is a neurological and/or psychiatric disorder associated with glutamate dysfunction. In a further aspect, the disorder is selected from dementia, delirium, amnestic disorders, age-related cognitive decline, schizophrenia, psychosis including schizophrenia, schizophreniform disorder, schizoaffective disorder, delusional disorder, brief psychotic disorder, substance-related disorder, movement disorders, epilepsy, chorea, pain, migraine, diabetes, dystonia, obesity, eating disorders, brain edema, sleep disorder, narcolepsy, anxiety, affective disorder, panic attacks, unipolar depression, bipolar disorder, and psychotic depression.

In one aspect, the mammal is a human. In a further aspect, the mammal has been diagnosed with a need for treatment of the disorder prior to the administering step.

d. Enhancing Cognition

Schizophrenia symptoms can be classified as positive, negative, or cognitive. Positive symptoms of schizophrenia include delusion and hallucination, which can be measured using, for example, the Positive and Negative Syndrome Scale (PANSS) (see Kay et al., 1987, Schizophrenia Bulletin 13, 261-276). Negative symptoms of schizophrenia include affect blunting, anergia, alogia, and social withdrawal, which can be measured for example, using the Scales for the Assessment of Negative Symptoms (SANS) (see Andreasen, 1983, Scales for the Assessment of Negative Symptoms, Iowa City, Iowa). Cognitive symptoms of schizophrenia include impairment in obtaining, organizing, and using intellectual knowledge which can be measured using the Positive and Negative Syndrome Scale-cognitive subscale (PANSS-cognitive subscale) (Lindenmayer et al., J Nerv Ment Dis 1994, 182, 631-638) or by assessing the ability to perform cognitive tasks such as, for example, using the Wisconsin Card Sorting Test (see, e.g., Green et al., Am J Psychiatry 1992, 149, 162-67; and Koren et al., Schizophr Bull 2006, 32(2), 310-26).

In one aspect, the invention relates to a method for enhancing cognition in a mammal comprising the step of administering to the mammal at least one compound having a structure represented by a formula:

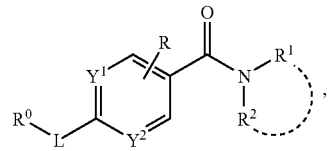

wherein each ----- is an optional covalent bond; wherein $Y^1$ and $Y^2$ are independently selected from N and C—R; wherein R comprises two to four substituents independently selected from hydrogen, halogen, hydroxyl, cyano, nitro, thiol, or an organic radical comprising 1 to 12 carbon atoms; wherein $R^1$ and $R^2$ are independently hydrogen or an optionally substituted organic radical comprising from 1 to 12 carbon atoms;

wherein R⁰ is an optionally substituted organic radical comprising 4 to 14 carbon atoms, wherein L is an organic divalent radical comprising 1 to 7 carbon atoms and is selected from:

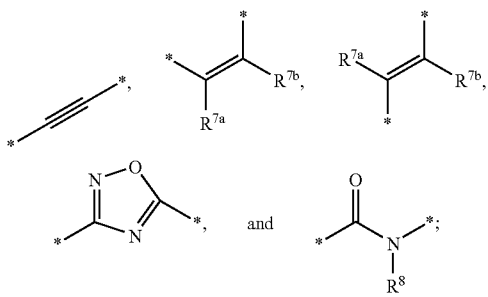

wherein R$^{7a}$ and R$^{7b}$ together form an optionally substituted carbocyclic or heterocyclic ring having from two to five carbons or are independently selected from hydrogen, halogen, hydroxyl, cyano, nitro, thiol, amino, and an organic radical comprising 1 to 5 carbon atoms selected from optionally substituted C1-C5 alkyl or C2-C5 alkenyl or C2-C5 alkynyl, optionally substituted C1-C5 heteroalkyl or C2-C5 heteroalkenyl or C2-C5 heteroalkynyl, optionally substituted C3-C5 cycloalkyl or C3-C5 cycloalkenyl, optionally substituted C3-C5 heterocycloalkyl or C3-C5 heterocycloalkenyl, optionally substituted aryl, optionally substituted heteroaryl, optionally substituted alkoxyl, optionally substituted thioalkyl, optionally substituted alkylsulfinyl, optionally substituted alkylsulfonyl, and optionally substituted amino, thioamido, amidosulfonyl, alkoxycarbonyl, carboxamide, aminocarbonyl, and alkylamine-carbonyl; or a pharmaceutically acceptable salt or N-oxide thereof, in a dosage and amount effective to enhance cognition in the mammal.

In one aspect, the mammal is a human. In a further aspect, the method further comprises identifying a mammal with a need for enhancing cognition. In a further aspect, the mammal has a need for enhancing cognition prior to administration. In a further aspect, the mammal has been diagnosed with a need for enhancing cognition prior to administration.

Figure 11:
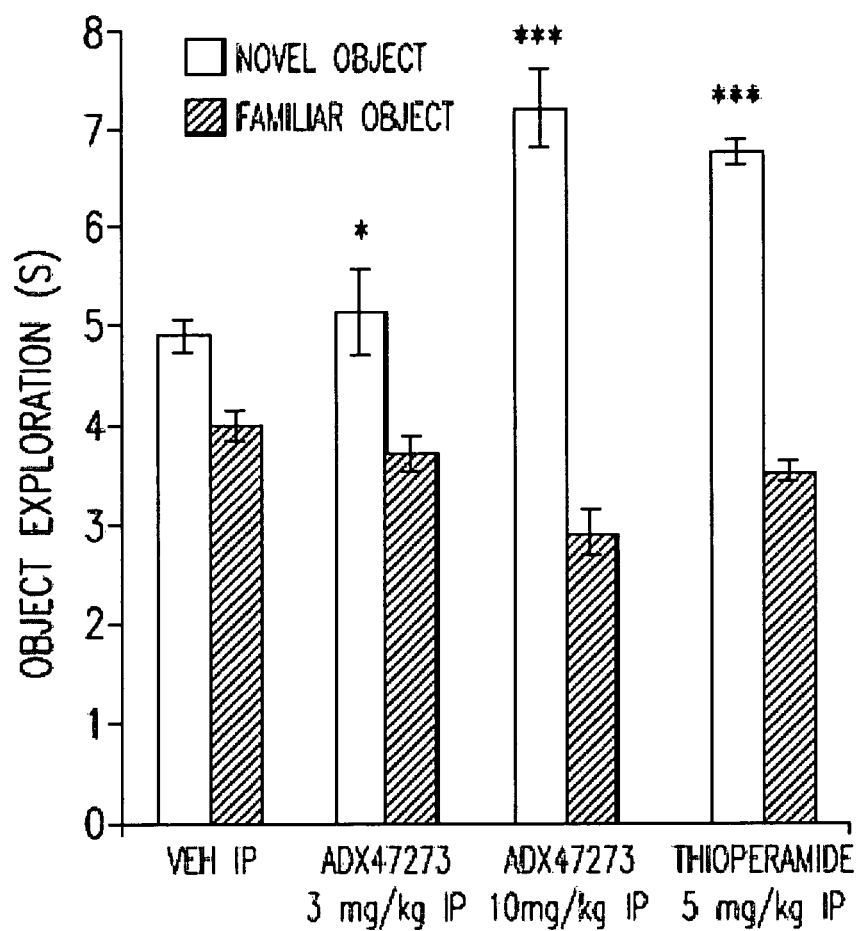
FIG. 11 shows cognitive improvement in a novel object recognition (NOR) paradigm by ADX47273.
Figure 17:
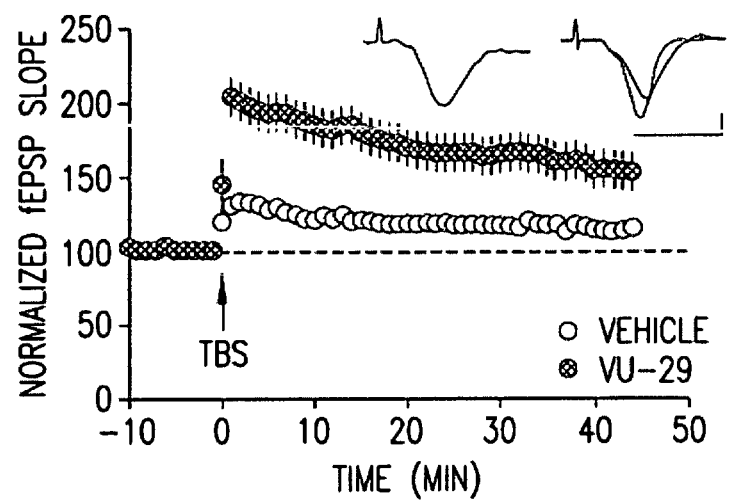
FIG. 17 shows the increase in strength of synaptic connections after applying a stimulus to the synapse in the absence and presence of two structurally distinct mGluR5 PAMs, VU29 (top panel) and ADX47273 (bottom panel).
Figure 17:
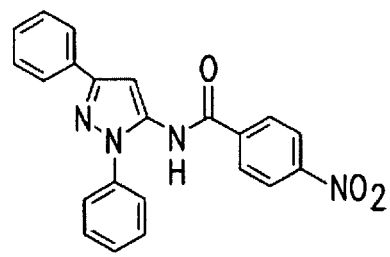
Figure 17:
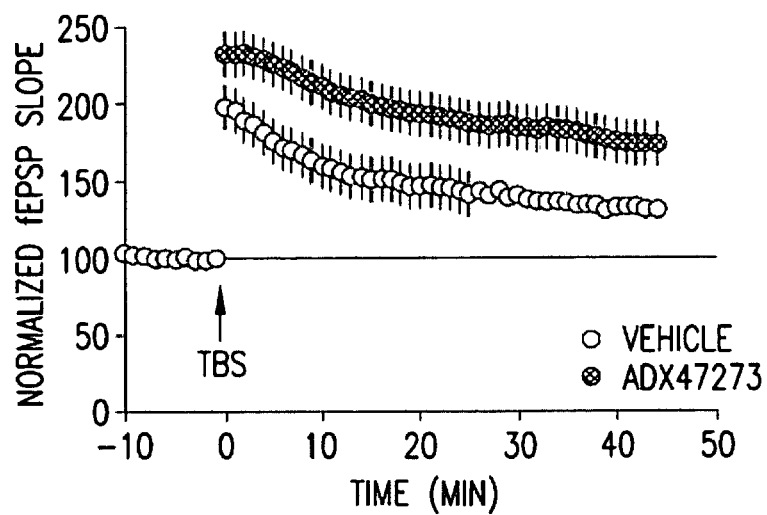

In a further aspect, the cognition enhancement is a statistically significant increase in Novel Object Recognition. In a further aspect, the cognition enhancement is a statistically significant increase in synaptic plasticity. In a further aspect, the cognition enhancement is a statistically significant increase in performance of the Wisconsin Card Sorting Test.

mGluR5 potentiation has also been linked to improvement of cognition (Kinney, G. G.; O'Brien, Lemaire, W.; Burno, M.' Bickel, D. J.; Clements, M. K.; Wisnoski, D. D.; Lindsley, C. W.; Tiller, P. R.; Smith, S.; Jacobson, M. A.; Sur, C.; Duggan, M. E.; Pettibone, D. J.; Williams, Jr., D. W. 'A novel selective allosteric modulator of metabotropic glutamate receptor subtype 5 (mGluR5) has an antipsychotic profile in rat behavioral models' *J. Pharmacol. Exp. Therapeut.* 2005, 313(1), 199; Lindsley, C. W.; Wisnoski, D. D.; Leister, W. H.; O'Brien, J. A.; Lemiare, W.; Williams, Jr., D. L.; Burno, M.; Sur, C.; Kinney, G. G.; Pettibone, D. J.; iller, P. R.; Smith, S.; Duggan, M. E.; Hartman, G. D.; Conn, P. J.; Huff, J. R. 'Discovery of positive allosteric modulators for the metabotropic glutamate receptor subtype from a series of N-(1,3-Diphenyl-1H-pyrazol-5-yl)benzamides that potentiate receptor function in vivo' *J. Med. Chem.* 2004, 47, 5825; Epping-Jordan M. P., Nayak, S., Derouet, F., Dominguez, H., Bessis A. S., Le Poul E., Ludwig B. L. Mutel V., Poli S. M. and Rocher J. P. In Vivo Characterization of mGluR5 Positive Allosteric Modulators as Novel Treatments for Schizophrenia and Cognitive Dysfunction *Neuropharmacology* 2005, 49, 243.). This theory was validated in a cellular model of the long lasting changes in transmission of synaptic transmission that are thought to underlie multiple forms of learning and memory. This model is termed hippocampal long term potentiation (LTP) and involves measurements of strengthen in synaptic connections between neurons in the brain that are critical for learning to occur. FIG. 17 shows the increase in strength of synaptic connections after applying a stimulus to the synapse in the absence and presence of two structurally distinct mGluR5 PAMs, VU29 (top panel) and ADX47273 (bottom panel). Both PAMs induced a robust increase in synaptic connections in a manner that would be predicted to enhance learning and memory. This could provide an approach to improving cognition in disorders involving impaired cognitive function, including schizophrenia, Alzheimers disease, Parkinson's disease, and multiple other human brain disorders. A representative mGluR5 PAM that enhances hippocampal LTP is also active in preclinical cognition model of Novel Object Recognition (NOR) wherein the mGluR5 PAM, ADX47273, displaying a robust and significant improvement in NOR, equivalent to the known cognitive enhancing H3 antagonist Thioperide (FIG. 11).

2. Manufacture of a Medicament

Also provided is a method for the manufacture of a medicament for treatment of a disorder in a mammal, for partial agonism of metabotropic glutamate receptor activity in a mammal, for enhancing cognition in a mammal, and/or for potentiation of metabotropic glutamate receptor activity in a mammal comprising combining at least one compound having a structure:

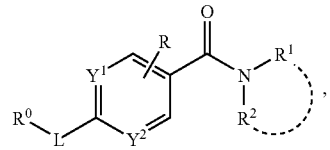

wherein ----- is an optional covalent bond; wherein Y$^1$ and Y$^2$ are independently selected from N and C—R; wherein R comprises two to four substituents independently selected from hydrogen, halogen, hydroxyl, cyano, nitro, thiol, or an organic radical comprising 1 to 12 carbon atoms; wherein R$^1$ and R$^2$ are independently hydrogen or an optionally substituted organic radical comprising from 1 to 12 carbon atoms; wherein R⁰ is an optionally substituted organic radical comprising 4 to 14 carbon atoms; and wherein L is an organic divalent radical comprising 1 to 7 carbon atoms and is selected from:

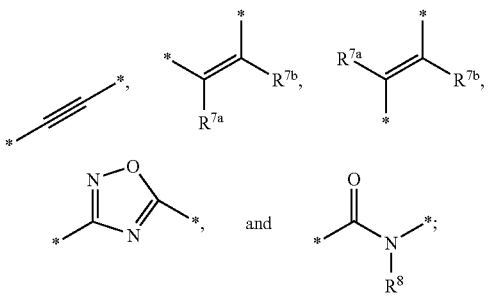

wherein R$^{7a}$ and R$^{7b}$ together form an optionally substituted carbocyclic or heterocyclic ring having from two to five carbons or are independently selected from hydrogen, halogen, hydroxyl, cyano, nitro, thiol, amino, and an organic radical comprising 1 to 5 carbon atoms selected from optionally substituted C1-C5 alkyl or C2-C5 alkenyl or C2-C5 alkynyl, optionally substituted C1-C5 heteroalkyl or C2-C5 heteroalkenyl or C2-C5 heteroalkynyl, optionally substituted C3-C5 cycloalkyl or C3-C5 cycloalkenyl, optionally substituted C3-C5 heterocycloalkyl or C3-C5 heterocycloalkenyl, optionally substituted aryl, optionally substituted heteroaryl, optionally substituted alkoxyl, optionally substituted thioalkyl, optionally substituted alkylsulfinyl, optionally substituted alkylsulfonyl, and optionally substituted amino, thioamido, amidosulfonyl, alkoxycarbonyl, carboxamide, aminocarbonyl, and alkylamine-carbonyl; or a pharmaceutically acceptable salt or N-oxide thereof, with a pharmaceutically acceptable carrier.

3. Use of Compounds

Also provided are uses of the disclosed compounds. For example, provided is the use of a compound having a structure:

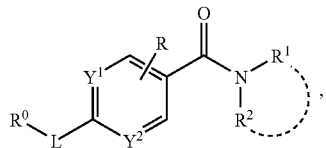

wherein ----- is an optional covalent bond; wherein $Y^1$ and $Y^2$ are independently selected from N and C—R; wherein R comprises two to four substituents independently selected from hydrogen, halogen, hydroxyl, cyano, nitro, thiol, or an organic radical comprising 1 to 12 carbon atoms; wherein $R^1$ and $R^2$ are independently hydrogen or an optionally substituted organic radical comprising from 1 to 12 carbon atoms; wherein $R^0$ is an optionally substituted organic radical comprising 4 to 14 carbon atoms; and wherein L is an organic divalent radical comprising 1 to 7 carbon atoms and is selected from:

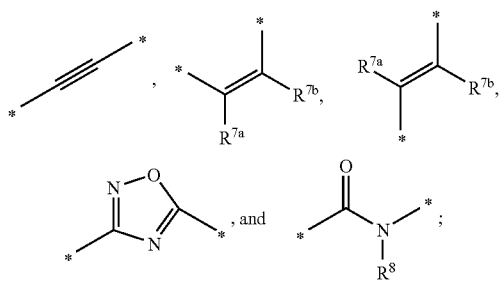

wherein $R^{7a}$ and $R^{7b}$ together form an optionally substituted carbocyclic or heterocyclic ring having from two to five carbons or are independently selected from hydrogen, halogen, hydroxyl, cyano, nitro, thiol, amino, and an organic radical comprising 1 to 5 carbon atoms selected from optionally substituted C1-C5 alkyl or C2-C5 alkenyl or C2-C5 alkynyl, optionally substituted C1-C5 heteroalkyl or C2-C5 heteroalkenyl or C2-C5 heteroalkynyl, optionally substituted C3-C5 cycloalkyl or C3-C5 cycloalkenyl, optionally substituted C3-C5 heterocycloalkyl or C3-C5 heterocycloalkenyl, optionally substituted aryl, optionally substituted heteroaryl, optionally substituted alkoxyl, optionally substituted thioalkyl, optionally substituted alkylsulfinyl, optionally substituted alkylsulfonyl, and optionally substituted amino, thioamido, amidosulfonyl, alkoxycarbonyl, carboxamide, aminocarbonyl, and alkylamine-carbonyl; or a pharmaceutically acceptable salt or N-oxide thereof.

In one aspect, the use is characterized in that the mammal is a human.

In one aspect, the use relates to a treatment of a disorder in a mammal.

In one aspect, the use is characterized in that the disorder is a neurological and/or psychiatric disorder associated with glutamate dysfunction.

In one aspect, the use relates to potentiation for partial agonism of metabotropic glutamate receptor activity in a mammal.

4. Subjects

The subject of the herein disclosed methods can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

In some aspects of the disclosed methods, the subject has been diagnosed with a need for treatment of one or more neurological and/or psychiatric disorder associated with glutamate dysfunction prior to the administering step.

In some aspects of the disclosed method, the subject has been diagnosed with a need for potentiation of metabotropic glutamate receptor activity prior to the administering step.

In some aspects of the disclosed method, the subject has been diagnosed with a need for partial agonism of metabotropic glutamate receptor activity prior to the administering step.

H. EXPERIMENTAL

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. ethyl 4-(phenylethynyl)benzoate

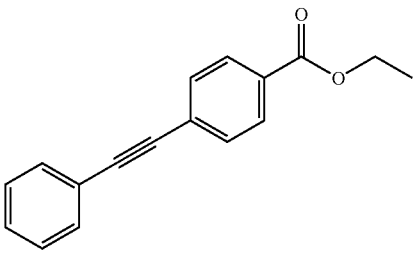 [SMILES: CCOC(=O)c1ccc(C#Cc2ccccc2)cc1]

To a solution of ethyl 4-iodobenzoate (5.0 g, 18.2 mmol) in DMF (8 mL) was added phenylacetylene (2.25 g, 22.1 mmol), Pd(Ph₃P)₄ (502 mg, 0.45 mmol), CuI (172 mg, 0.91 mmol) and diethylamine (2 mL). The reaction vessel was sealed and heated at 60° C. for 1 h in a microwave reactor. The reaction was cooled to room temperature, diluted with EtOAc:hexanes (2:1, 150 mL) and washed with water (2×100 mL) and brine (100 mL). The organic phase was dried over MgSO₄, filtered and concentrated under vacuum. The crude product was purified by column chromatography (silica gel) using 0 to 10% EtOAc/hexanes to afford ethyl 4-(phenylethynyl)benzoate (7.89 g, 86%) as a pale yellow solid; ¹H-nmr (400 MHz, CDCl₃) δ 8.05 (d, J=8.0 Hz, 2H), 7.61 (d, J=8.0 Hz, 2H), 7.56 (dd, J=8.0, 2.0 Hz, 2H), 7.41-7.37 (m, 3H), 4.41 (q, J=7.0 Hz, 2H), 1.44 (t, J=7.0 Hz, 3H); LC (275 nM) 5.79 min (>98%); MS (ESI) m/z=250.9.

2. 4-(phenylethynyl)benzoic acid

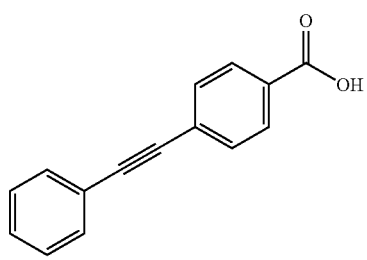 [SMILES: O=C(O)c1ccc(C#Cc2ccccc2)cc1]

To a solution of ethyl 4-(phenylethynyl)benzoate (7.81 g, 31.2 mmol) in THF (80 mL) was added MeOH (15 mL) and a solution of LiOH (5.24 g, 124 mmol) in water (15 mL). The reaction was stirred at room temperature and for 4 h. The reaction was acidified with 1 N HCl (50 mL), and 4-(phenylethynyl)benzoic acid was isolated (5.78 g, 83%) as a white solid; ¹H-nmr (400 MHz, CDCl₃) δ 8.11 (d, J=8.0 Hz, 2H), 7.75-7.68 (m, 1H), 7.64 (d, J=8.0 Hz, 2H), 7.62-7.56 (m, 2H), 7.52-7.47 (m, 1H), 7.43-7.36 (m, 3H); LC (275 nM) 5.12 min (>98%); MS (ESI) m/z=222.9.

3. (4-hydroxypiperidin-1-yl)(4-phenylethynyl)phenyl)methanone

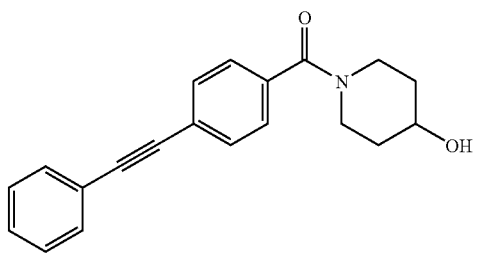

To a solution of 4-(phenylethynyl)benzoic acid (1.40 g, 6.30 mmol) and DIPEA (2.70 g, 20.8 mmol) in DMF (25 mL) was added EDC (1.41 g, 7.56 mmol), HOBt (850 mg, 6.30 mmol) and 4-hydroxypiperidine hydrochloride (1.29 g, 9.46 mmol). The reaction was stirred at room temperature for 18 h. The reaction was diluted with water (100 mL) and (4-hydroxypiperidin-1-yl)(4-phenylethynyl)phenyl)methanone was isolated (1.84 g, 98%) as a white solid by vacuum filtration; ¹H-nmr (400 MHz, CDCl₃) δ 7.58 (d, J=8.0 Hz, 2H), 7.56-7.52 (m, 2H), 7.44-7.34 (m, 5H), 4.21-4.08 (m, 1H), 4.03-3.96 (m, 1H), 3.81-3.48 (m, 1H), 3.47-3.16 (m, 2H), 2.08-1.79 (m, 2H), 1.71-1.42 (m, 2H); LC (275 nM) 5.01 min (>98%); MS (ESI) m/z=305.9.

4. 4-((3-fluorophenyl)ethynyl)benzoic acid

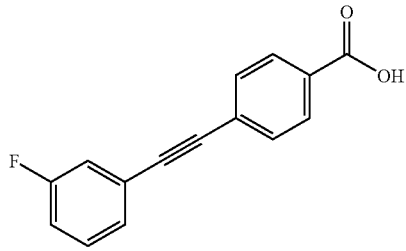 [SMILES: O=C(O)c1ccc(C#Cc2cccc(F)c2)cc1]

To a solution of ethyl 4-Iodobenzoate (10.0 g, 36.2 mmol) in DMF (30 mL) was added 3-fluorophenylacetylene (5.22 g, 43.4 mmol), Pd(Ph₃P)₄ (1.04 g, 0.91 mmol), CuI (346 mg, 1.82 mmol) and diethylamine (6 mL). The reaction vessel was sealed and heated at 60° C. for 1 h in a microwave reactor. The reaction was cooled to room temperature, diluted with EtOAc:hexanes (2:1, 250 mL) and washed with water (2×200 mL) and brine (200 mL). The organic phase was dried over MgSO₄, filtered and concentrated under vacuum. The crude product was dissolved in THF (130 mL) added MeOH (28 mL) and a solution of LiOH (3.04 g, 72.4 mmol) in water (28 mL). The reaction was stirred at room temperature and for 4 h. The reaction was acidified with 1 N HCl (100 mL) and 4-((3-fluorophenyl)ethynyl)benzoic acid was isolated (6.89 g, 79%) as a light tan solid; ¹H-nmr (400 MHz, d₆-DMSO) δ 7.97 (d, J=8.5 Hz, 2H), 7.68 (d, J=8.5 Hz, 1H), 7.55-7.42 (m, 3H), 7.21 (td, J=8.0, 2.0 Hz, 1H); LC (290 nM) 5.27 min (>98%); MS (ESI) m/z=240.7.

5. (4-((3-fluorophenyl)ethynyl)phenyl)(morpholino)methanone

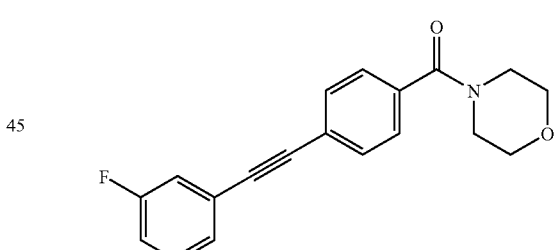

To a solution of 4-((3-fluorophenyl)ethynyl)benzoic acid (2.0 g, 8.33 mmol) and DIPEA (2.38 g, 18.3 mmol) in DMF (35 mL) was added EDC (1.86 g, 10.0 mmol), HOBt (1.35 g, 10.0 mmol) and morpholine (1.07 g, 12.5 mmol). The reaction was stirred at room temperature for 18 h. The reaction was diluted with water (200 mL) and extracted with EtOAc (2×150 mL). The combined organic extracts were washed with water (2×100 mL) and brine (100 mL), dried over MgSO₄, filtered and concentrated under vacuum. The residue was purified by column chromatography (silica gel) using 0 to 90% EtOAc/hexanes to afford (4-((3-fluorophenyl)ethynyl)phenyl)(morpholino)methanone (2.35 g, 89%) as a light tan solid; ¹H-nmr (400 MHz, CDCl₃) δ 7.57 (d, J=8.5 Hz, 2H), 7.41 (d, J=8.5 Hz, 2H), 7.38-7.31 (m, 1H), 7.28-7.21 (m, 1H), 7.13-7.05 (m, 1H), 4.00-3.31 (bd s, 8H); LC (290 nM) 5.08 min (>98%); MS (ESI) m/z=310.

6. (4((3-fluorophenyl)ethynyl)phenyl)(4-hydroxylpiperidin-1-yl-methanone

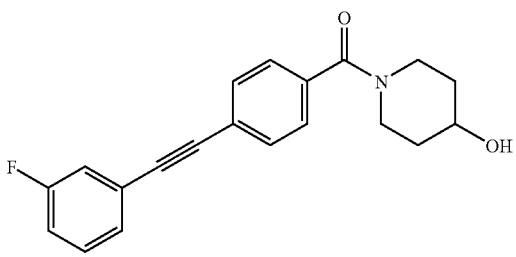 [SMILES: O=C(c1ccc(C#Cc2cccc(F)c2)cc1)N1CCC(O)CC1]

(4((3-fluorophenyl)ethynyl)phenyl)(4-hydroxylpiperidin-1-yl-methanone (2.61 g, 97%) light cream solid as prepared in identical fashion to (4((3-fluorophenyl)ethynyl)phenyl)(4-hydroxylpiperidin-1-yl-methanone; $^1$H-nmr (400 MHz, CDCl$_3$) δ 7.57 (d, J=8.5 Hz, 2H), 7.41 (d, J=8.5 Hz, 2H), 7.38-7.31 (m, 2H), 7.28-7.21 (m, 1H), 7.11-7.03 (m, 1H), 4.21-4.08 (m, 1H), 4.03-3.96 (m, 1H), 3.81-3.48 (m, 1H), 3.47-3.15 (m, 2H), 2.05-1.78 (m, 2H), 1.71-1.42 (m, 2H); LC (290 nM) 4.86 min (>98%); LC (290 nM) 4.93 min (>98%); MS (ESI) m/z=324.

7. (4-((3-fluorophenyl)ethynyl)phenyl)(4-hydroxymethyl)piperidin-1-yl)methanone

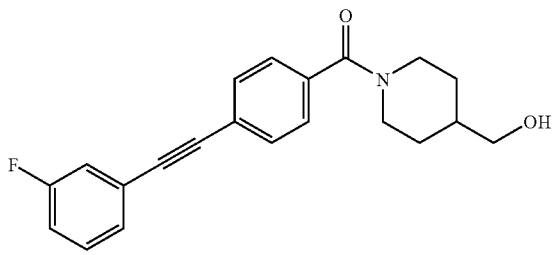 [SMILES: O=C(c1ccc(C#Cc2cccc(F)c2)cc1)N1CCC(CO)CC1]

Amide (4-((3-fluorophenyl)ethynyl)phenyl)(4-hydroxymethyl)piperidin-1-yl)methanone (2.32 g, 78%) light cream solid as prepared in identical fashion to (4-((3-fluorophenyl)ethynyl)phenyl)(morpholino)methanone; $^1$H-nmr (400 MHz, CDCl$_3$) δ 7.56 (d, J=8.5 Hz, 2H), 7.40 (d, J=8.5 Hz, 2H), 7.38-7.30 (m, 2H), 7.28-7.21 (m, 1H), 7.09-7.02 (m, 1H), 3.89-3.71 (m, 1H), 3.61-3.52 (m, 2H), 3.12-2.71 (m, 2H), 1.96-1.69 (m, 3H), 1.41-1.12 (m, 3H); LC (290 nM) 4.98 min (>98%); MS (ESI) m/z=338.

8. 4-((3,4-difluorophenyl)ethynyl)benzoic acid

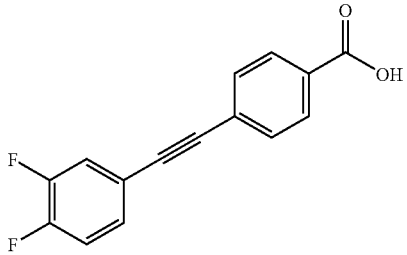 [SMILES: O=C(O)c1ccc(C#Cc2ccc(F)c(F)c2)cc1]

To a solution of ethyl 4-iodobenzoate (5.0 g, 18.1 mmol) in DMF (15 mL) was added 3,4-difluorophenylacetylene (2.99 g, 21.7 mmol), Pd(Ph$_3$P)$_4$ (520 mg, 0.45 mmol), CuI (173 mg, 0.90 mmol) and diethylamine (3 mL). The reaction vessel was sealed and heated at 60° C. for 1 h in a microwave reactor. The reaction was cooled to room temperature, diluted with EtOAc:hexanes (2:1, 150 mL) and washed with water (2×100 mL) and brine (100 mL). The organic phase was dried over MgSO$_4$, filtered and concentrated under vacuum. The crude product was dissolved in THF (60 mL) added MeOH (14 mL) and a solution of LiOH (1.52 g, 36.2 mmol) in water (14 mL). The reaction was stirred at room temperature and for 4 h. The reaction was acidified with 1 N HCl (60 mL) and 4-((3,4-difluorophenyl)ethynyl)benzoic acid was isolated (2.45 g, 57%) as a white solid; $^1$H-nmr (400 MHz, d$_6$-DMSO) δ 7.96 (d, J=8.5 Hz, 2H), 7.73 (td, J=8.5, 2.0 Hz, 1H), 7.67 (d, J=8.5 Hz, 2H), 7.55-7.43 (m, 2H); LC (290 nM) 5.08 min (>98%); MS (ESI) m/z=258.7.

9. (4-((3,4-difluorophenyl)ethynyl)phenyl)(morpholino)methanone

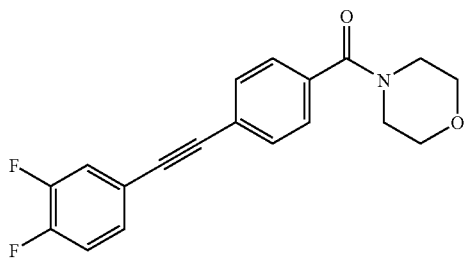 [SMILES: O=C(c1ccc(C#Cc2ccc(F)c(F)c2)cc1)N1CCOCC1]

To a solution of acid 7 (2.40 g, 9.30 mmol) and DIPEA (3.34 g, 18.6 mmol) in DMF (35 mL) was added EDC (2.07 g, 11.2 mmol), HOBt (1.25 g, 9.3 mmol) and morpholine (1.04 g, 12.1 mmol). The reaction was stirred at room temperature for 18 h. The reaction was diluted with water (100 mL) and (4-((3,4-difluorophenyl)ethynyl)phenyl)(morpholino)methanone was isolated (2.91 g, 96%) as a white solid by vacuum filtration; $^1$H-nmr (400 MHz, CDCl$_3$) δ 7.56 (d, J=8.5 Hz, 2H), 7.41 (d, J=8.5 Hz, 2H), 7.35 (t, J=8.0 Hz, 1H), 7.31-7.25 (m, 1H), 7.15 (dd, J=18.0, 8.0 Hz, 1H), 4.00-3.31 (bd s, 8H); LC (290 nM) 5.10 min (>98%); MS (ESI) m/z=327.9.

10. methyl 4-(3-phenyl-1,2,4-oxadiazol-5-yl)benzoate

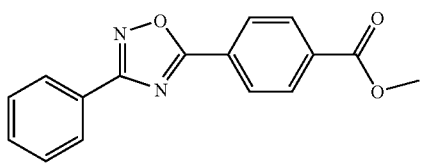 [SMILES: COC(=O)c1ccc(-c2nc(-c3ccccc3)no2)cc1]

To a suspension of mono-methyl terephthalate (1.50 g, 8.33 mmol) in acetonitrile (16 mL) was added EDC (4.65 g, 25.0 mmol), HOBt (1.12 g, 8.33 mmol), DIPEA (3.24 g, 25.0 mmol) and N-hydroxybenzimidamide (1.36 g, 10.0 mmol). The reaction was heated at 100° C. for 30 mins in a microwave. The reaction was then cooled to rt, diluted with water (60 mL) and isolated the crude white precipitate by vacuum filtration. Dissolved in CH$_2$Cl$_2$ and passed through a plug of silica to afford methyl 4-(3-phenyl-1,2,4-oxadiazol-5-yl)benzoate as an off-white solid (640 mg, 23%). $^1$H-nmr (400 MHz, CDCl$_3$) δ 8.33 (d, J=8 Hz, 2H), 8.24 (d, J=8 Hz, 2H), 8.21-8.11 (m, 2H), 7.59-7.51 (m, 3H), 4.00 (s, 3H); MS (ESI) m/z 280.9

11. 4-(3-phenyl-1,2,4-oxadiazol-5-yl)benzoic acid

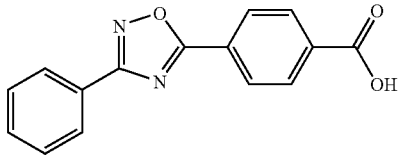 [SMILES: O=C(O)c1ccc(-c2nc(-c3ccccc3)no2)cc1]

To a solution of methyl 4-(3-(4-fluorophenyl) 1,2,4-oxadiazol-5-yl)benzoate (600 mg, 2.14 mmol) in THF (12 mL) was added MeOH (3 mL) and a solution of LiOH (351 mg, 8.57 mmol) in $H_2O$ (3 mL). The reaction was stirred at room temperature for 2 h. The reaction was quenched upon the addition of 1N HCl (30 mL) and extracted with EtOAc (2×30 mL). The organic extracts were dried over $MgSO_4$, and concentrated under vacuum to afford 4-(3-phenyl-1,2,4-oxadiazol-5-yl)benzoic acid (550 mg, 87%) as a white solid. $^1$H-nmr (400 MHz, $CDCl_3$) δ 8.37 (d, J=8 Hz, 2H), 8.30 (d, J=8 Hz, 2H), 8.26-8.19 (m, 2H), 7.62-7.52 (m, 3H); MS (ESI) m/z 266.8

12. N-(3,3-dimethylbutyl)-4-(3-phenyl-1,2,4-oxadiazol-5-yl-benzamide

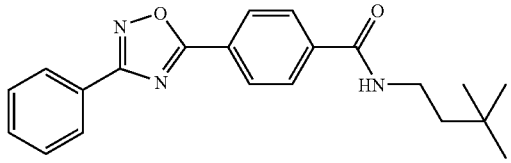 [SMILES: CC(C)(C)CCNC(=O)c1ccc(-c2nc(-c3ccccc3)no2)cc1]

To a solution of 4-(3-phenyl-1,2,4-oxadiazol-5-yl)benzoic acid (200 mg, 0.75 mmol) in DMF (2 mL) was added EDC (167 mg, 0.90 mmol), HOBt (122 mg, 0.90 mmol), DIPEA (200 mg, 1.50 mmol) and 3,3-dimethylbutylamine (113 mg, 1.12 mmol). The reaction was stirred at room temperature for 18 h. The reaction was diluted with water (10 mL) and isolated the white precipitate by vacuum filtration to afford N-(3,3-dimethylbutyl)-4-(3-phenyl-1,2,4-oxadiazol-5-yl-benzamide (248 mg, 95%). $^1$H-nmr (400 MHz, $CDCl_3$) δ 8.31 (d, J=8 Hz, 2H), 8.23-8.17 (m, 2H), 7.95 (d, J=8 Hz, 2H), 7.59-7.52 (m, 3H), 6.12 (s, 1H), 3.57-3.51 (m, 2H) 1.62-1.58 (m, 2H), 1.02 (s, 9H); MS (ESI) m/z 349.9.

13. (E)-ethyl 4-styrylbenzoate

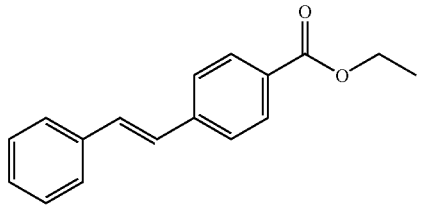 [SMILES: CCOC(=O)c1ccc(/C=C/c2ccccc2)cc1]

To a solution of ethyl 4-iodobenzoate (1.0 g, 3.6 mmol) in DMF (4 mL) was added commercial (E)-styrylboronic acid (538 mg, 3.6 mmol) and catalytic Pd(tBuP)$_2$. The reaction vessel was sealed and heated at 160° C. for 10 minutes in a microwave reactor. The reaction was cooled to rt, diluted with EtOAc:hexanes (2:1, 20 mL) and washed with water (2×20 mL) and brine (20 mL). The organic phase was dried over $MgSO_4$, filtered and concentrated under vacuum. The crude product was purified by column chromatography (silica gel) using 0 to 10% EtOAc/hexanes to afford (E)-ethyl 4-styrylbenzoate (771 mg, 85%) as a pale yellow solid; $^1$H-nmr (400 MHz, $CDCl_3$) δ 8.05 (d, J=8.0 Hz, 2H), 7.61 (d, J=8.0 Hz, 2H), 7.56 (dd, J=8.0, 2.0 Hz, 2H), 7.41-7.37 (m, 3H), 6.95 (d, 1H), 6.89 (d, 1H), 4.41 (q, J=7.0 Hz, 2H), 1.44 (t, J=6.8 Hz, 3H); LCMS (214 nM) 3.58 min (>98%); MS (ESI) m/z=253.1.

14. (E)-ethyl 4-styrylbenzoic acid

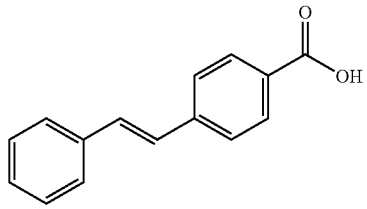 [SMILES: O=C(O)c1ccc(/C=C/c2ccccc2)cc1]

To a solution of ester (E)-ethyl 4-styrylbenzoate (600 mg, 2.3 mmol) in THF (5 mL) was added MeOH (2 mL) and a solution of LiOH (360 mg, 10 mmol) in water (25 mL). The reaction was stirred at room temperature and for 4 h. The reaction was acidified with 1 N HCl (10 mL) and isolated (E)-ethyl 4-styrylbenzoic acid (440 mg, 83%) as a white solid; $^1$H-nmr (400 MHz, $CDCl_3$) δ 8.11 (d, J=8.0 Hz, 2H), 7.75-7.68 (m, 1H), 7.64 (d, J=8.0 Hz, 2H), 7.62-7.56 (m, 2H), 7.52-7.47 (m, 1H), 7.43-7.36 (m, 3H), 6.97 (d, 1H), 6.88 (d, 1H); LCMS (214 nM) 3.22 min (>98%); MS (ESI) m/z=225.1.

15. (4-hydroxypiperidin-1-yl)(4-styrylphenyl)methanone

To a solution of (E)-ethyl 4-styrylbenzoic acid (300 mg, 1.3 mmol) and DIPEA (270 uL, 2.1 mmol) in DMF (5 mL) was added EDC (280 mg, 1.5 mmol), HOBt (270 mg, 2.0 mmol) and 4-hydroxypiperidine hydrochloride (258 mg, 1.8 mmol). The reaction was stirred at room temperature for 18 h. The reaction was diluted with water (10 mL) and (4-hydroxypiperidin-1-yl)(4-styrylphenyl)methanone was isolated (390 mg, 98%) as a white solid by vacuum filtration; $^1$H-nmr (400 MHz, $CDCl_3$) δ 7.58 (d, J=8.0 Hz, 2H), 7.56-7.52 (m, 2H), 7.44-7.34 (m, 5H), 6.95 (d, 1H), 6.89 (d, 1H), 4.21-4.08 (m, 1H), 4.03-3.96 (m, 1H), 3.81-3.48 (m, 1H), 3.47-3.16 (m, 2H), 2.08-1.79 (m, 2H), 1.71-1.42 (m, 2H); LCMS (214 nM) 3.32 min (>98%); MS (ESI) m/z=308.1.

16. methyl 4-(4-fluorophenylcarbamoyl)benzoate

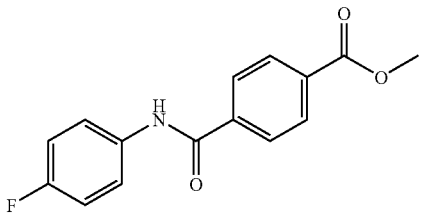 [SMILES: COC(=O)c1ccc(C(=O)Nc2ccc(F)cc2)cc1]

To a suspension of mono-methyl terephthalate (2.0 g, 11.1 mmol) in DMF (10 mL) was added EDC (2.48 g, 13.3 mmol), HOBt (1.80 g, 13.3 mmol), and 4-fluoroaniline (1.48 g, 13.3 mmol). The reaction was stirred at room temperature for 72 h. The reaction was diluted with water (80 mL) and isolated methyl 4-(4-fluorophenylcarbamoyl)benzoate (3.00 g, 98%) as a white precipitate by vacuum filtration. $^1$H-nmr (400 MHz, CDCl$_3$) δ 8.18 (d, J=8 Hz, 2H), 7.95 (d, J=8 Hz, 2H), 7.82 (br s, 1H), 7.66-7.59 (m, 2H), 7.15-7.07 (m, 2H), 3.99 (s, 3H); MS (ESI) m/z 273.9.

17. 4-(4-fluorophenylcarbamoyl)benzoic acid

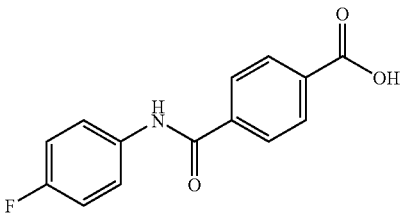 [SMILES: O=C(O)c1ccc(C(=O)Nc2ccc(F)cc2)cc1]

To a solution of methyl 4-(4-fluorophenylcarbamoyl)benzoate (2.98 g, 10.9 mmol) in THF (35 mL) was added MeOH (8 mL) and a solution of LiOH (1.79 g, 43.6 mmol) in H$_2$O (8 mL). The reaction was stirred at room temperature for 2 h. The reaction was quenched upon the addition of 1N HCl (50 mL) and extracted with EtOAc (2×60 mL). The organic extracts were dried over MgSO$_4$, and concentrated under vacuum to afford 4-(4-fluorophenylcarbamoyl)benzoic acid (2.43 g, 86%) as a white solid. $^1$H-nmr (400 MHz, d$_6$-DMSO) δ 10.49 (s, 1H), 8.11-8.02 (m, 4H), 7.87-7.77 (m, 2H), 7.25-7.16 (m, 2H); MS (ESI) m/z 259.9.

18. N-(4-fluorophenyl)-4-(2-methylpiperidine-1-carbonyl)benzamide

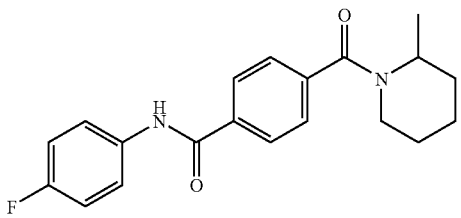 [SMILES: CC1CCCCN1C(=O)c1ccc(C(=O)Nc2ccc(F)cc2)cc1]

To a solution of 4-(4-fluorophenylcarbamoyl)benzoic acid (50 mg, 0.19 mmol) in DMF (1 mL) was added PS-Carbodiimide (125 mg, 0.25 mmol), HOBt (26 mg, 0.19 mmol), DIPEA (52 mg, 0.40 mmol) and 2-methylpiperidine (25 mg, 0.25 mmol). The reaction was agitated at room temperature for 18 h. To the reaction was added MP-carbonate and agitated for a further 8 h. The reaction was filtered and concentrated under vacuum to afford diluted with water (10 mL) and isolated the white precipitate by vacuum filtration to afford N-(4-fluorophenyl)-4-(2-methylpiperidine-1-carbonyl)benzamide (248 mg, 95%). $^1$H-nmr (400 MHz, d$_6$-DMSO) δ 10.37 (br s, 1H), 8.00 (d, J=7 Hz, 2H), 7.83-7.72 (m, 2H), 7.49 (d, J=7 Hz, 2H), 7.21 (t, J=8 Hz, 2H), 3.52-3.01 (m, 3H), 1.75-1.29 (m, 6H), 1.21 (m, 3H); MS (ESI) m/z 341.4.

19. In Vitro Studies

Human embryonic kidney (HEK) cells transfected with rat mGluR5 were plated in clear-bottomed, poly-D-lysine-coated assay plates in glutamate-glutamine-free medium growth and incubated overnight at 37° C. in 5% CO$_2$. The following day, cells were loaded with 2 µM calcium indicator dye, fluo-4 AM, for 1 h at 37° C. Dye was removed and replaced with assay buffer containing 1× Hanks balanced salt solution (Invitrogen, Carlsbad, Calif.), 20 mM HEPES, and 2.5 mM probenecid, pH 7.4. Cell plates were then loaded into the Functional Drug Screening System 6000 (FDSS 6000, Hamamatsu, Japan). After establishment of a fluorescence baseline for twelve seconds, the compounds of the present invention were added to the cells, and the response in cells was measured. Five minutes later, an mGluR5 agonist (e.g., glutamate, 3,5-dihydroxyphenylglycine, or quisqualate) was added to the cells, and the response of the cells was measured during a 1 minute incubation with agonists. Typically, the effect of test compounds of the present invention was on an EC$_{20}$ concentration of glutamate was measured. All test compounds were dissolved and diluted in 100% DMSO and then serially diluted into assay buffer for a 2.5× stock in 0.25% DMSO; stock compounds were then added to the assay for a final DMSO concentration of 0.1%. Calcium fluorescence measures were recorded as fold over basal fluorescence; raw data was then normalized to the maximal response to agonist. Potentiation of the agonist response of mGluR5 by the compounds in the present invention was observed as an increase in response to non-maximal concentrations of agonist (here, glutamate) in the presence of compound compared to the response to agonist in the absence of compound.

20. Behavior Evaluation

Locomotor activity can be assessed as mean distance traveled (cm) in standard 16×16 photocell testing chambers measuring 43.2 cm (L)×43.2 cm (W)×30.5 cm (H) (Med Associates, St. Albans, Vt.). Animals can be habituated to individual activity chambers for at least 60 min prior to drug administration. Following administration of appropriate drugs or vehicle, activity can be recorded for a 3 hr time period. Data can be expressed as the mean (±SEM) distance traveled recorded in 10 min intervals over the test period. The data can be analyzed using repeated measures analysis of variance (ANOVA) followed by post-hoc testing using Tukey's HSD test, when appropriate. A difference can be considered significant when p≤0.05.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having a structure represented by a formula:

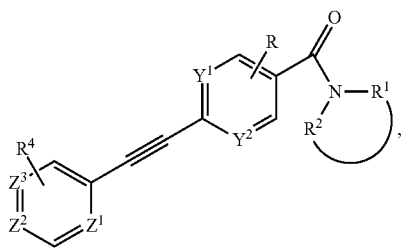

wherein N, $R^1$, and $R^2$ together form an optionally substituted heterocyclic ring having from two to seven carbons;
wherein both of $Y^1$ and $Y^2$ are carbon;
wherein R represents four substituents independently selected from hydrogen, halogen, hydroxyl, cyano, nitro, thiol, or an organic radical comprising 1 to 12 carbon atoms;
wherein all of $Z^1$, $Z^2$, and $Z^3$ are carbon; and
wherein $R^4$ represents five substituents independently selected from hydrogen, halogen, and cyano, wherein at least one of $R^4$ is halogen selected from F and Cl;
or a pharmaceutically acceptable salt or N-oxide thereof,
wherein the compound exhibits potentiation of mGluR5 response to glutamate as an increase in response to non-maximal concentrations of glutamate in human embryonic kidney cells transfected with rat mGluR5 in the presence of the compound, compared to the response to glutamate in the absence of the compound.

2. The compound of claim 1, wherein R represents four substituents independently selected from hydrogen, halogen, and lower alkyl.

3. The compound of claim 1, wherein N, $R^1$, and $R^2$ together form a cyclic optionally substituted alkyl residue selected from (E)-4-hydroxypiperidin-1-yl; (S)-(4-(1-cyclohexylethylamino)piperidin-1-yl; 1-(piperidin-4-yl)-1H-benzo[d]imidazol-2(3H)-one; 1-(piperidin-4-yl)ethanone; 2-(piperazin-1-yl)benzonitrile; 2,6-dimethylmorpholino; 2-morpholinoethyl; 3-hydroxy-3-(thiophen-2-yl)azetidin-1-yl; 3-hydroxy-3-methylazetidin-1-yl; 3-hydroxy-3-propylazetidin-1-yl; 3-hydroxyazetidin-1-yl; 3-hydroxypiperidin-1-yl; 4-(2-fluorophenyl)piperazin-1-yl; 4-(2-methoxyethylamino)piperidin-1-yl; 4-(2-methoxyphenyl)piperazin-1-yl; 4-(2-morpholinoethylamino)piperidin-1-yl; 4-(3-fluorophenyl)-4-hydroxypiperidin-1-yl; 4-(4-(pyridin-4-yl)piperazin-1-yl)piperidin-1-yl; 4-(4-bromophenyl)-4-hydroxypiperidin-1-yl; 4-(4-chloro-2-(trifluoromethyl)phenyl)-4-hydroxypiperidin-1-yl; 4-(4-chlorophenyl)-4-hydroxypiperidin-1-yl; 4-(4-fluorophenyl)-4-hydroxypiperidin-1-yl; 4-(4-methylpiperazin-1-yl)piperidin-1-yl; 4-(azetidin-1-yl)piperidin-1-yl; 4-(cyclobutylamino)piperidin-1-yl; 4-(cyclopropylmethylamino)piperidin-1-yl; 4-(hydroxymethyl)piperidin-1-yl; 4-(pyridin-2-yl)piperazin-1-yl; 4-(pyrrolidin-1-yl)piperidin-1-yl; 4-hydroxy-4-(4-methoxyphenyl)piperidin-1-yl; 4-hydroxy-4-(thiophen-2-yl)piperidin-1-yl; 4-hydroxy-4-isopropylpiperidin-1-yl; 4-hydroxy-4-methylpiperidin-1-yl; 4-hydroxypiperidin-1-yl; 4-isopropylpiperazin-1-yl; 4-methylpiperazin-1-yl; 4-phenyl-1-piperidine-4-carbonitrile; 6-chloro-1-(piperidin-4-yl)-1H-benzo[d]imidazol-2(3H)-one; morpholino; octahydroisoquinolin-2(1H)-yl; and piperazin-1-yl.

4. The compound of claim 1, wherein the compound exhibits potentiation of mGluR5 response to glutamate with an $EC_{50}$ of less than $1.0 \times 10^{-6}$.

5. The compound of claim 1, wherein the compound exhibits potentiation of mGluR5 response to glutamate with an $EC_{50}$ of less than $1.0 \times 10^{-7}$.

6. The compound of claim 1, wherein the compound exhibits potentiation of mGluR5 response to glutamate with an $EC_{50}$ of less than $1.0 \times 10^{-8}$.

7. The compound of claim 1, wherein R represents four hydrogens.

8. The compound of claim 1, having a structure represented by a formula:

163
-continued
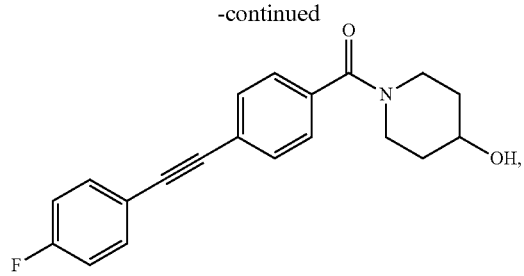
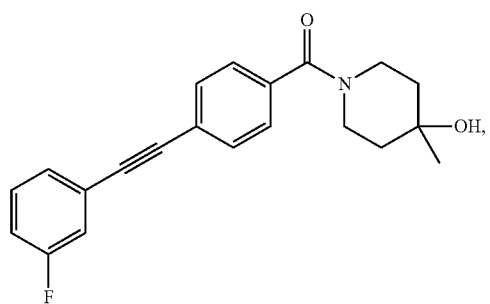
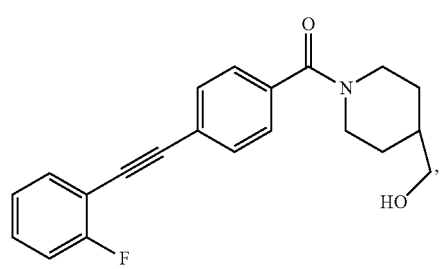
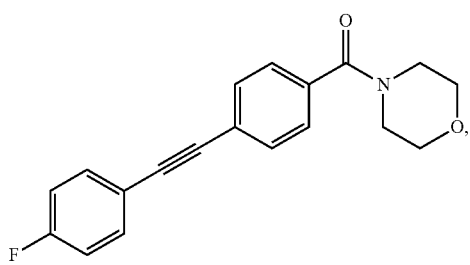
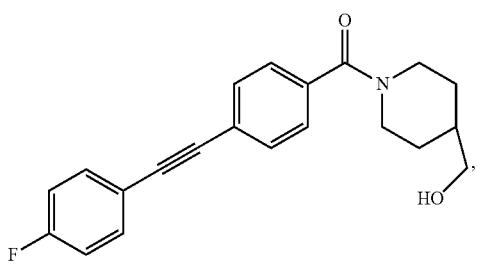
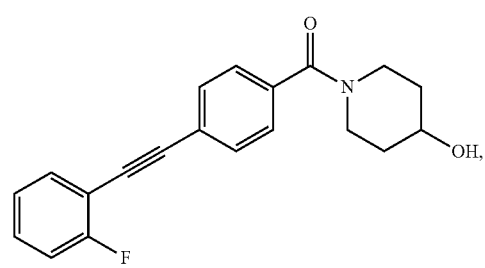
164
-continued
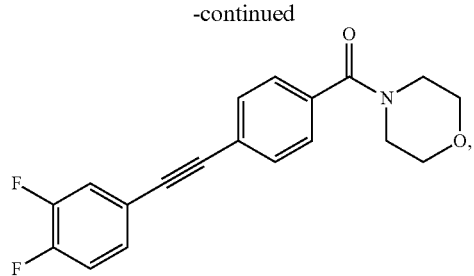
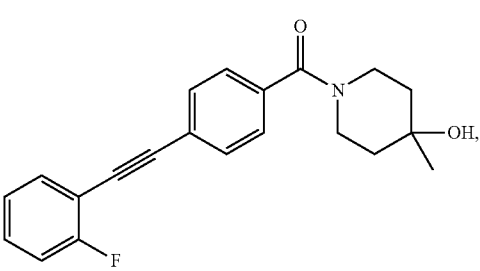
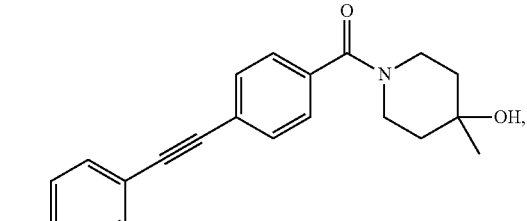
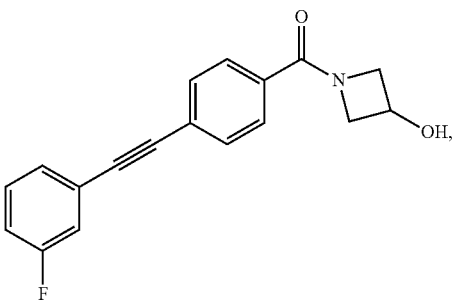
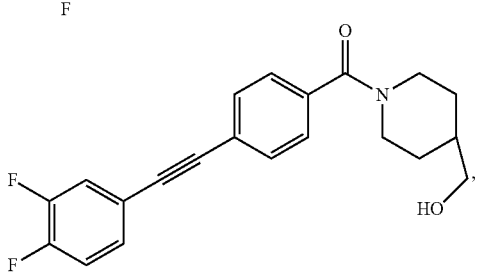

-continued
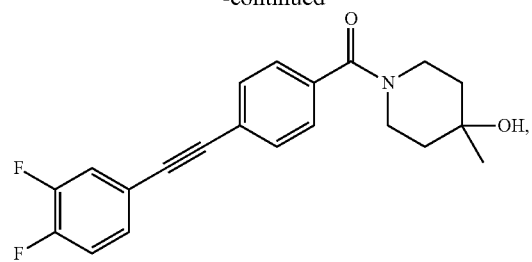
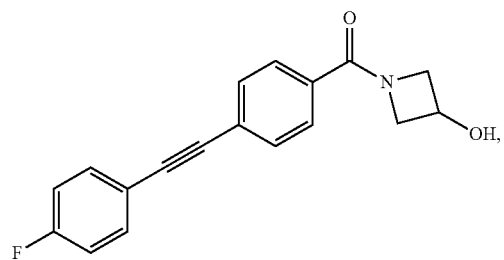
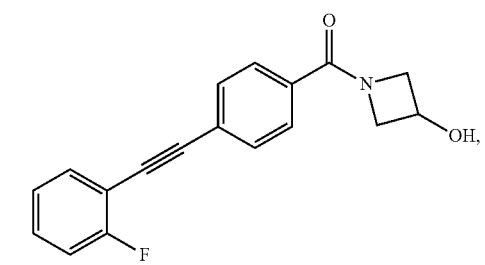
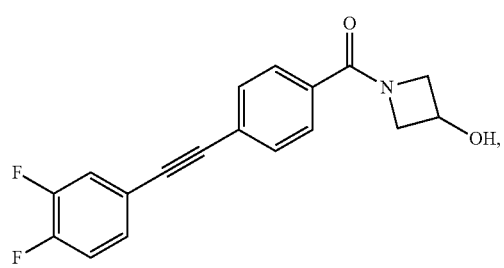
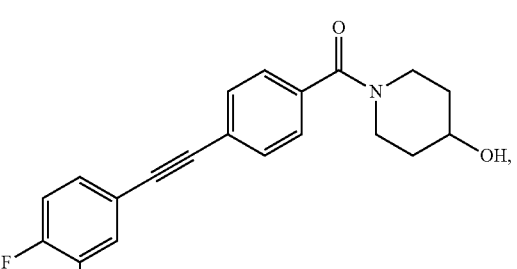
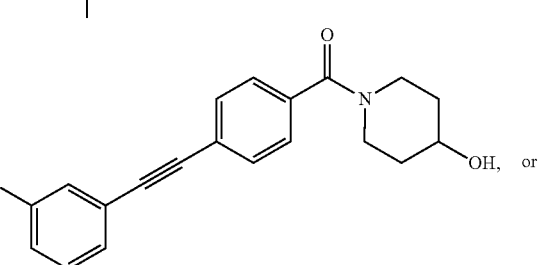 or
-continued
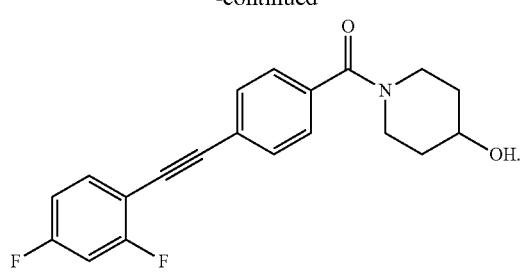
9. A compound having a structure represented by a formula:
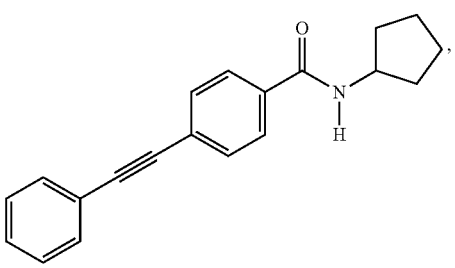
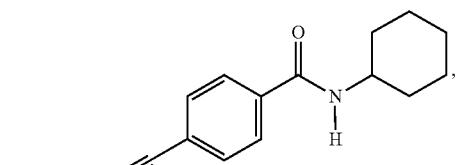
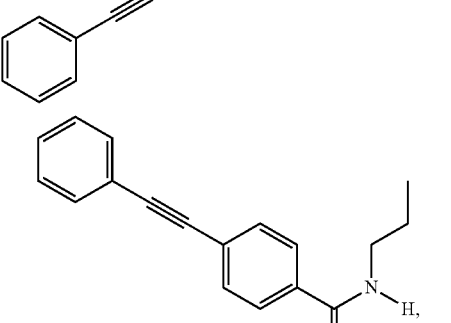
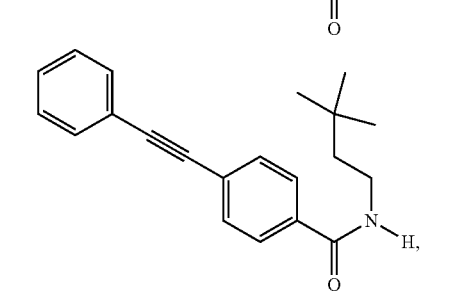
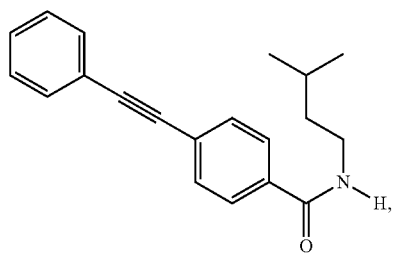

167
-continued
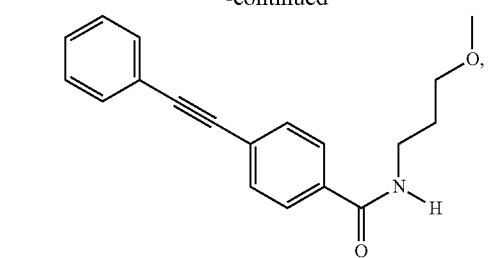
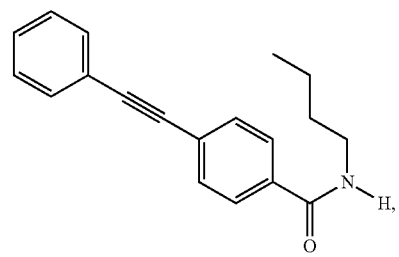
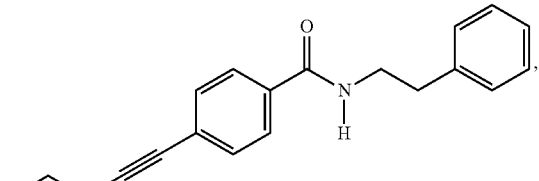
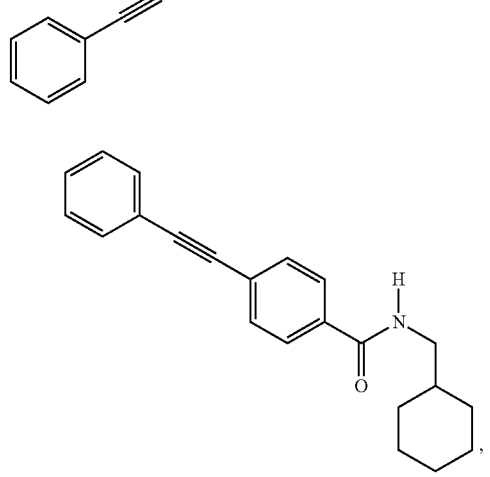
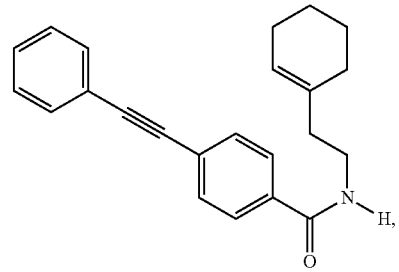
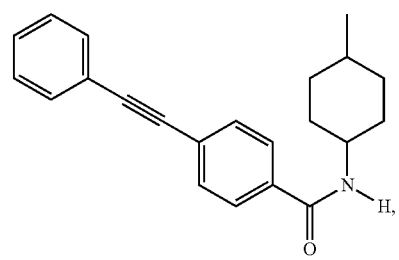
168
-continued
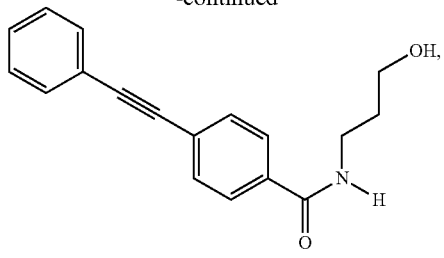
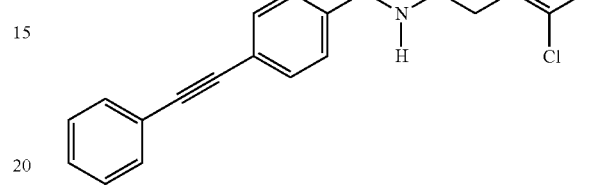
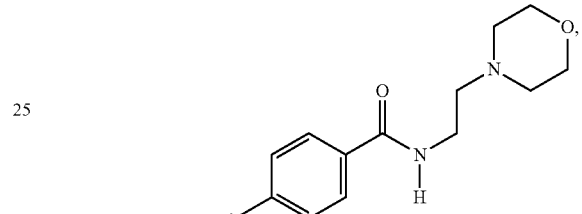
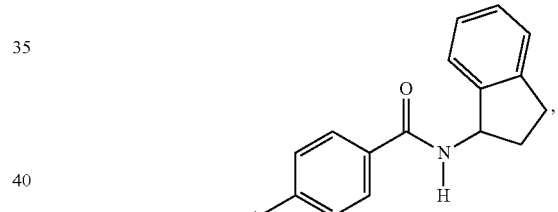
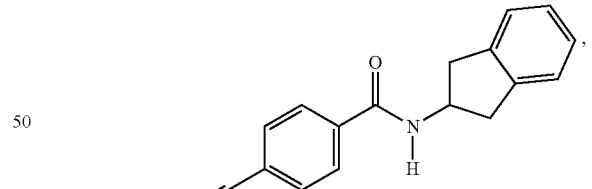
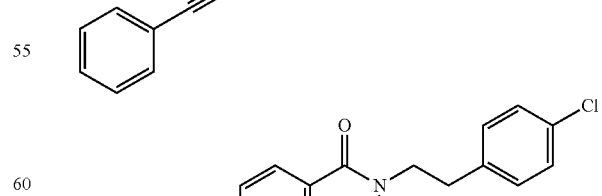

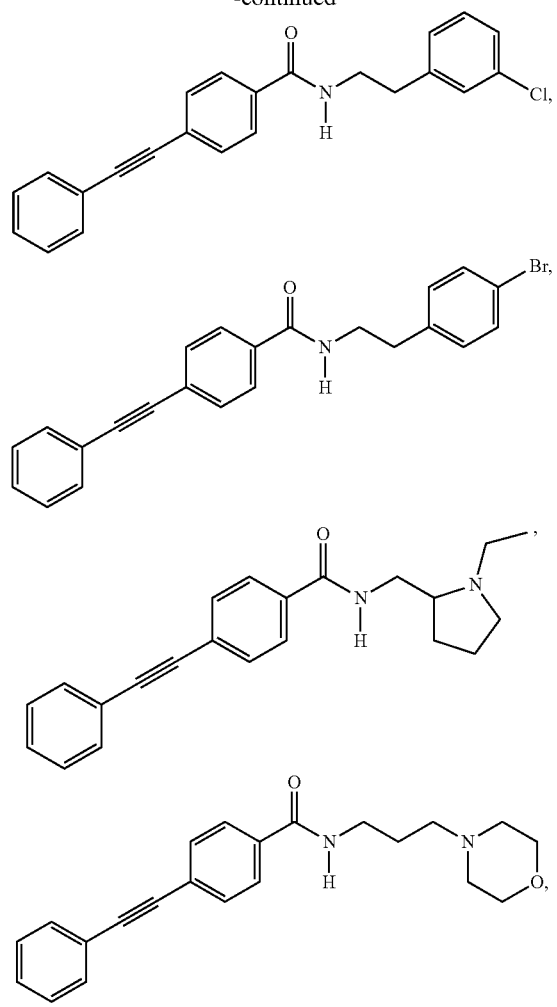
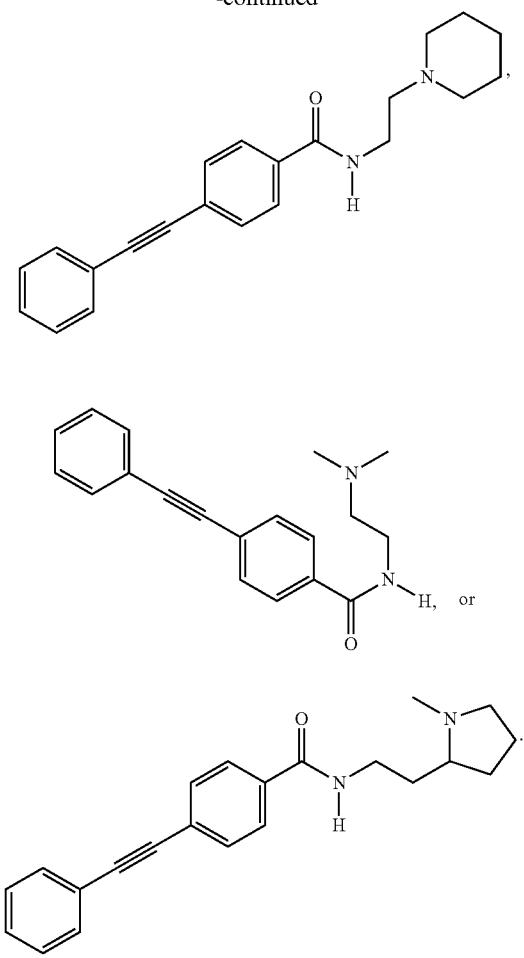
* * * * *

UNITED STATES PATENT AND TRADEMARK OFFICE
CERTIFICATE OF CORRECTION

PATENT NO. : 8,853,392 B2  Page 1 of 1
APPLICATION NO. : 12/132289
DATED : October 7, 2014
INVENTOR(S) : P. Jeffrey Conn et al.

It is certified that error appears in the above-identified patent and that said Letters Patent is hereby corrected as shown below:

Claims

In column 167, line 25, claim 9, replace " 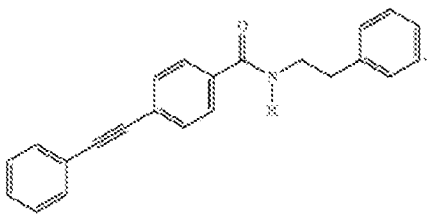 " with

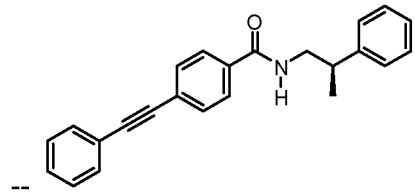

--     --

Signed and Sealed this
Fifth Day of April, 2016

Michelle K. Lee
*Director of the United States Patent and Trademark Office*